US006936606B2

(12) United States Patent
Bekkali et al.

(10) Patent No.: US 6,936,606 B2
(45) Date of Patent: Aug. 30, 2005

(54) CYANOAMIDO-CONTAINING HETEROCYCLIC COMPOUNDS USEFUL AS REVERSIBLE INHIBITORS OF CYSTEINE PROTEASES

(75) Inventors: Younes Bekkali, Danbury, CT (US); Denice Mary Spero, West Redding, CT (US); Sanxing Sun, Danbury, CT (US); David S. Thomson, Ridgefield, CT (US); Yancey D. Ward, Sandy Hook, CT (US); Erick R. R. Young, Danbury, CT (US); Eugene R. Hickey, Danbury, CT (US); Weimin Liu, Sandy Hook, CT (US); Usha R. Patel, Brookfield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 174 days.

(21) Appl. No.: 10/256,512

(22) Filed: Sep. 27, 2002

(65) Prior Publication Data

US 2004/0063679 A1 Apr. 1, 2004

Related U.S. Application Data

(60) Provisional application No. 60/326,538, filed on Oct. 2, 2001.

(51) Int. Cl.[7] .................. C07D 239/95; C07D 265/24; C07D 401/12; A61K 31/517; A61K 31/536
(52) U.S. Cl. ................ 514/226.8; 514/229.8; 514/230.5; 514/266.3; 514/267; 514/373; 514/416; 544/54; 544/89; 544/91; 544/92; 544/250; 544/286; 548/212; 548/472
(58) Field of Search .................. 514/226.8, 229.8, 514/230.5, 266.3, 267, 373, 416; 544/54, 89, 91, 92, 250, 286; 548/212, 472

(56) References Cited

U.S. PATENT DOCUMENTS

| 5,776,718 | A | 7/1998 | Palmer et al. |
| 6,395,897 | B1 | 5/2002 | Cywin et al. |
| 6,420,364 | B1 | 7/2002 | Emmanuel et al. |
| 2003/0158256 | A1 * | 8/2003 | Cowen et al. ............ 514/521 |

FOREIGN PATENT DOCUMENTS

| WO | WO 99/24460 | 5/1999 |
| WO | WO 00/55125 | 9/2000 |
| WO | WO 00/55126 | 9/2000 |
| WO | WO 01/19796 A1 | 3/2001 |
| WO | WO 01/19808 | 3/2001 |
| WO | WO 01/19816 A1 | 3/2001 |

OTHER PUBLICATIONS

Marquis, Robert W., Ann. Reports Med. Chem., vol. 35, pp. 309–320, 2000.*
Rasnick et al "Small synthetic inhibitors of cysteine proteases"; Perspectives in Drug Discovery and Design, vol. 6, pp. 47 63 (1996).*

Riese R.J. et al, J. Clin. Invest., 101(11), pp. 2351–2363, 1998.*

Saegusa K,, et al, J. Clin Invest. Aug. 2002;110(3):361–9.*

Thurmond RL et al, J Pharmacol Exp Ther. Oct. 17, 2003, abstract cited in PMID: 14566006.*

Vitas–M Screening Collection, Mar. 22, 2001, cited in Chemical Abstracts, 2001:473994 CHEMCATS.*

Robin L. Thurmond, et al; Identification of a Potent and Selective Noncovalent Cathepsin S Inhibitor; Journal of Pharmacology and Experimental Therapeutics, vol. 308, No. 1 pp 268–276.

H. Beck, et al; Cathepsin S and an asparagine–specific endoprotease dominate the proteolytic processing of human myelin basic protein in vitro; Eur. J. Immunol., 2001, 31: 3726–3736.

Terry Y. Nakagawa, et al; Impaired Invariant Chain Degradation and Antigen Presentation and Diminished Collagen––induced Arthritis in Cathepsin S Null Mice; Immunity, vol. 10, 207–217, Feb. 1999.

Francesca Lazner, et al; Osteropetrosis and Osteoporosis: two sides of the same coin; Human Molecular Genetics 1999, vol. 8 No. 10 Review 1839–1846.

Galina K. Sukhova, et al; Expression of the Elastolytic Cathepsins S and K in Human Atheroma and Regulation of their Production in Smooth Muscle Cells; J. Clin. Invest. vol. 102, No. 2, Aug. 1998, pp. 576–583.

(Continued)

*Primary Examiner*—Thomas C. McKenzie
(74) *Attorney, Agent, or Firm*—M. P. Morris; A. P. Bottino; P. I. Datlow

(57) ABSTRACT

Disclosed are novel cathepsin S, K, F, L and B reversible inhibitory compounds of the formulas (Ia) and (Ib) where $R_1$, $R_2$, $R_3$, $R_4$, $R_5$, $R_6$, $R_8$, $R_9$ and X are defined herein. The compounds are useful for treating autoimmune and other diseases. Also disclosed are processes for making such novel compounds

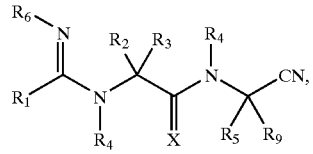

(Ia)

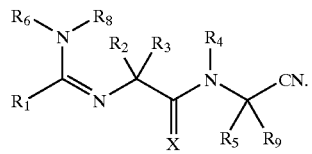

(Ib)

12 Claims, No Drawings

OTHER PUBLICATIONS

Harold A. Chapman, et al; Emerging Rofes for Cysteine Proteases in Human Biology; Annu. Rev. Physiol. 1997, 59, 63–88.

Ulf Mueller–Ladner, et al; Cysteine Proteinases in Arthritis and Inflammation: Perspectives in Drug Discovery and Design, vol. 6, pp. 87–98.

Woomi Kim and Kooli Kang; Recent developments of Cathepsin Inhibitors and Their Sensitivity; Expert Opinion Ther. Patents (2002) 12(3), pp 421–432.

Revised by Richard J. Lewis, Sr., Hawley's Condensed Chemical Dictionary, Thirteen Edition, pp 515–516.

* cited by examiner

CYANOAMIDO-CONTAINING HETEROCYCLIC COMPOUNDS USEFUL AS REVERSIBLE INHIBITORS OF CYSTEINE PROTEASES

APPLICATION DATA

This application claims benefit to U.S. provisional application Ser. No. 60/326,538 filed Oct. 2, 2001.

TECHNICAL FIELD OF THE INVENTION

This invention relates to amidino and guanidino peptidyl compounds active as cysteine protease inhibitors. The compounds are reversible inhibitors of the cysteine protease cathepsin S, K, F, L and B are therefore useful in the treatment of autoimmune and other diseases. The invention also relates to processes for preparing such compounds and pharmaceutical compositions comprising them.

BACKGROUND OF THE INVENTION

Cathepsin S and cathepsin K are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et at, 1999, Immunity, 10, 207). The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immunoregulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999).

A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation, 1998, 101, 2351).

Another cysteine protease, cathepsin F has been found in macrophages and is also involved in antigen processing. It has been postulated that cathepsin F in stimulated lung macrophages and possibly other antigen presenting cells could play a role in airway inflammation (G.-P. Shi et al., J. Exp. Med., 2000, 191, 1177).

Cathepsin K, another cysteine protease has been found to be highly expressed in osteoclasts and to degrade bone collagen and other bone matrix proteins. Inhibitors of cathepsin K have been shown to inhibit bone resorption in mice. Therefore, cathepsin K may play a role in osteoclastic bone resorption and cathepsin K inhibitors may be useful in the treatment of diseases involving bone resorption such as osteoporosis (F. Lazner et al., Human Molecular Genetics, 1999, 8, 1839).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al., there is disclosed in it's broadest generic aspect a protease inhibitor comprising a targeting group linked through a two carbon atom chain to an electron withdrawing group (EWG). The compounds of the present application are structurally distinct and thus excluded from the U.S. Pat. No. 5,776,718 with particular embodiments possessing unexpectedly greater activity than the closest compounds of the prior art. Other examples of cathepsin S inhibitors have been reported by E. T. Altmann et al, (WO 9924460, 1999) which describes dipeptide nitriles asserted to have activity as inhibitors of Cathepsins B, K, L and S. Axys publications WO 00/55125 and 00/55126 disclose peptidyl nitrites for cathepsin inhibition which possess spirocarbocyclic and spiroheterocyclic moieties at P1, Axys publications WO 01/19808 and WO 01/19796 disclose peptidyl nitriles possessing mandatory sulfonyl groups at P2. Additional peptidyl nitrites have been reported as protease inhibitors. For example, both nitriles and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain.

None of the aforementioned publications disclose compounds possessing a mandatory guanidino or amidino structure at the P3 position.

A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases such as cathepsin S and cathepsin K for indications in which these proteases exacerbate disease.

BRIEF DESCRIPTION OF THE INVENTION

It is therefore an object of this invention to provide novel compounds according to the formula (Ia/Ib) as described herein which reversibly inhibit the cysteine proteases cathepsin S, K, F, L and B. It is a further object of the invention to provide methods for treating diseases and pathological conditions exacerbated by these cysteine proteases such as, but not limited to, rheumatoid arthritis, multiple sclerosis, asthma and osteoporosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases such as cathepsin S, K, F, L and B may be determined by the screens described in the section entitled "Assessment of Biological Properties."

Accordingly, in a first generic aspect of the invention, there are provided compounds of formula (Ia) or (Ib):

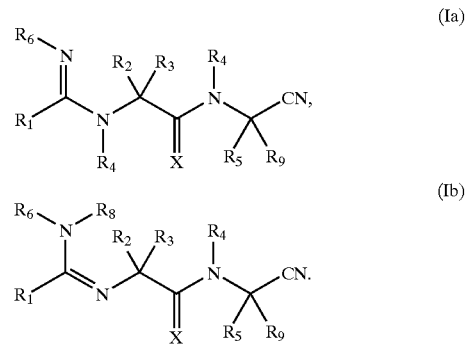

wherein:
$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, heterocyclyl selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, heterocyclyloxy wherein the heterocyclyl moiety is selected from those herein described in this paragraph, hydroxy or amino; wherein $R_1$ is optionally substituted by one or more $R_a$;

$R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10 alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$; with the proviso that $R_1$ and $R_a$ simultaneously cannot be a bond;

$R_b$ is a C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1–4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;

or $R_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;

$R_2$ is hydrogen or C1–3 alkyl;

$R_3$ is a bond, hydrogen, alkyl wherein one or more carbon atoms are optionally replaced by O, S or N wherein it shall be understood if N is not substituted by $R_c$ then it is NH, or $R_3$ is C2–10alkylene, heterocyclylC1–5 alkyl wherein the heterocyclic moiety is selected from pyrrolidinyl, piperidinyl, morpholinyl, thiomorpholinyl, 8-aza-bicyclo [3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl and quinoxalinyl, C3–8 cycloalkyl, arylC1–5alkyl or aryl wherein $R_3$ is optionally substituted by one or more $R_c$;

$R_c$ is C3–8 cycloalkyl, aryl, indanyl, indenyl, bicyclo [2.2.1]heptanyl, bicyclo[2.2.2]octanyl, bicyclo[4.1.0] heptanyl, bicyclo[3.1.0]hexanyl, bicyclo[1.1.1] pentanyl, spiroC8–12 cycloalkyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, aryloxy, aroyl, aryloxycarbonyl, aroyloxy, or $R_c$ is aroylamino, alkylthio, arylthio, aryloxycarbonylamino, arylcarbamoyloxy, arylsulfonylamino, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyi, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

each $R_4$ is independently hydrogen, hydroxy or C1–3 alkyl;

$R_5$ is hydrogen, alkyl, alkoxy, alkoxyalkyl or arylalkyl;

$R_9$ is hydrogen, alkyl wherein one or more carbon atoms are optionally replaced by O, S or N wherein it shall be understood if N is not substituted by $R_e$ then it is NH, or $R_9$ is cycloalkyl, aryl, heterocyclyl, aryl, heteroaryl or cyano, wherein $R_9$ is optionally substituted by one or more $R_e$;

$R_e$ is selected from alkyl, cycloalkyl, aryl, aroyl, heterocyclyl, heteroaryl, halogen, hydroxy, oxo, carboxy, cyano, nitro, amidino and guanidino, $R_e$ may be further optionally substituted by one or more $R_f$;

$R_f$ is selected from alkyl, cycloalkyl, aryl optionally substituted by one or more groups selected from halogen, methyl or methoxy, heterocyclyl, heteroaryl, alkoxy, aryloxy, aroyl, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl, heteroaryl, halogen, hydroxy, carboxy and cyano;

$R_6$ is hydrogen, hydroxy, nitrile or a C1–6 saturated or unsaturated branched or unbranched alkyl optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C1–4 alkyl, C3–7 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formulas (Ia) or (Ib) optionally form a 4 to 8 membered mono- or 7–14 membered polycyclo heteroring system, each aromatic or nonaromatic, wherein each ring is optionally substituted by one or more $R_7$;

each $R_7$ and $R_8$ are independently:

hydrogen, C1–5 alkyl chain optionally interrupted by one or two N, O or S(O)$_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated, halogen, hydroxy, oxo, carboxy, nitrile, nitro or NH$_2$C(O)—;

m is 0, 1 or 2;

X is =O, =S or =N—$R_6$ wherein $R_6$ is as defined above, and pharmaceutically acceptable derivatives thereof.

In another embodiment of the invention, there are provided novel compounds of the formula (Ia) or formula (Ib) as described immediately above, and wherein:

$R_1$ and $R_6$ of the formula (Ia) or formula (Ib) form:

a monocyclic 5, 6 or 7 membered aromatic or nonaromatic heterocyclic ring optionally substituted by $R_7$;

a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

or a tricyclic ring wherein the abovementioned bicyclic ring is further fused to a third 5–7 membered aromatic or nonaromatic heterocyclic or carbocyclic ring wherein each ring is optionally independently substituted by one or more $R_7$;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein $R_3$ is optionally substituted by one or more $R_c$;

$R_c$ is C3–7 cycloalkyl, aryl, indanyl, indenyl, bicyclo [2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, aryl or cyano, wherein $R_9$ is optionally substituted by one or more $R_e$;

$R_e$ is selected from C1–8 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from C1–8 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, aroyl, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, carboxy and cyano;

$R_7$ and $R_8$ are independently hydrogen, C1–5 alkyl, C3–6 cycloalkyl, aryl, C1–5 alkoxy, aryloxy, benzyloxy each of the aforementioned are optionally halogenated, halogen, hydroxy, oxo, carboxy, nitrile, nitro or $NH_2C(O)$—;

m is 0, 1 or 2 and

X is O or S.

In yet another embodiment of the invention, there are provided novel compounds of the formulas (Ia) or (Ib) as described immediately above, and wherein:

$R_1$ and $R_6$ of the formula (Ia) or Formula (Ib) form:

a monocyclic 5 or 6 membered aromatic or nonaromatic heterocyclic ring optionally substituted by $R_7$;

a bicyclic ring having one 5, 6 or 7 membered aromatic or nonaromatic heterocyclic ring fused to a second 5–6 membered aromatic or nonaromatic heterocyclic or carbocyclic ring wherein each ring is optionally independently substituted by one or more $R_7$;

or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring;

$R_2$ is hydrogen or methyl;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3∝6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is hydrogen, C1–8 alkyl, C1–3 alkoxyC1–3 alkyl, C1–8 alkoxy, phenylC1–5 alkyl or naphthylC1–5 alkyl;

$R_9$ is hydrogen, C1–12 alkyl wherein one or more carbon atoms are optionally replaced by O, S or N, C3–cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, aryl or cyano, wherein $R_9$ is optionally substituted by one or more $R_e$;

$R_e$ is selected from C1–5 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_e$ may be further optionally substituted by one or more $R_f$;

$R_f$ is selected from C1–5 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, carboxy and cyano;

$R_7$ and $R_8$ are independently hydrogen, C1–4 alkyl, C5–6 cycloalkyl, C1–4 alkoxy, halogen, hydroxy, oxo, carboxy, nitrile, nitro or $NH_2C(O)—$; and X is O.

In yet still another embodiment of the invention, there are provided novel compounds of the formulas (Ia) or (Ib) as described immediately above, and wherein:

$R_1$ and $R_6$ of the formula (Ia) or formula (Ib) form:
a bicyclic ring having one 5 or 6 membered aromatic or nonaromatic heterocyclic ring fused to a second 5–6 membered heteroaryl, heterocycle or phenyl ring;
or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring; wherein each ring is optionally independently substituted by one or two $R_7$ $R_2$ is hydrogen;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is hydrogen, C1–5 alkyl, C1–3 alkoxyC1–3 alkyl, benzyl or phenethyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, phenyl, naphthyl or cyano, wherein $R_9$ is optionally substituted by one or more $R_e$;.

$R_e$ is selected from C1–5 alkyl, C3–7 cycloalkyl, phenyl, naphthyl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1-alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, nitro, carboxy and cyano, $R_e$ may be further optionally substituted by one or more $R_f$;

$R_f$ is selected from C1 —S alkyl, C3–7 cycloalkyl, phenyl optionally substituted by one or more groups selected from halogen, methyl or methoxy, naphthyl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl, naphthyl, arylC1–3alkyl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, carboxy and cyano.

In yet a further embodiment of the invention, there are provided novel compounds of the formulas (Ia) or (Ib) as described immediately above, and wherein:

$R_1$ and $R_6$ of the formula (Ia) or Formula (Ib) form:

a bicyclic ring having one 5–6 membered aromatic or nonaromatic heterocyclic ring fused to a phenyl or 5–6 membered aromatic or nonaromatic heterocyclic ring;

a tricyclic ring having one 5–6 membered aromatic or nonaromatic heterocyclic ring fused to a 6-membered aromatic or nonaromatic carbocyclic ring which in turn is fused to a 5–6 membered aromatic or nonaromatic heterocyclic ring;

wherein each ring is optionally independently substituted by one or two $R_7$.

$R_3$ is a bond, C1–10 alkyl wherein one or more carbon atoms are optionally replaced by O, S or N, or $R_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_9$ is hydrogen, C1–12 alkyl wherein one or more carbon atoms are optionally replaced by O, S or N, C3–6 cycloalkyl, phenyl or cyano, wherein $R_9$ is optionally substituted by one or more $R_e$;

$R_e$ is selected from C1–3 alkyl, C3–6 cycloalkyl, phenyl, naphthyl, aroyl, heterocyclyl selected from pyrrolidinyl, piperidinyl, morpholinyl, thio morpholinyl and piperazinyl; heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, halogen, hydroxy, oxo, nitro, carboxy and cyano, $R_e$ may be further optionally substituted by one or more $R_f$;

$R_f$ is selected from C1–3 alkyl, C5–6 cycloalkyl, phenyl optionally substituted by one or more groups selected from halogen or methyl, heterocyclyl selected from pyrrolidinyl, piperidinyl, morpholinyl and piperazinyl, heteroaryl selected from furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano;

or $R_5$ and $R_9$ together with the carbon they are attached form a carbocyclic ring selected from:

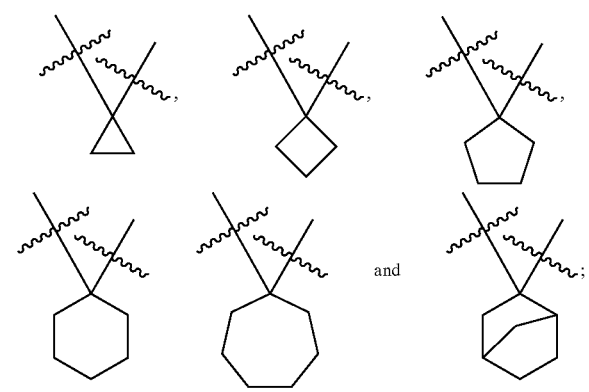

each carbocyclic ring being optionally benzofused and optionally substituted with one or more $R_g$;

$R_g$ is selected from C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl or arylC1–3alkyl; halogen, hydroxy, carboxy and cyano.

In yet still a further embodiment of the invention, there are provided novel compounds of the formula (Ia) as described immediately above, and wherein:
$R_1$ and $R_6$ of the formula (Ia) form:
the bicyclic ring:

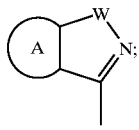

wherein W is —S(O)$_n$—, >(O), —O—C(O)—, —S—C(O)— or —NH—C(O)—, n is 0, 1 or 2, fused ring A is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$.
or the tricyclic ring:

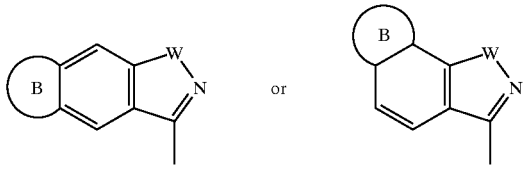

wherein W is —S(O)$_n$—, >C(O), —O—C(O)—, —S—C(O)— or —NH—C(O)—, n is 0, 1 or 2, fused ring B is selected from phenyl, morpholinyl, pyridinyl, pyrimidinyl, pyrazinyl, piperidinyl, pyrazolyl, pyrrolyl, pyrrolidinyl, imidazolyl, oxazolyl, thienyl, furanyl and thiazinyl and wherein each ring is optionally independently substituted by one or two $R_7$.

$R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5] octanyl, spiro[3.5] nonyl, spiro[4.5]decanyl, cubanyl, 1,2,3,4-tetrahydronaphthyl, phenoxy, benzoyl, phenoxycarbonyl, benzoyloxy, phenylthio, fluoro or chloro;

$R_9$ is hydrogen, C1–5 alkyl, C1–5 alkylene, C1–5 alkoxyC1–5 alkyl, C1–5 alkoxycarbonylC1–5 alkyl, C1–5 alkylthioC1–5 alkyl, C1–5 alkylsulfinylC1–5 alkyl, C1–5 alkylsulfonylC1–5 alkyl, aminoC1–5 alkyl, mono or di-C1–5alkylaminoC1–5 alkyl, mono or di-C1–5 alkylamidoC1–5 alkyl, phenyl, furanyl, thienyl, thiazolyl, imidazolyl, pyridinyl, indolyl or cyano wherein $R_9$ is optionally substituted by one to two groups of the formula $R_e$;

$R_e$ is selected from C1–3 alkyl, C3–6 cycloalkyl, phenyl, naphthyl, benzoyl, furanyl, thienyl, thiazolyl, imidazolyl, pyridinyl, piperidinyl, piperazinyl, morpholinyl, thiomorpholinyl, indolyl, halogen, hydroxy, oxo, carboxy and cyano, $R_e$ may be further optionally substituted by one or more $R_f$;

$R_f$ is selected from C1–3 alkyl, phenyl optionally substituted by one or more groups selected from halogen and methyl, heterocyclyl selected from piperidinyl, morpholinyl and piperazinyl; heteroaryl selected from furanyl, thienyl, pyrrolyl and pyridinyl, C1–3 alkoxy, aryloxy, benzoyl, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl, halogen, hydroxy, oxo, nitro, carboxy and cyano;

$R_g$ is selected from C1–3 alkyl, phenyl, C1–3 alkoxycarbonyl, phenoxyoxycarbonyl, benzyloxy, carbamoyl wherein the nitrogen atom may be optionally mono or di-substituted with a group selected from C1–5 alkyl, phenyl and benzyl, halogen, hydroxy, carboxy and cyano.

In a further embodiment of the invention, there are provided novel compounds of the formulas (Ia) as described immediately above, and wherein:
$R_1$ and $R_6$ of the formula (Ia) form the bicyclic ring selected from:

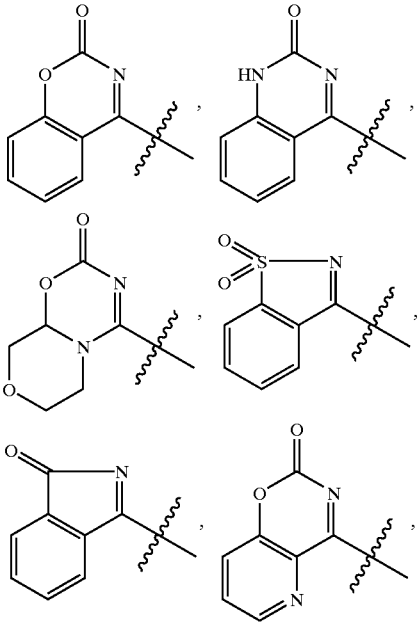

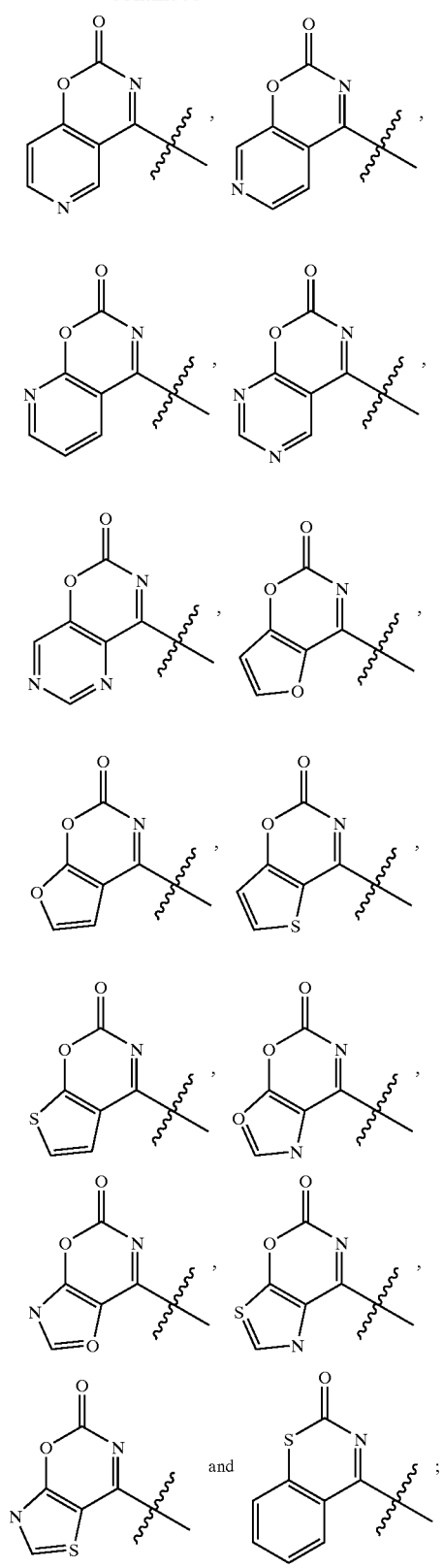
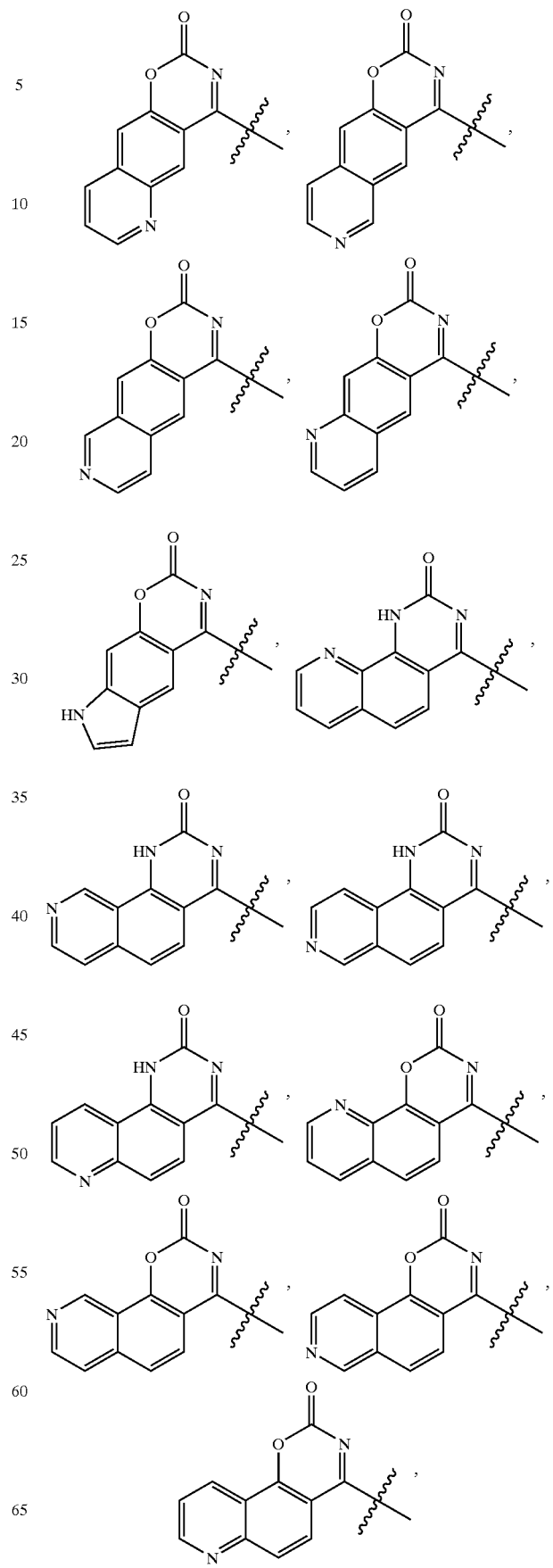
or $R_1$ and $R_6$ of the same formulas (Ia) form the tricyclic ring selected from;

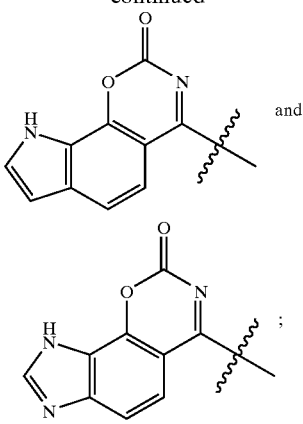 and

;

wherein each ring is optionally independently substituted by one or two $R_7$;

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_e$ is methyl, cyclohexyl, cyclopentyl, indanyl, 1,2,3,4-tetrahydronaphthyl, spiro[2.5] octanyl, spiro[3.5] nonyl, spiro[4.5] decanyl, fluoro or chloro;

$R_9$ is hydrogen, C1–4 alkyl, C1–5 alkylene, C1–3 alkoxyC1–3 alkyl, C1–3 alkoxycarbonylC 1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, phenyl, furanyl, thienyl, thiazolyl, imidazolyl, pyridinyl, indolyl or cyano wherein $R_9$ is optionally substituted by one to two groups of the formula $R_e$;

$R_e$ is selected from methyl, C3–6 cycloalkyl, phenyl, benzoyl, naphthyl, furanyl, thienyl, thiazolyl, imidazolyl, pyridinyl, piperidinyl, piperazinyl, morpholinyl, thiomorpholinyl, indolyl, halogen, hydroxy, carboxy and cyano, $R_e$ may be further optionally substituted by one or more $R_f$.

$R_f$ is selected from C1–3 alkyl, phenyl or phenylsulfonyl each optionally substituted by one or more groups selected from halogen or methyl, C1–3 alkoxy, aryloxy, benzoyl, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, nitro, carboxy and cyano;

and $R_g$ is selected from C1–3 alkyl, phenyl, C1–3 alkoxycarbonyl, benzyloxy and carboxy.

In another embodiment of the invention, there are provided novel compounds of the formulas (Ia) or I(b) as described for the broadest generic aspect above and wherein: $R_1$ and $R_6$ remain acyclic:

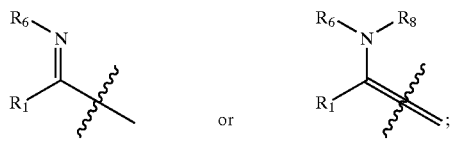

or ;

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein $R_3$ is optionally substituted by one or more $R_c$;

$R_c$ is C3–7 cycloalkyl, aryl, indanyl, indenyl, bicyclo [2.2.1]heptanyl, bicyclo[2.2.2]octanyl, bicyclo[4.1.0] heptanyl, bicyclo[3.1.0]hexanyl, bicyclo 1.1.1 pentanyl, spiroC8–10 cycloalkyl, cubanyl, 1,2,3,4- tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, aryl or cyano, wherein $R_9$ is optionally substituted by one or more $R_e$;

$R_e$ is selected from C1–8 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from C1–8 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, aroyl, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C 1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, carboxy and cyano;

$R_6$ is hydroxy, nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with 1–2 oxo groups, $NH_2$, one or more C1–4 alkyl, C3–6 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolinyl or quinoxalinyl;

$R_8$ is hydrogen, C1–5 alkyl, C3–6 cycloalkyl, aryl, C1–5 alkoxy, aryloxy, benzyloxy each of the aforementioned are optionally halogenated or hydroxy; and X is O.

In another embodiment of the invention, there are provided novel compounds of the formula (Ia) or (Ib) as described immediately above, and wherein:

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_5$ is hydrogen, C1–8 alkyl, C1–3 alkoxyC1–3 alkyl, C1–8 alkoxy, C1–5phenyl or C1–5naphthyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, aryl or cyano, wherein $R_9$ is optionally substituted by one or more $R_e$;

$R_e$ is selected from C1–5 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_e$ may be further optionally substituted by one or more $R_f$;

$R_f$ is selected from C1–5 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, carboxy and cyano;

$R_6$ is nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with oxo, $-NH_2$, C3–6 cycloalkyl, piperidinyl, morpholinyl, thiomorpholinyl, piperazinyl, pyridinyl, pyrimidinyl or pyrazinyl; and $R_8$ is hydrogen, C1–3 alkyl, C3–6 cycloalkyl, phenyl, C1–3 alkoxy, benzyloxy each of the aforementioned are optionally halogenated or hydroxy.

In yet another embodiment of the invention, there are provided novel compounds of the formula (Ia) or formula (Ib) as described immediately above, and wherein:

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo [2.2.1]heptanyl, bicyclo[2.2.2]octanyl, bicyclo[4.1.0] heptanyl, bicyclo[3.1.0]hexanyl, bicyclo[1.1.1] pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is hydrogen, C1–5 alkyl, C1–3 alkoxyC1–3 alkyl, benzyl or phenethyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, phenyl, naphthyl or cyano, wherein $R_9$ is optionally substituted by one or more $R_e$.

$R_e$ is selected from C1–5 alkyl, C3–7 cycloalkyl, phenyl, naphthyl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1-alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, nitro, carboxy and cyano, $R_e$ may be further optionally substituted by one or more $R_f$;

$R_f$ is selected from C1–5 alkyl, C3–7 cycloalkyl, phenyl optionally substituted by one or more groups selected from halogen, methyl or methoxy, naphthyl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl, naphthyl, arylC1–3alkyl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, carboxy and cyano;

$R_6$ is nitrile or a C1–5 saturated or unsaturated branched or unbranched alkyl optionally partially or fully halogenated wherein one or more C atoms are optionally replaced by O, NH, or $S(O)_2$ and wherein said chain is optionally independently substituted with oxo, $-NH_2$, C3–6 cycloalkyl, morpholinyl or piperazinyl; and $R_g$ is hydrogen, C1–3 alkyl, C1–3 alkoxy or hydroxy.

In yet still another embodiment of the invention, there are provided novel compounds of the formulas (Ia) or (Ib) as described immediately above, and wherein:

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is a bond, C1–10 alkyl wherein one or more carbon atoms are optionally replaced by O, S or N, or $R_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.11]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_9$ is hydrogen, C1–12 alkyl wherein one or more carbon atoms are optionally replaced by O, S or N, C3–6 cycloalkyl, phenyl or cyano, wherein $R_9$ is optionally substituted by one or more $R_e$;

$R_e$ is selected from C1–3 alkyl, C3–6 cycloalkyl, phenyl, naphthyl, aroyl, heterocyclyl selected from pyrrolidinyl, piperidinyl, morpholinyl, thio morpholinyl and piperazinyl; heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, halogen, hydroxy, oxo, nitro, carboxy and cyano, $R_e$ may be further optionally substituted by one or more $R_f$;

$R_f$ is selected from C1–3 alkyl, C5–6 cycloalkyl, phenyl optionally substituted by one or more groups selected from halogen or methyl, heterocyclyl selected from pyrrolidinyl, piperidinyl, morpholinyl and piperazinyl, heteroaryl selected from furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano;

or $R_5$ and $R_9$ together with the carbon they are attached form a carbocyclic ring selected from

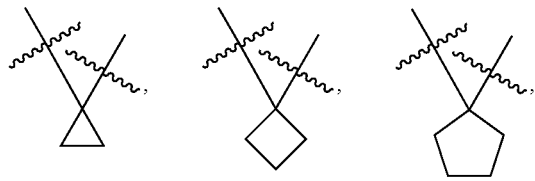

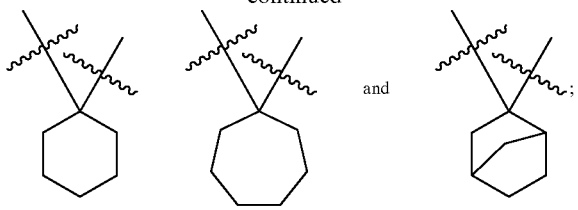

each carbocyclic ring being optionally benzofused and optionally substituted with one or more $R_g$;

$R_g$ is selected from C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl or arylC1–3alkyl; halogen, hydroxy, carboxy and cyano;

$R_6$ is C3–6 cycloalkyloxycarbonyl, acetyl, C1–3alkylaminocarbonyl or C1–3alkoxycarbonyl; and $R_g$ is hydrogen, C1–3 alkyl or C1–3 alkoxy.

In yet a further embodiment of the invention, there are provided novel compounds of the formulas (Ia) or (Ib) as described immediately above, and wherein:

$R_1$ is morpholin-4-yl, p-fluorophenyl or p-methoxyphenyl;

$R_3$ is a bond, methyl, ethyl, n-propyl, propenyl, butenyl, i-butenyl, C1–5 alkoxyC1–5 alkyl, C1–5 alkoxycarbonylC1–5 alkyl, C1–5 alkylthioC1–5 alkyl, C1–5alkylsulfinylC1–5 alkyl, C1–5 alkylsulfonylC1–5 alkyl, aminoC1–5 alkyl, mono or di-alkylaminoC1–5 alkyl, mono or di-alkylamidoC1–5 alkyl, cyclohexyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5] octanyl, spiro[3.5] nonyl, spiro[4.5] decanyl, cubanyl, 1,2,3,4-tetrahydronaphthyl, phenoxy, benzoyl, phenoxycarbonyl, benzoyloxy, phenylthio, fluoro or chloro;

$R_9$ is hydrogen, C1–5 alkyl, C1–5 alkylene, C1–5 alkoxyC1–5 alkyl, C1–5 alkoxycarbonylC1–5 alkyl, C1–5 alkylthioC1–5 alkyl, C1–5 alkylsulfonylC1–5 alkyl, C1–5 alkylsulfonylC1–5 alkyl, aminoC1–5 alkyl, mono or di-C1–5alkylaminoC1–5 alkyl, mono or di-C1–5 alkylamidoC1–5 alkyl, phenyl, furanyl, thienyl, thiazolyl, imidazolyl, pyridinyl, indolyl or cyano wherein $R_9$ is optionally substituted by one to two groups of the formula $R_e$;

$R_e$ is selected from C1–3 alkyl, C3–6 cycloalkyl, phenyl, naphthyl, benzoyl, furanyl, thienyl, thiazolyl, imidazolyl, pyridinyl, piperidinyl, piperazinyl, morpholinyl, thiomorpholinyl, indolyl, halogen, hydroxy, oxo, carboxy and cyano, $R_e$ may be further optionally substituted by one or more $R_f$;

$R_f$ is selected from C1–3 alkyl, phenyl optionally substituted by one or more groups selected from halogen and methyl, heterocyclyl selected from piperidinyl, morpholinyl and piperazinyl; heteroaryl selected from furanyl, thienyl, pyrrolyl and pyridinyl, C1–3 alkoxy, aryloxy, benzoyl, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl, halogen, hydroxy, oxo, nitro, carboxy and cyano;

$R_g$ is selected from C1–3 alkyl, phenyl, C1–3 alkoxycarbonyl, phenoxyoxycarbonyl, benzyloxy, carbamoyl wherein the nitrogen atom may be optionally mono or di-substituted with a group selected from C1–5 alkyl, phenyl and benzyl, halogen, hydroxy, carboxy and cyano;

$R_6$ is C3–6 cycloalkyloxycarbonyl, acetyl, ethylaminocarbonyl or ethoxycarbonyl; and $R_8$ is hydrogen.

In a further embodiment of the invention, there are provided novel compounds of the formulas (Ia) or (Ib) as described immediately above, and wherein:

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl1 mono ordi-C1–3 alkylaminoC1–3 alkyl, mono or di-C 1–3 alkylamidoC1–3 alkyl, heterocyclylC 1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4-tetrahydronaphthyl, spiro[2.5] octanyl, spiro[3.5] nonyl, spiro[4.5] decanyl, fluoro or chloro;

$R_9$ is hydrogen, C1–4 alkyl, C1–5 alkylene, C1–3 alkoxycl-3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, phenyl, furanyl, thienyl, thiazolyl, imidazolyl, pyridinyl, indolyl or cyano wherein $R_9$ is optionally substituted by one to two groups of the formula $R_e$;

$R_e$ is selected from methyl, C3–6 cycloalkyl, phenyl, benzoyl, naphthyl, furanyl, thienyl, thiazolyl, imidazolyl, pyridinyl, piperidinyl, piperazinyl, morpholinyl, thiomorpholinyl, indolyl, halogen, hydroxy, carboxy and cyano, $R_e$ may be further optionally substituted by one or more $R_f$.

$R_f$ is selected from C1–3 alkyl, phenyl or phenylsulfonyl each optionally substituted by one or more groups selected from halogen or methyl, C1–3 alkoxy, aryloxy, benzoyl, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, nitro, carboxy and cyano;

$R_g$ is selected from C1–3 alkyl, phenyl, C1–3 alkoxycarbonyl, benzyloxy and carboxy.

Further compounds of Formula (Ia), made up of components A, B, and C are provided in Tables I & II below. Any and all combinations of A, B, and C components within the structural limitations of Formula (Ia), comprise a compound of the invention, and their pharmaceutically acceptable derivatives. For example, the compound:

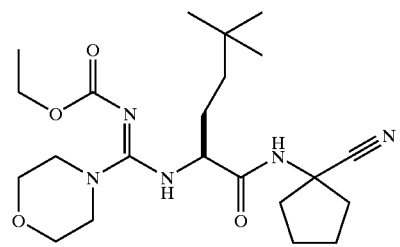

would represent the combination of A24,B32,C4.

These compounds can be synthesized by the General schemes, methods described in the experimental section of this document and analogous methods known to those skilled in the art without undue experimentation. Preferred compounds will possess desirable inhibition activity of Cathepsin S in a cell based assay as described in Riese, R. J. et al., Immunity, 1996, 4, 357–366, incorporated herein by reference.

FORMULA (Ia)

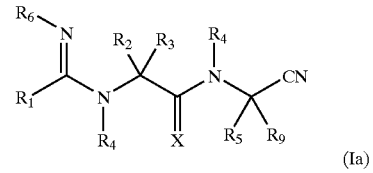

(Ia)

wherein for the Formula (Ia), the components

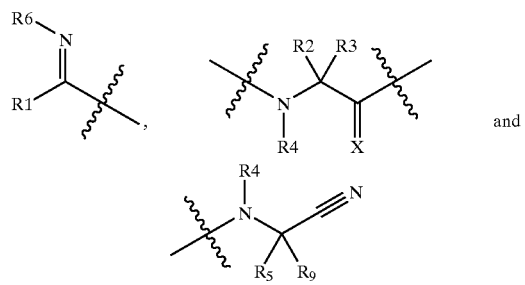

and are chosen from any combination of A, B and C as follows:

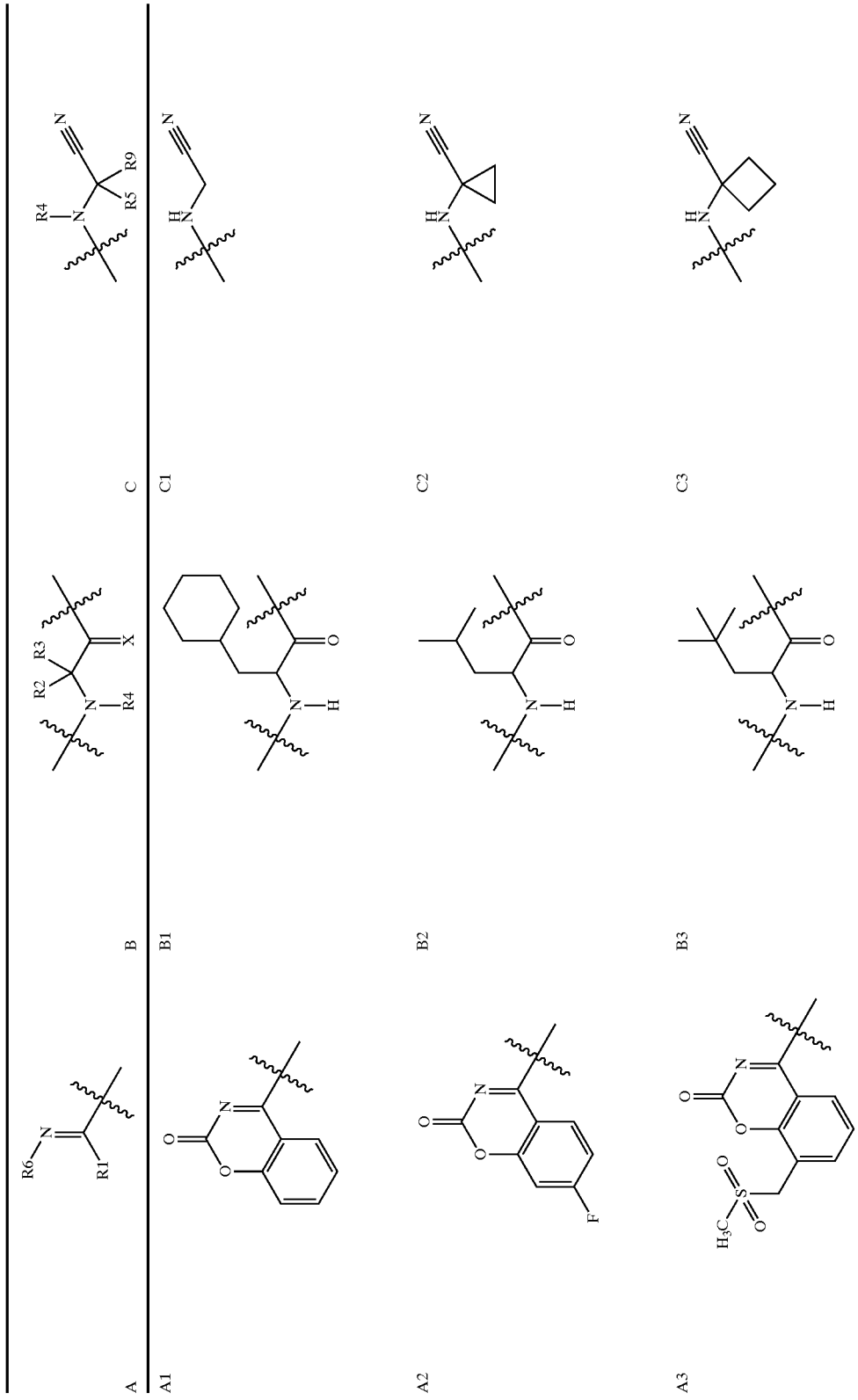

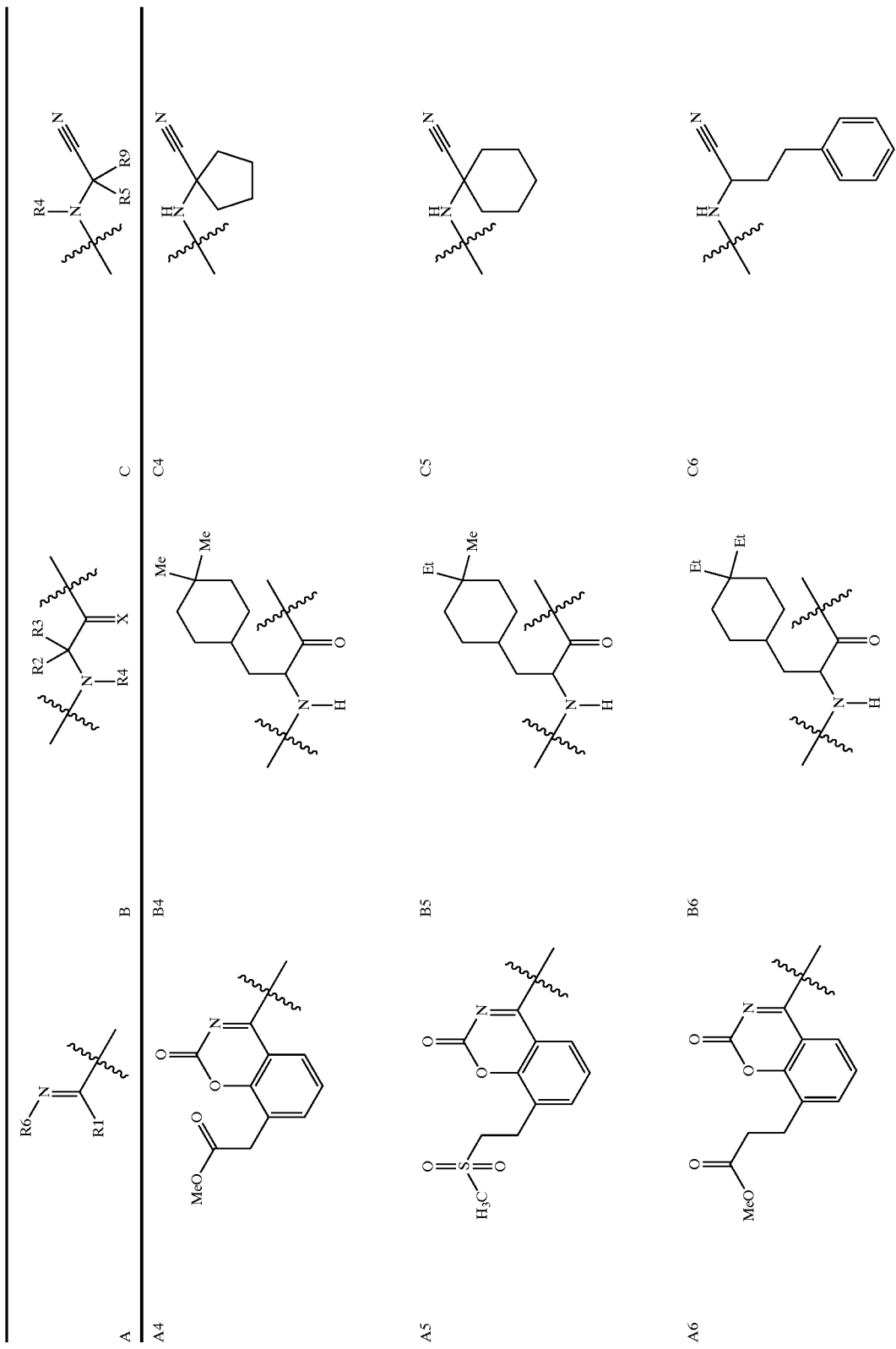

TABLE I-continued

| A | B | C |
|---|---|---|
| A7 | B7 | C7 |
| A8 | B8 | C8 |
| A9 | B9 | C9 |

TABLE I-continued
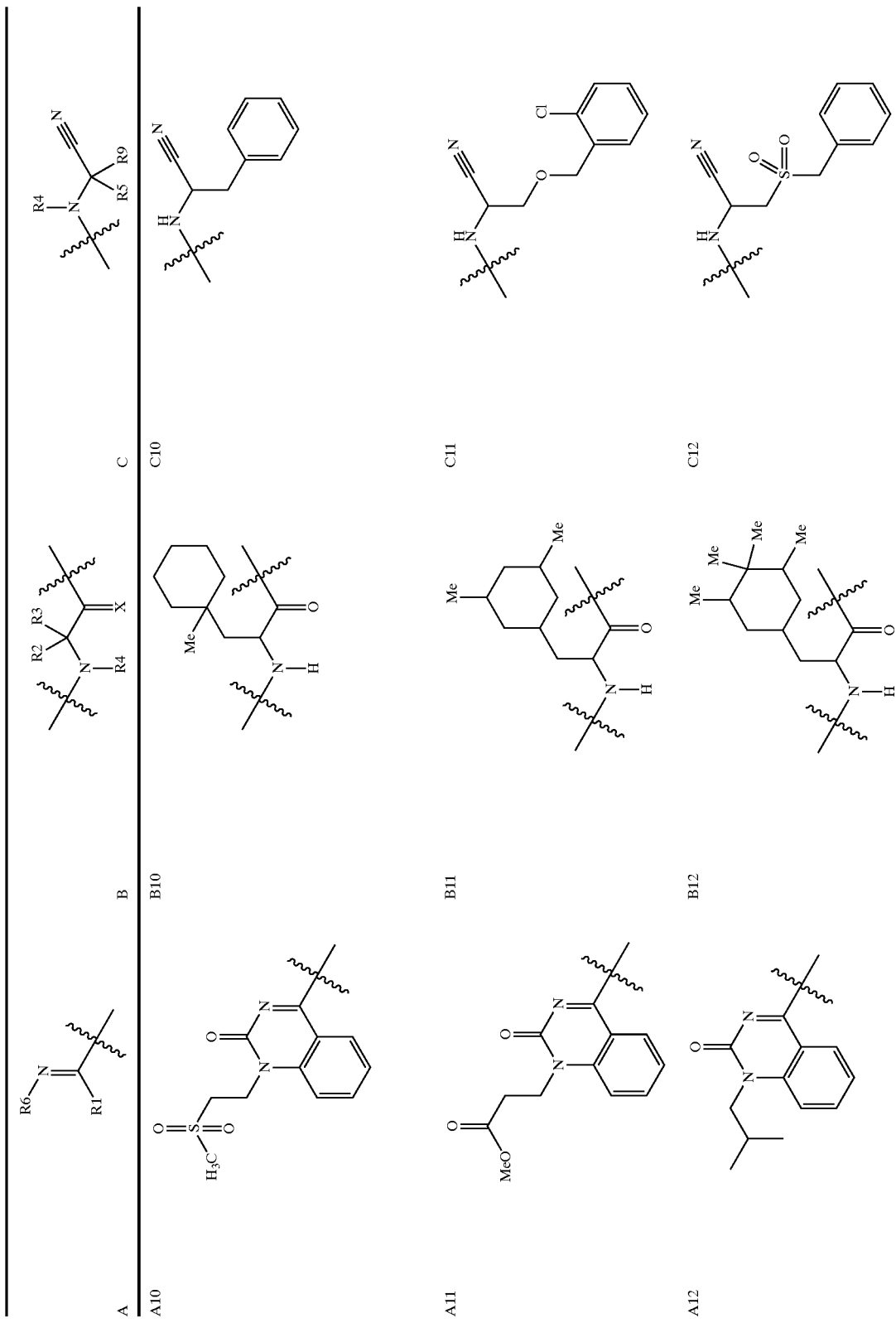

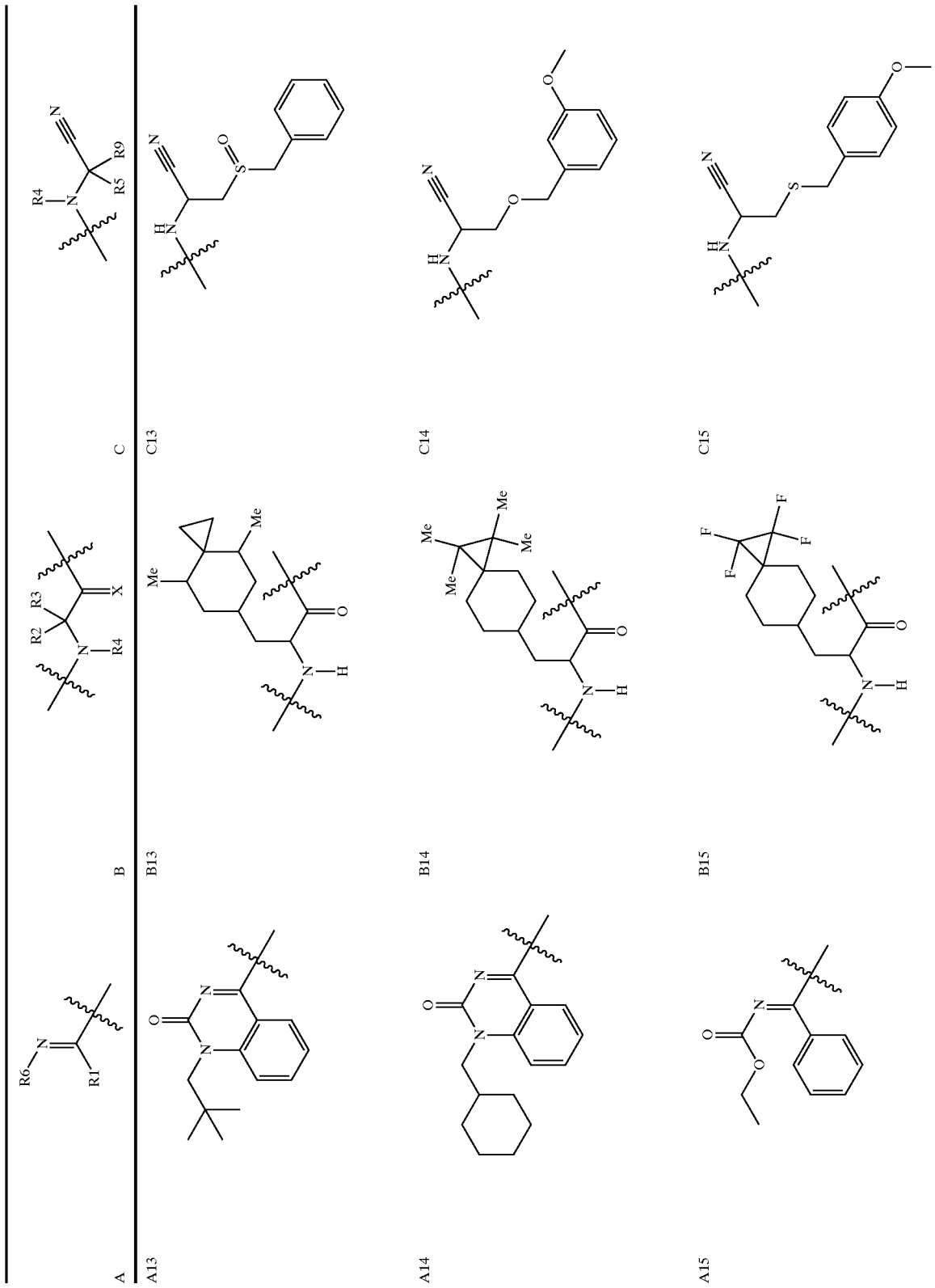

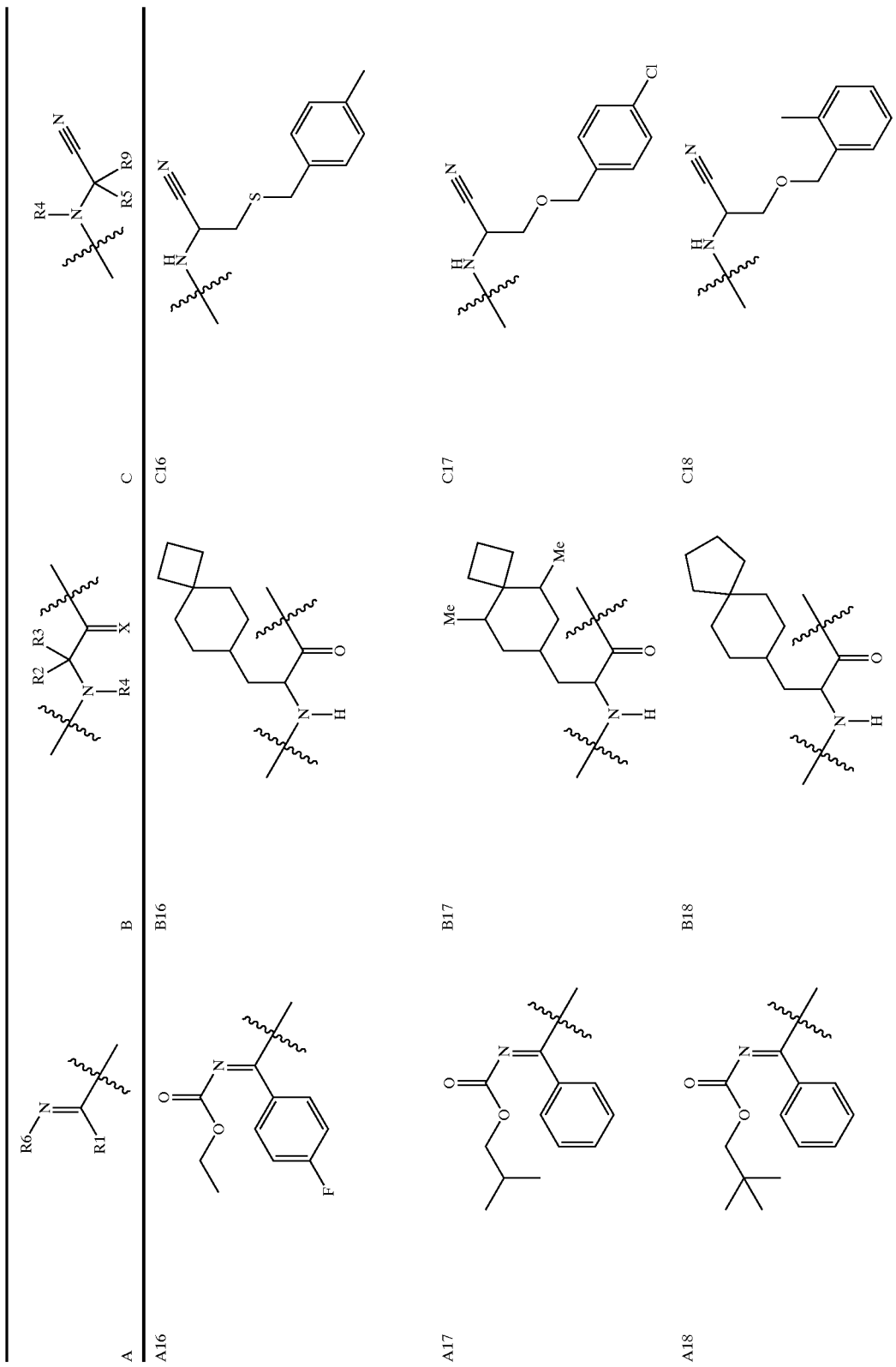

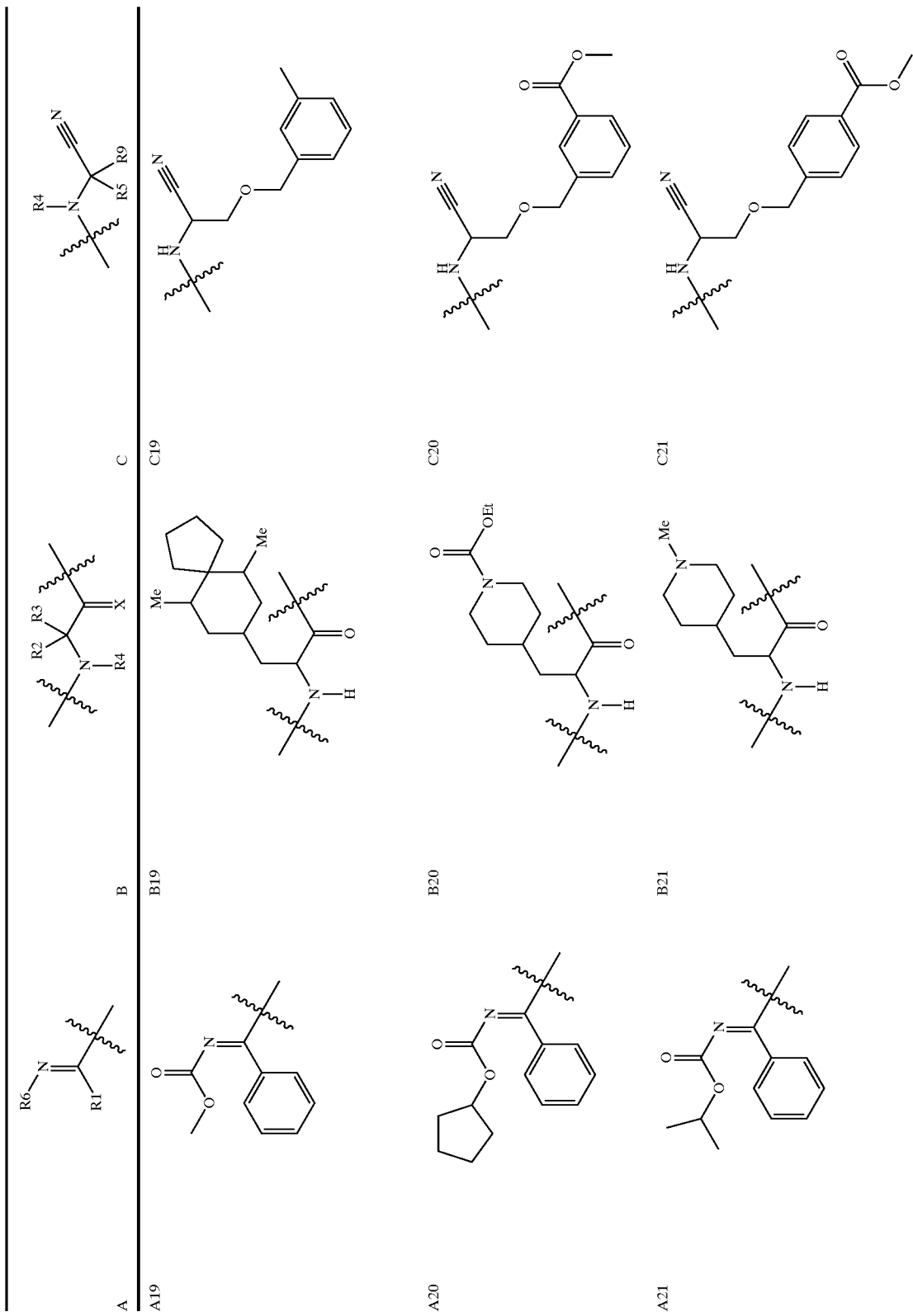

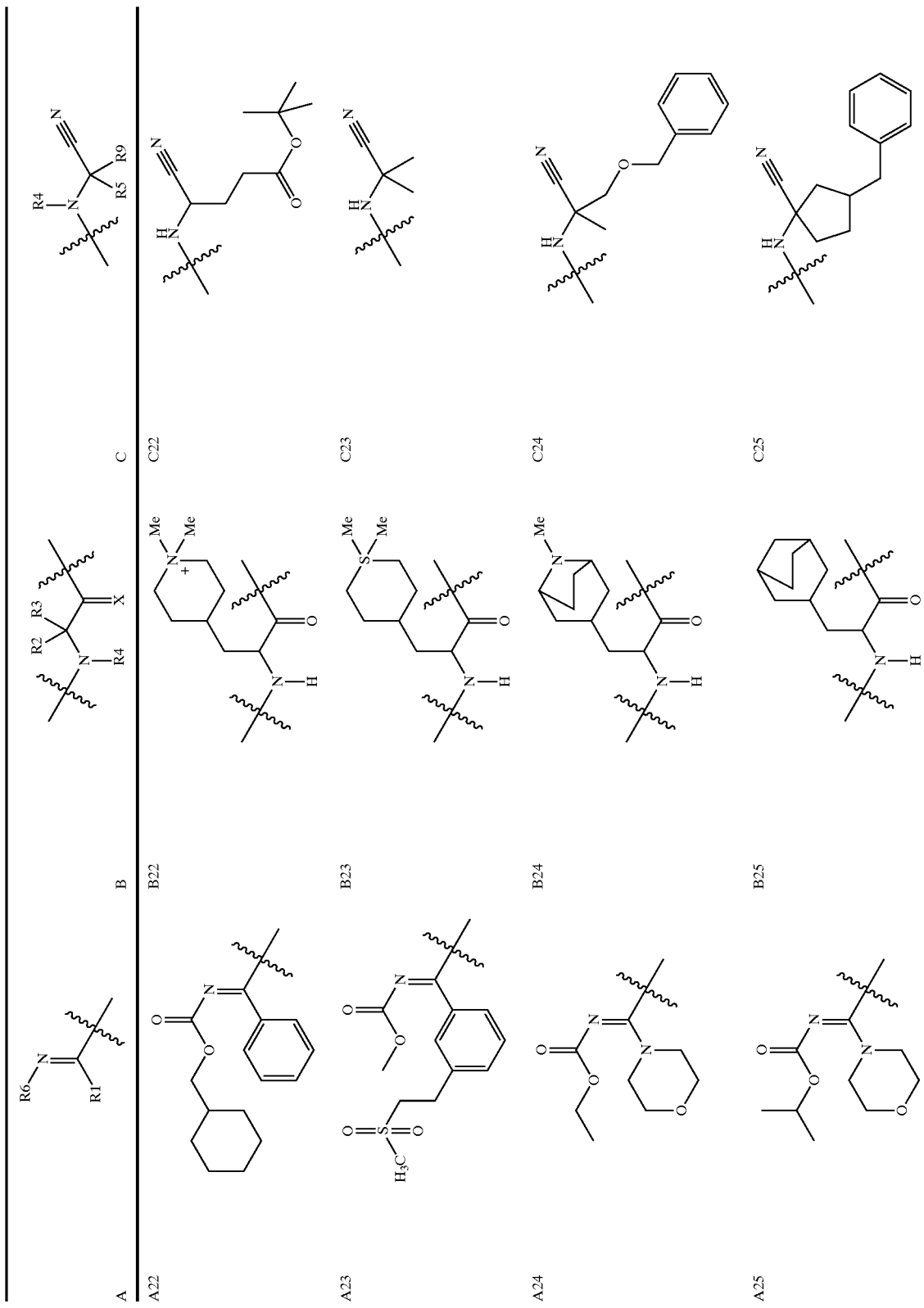

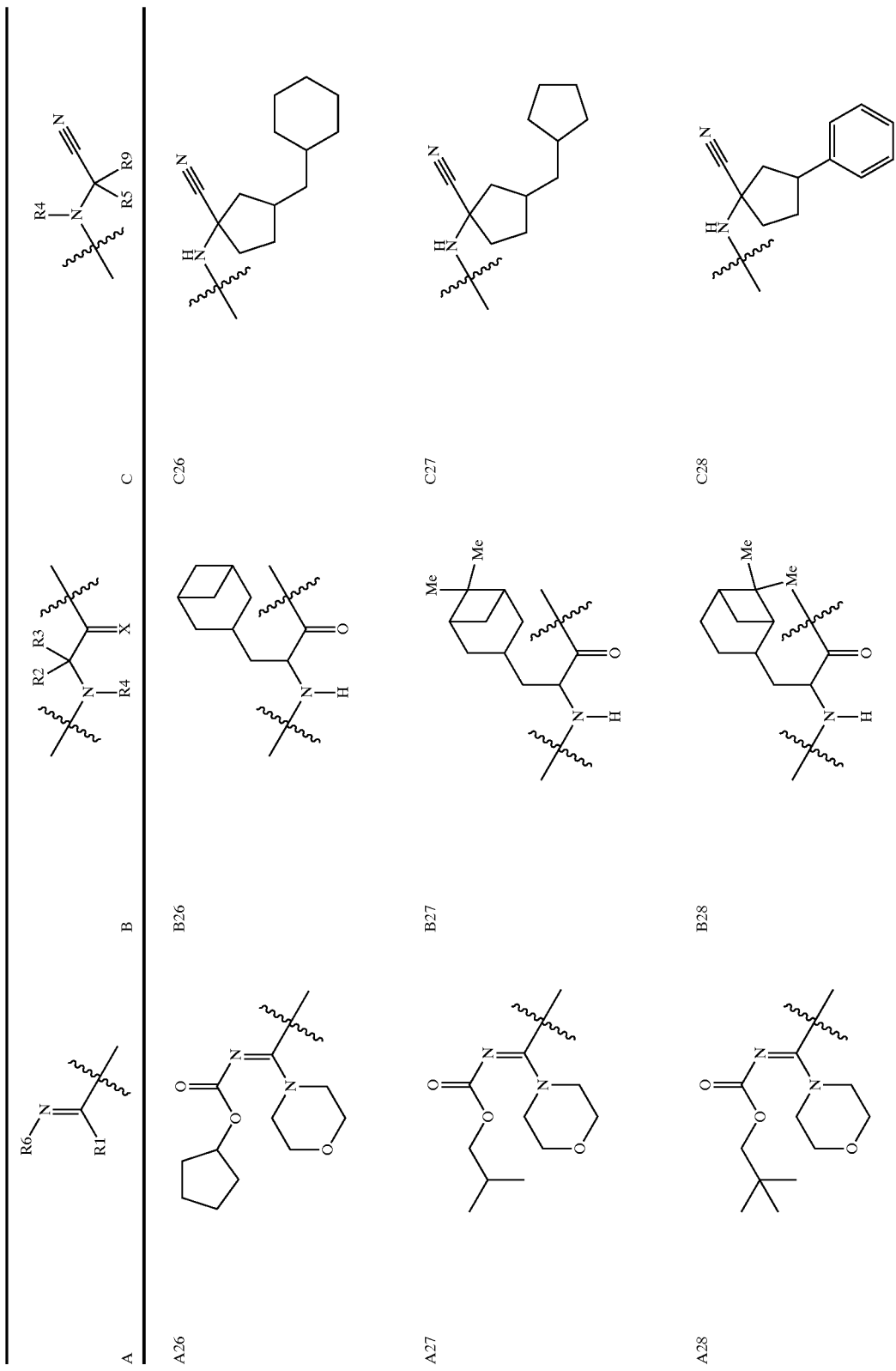

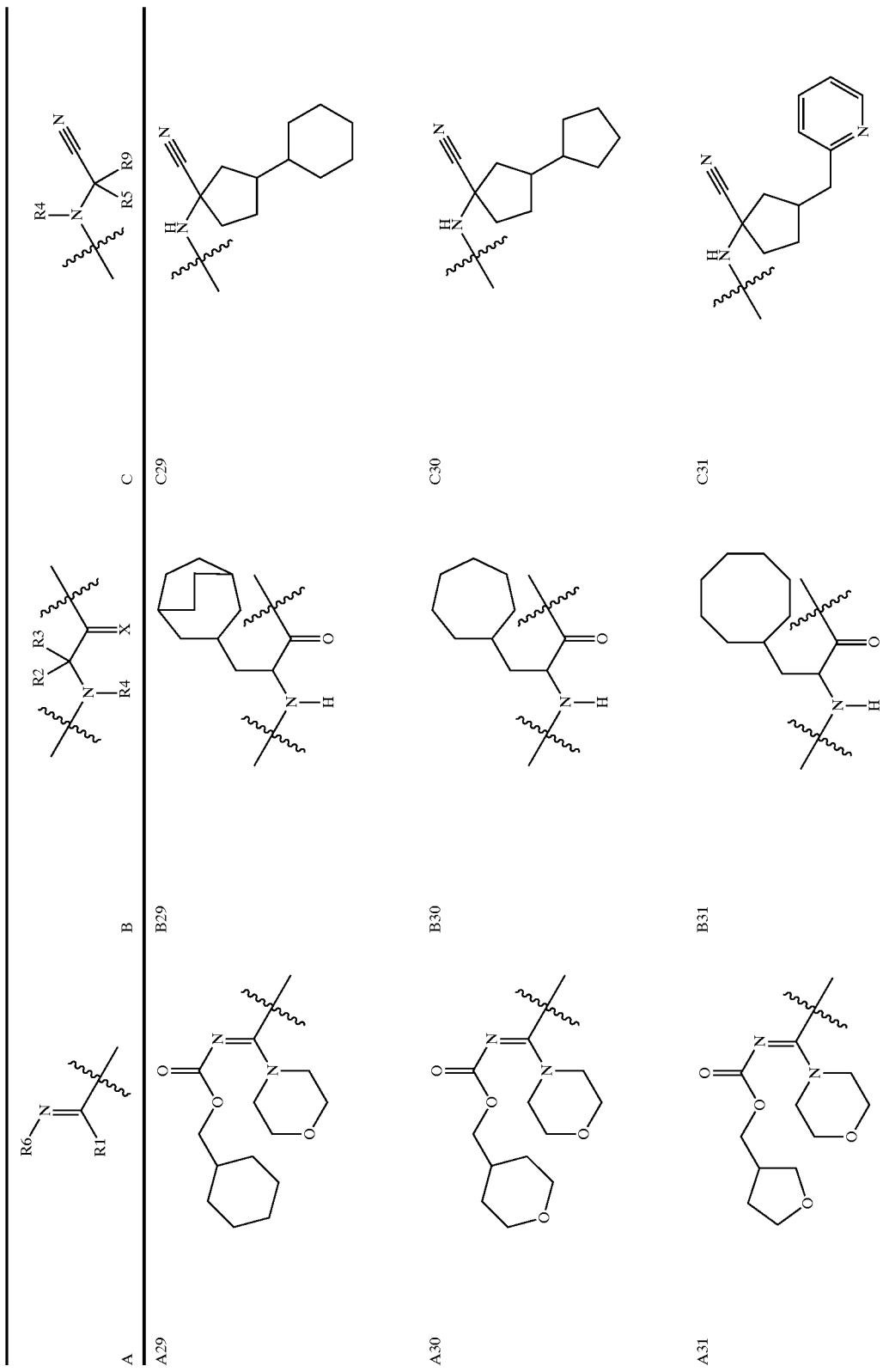

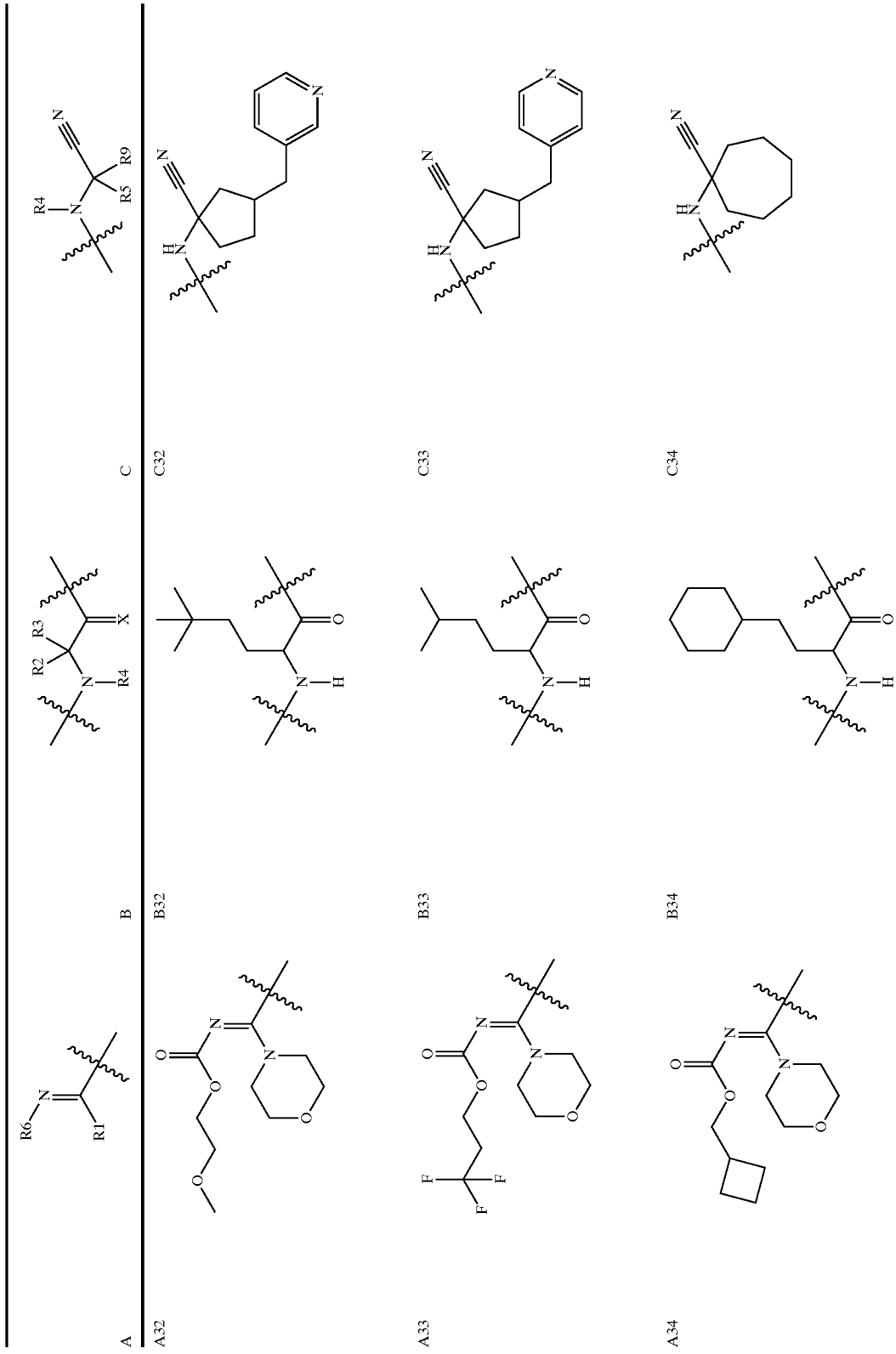

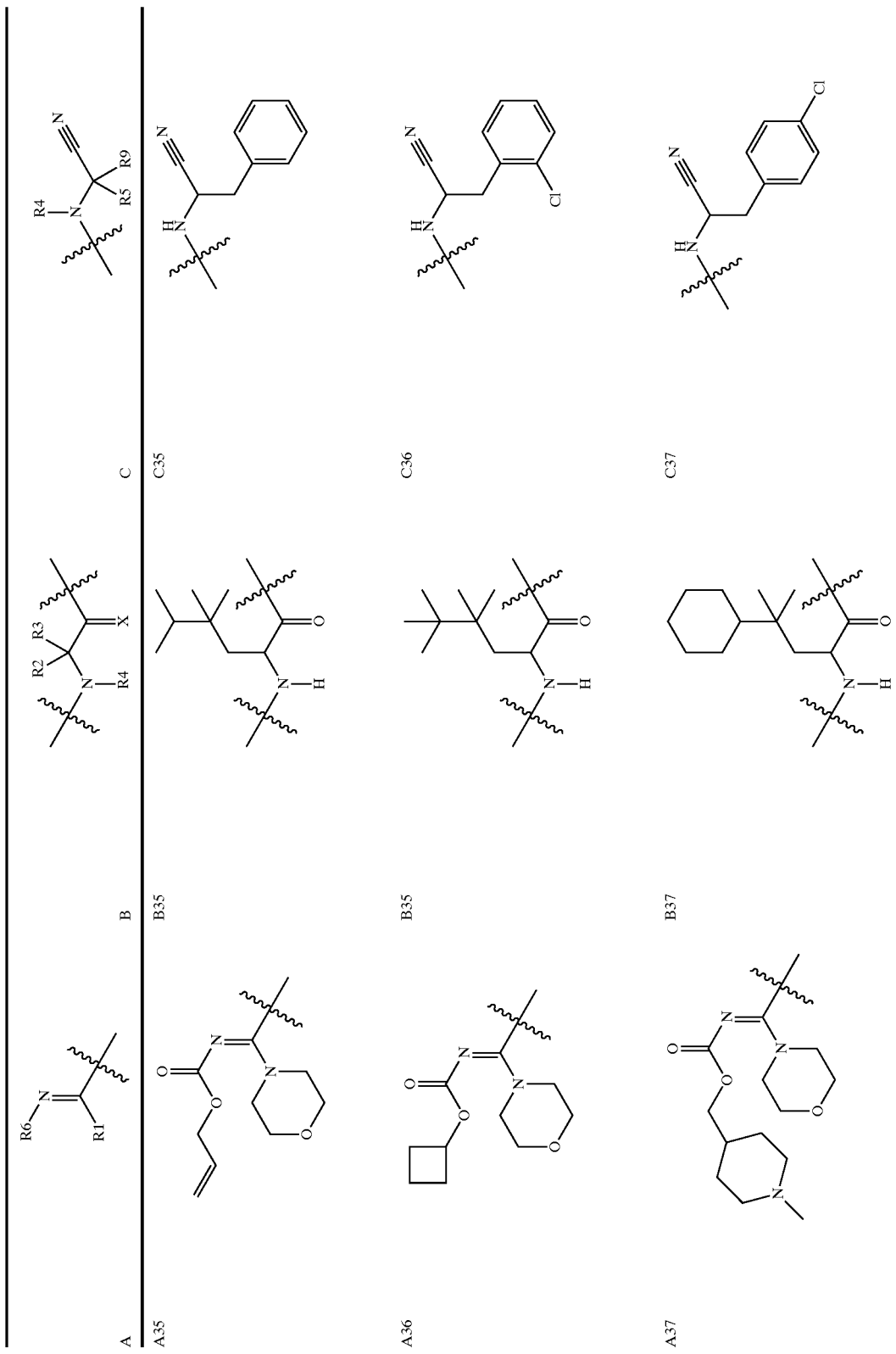

TABLE I-continued

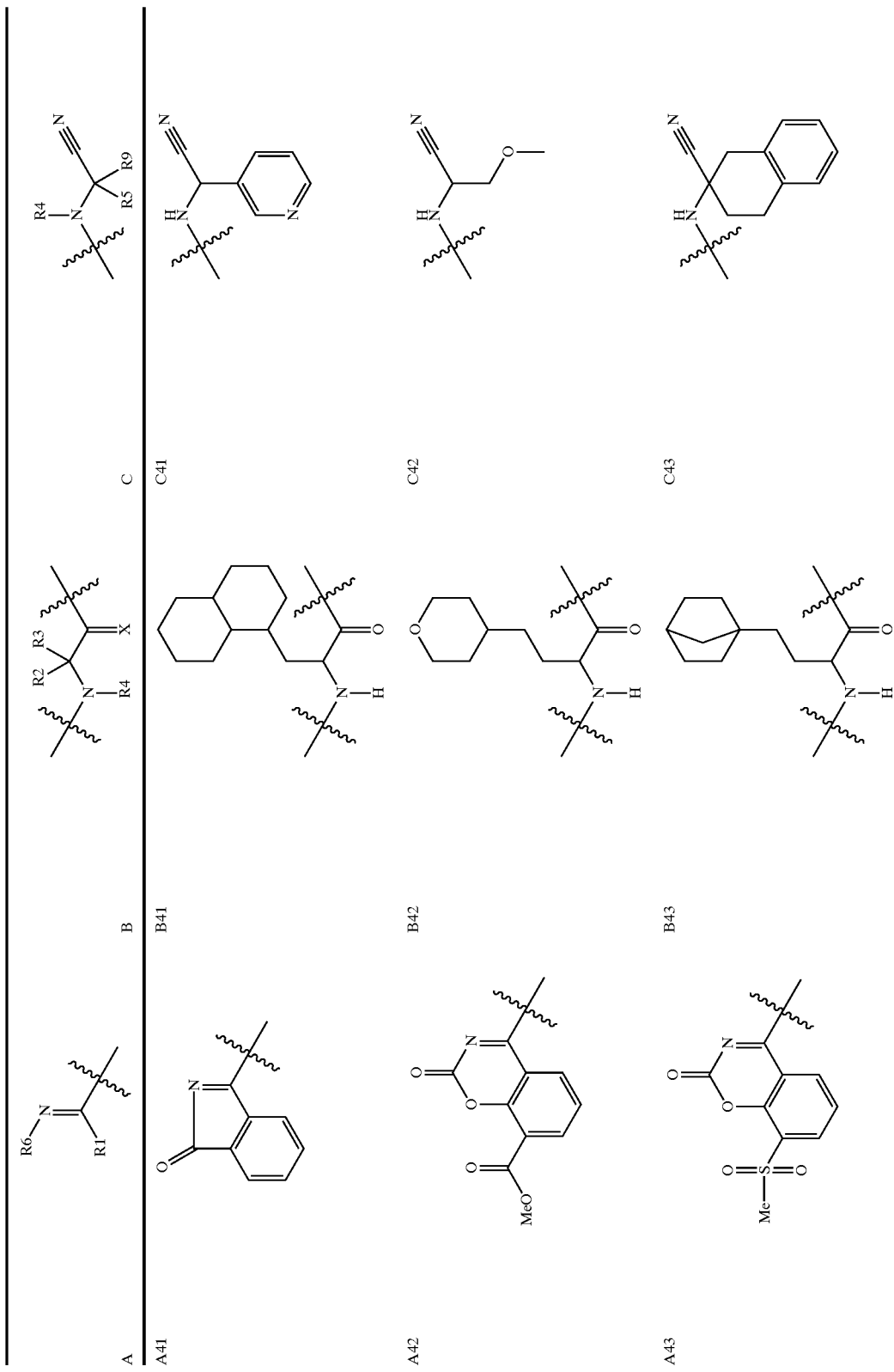

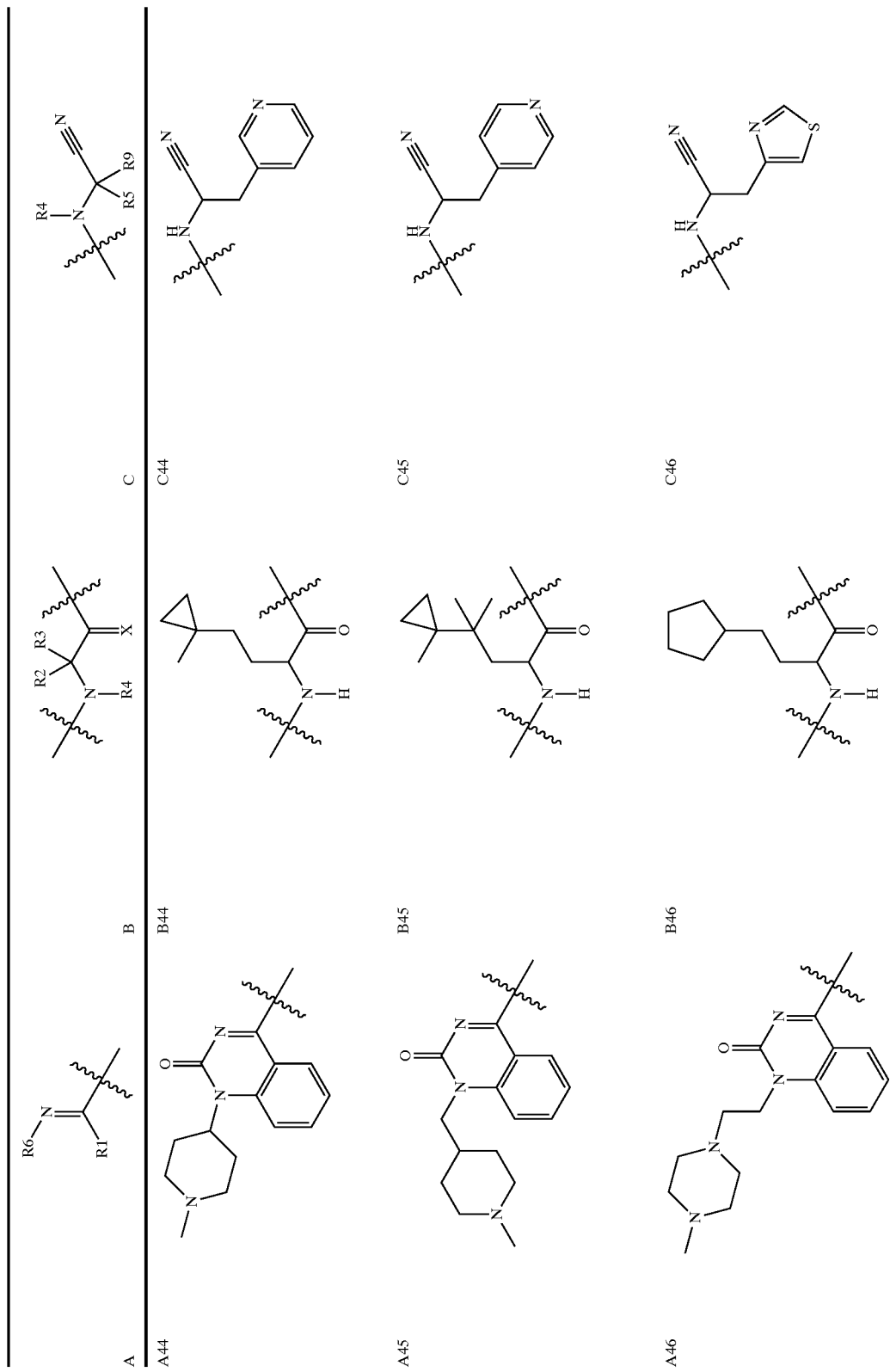

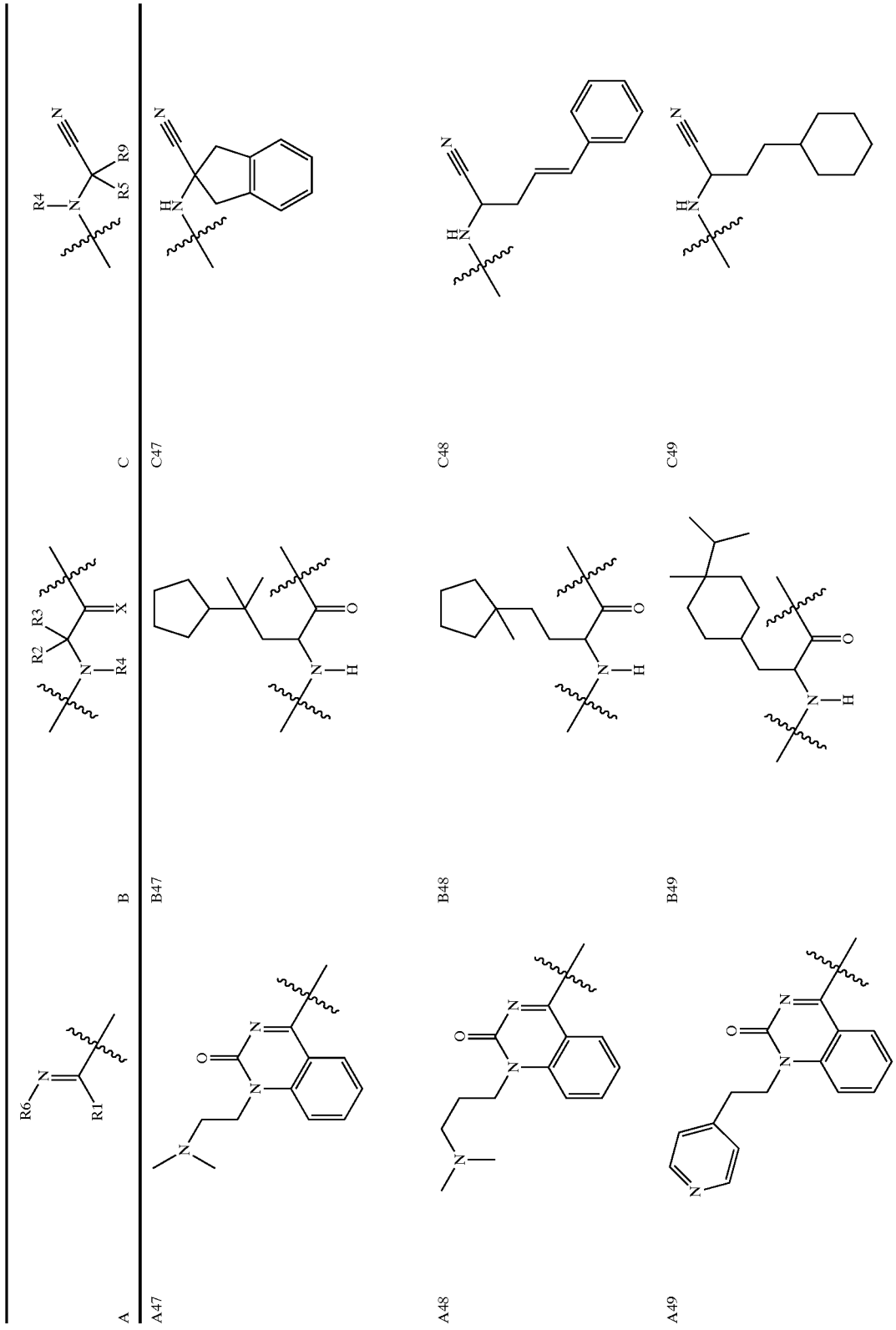

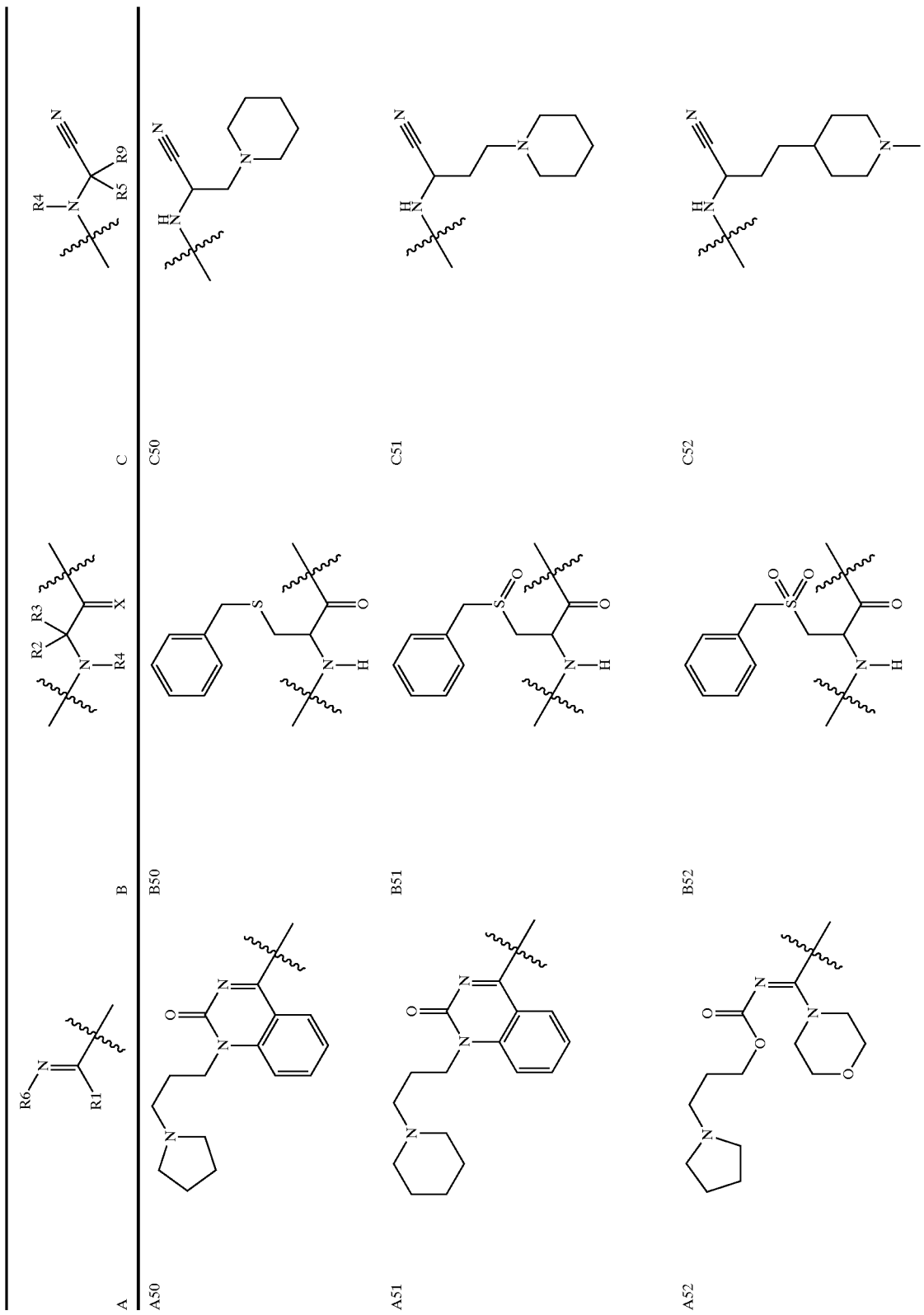

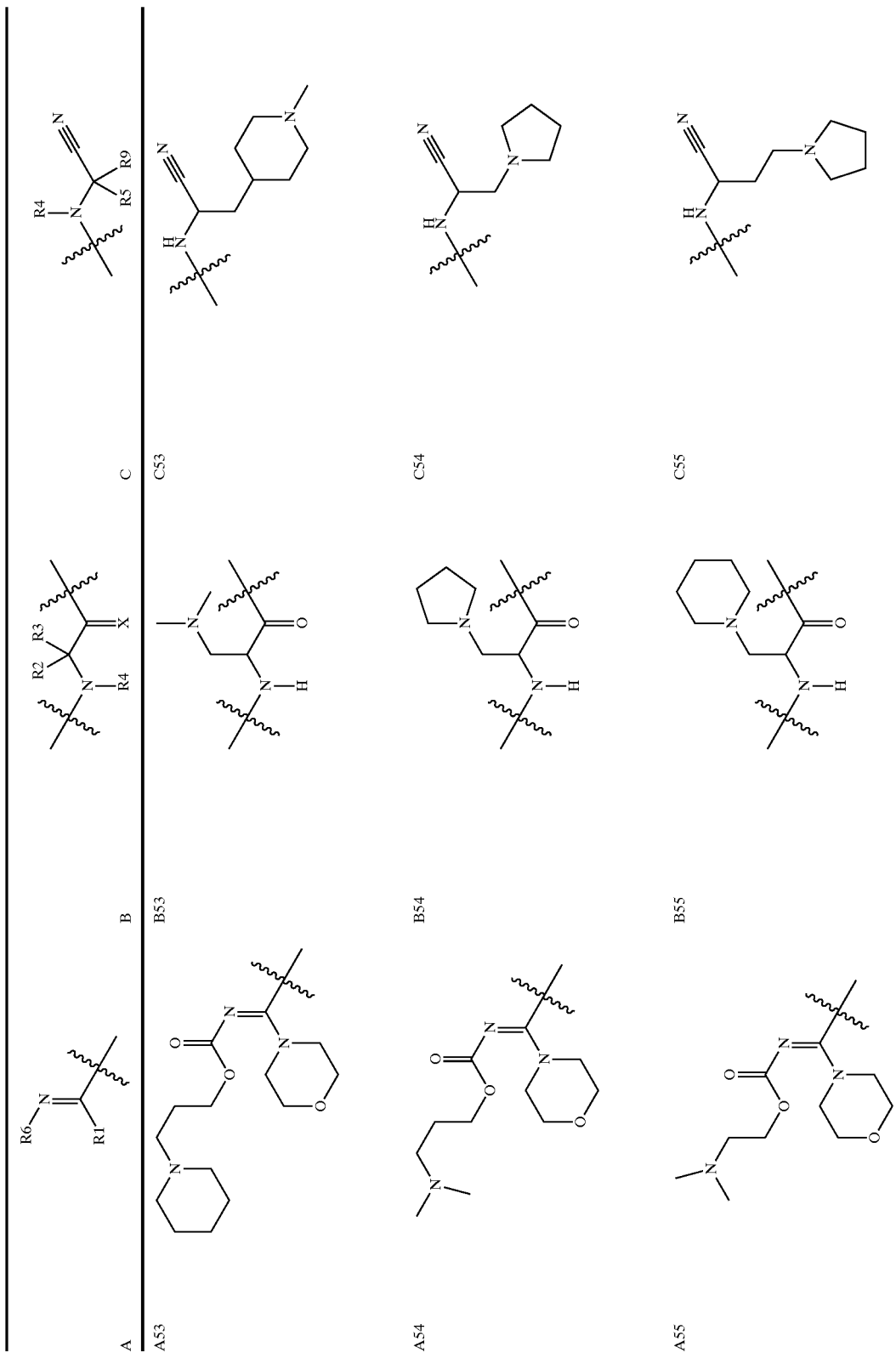

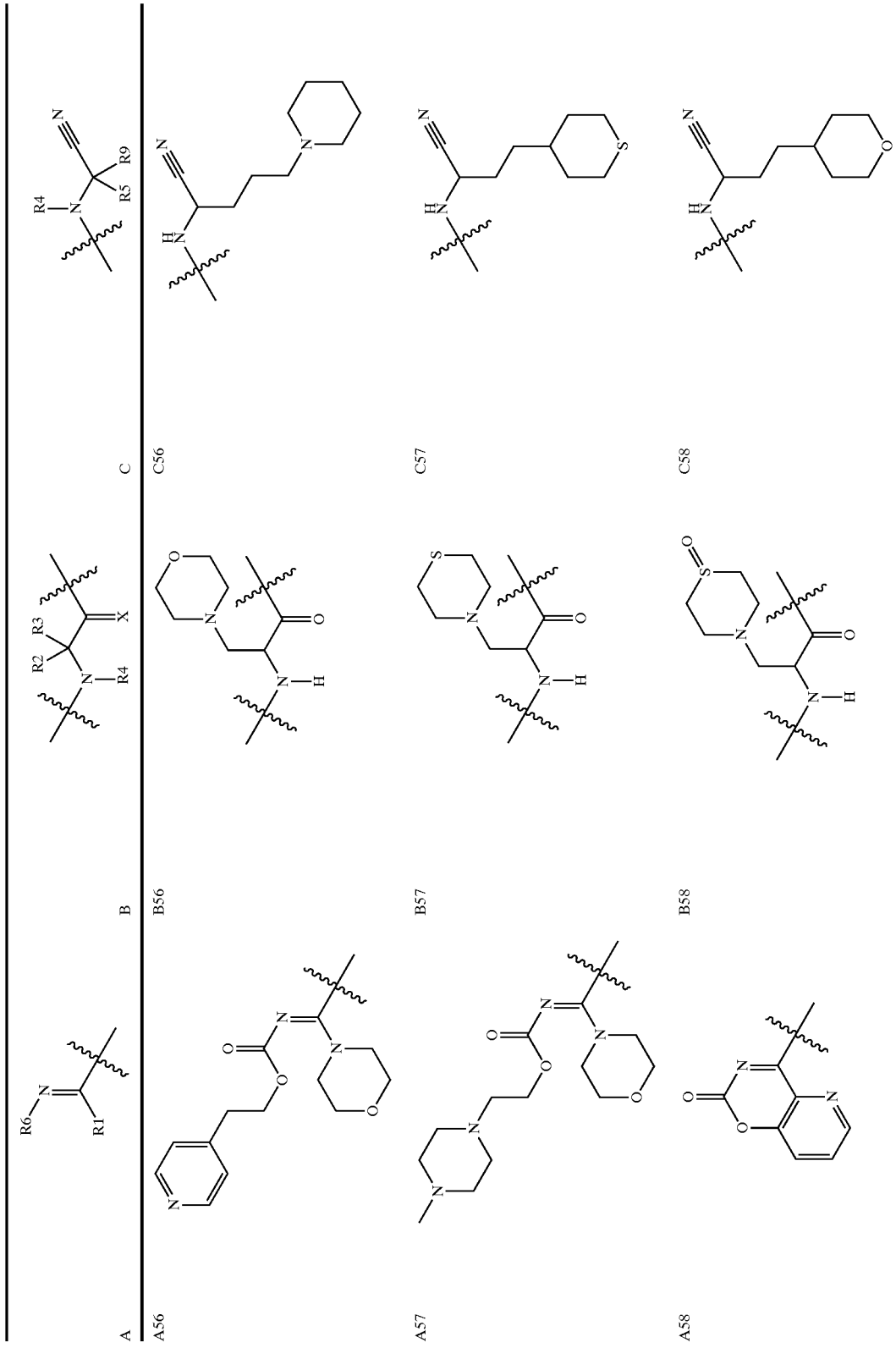

TABLE I-continued

| A | B | C |
|---|---|---|
| A59 | B59 | C59 |
| A60 | B60 | C60 |
| A61 | B61 | C61 |

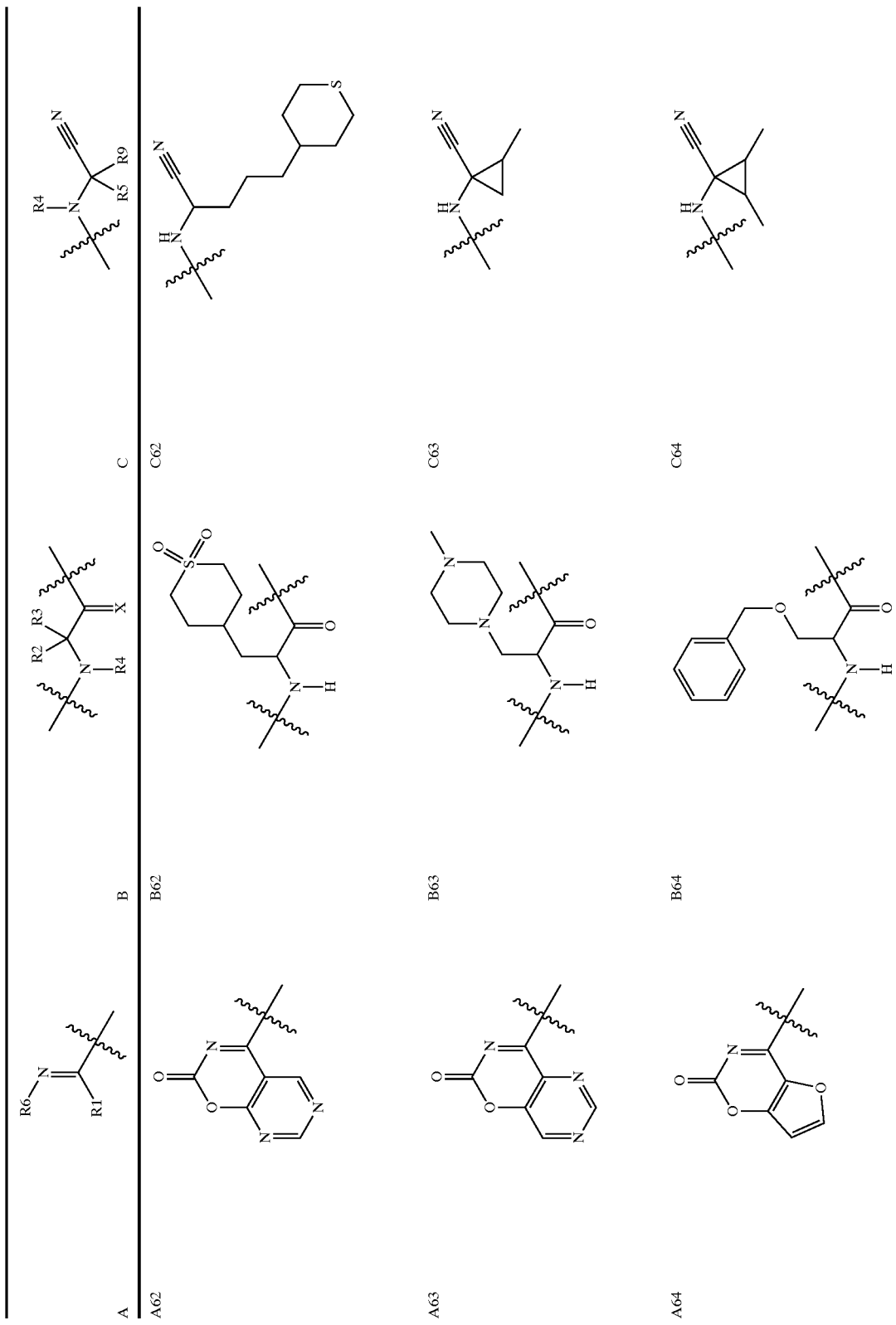

TABLE I-continued

| A | | B | | C | |
|---|---|---|---|---|---|
| A65 | | B65 | | C65 | |
| A66 | | B66 | | C66 | |
| A67 | | B67 | | C67 | |

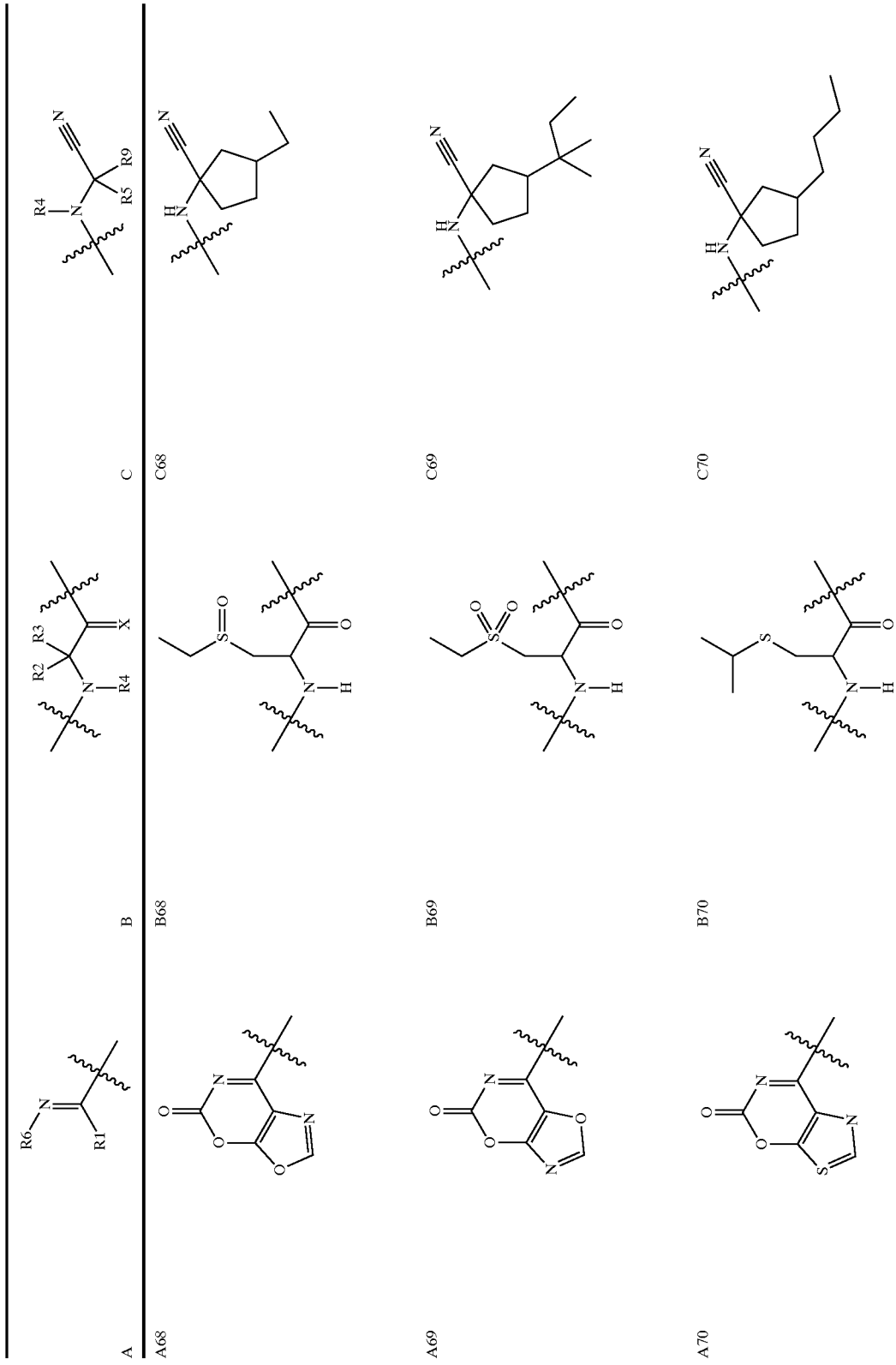

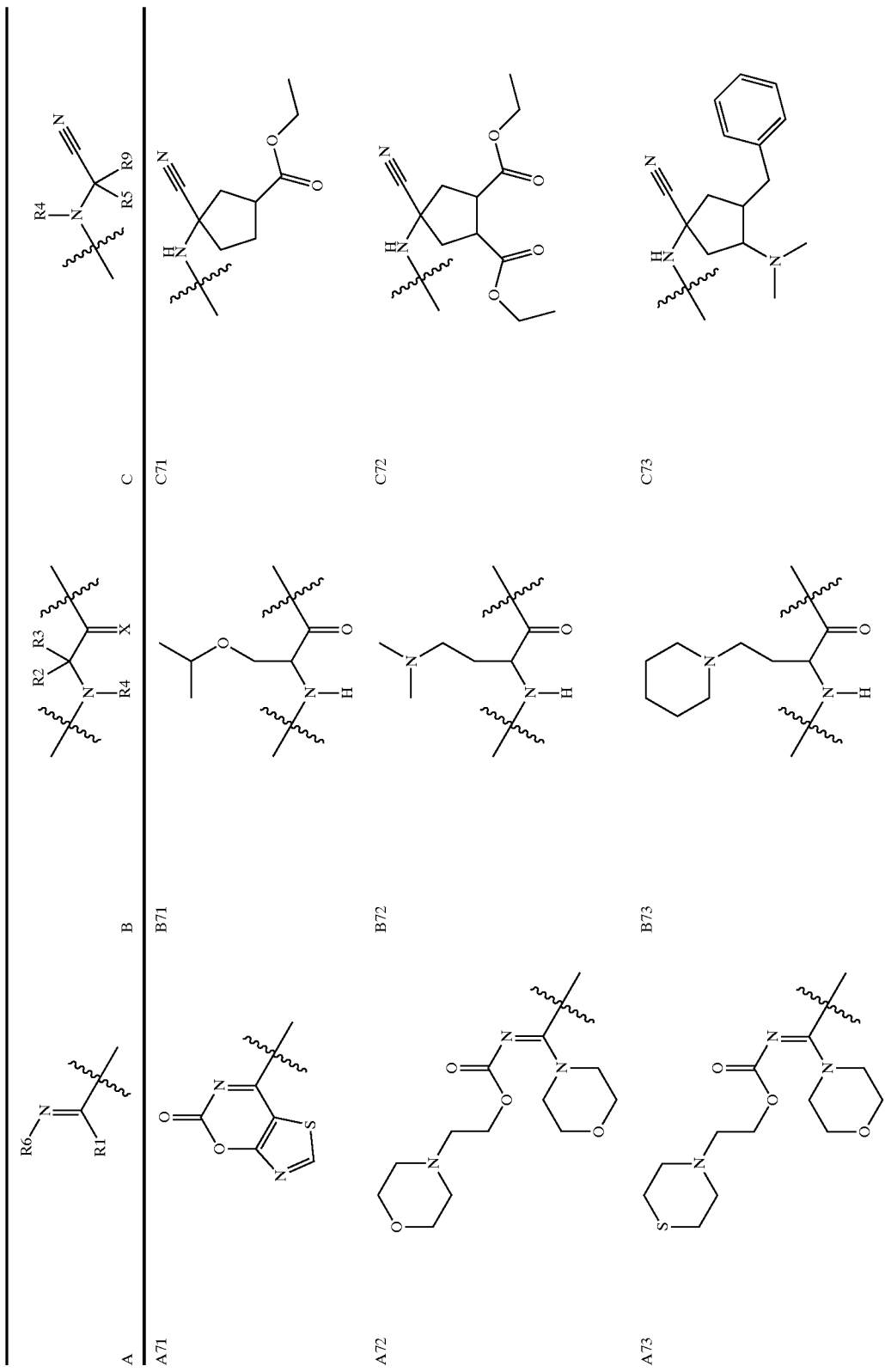

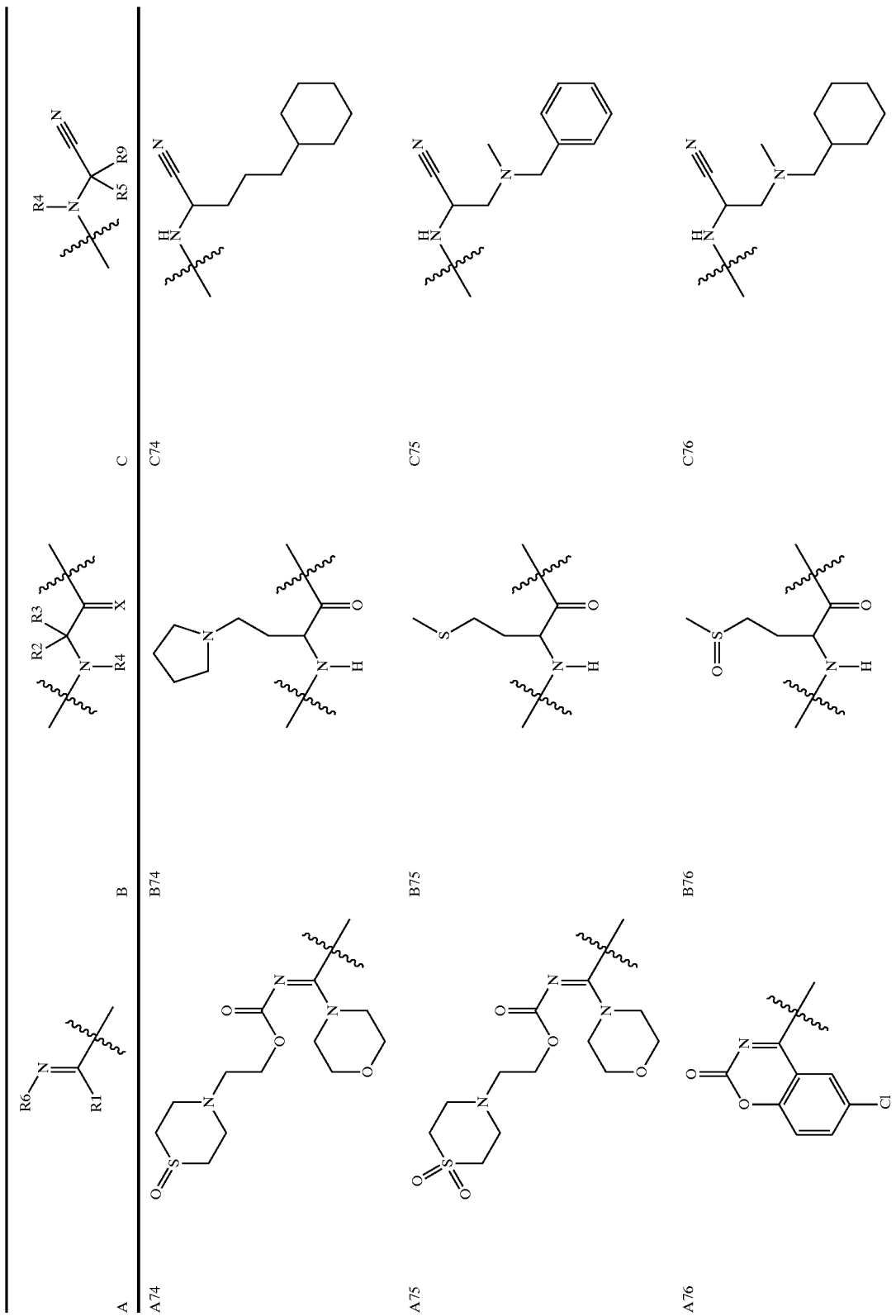

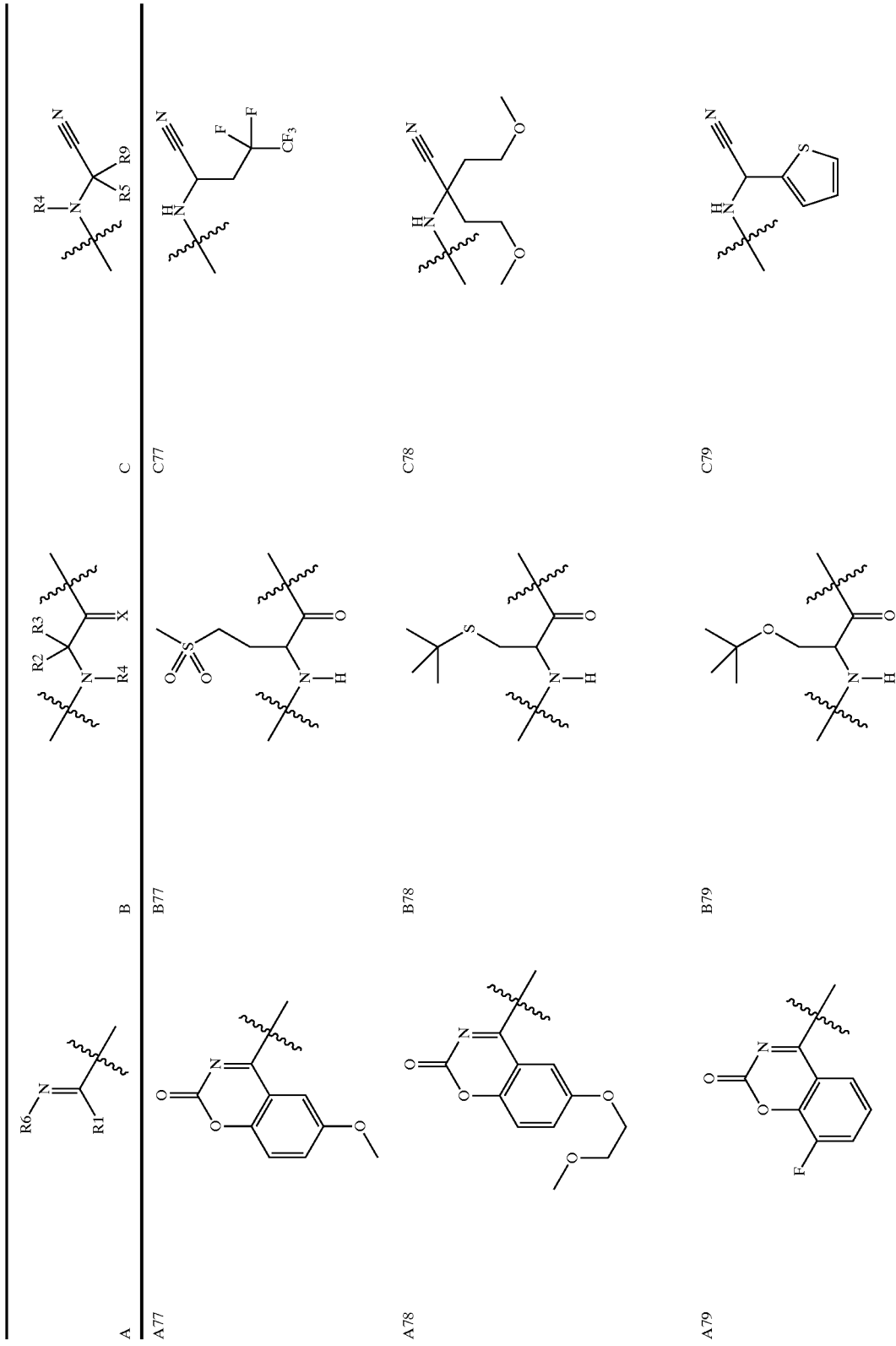

TABLE I-continued
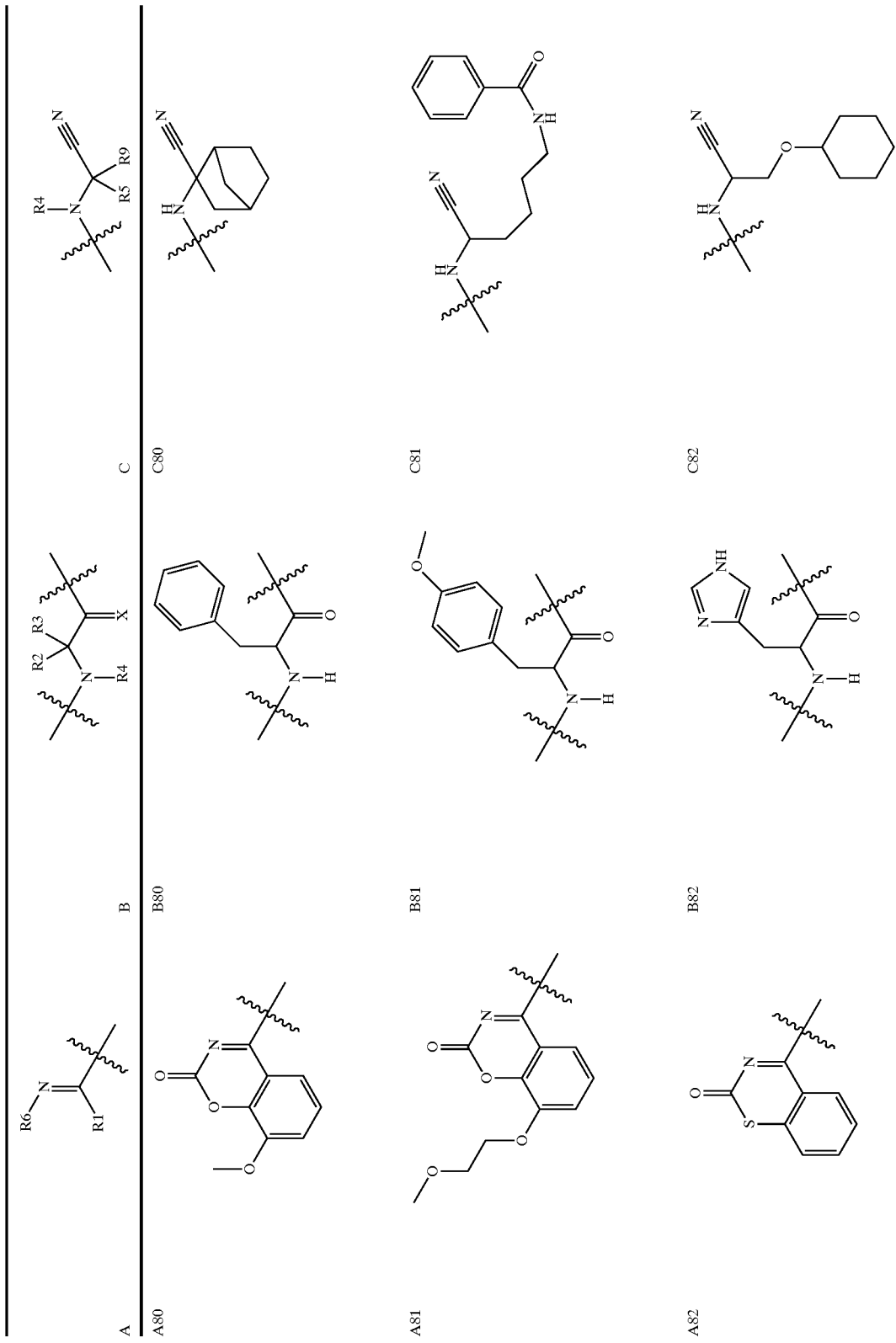

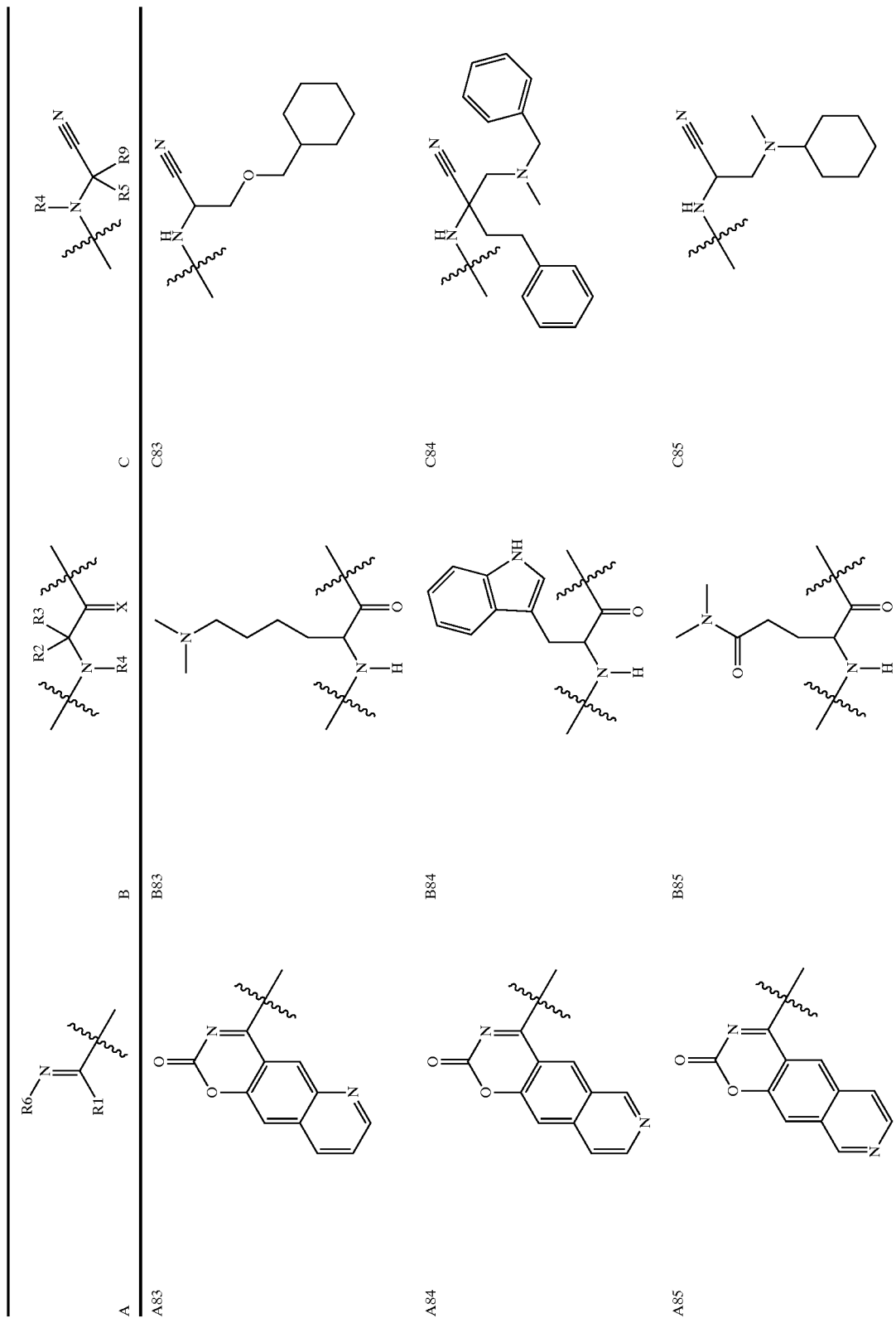

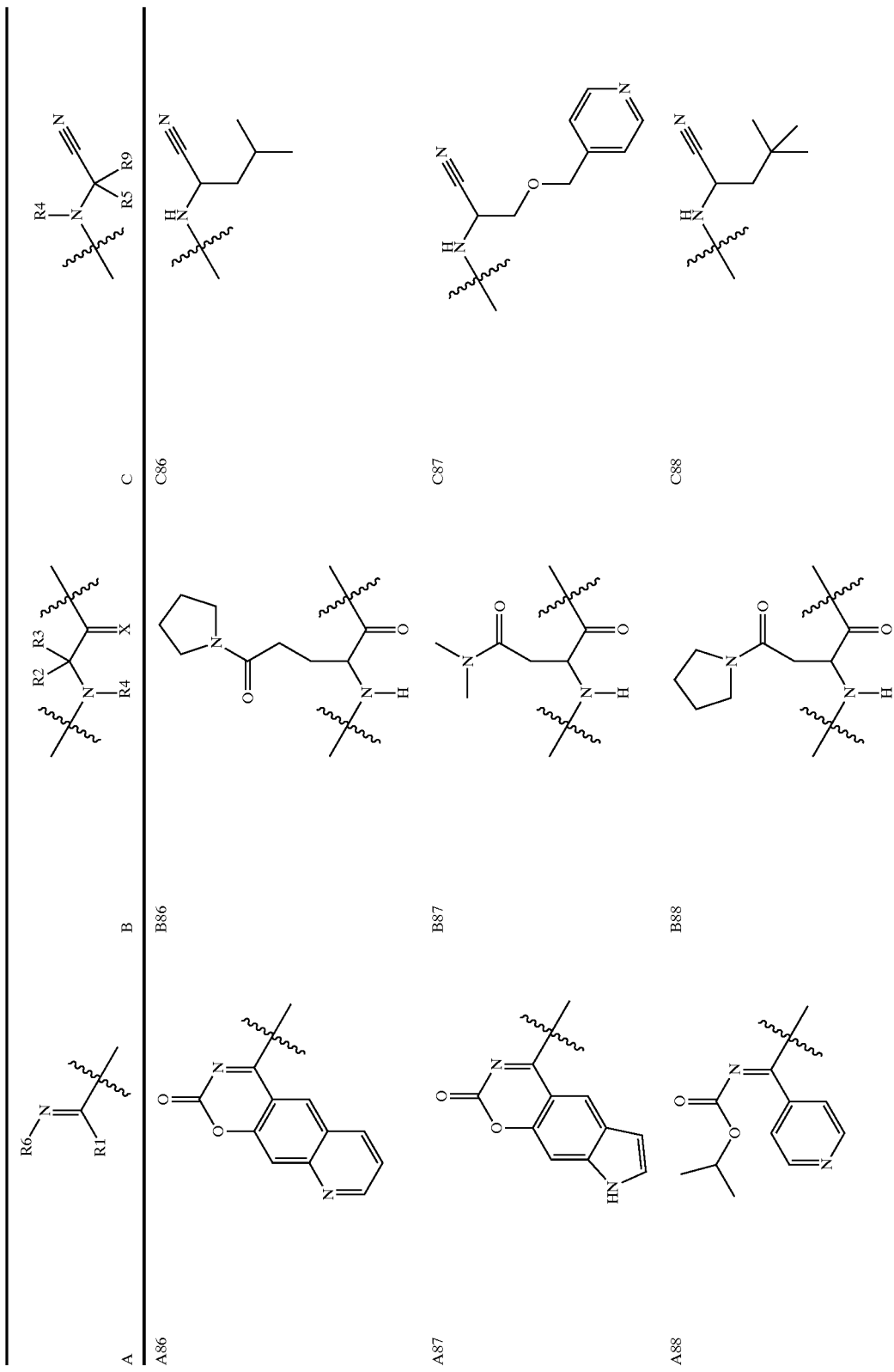

TABLE I-continued

| A | B | C |
|---|---|---|
| A89 | B89 | C89 |
| A90 | B90 | C90 |
| A91 | B91 | C91 |

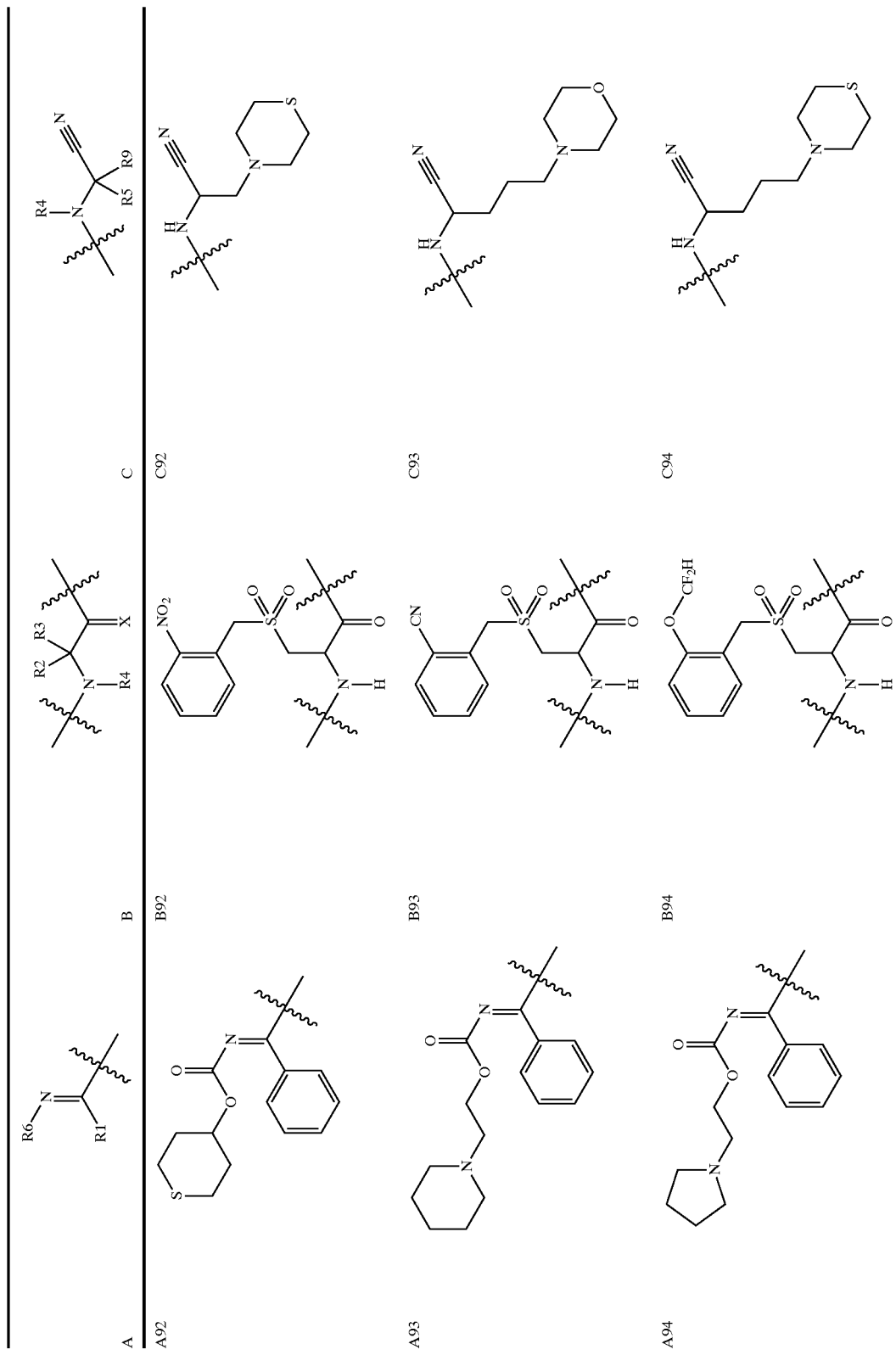

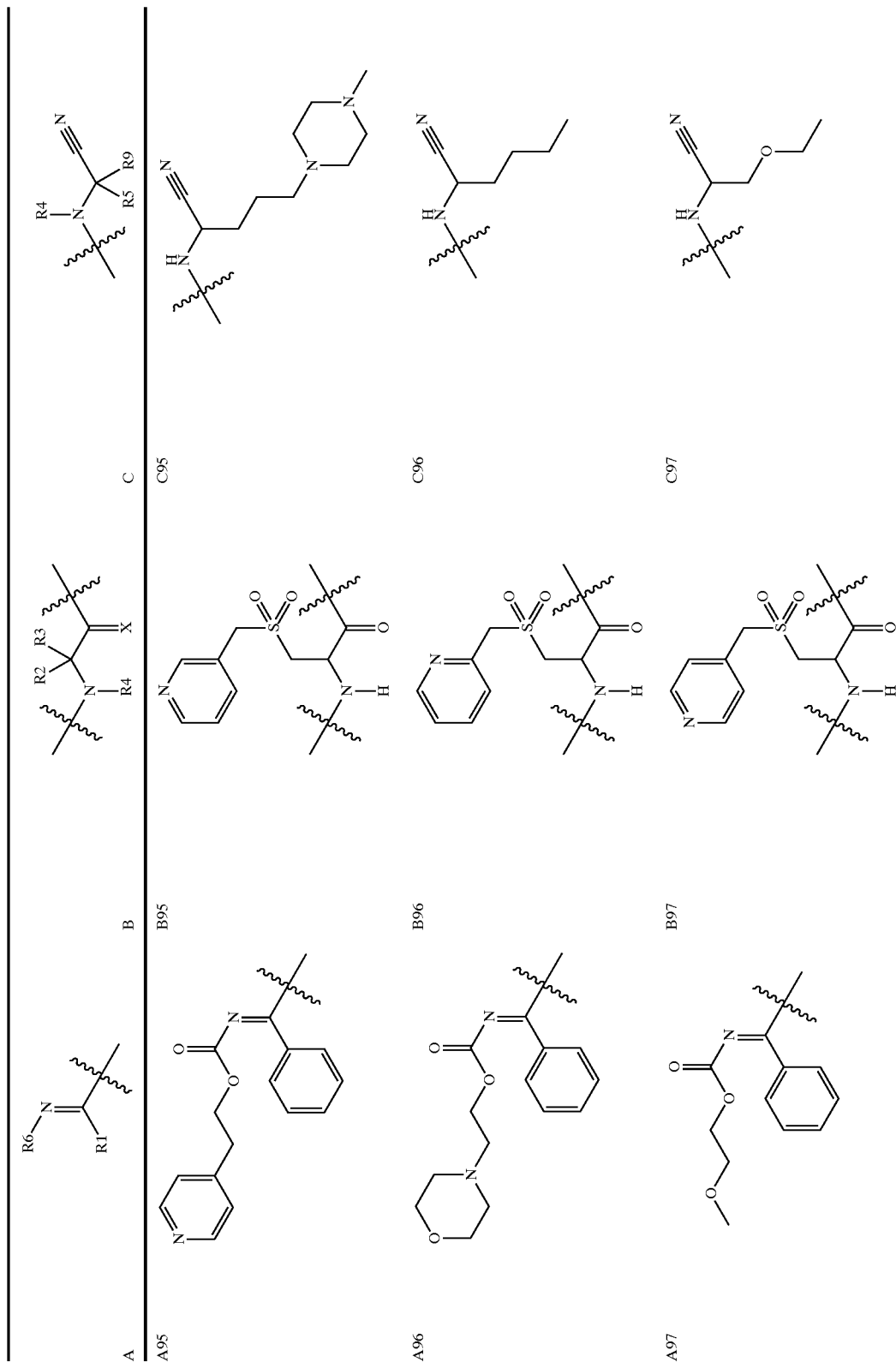

TABLE I-continued

| A | B | C |
|---|---|---|
| A98 | B98 | C98 |
| A99 | B99 | C99 |
| A100 | B100 | C100 |

TABLE I-continued

TABLE I-continued

| A | B | C |
|---|---|---|
| A104 | B104 | C104 |
| A105 | B105 | C105 |
| A106 | B106 | C106 |

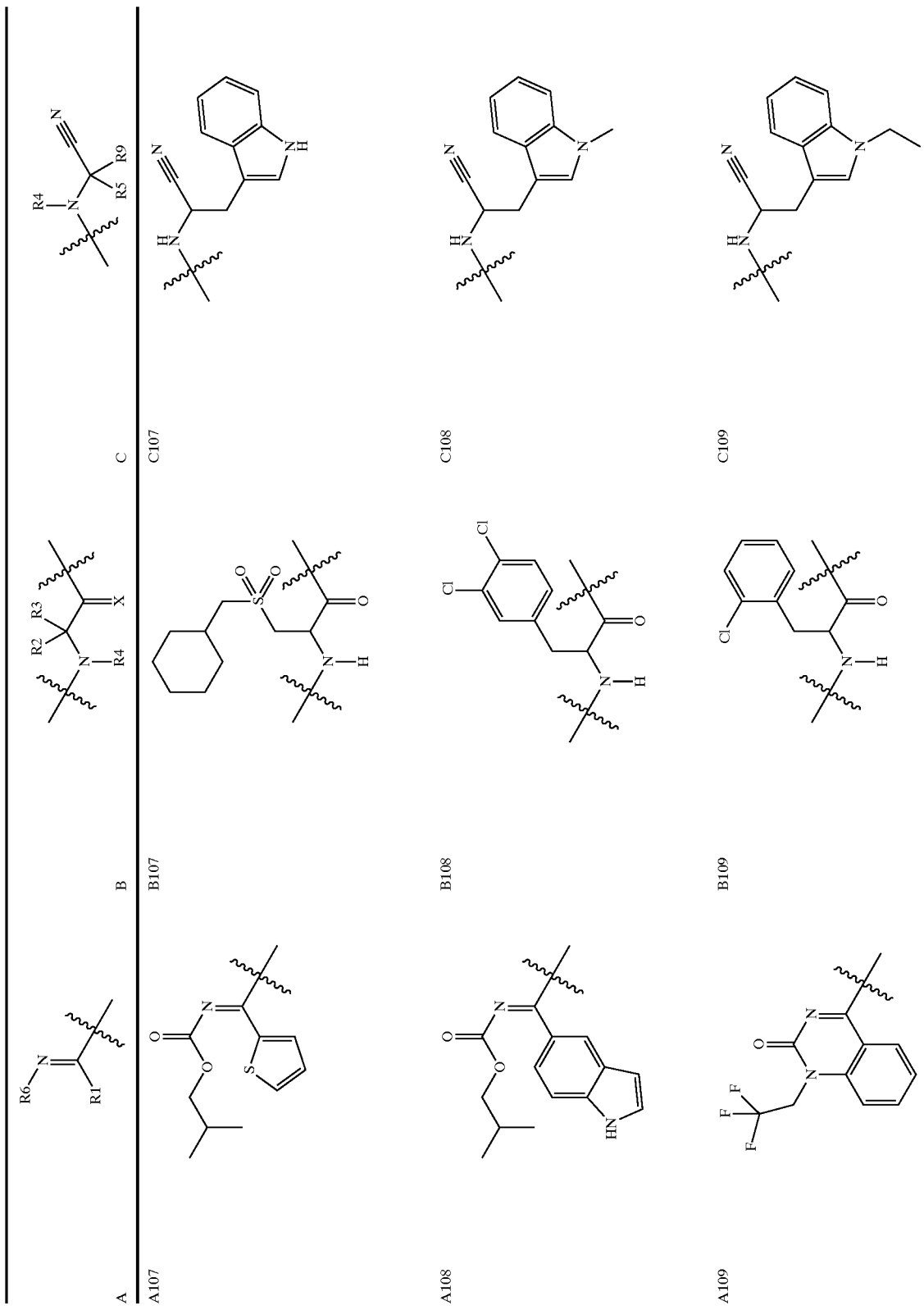

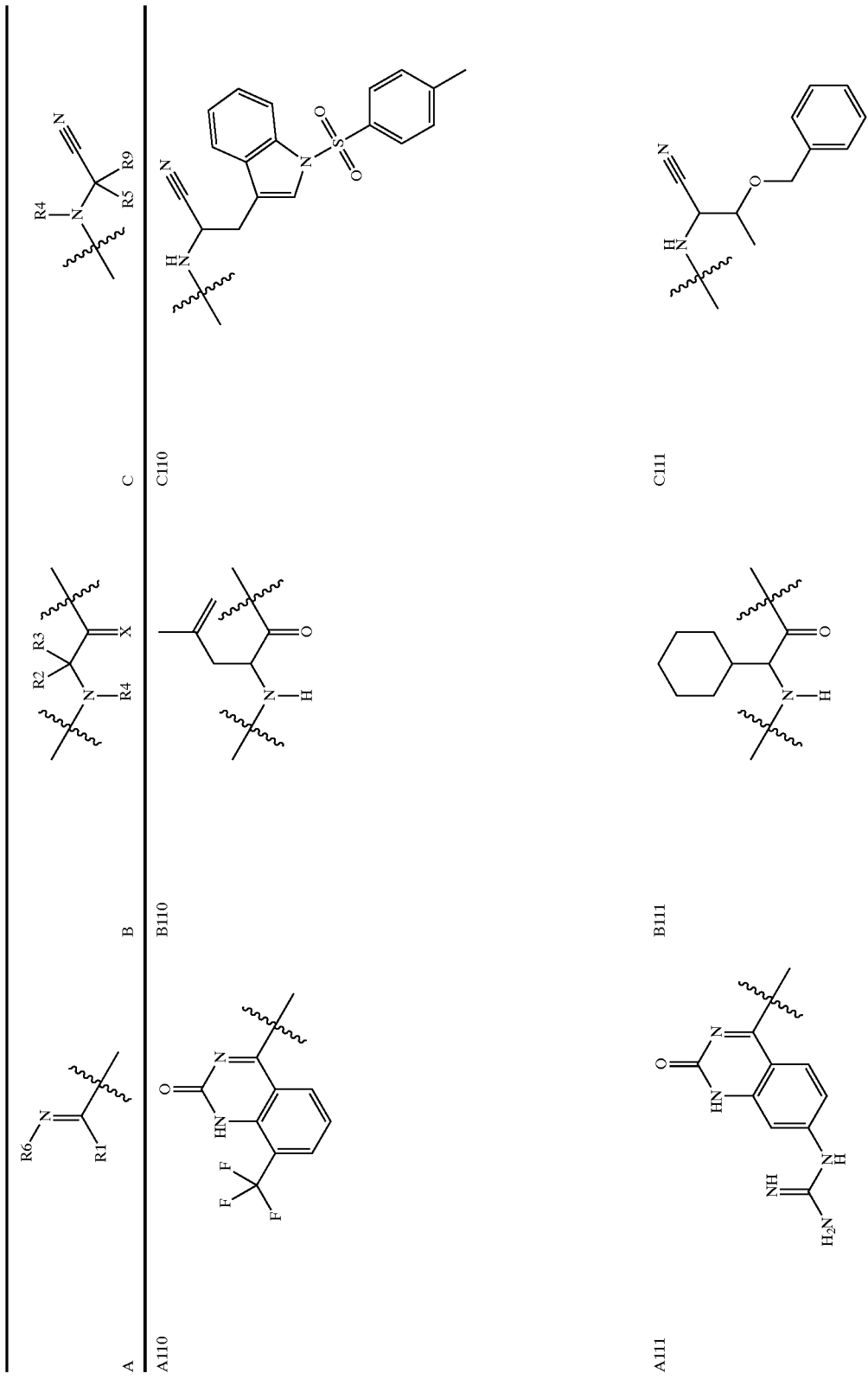

TABLE I-continued

| A | B | C |
|---|---|---|
| A112 | B112 | C112 |
| A113 | B113 | C113 |

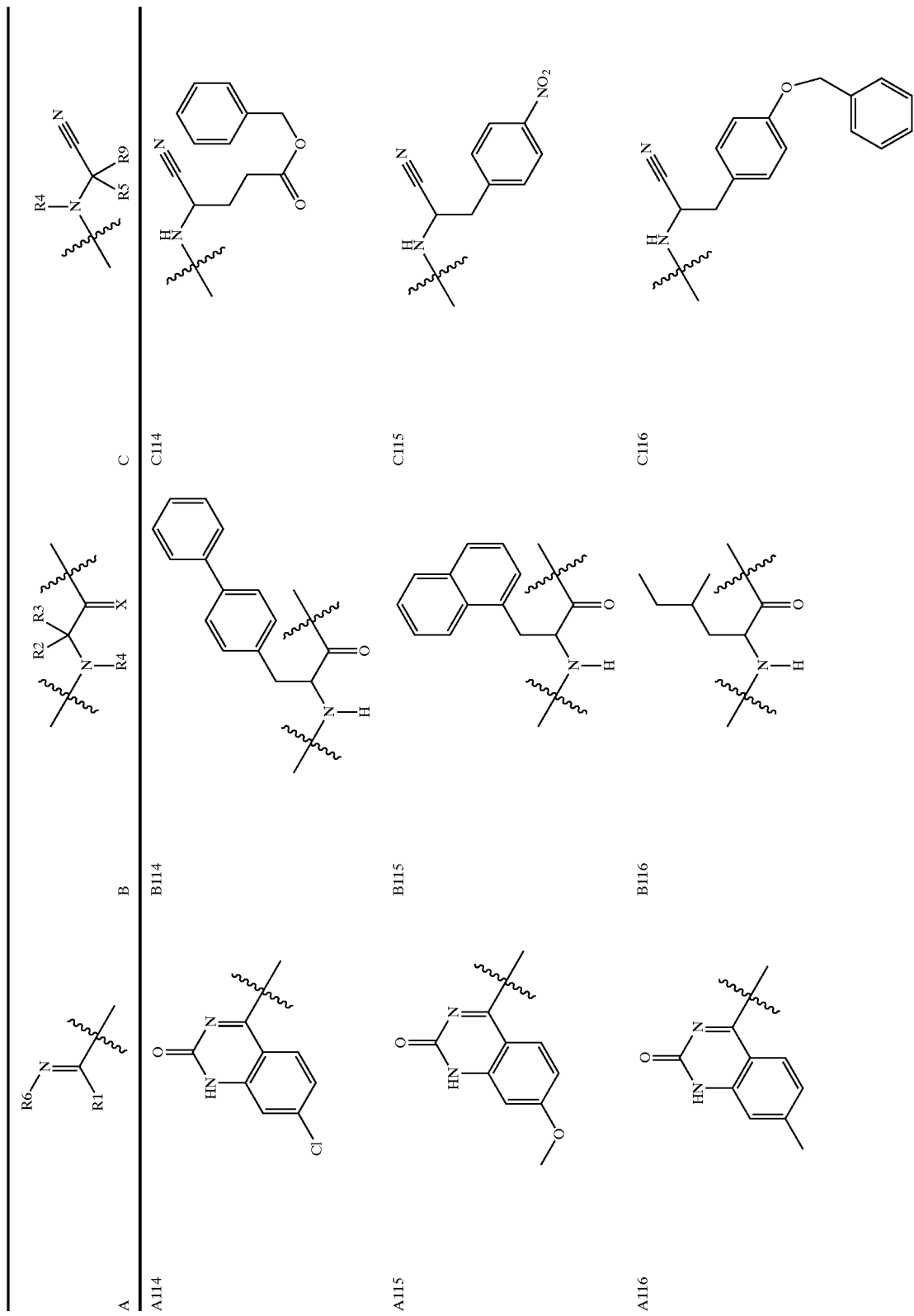

TABLE I-continued
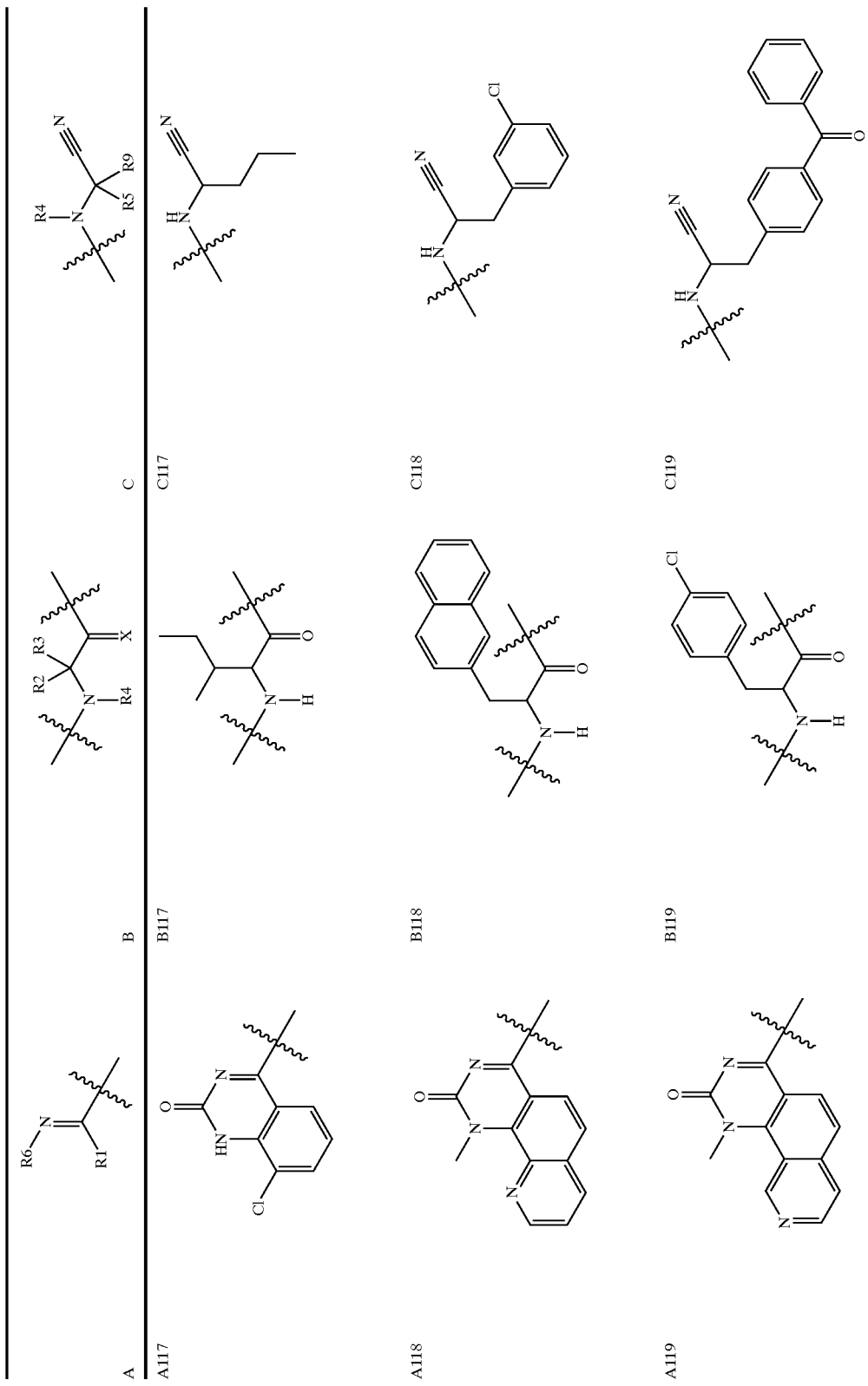

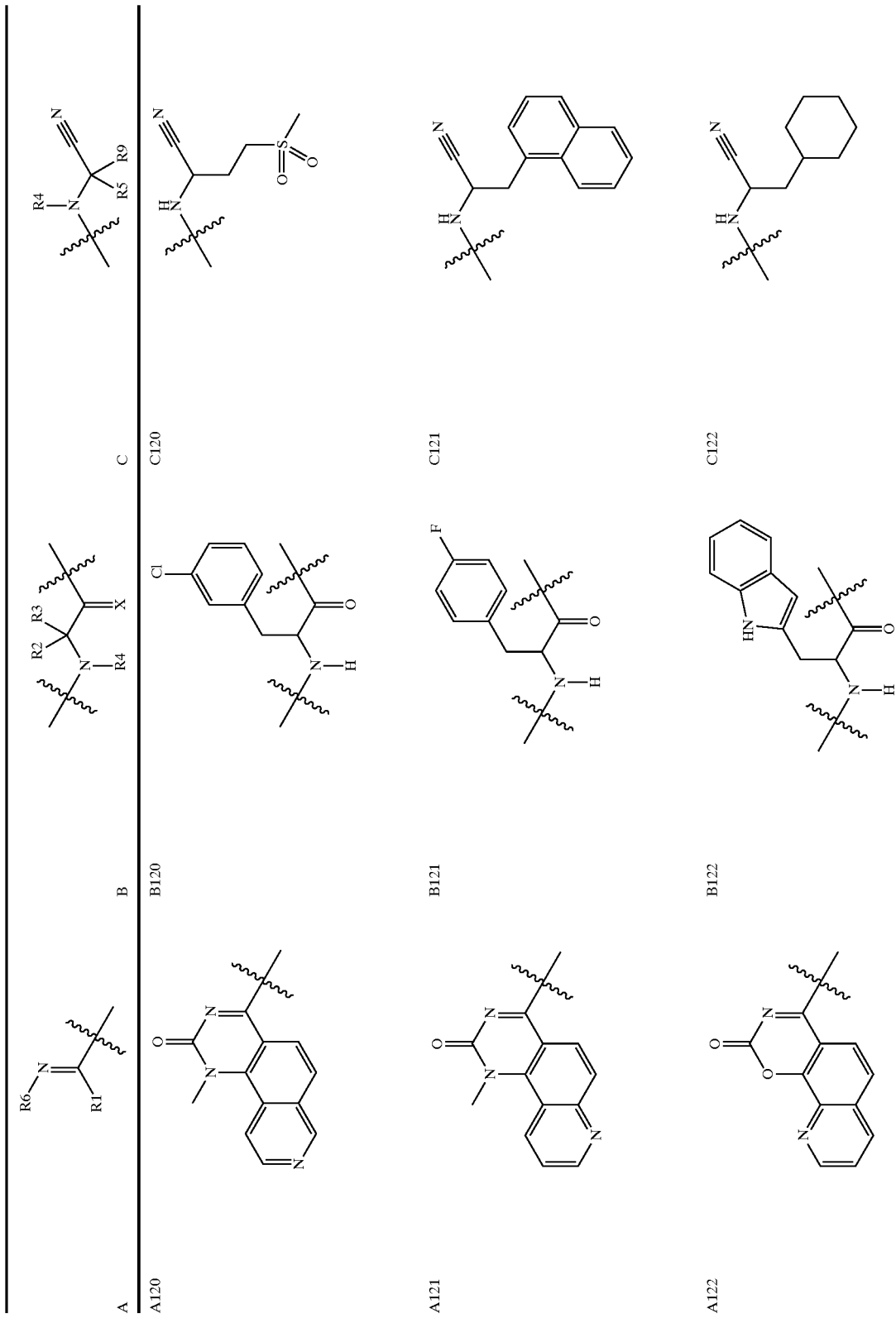

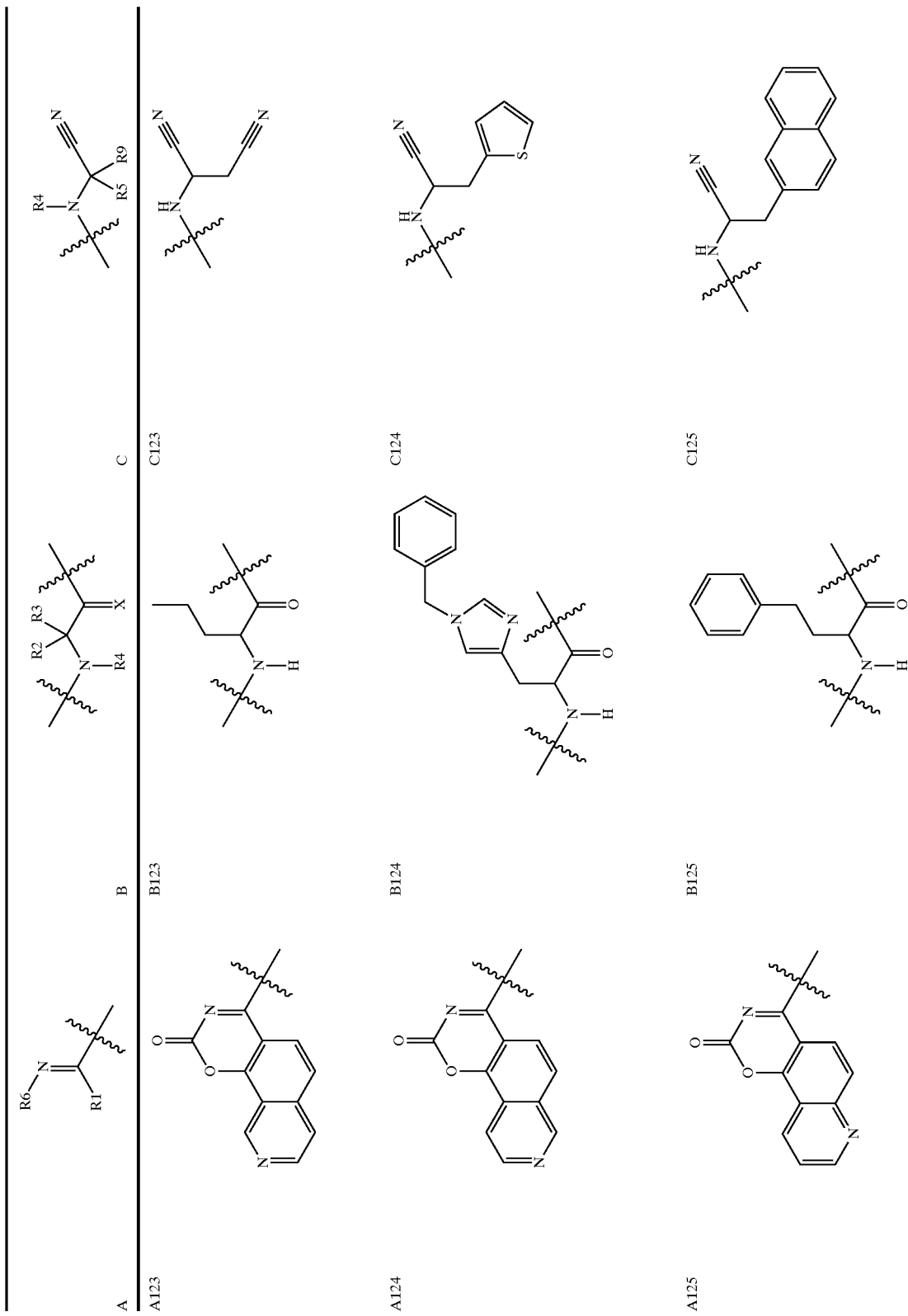

TABLE I-continued

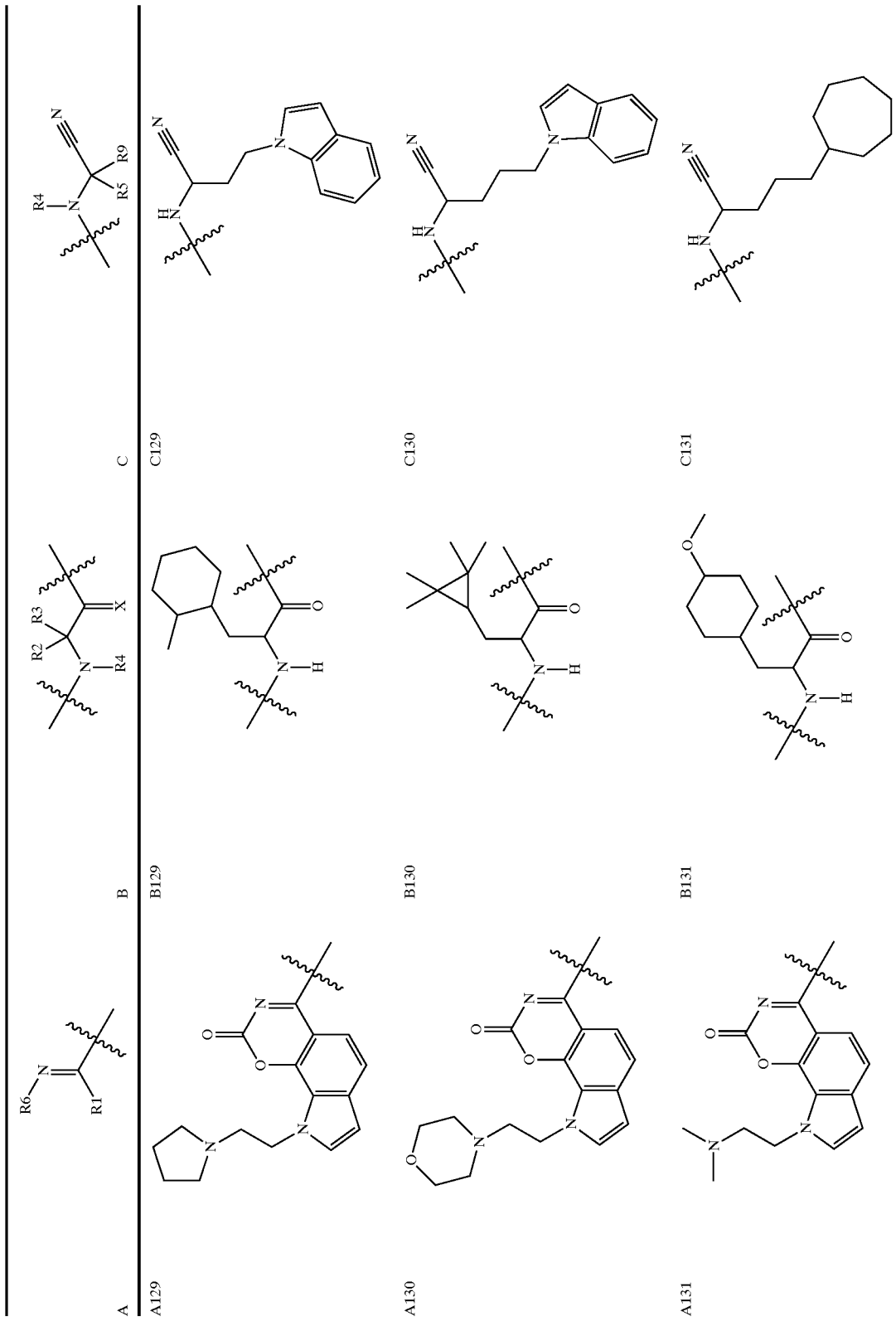

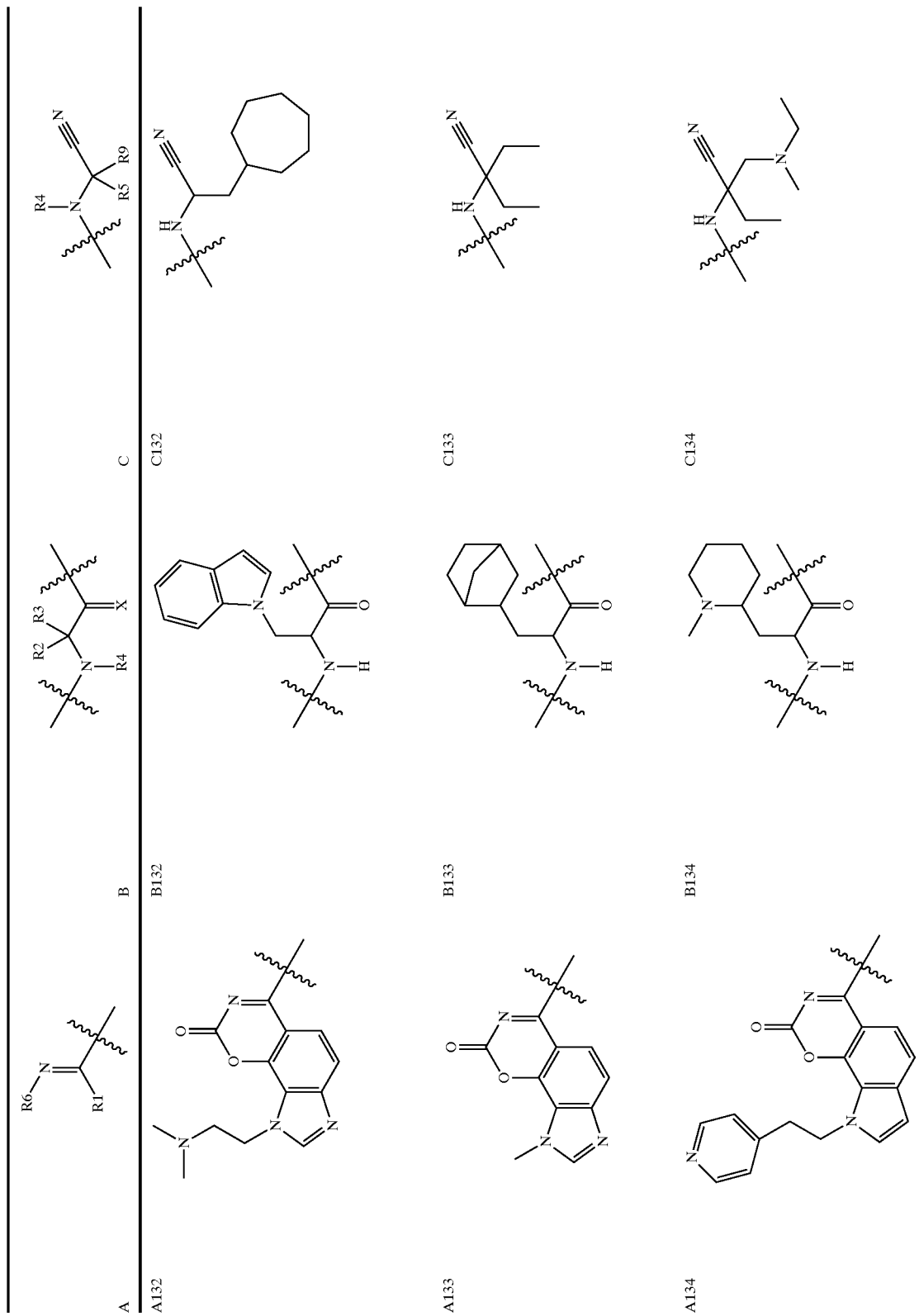

TABLE I-continued
| A | B | C |
|---|---|---|
| A135 | 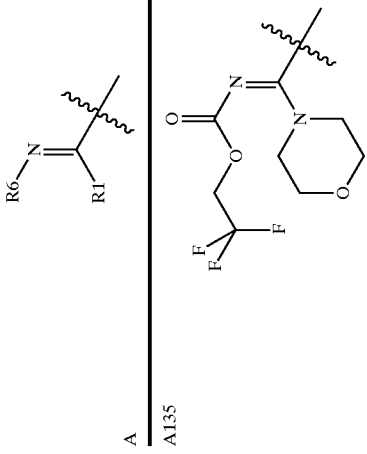 | |
| A136 | 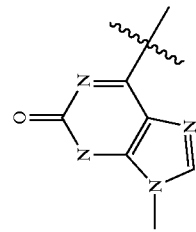 | |
| A137 | 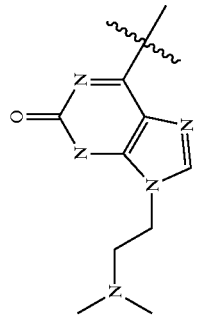 | |
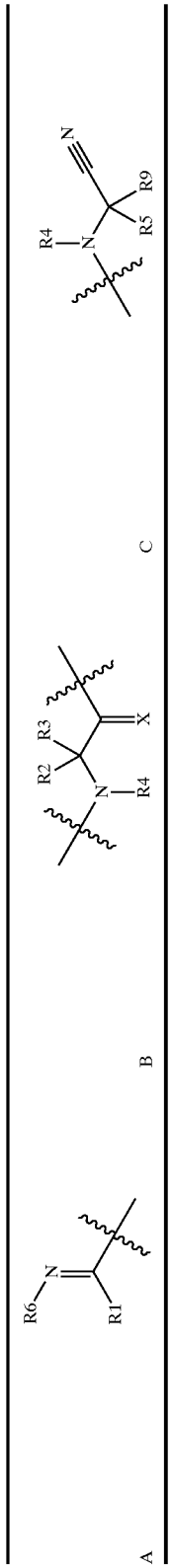

TABLE I-continued
| A | B | C |
|---|---|---|
| A138 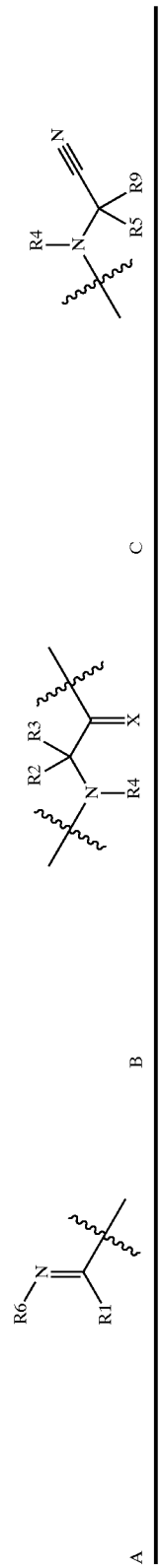 |  | |
| A139 |  | |
| A140 |   R is hydrogen or alkyl | | and the pharmaceutically acceptable derivatives thereof.

The following compounds can be synthesized by the General schemes, methods described in the experimental section of this document and analogous methods known to those skilled in the art without undue experimentation. Preferred compounds will possess desirable inhibition activity of Cathepsin S in a cell based assay as described in Riese, R. J. et al., Immunity, 1996, 4, 357–366, incorporated herein by reference.

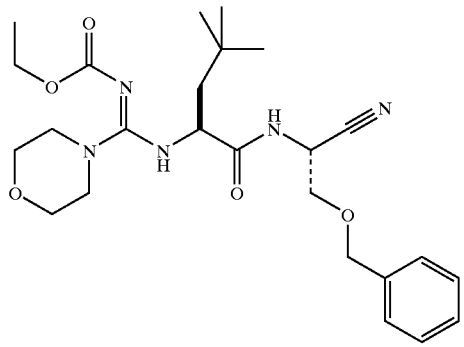

({1[(Benzyloxymethyl-cyano-methyl)-carbamoyl]-3,3-dimethyl-butylimino}-morpholin-4-yl-methyl)-carbamic acid ethyl ester

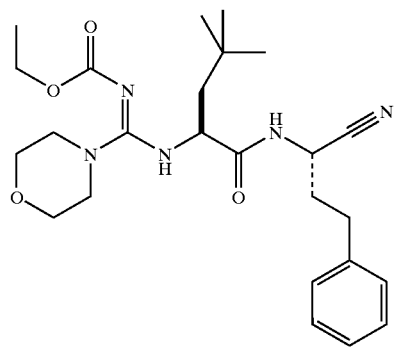

{[1-(1-Cyano-3-phneyl-propylcarbamoyl)-3,3-dimethyl-butylimino]-morpholin-4-yl-methyl}-carbamic acid ethyl ester

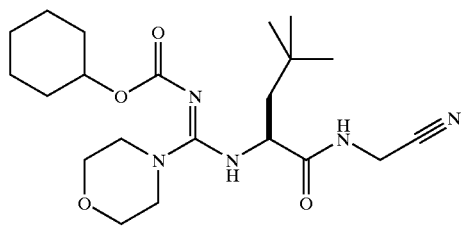

{[1-(Cyanomethyl-carbamoyl)-3,3-dimethyl-butylimino]-morpholin-4-yl-methyl}-carbamic acid cyclohexyl ester

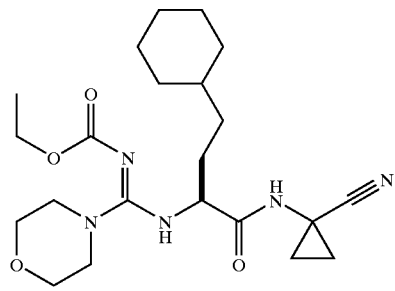

{[1-(1-Cyano-cyclopropylcarbamoyl)-3-cyclohexyl-propylimino]-morpholin-4-yl-methyl}-carbamic acid ethyl ester

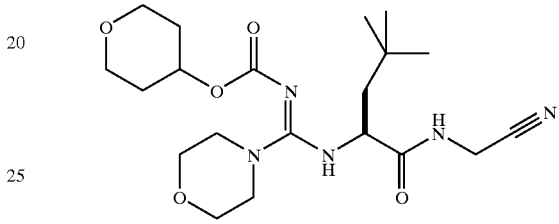

{[1-(Cyanomethyl-carbamoyl)-3,3-dimethyl-butylimino]-morpholin-4-yl-methyl}-carbamic acid tetrahydro-pyran-4-yl ester

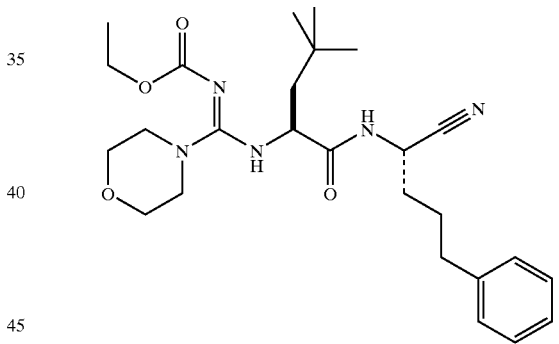

{[1-(1-Cyano-4-phenyl-butylcarbamoyl)-3,3-dimethyl-butylimino]-morpholin-4-yl-methyl}-carbamic acid ethyl ester

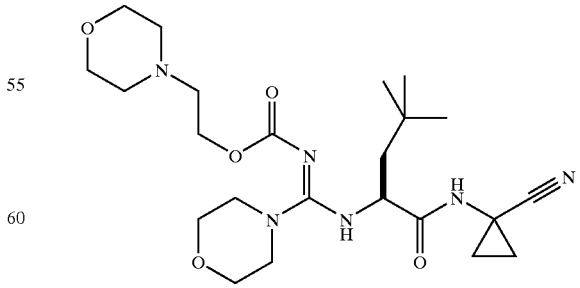

{[1-(1-Cyano-cyclopropylcarbamoyl)-3,3-dimethyl-butylimino]-morpholin-4-yl-methyl}-carbamic acid 2-morpholin-4-yl-ethyl ester

131

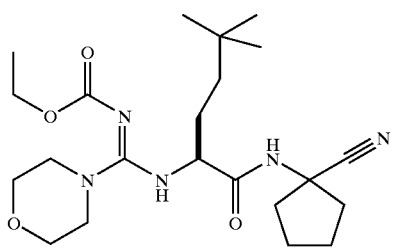

{[1-(1-Cyano-cyclopentylcarbamoyl)-4,4-dimethyl-pentylimino]-morpholin-4-yl-methyl}-carbamic acid ethyl ester

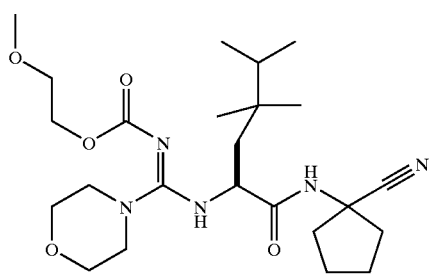

{[1-(1-Cyano-cyclopentylcarbamoyl)-3,3,4-trimethyl-pentylimino]-morpholin-4-yl-methyl}-carbamic acid 2-methoxy-ethyl ester

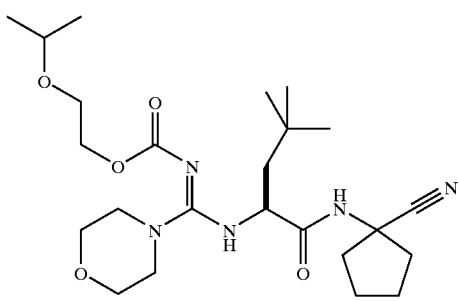

{[1-(1-Cyano-cyclopentylcarbamoyl)-3,3-dimethyl-butylimino]-morpholin-4-yl-methyl}-carbamic acid 2-isopropoxy-ethyl ester

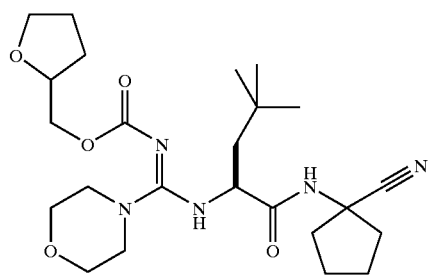

{[1-(1-Cyano-cyclopentylcarbamoyl)-3,3-dimethyl-butylimino]-morpholin-4-yl-methyl}-carbamic acid tetrahydro-furan-2-ylmethyl ester

132

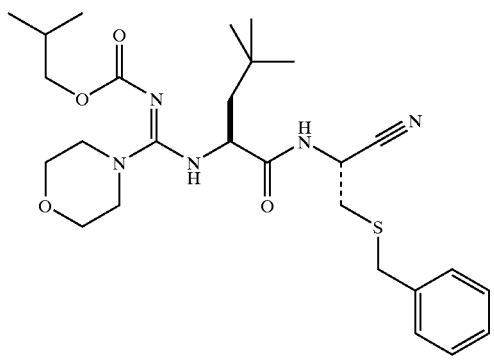

({1-[(Benzylsulfanylmethyl-cyano-methyl)-carbamoyl]-3,3-dimethyl-butylimino}-morpholin-4-yl-methyl)-carbamic acid isobutyl ester

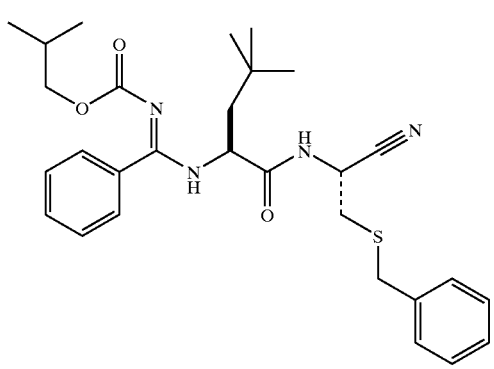

({1-[Benzylsulfanylmethyl-cyano-methyl)-carbamoyl]-3,3-dimethyl-butylimino}-phenyl-methyl)-carbamic acid isobutyl ester

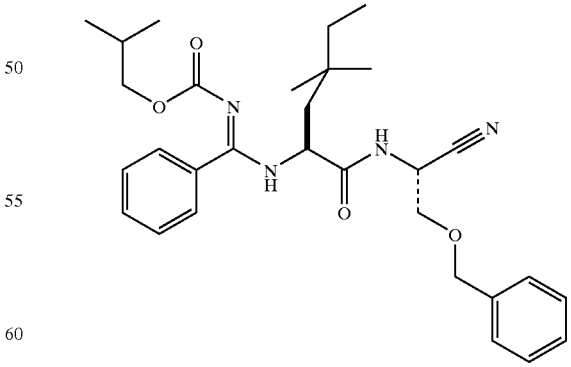

({1-[(Benzyloxymelthyl-cyano-methyl)-carbamoyl]-3,3-dimethyl-pentylimino}-phenylmethyl)-carbamic acid isobutyl ester

133

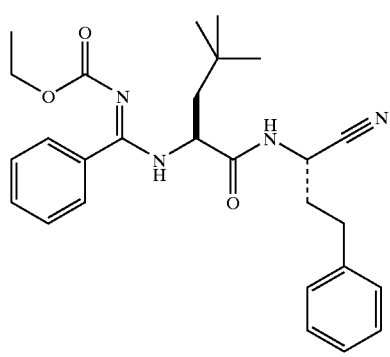

{[1-(1-Cyano-3-phenyl-propylcarbamoyl)-3,3-dimethyl-butylimino]-phenyl-methyl}-carbamic acid ethyl ester

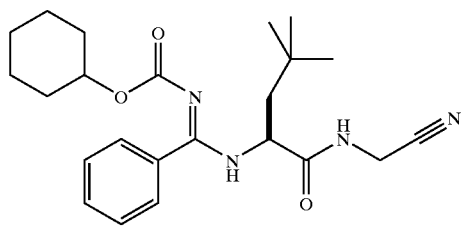

{[1-(Cyanomethyl-carbamoyl)-3,3-dimethyl-butylimino]-phenyl-methyl}-carbamic acid cyclohexyl ester

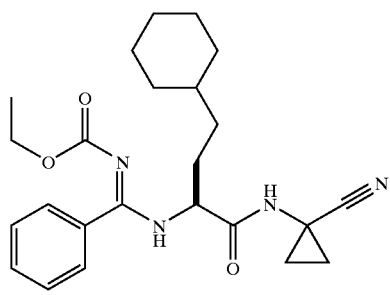

{[1-(1-Cyano-cyclopropylcarbamoyl)-3-cyclohexyl-propylimino]-phenyl-methyl}-carbamic acid ethyl ester

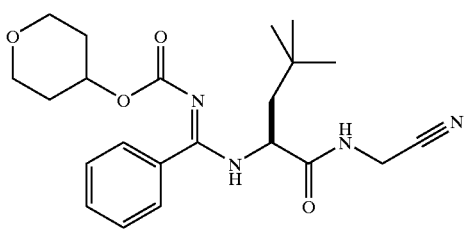

{[1-(Cyanomethyl-carbamoyl)-3,3-dimethyl-butylimino]-phenyl-methyl}-carbamic acid tetrahydro-pyran-4-yl ester

134

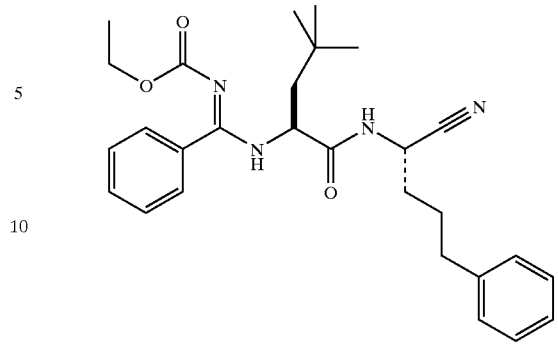

{[1-(1-Cyano-4-phenyl-butylcarbamoyl)-3,3-dimethyl-butylimino]-phenyl-methyl}-carbamic acid ethyl ester

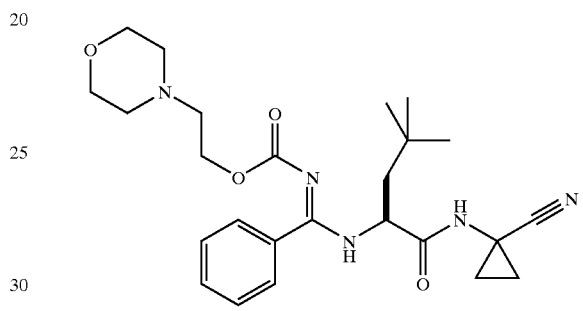

{[1-(1-Cyano-cyclopropylcarbamoyl)-3,3-dimethyl-butylimino]-phenyl-methyl}-carbamic acid 2-morpholin-4-yl-ethyl ester

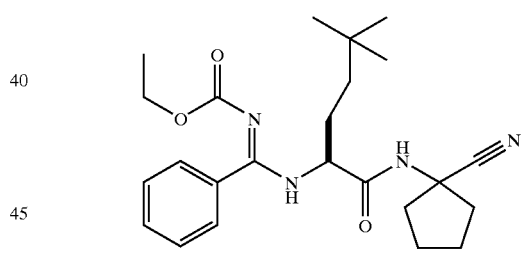

{[1-(1-Cyano-cyclopentylcarbamoyl)-4,4-dimethyl-pentylimino]-phenyl-methyl}-carbamic acid ethyl ester

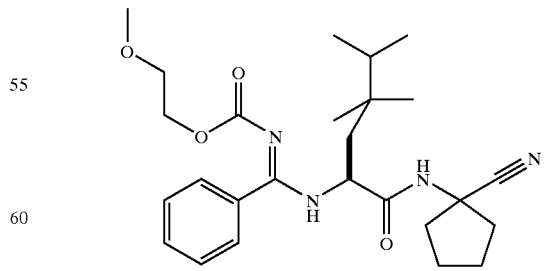

{[1-(1-Cyano-cyclopentylcarbamoyl)-3,3,4-trimethyl-pentylimino]-phenyl-methyl}-carbamic acid 2-methoxy-ethyl ester

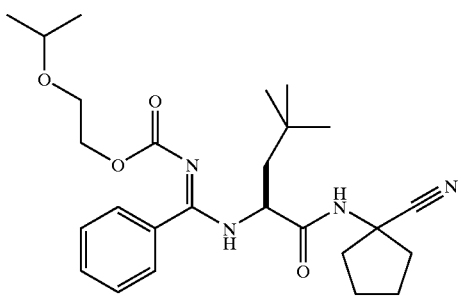

{[1-(1-Cyano-cyclopentylcarbamoyl)-3,3-dimethyl-butylimino]-phenyl-methyl}-carbamic acid 2-isopropoxy-ethyl ester

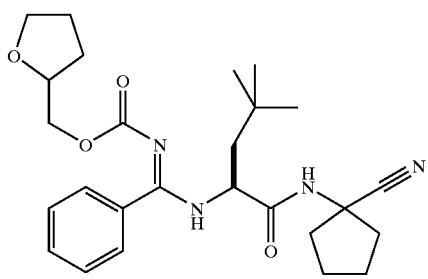

{[1-(1-Cyano-cyclopentylcarbamoyl)-3,3-dimethyl-butylimino]-phenyl-methyl}-carbamic acid tetrahydro-furan-2-ylmethyl ester

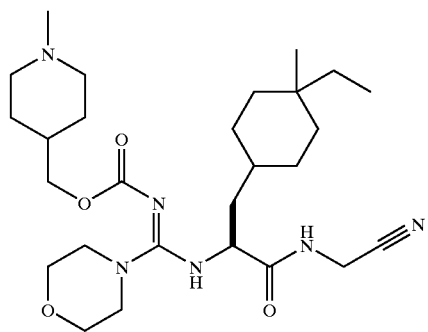

{[1-(Cyanomethyl-carbamoyl)-2-(4-ethyl-4-methyl-cyclohexyl)-ethylimino]-morpholin-4-yl-methyl}-carbamic acid 1methyl-piperidin-4-ylmethyl ester

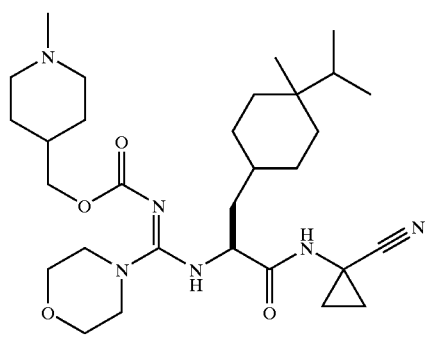

{[1-(1-Cyano-cyclopropylcarbamoyl)-2-(4-isopropyl-4-methyl-cyclohexyl)-ethylimino]-morpholin-4-yl-methyl}-carbamic acid 1-methyl-piperidin-4-ylmethyl ester

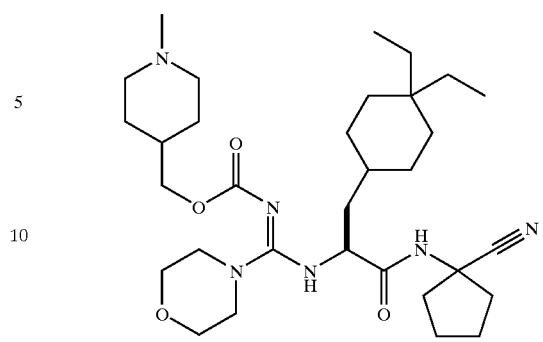

{[1-(1-Cyano-cyclopentylcarbamoyl)-2-(4,4-diethyl-cyclohexyl)-ethylimino]-morpholin-4-yl-methyl}-carbamic acid 1-methyl-piperidin-4-ylmethyl ester

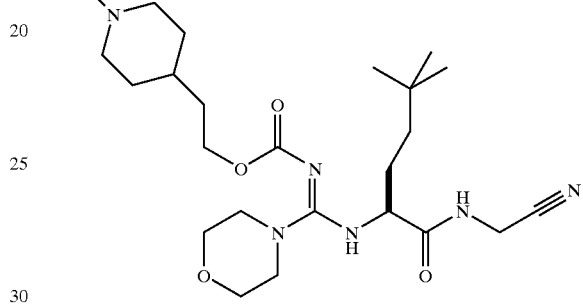

{[1-(Cyanomethyl-carbamoyl)-4,4-dimethyl-pentylimino]-morpholin-4-yl-methyl}-carbamic acid 2-(1-methyl-piperidin-4-yl)-ethyl ester

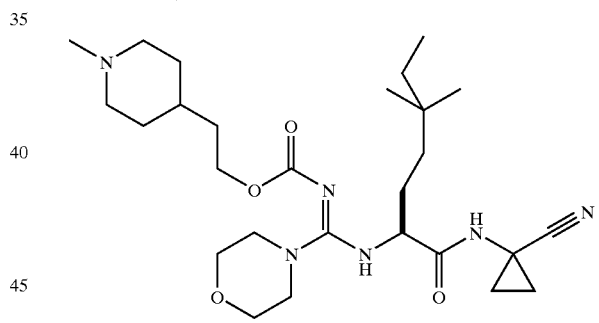

{[1-(1-Cyano-cyclopropylcarbamoyl)-4,4-dimethyl-hexylimino]-morpholin-4-yl-methyl}-carbamic acid 2-(1-methyl-piperidin-4-yl)-ethyl ester

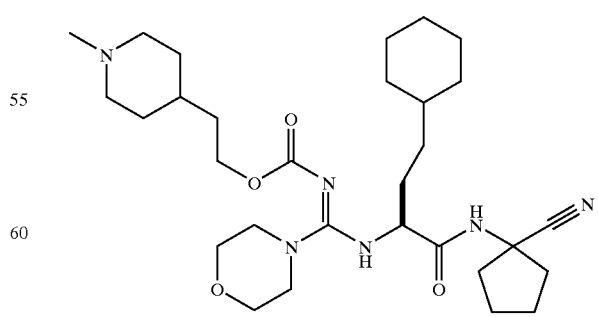

{[1-(1-Cyano-cyclopentylcarbamoyl)-3-cyclohexyl-propylimino]-morpholin-4-yl-methyl}-carbamic acid 2-(1-methyl-piperidin-4-yl)-ethyl ester

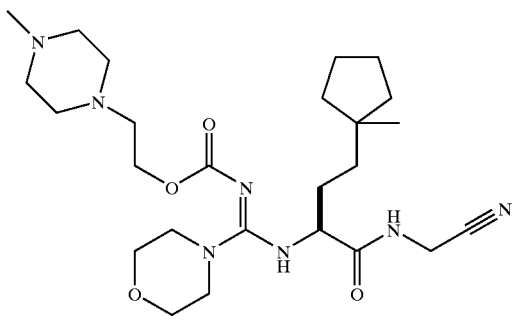

{[1-(Cyanomethyl-carbamoyl)-3-(1-methyl-cyclopentyl)-propylimino]-morpholin-4-yl-methyl}-carbamic acid 2-(4-methyl-piperazin-1-yl)-ethyl ester

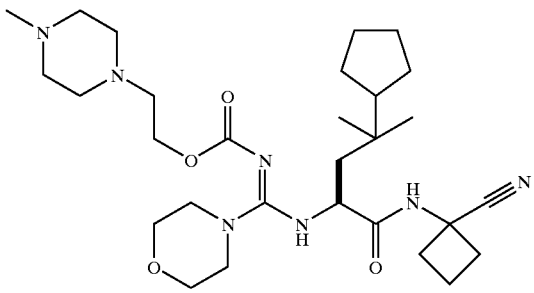

{[1-(1-Cyano-cyclobutylcarbamoyl)-3-cyclopentyl-3-methyl-butylimino]-morpholin-4-yl-methyl}-carbamic acid 2-(4-methyl-piperazin-1-yl)-ethyl ester

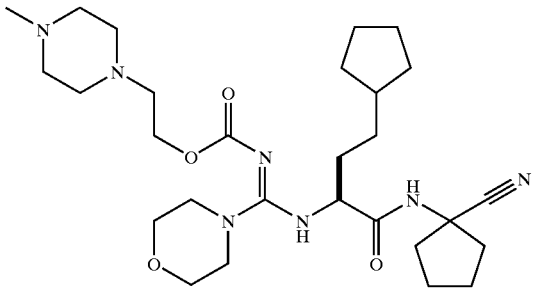

{[1-(1-Cyano-cyclopentylcarbamoyl)-3-cyclopentyl-propylimino]-morpholin-4-yl-methyl}-carbamic acid 2-(4-melthyl-piperazin-1-yl)-ethyl ester

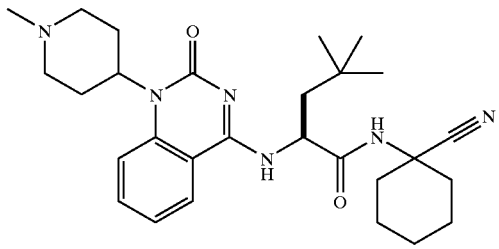

4,4-Dimethyl-2-[1-(1-methyl-piperidine-4-yl)-2-oxo-2,3-dihydro-1H-quinazolin-4-ylideneamino]-pentanoic acid (1-cyano-cyclohexyl)-amide

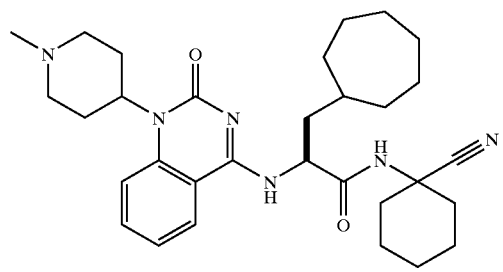

N-(1-Cyano-cyclohexyl)-3-cycloheptyl-2-[1-(1-methyl-piperidin-4-yl)-2-oxo-2,3-dihydro-1H-quniazolin-4-ylideneamino]-propionamide

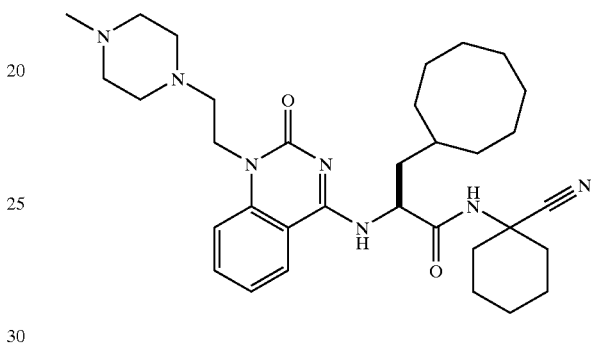

N-(1-Cyano-cyclohexyl)-3-cyclooctyl-2-{1-[2-(4-methyl-piperazin-1-yl)-ethyl]-2-oxo-2,3-dihydro-1H-quinazolin-4-ylideneamino}-propionamide

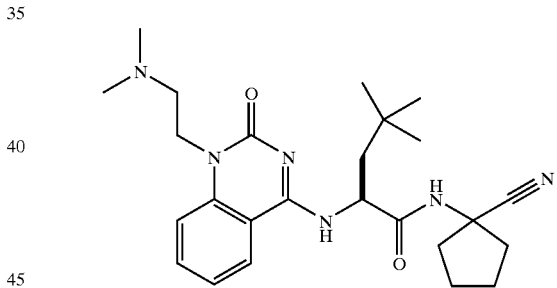

2-[1-(2-Dimethylamino-ethyl)-2-oxo-2,3-dihydro-1H-quinazolin-4-ylideneamino]-4,4-dimethyl-pentanoic acid (1-cyano-cyclopentyl)-amide

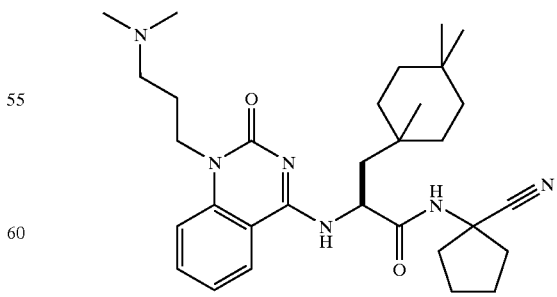

N-(1-Cyano-cyclopentyl)-2-[1-(3-dimethylamino-propyl)-2-oxo-2,3-dihydro-1H-quinazolin-4-ylideneamino]-3-(1,4,4-trimethyl-cyclohexyl)-propionamide

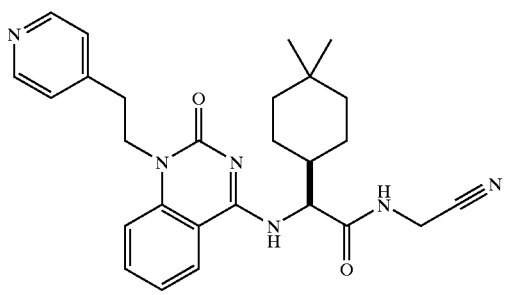

N-Cyanomethyl-2-(4,4-dimethyl-cyclohexyl)-2-[2-oxo-1-
(2-pyridin-4-yl-ethyl)-2,3-dihydro-1H-quinazolin-4-
ylideneamino]-acetamide

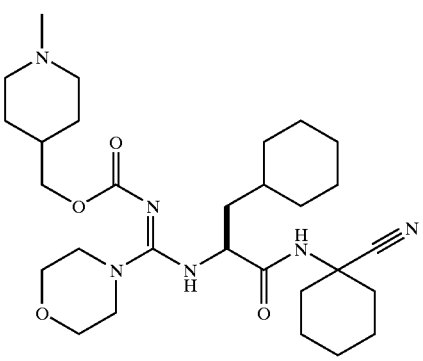

{[1-(1-Cyano-cyclohexylcarbamoyl)-2-cyclohexyl-
ethylimino]-morpholin-4-yl-methyl}-carbamic acid
1-methyl-piperidin-4-ylmethyl ester

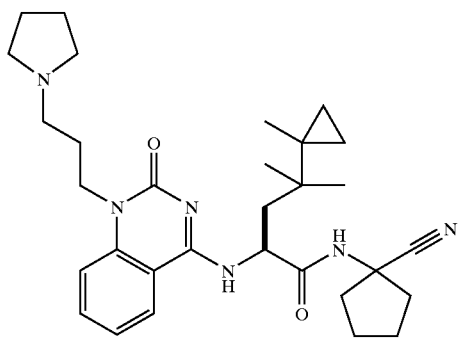

4-Methyl-4-(1-methyl-cyclopropyl)-2-[2-oxo-1-(3-
pyrrolidin-1-yl-propyl)-2,3-dihydro-1H-quniazolin-4-
ylideneamino]-pentanoic acid (1-cyano-cyclopentyl)-amide {[1-(1-Cyano-cyclohexylcarbamoyl)-2-cyclohexyl-
ethylimino]-morpholin-4-yl-methyl}-carbamic acid 2-(1-
methyl-piperidin-4-yl)-ethyl ester

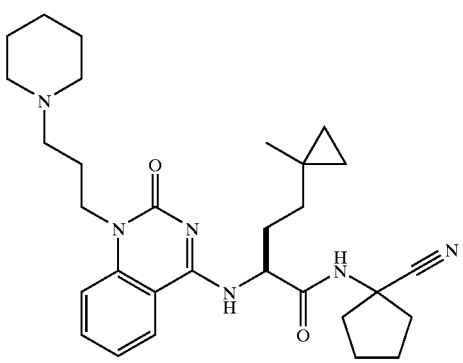

N-(1-Cyano-cyclopentyl)-4-(1-methyl-cyclopropyl)-2-[2-
oxo-1-(3-piperidin-1-yl-propyl)-2,3-dihydro-1H-
quinazolin-4-ylideneamino]-butyramide {[1-(1-Cyano-cyclohexylcarbamoyl)-2-cyclohexyl-
ethylimino]-morpholin-4-yl-methyl}-carbamic acid 2-(4-
methyl-piperazin-1-yl)-ethyl ester

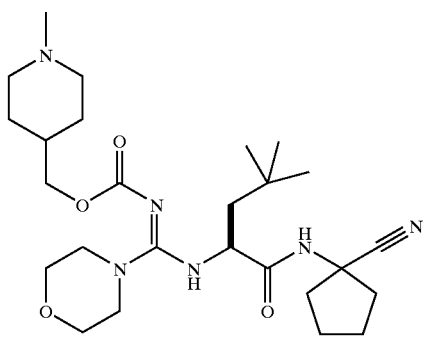

{[1-(1-Cyano-cyclopentylcarbamoyl)-3,3-dimethyl-butylimino]-morpholin-4-yl-methyl}-carbamic acid 1-methyl-piperidin-4-ylmethyl ester

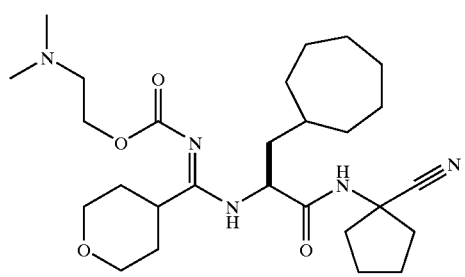

[[1-(1-Cyano-cyclopentylcarbamoyl)-2-cycloheptyl-ethylimino]-(tetrahydro-pyran-4-yl)-methyl]-carbamic acid 2-dimethylamino-ethyl ester

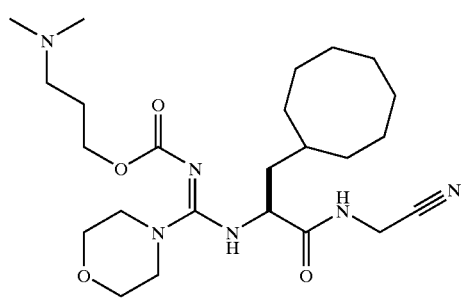

{[1-(Cyanomethyl-carbamoyl)-2-cyclooctyl-ethylimino]-morpholin-4-yl-methyl}-carbamic acid 3-dimethylamino-propyl ester

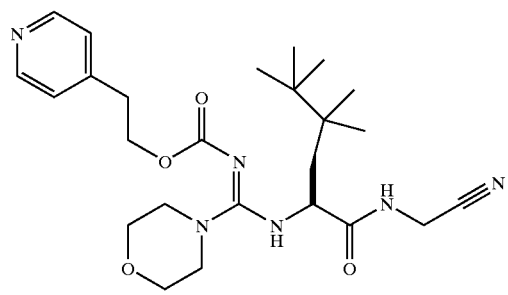

{[1-(Cyanomethyl-carbamoyl)-3,3,4,4-tetramethyl-pentylimino]-morpholin-4-yl-methyl}-carbamic acid 2-pyridin-4-yl-ethyl ester

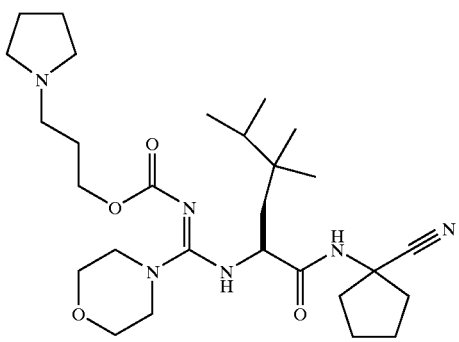

{[1-(1-Cyano-cyclopentylcarbamoyl)-3,3,4-trimethyl-pentylimino]-morpholin-4-yl-methyl}-carbamic acid 3-pyrrolidin-1-yl-propyl ester

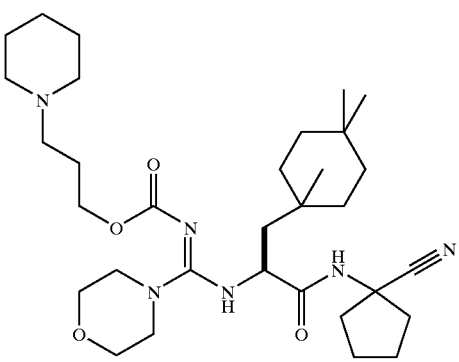

{[1-(1-Cyano-cyclopentylcarbamoyl)-2-(1,4,4-trimethyl-cyclohexyl)-ethylimino]-morpholin-4-yl-methyl}-carbamic acid 3-piperidin-1-yl-propyl ester

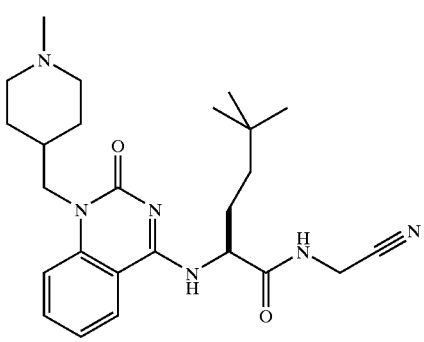

5,5-Dimethyl-2-[1-(1-methyl-piperidin-4-ylmethyl)-2-oxo-2,3-dihydro-1H-quinazolin-4-ylideneamino]-hexanoic acid cyanomethyl-amide

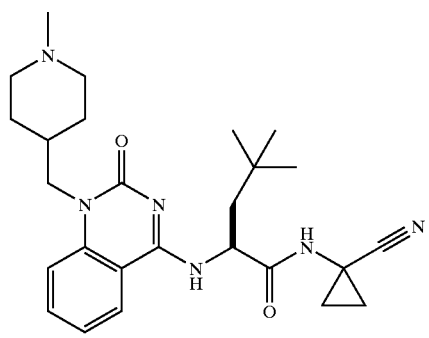

4,4-Dimethyl-2-[1-(1-methyl-piperidin-4-ylmethyl)-2-oxo-2,3-dihydro-1H-quinazolin-4-ylideneamino]-pentanoic acid (1-cyano-cyclopropyl)-amide

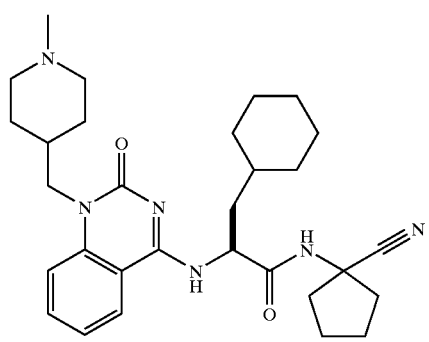

N-(1-Cyano-cyclopentyl)-3-cyclohexyl-2-[1-(1-methyl-piperidin-4-ylmethyl)-2-oxo-2,3-dihydro-1H-quinazolin-4-ylideneamino]-propionamide

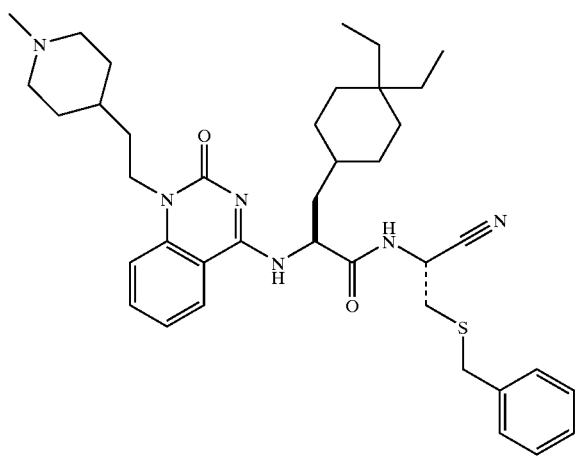

N-(Benzylsulfanylmethyl-cyano-methyl)-3-(4,4-diethyl-cyclohexyl)-2-{1-[2-(1-methyl-piperidin-4-yl)-ethyl]-2-oxo-2,3-dihydro-1H-quinazolin-4-ylideneamino}-pripionamide

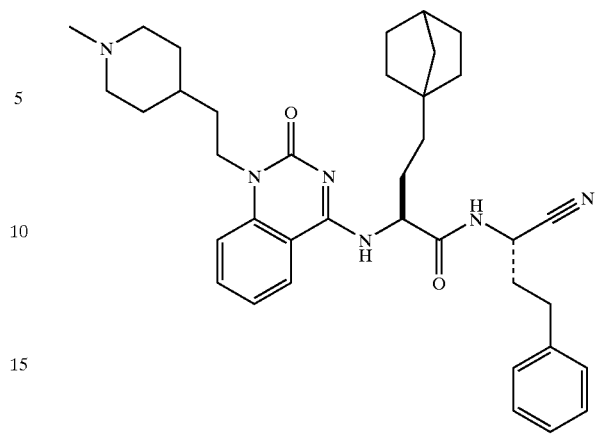

4-Bicyclo[2.2.1]hept-1-yl-N-(1-cyano-3-phenyl-propyl)-2-{1-[2-(1-methyl-piperidin-4-yl)-ethyl]-2-oxo-2,3-dihydro-1H-quinazolin-4-ylideneamino}-butyramide

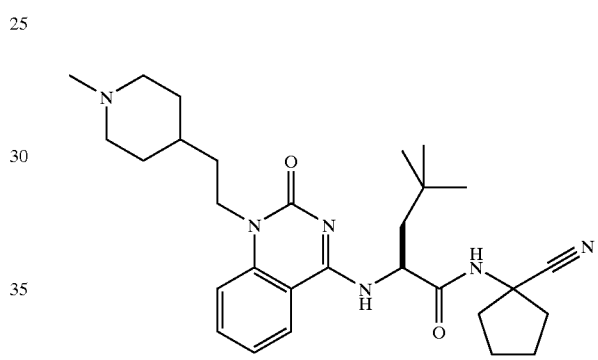

4,4-Dimethyl-2-{1-[2-(1-methyl-piperidin-4-yl)-ethyl]-2-oxo-2,3-dihydro-1H-quinazolin-4-ylideneamino}-pentanoic acid (1-cyano-cyclopentyl)-amide

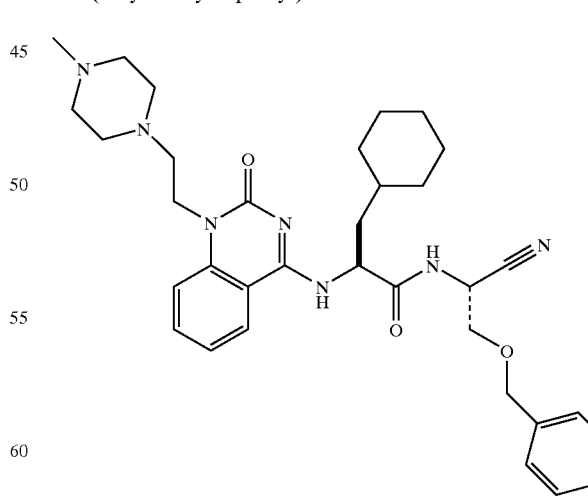

N-(Benzyloxymethyl-cyano-methyl)-3-cyclohexyl-2-{1-[2-(4-methyl-piperazin-1-yl)-ethyl]-2-oxo-2,3-dihydro-1H-quniazolin-4-ylideneamino}-propionamide

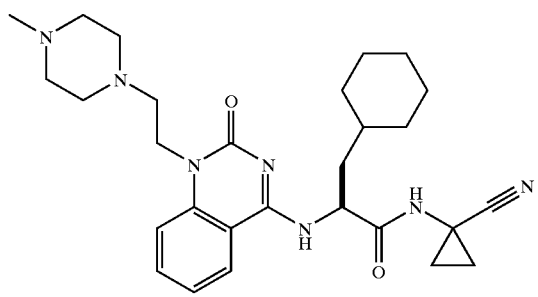

N-(1-Cyano-cyclopropyl)-3-cyclohexyl-2-{1-[2-(4-methyl-piperazin-1-yl)-ethyl]-2-oxo-2,3-dihydro-1H-quinazolin-4-ylideneamino}-propionamide

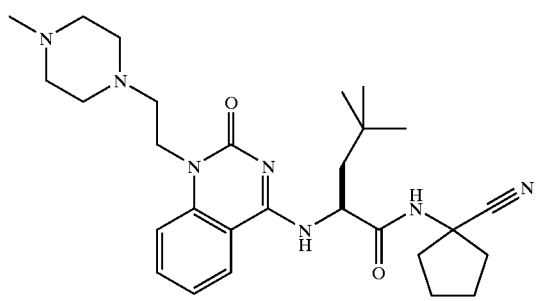

4,4-Dimethyl-2-{1-[2-(4-methyl-piperazin-1-yl)-ethyl]-2-oxo-2,3-dihydro-1H-quinazolin-4-ylideneamino}-pentanoic acid (1-cyano-cyclopentyl)-amide

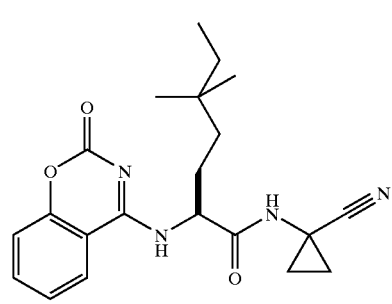

(S)-5,5-Dimethyl-2-(2-oxo-2H-benzo[e][1,3]oxazin-4-ylamino)-heptanoic acid (1-cyano-cyclopropyl)-amide

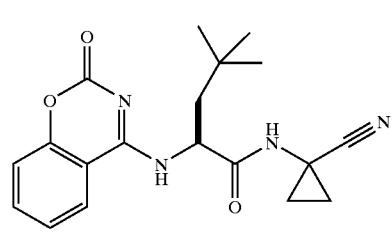

(S)-4,4-Dimethyl-2-(2-oxo-2H-benzo[e][1,3]oxazin-4-ylamino)-pentanoic acid (1-cyano-cyclopropyl)-amide

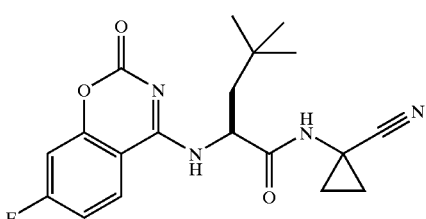

(S)-2-(7-Fluoro-2-oxo-2H-benzo[e][1,3]oxazin-4-ylamino)-4,4-dimethyl-pentanoic acid (1-cyano-cyclopropyl)-amide

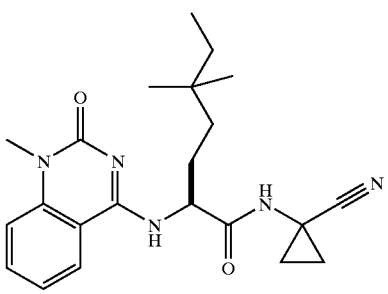

(S)-5,5-Diumethyl-2-(1-melthyl-2-oxo-1,2-dihydro-quniazolin-4-ylamino)-heptanoic acid (1-cyano-cyclopropyl)-amide

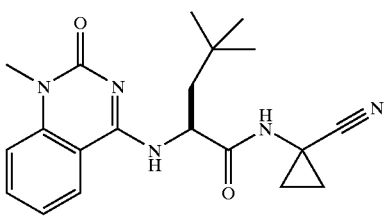

(S)-4,4-Dimethyl-2-(1-methyl-2-oxo-1,2-dihydro-quinazolin-4-ylamino)-pentanoic acid (1-cyan-cyclopropyl)-amide

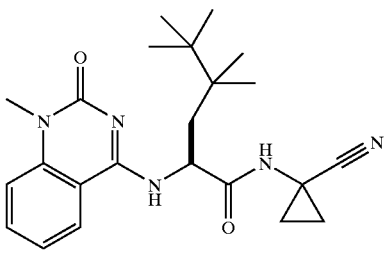

(S)-4,4,5,5-Tetramethyl-2-(1-methyl-2-oxo-1,2-dihydro-quniazolin-4-ylamino)-hexanoic acid (1-cyano-cyclopropyl)-amide

147

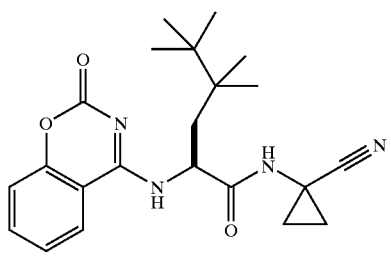

(S)-4,4,5,5-Tetramethyl-2-(2-oxo-2H-benzo[e][1,3]oxazin-4-ylamino)-hexanoic acid (1-cyano-cyclopropyl)-amide

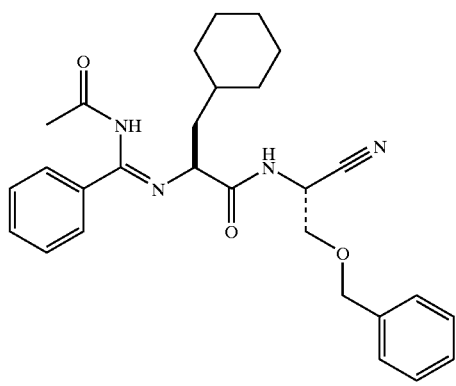

2-[(Acetylimino-phenyl-methyl)-amino]-N-(benzyloxymethyl-cyano-methyl)-3-cyclohexyl-propionamide

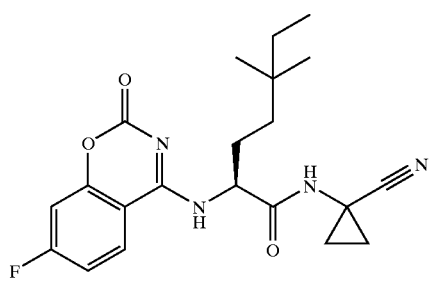

2-(7-Fluoro-2-oxo-2H-benzo[e][1,3]oxazin-4-ylamino)-5,5-dimethyl-heptanoic acid (1-cyano-cyclopropyl)-amide

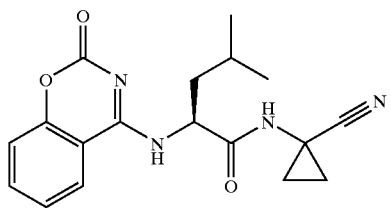

4-Methyl-2-(2-oxo-2H-benzo[e][1,3]oxazin-4-ylamino)-pentanoic acid (1-cyano-cyclopropyl)-amide

148

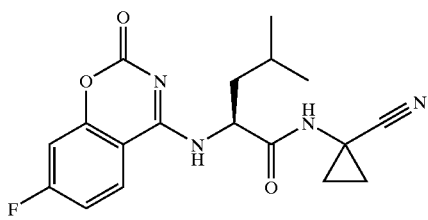

2-(7-Fluoro-2-oxo-2H-benzo[e][1,3]oxazin-4-ylamino)-4-methyl-pentanoic acid (1-cyano-cyclopropyl)-amide

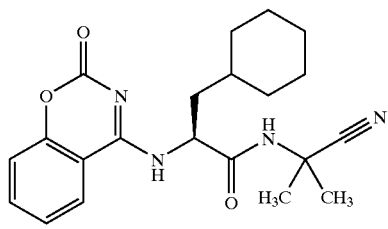

N-(Cyano-dimethyl-methyl)-3-cyclohexyl-2-(2-oxo-2H-benzo[e][1,3]oxazin-4-ylamino)-propionamide

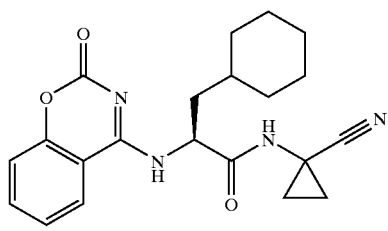

N-(1-Cyano-cyclopropyl)-3-cyclohexyl-2-(2-oxo-2H-benzo[e][1,3]oxazin-4-ylamino)-propionamide

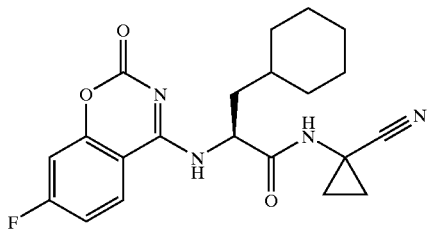

N-(1-Cyano-cyclopropyl)-3-cyclohexyl-2-(7-fluoro-2-oxo-2H-benzo[e][1,3]oxazin-4-ylamino)-propionamide

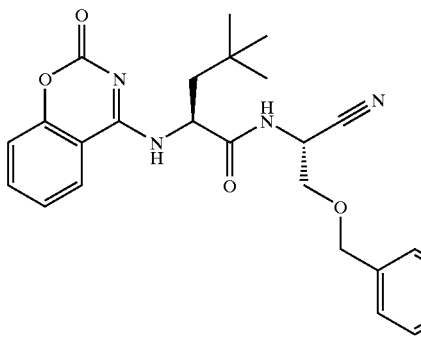

N-(Cyano-benzyloxymethyl-methyl)-3-cyclohexyl-2-(2-oxo-2H-benzo[e][1,3]oxazin-4-ylamino)-propionamide

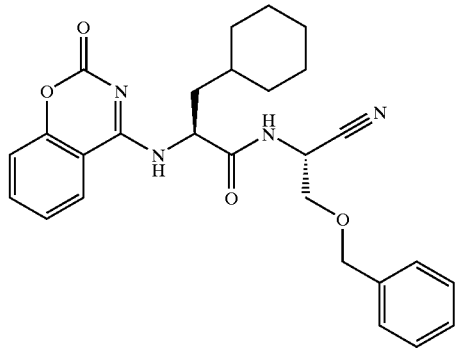

4,4-Dimethyl-2-(2-oxo-2H-benxo[e][1,3]oxazin-4-ylamino)-pentanoic acid (cyano-benzyloxymethyl-methyl)-amide

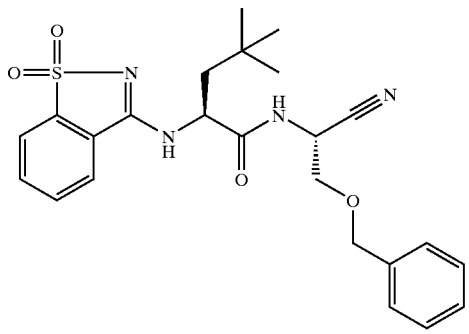

2-(1,1-Dioxo-1H-1λ⁶-benzo[d]isothiazol-3-ylamino)-4,4-dimethyl-pentanoic acid (cyano-benzyloxymethyl-methyl)-amide

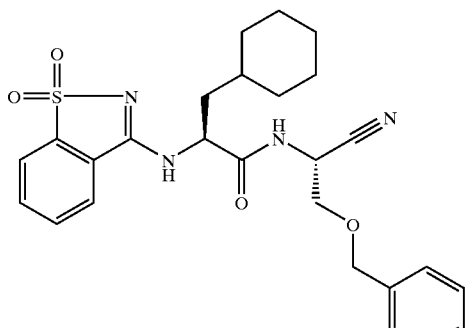

M-(Cyano-benzyloxymethyl-methyl)-3-cyclohexyl-2-(1,1-dioxo-1H-1λ⁶-benzo[d]isothiazol-3-ylamino)-pripionamide

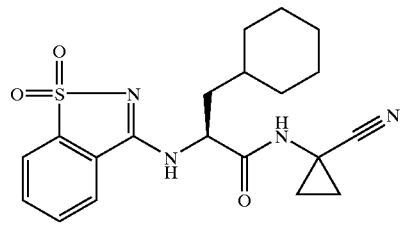

N-(1-Cyano-cyclopropyl)-3-cyclohexyl-2-(1,1-dioxo-1H-1λ⁶-benzo[d]isothiazol-3-ylamino)-pripionamide

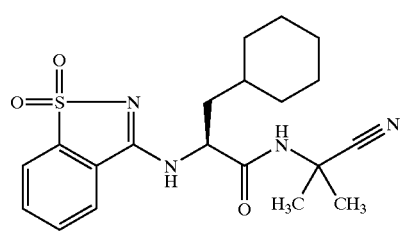

N-(Cyano-dimethyl-methyl)-3-cyclohexyl-2-(1,1-dioxo-1H-1λ⁶-benzo[d]isothiazol-3-ylamino)-pripionamide

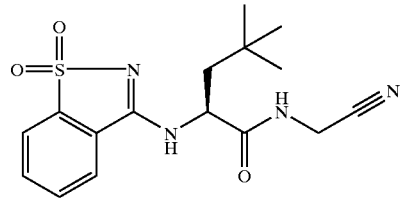

2-(1,1-Dioxo-1H-1λ⁶-benzo]d]isothiazol-3-ylamino)-4,4-dimethyl-pentanoic acid cyanomethyl-amide

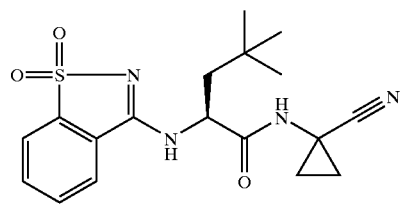

2-(1,1-Dioxo-1H-1λ⁶-benzo[d]isothiazol-3-ylamino)-4,4-dimethyl-pentanoic acid (1-cyano-cyclopropyl)-amide

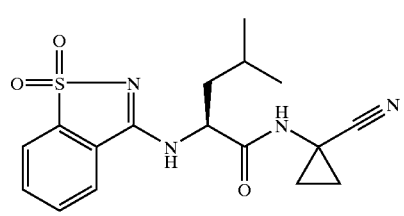

2-(1,1-Dioxo-1H-1λ⁶-benzo[d]isothiazol-3-ylamino)-4-methyl-pentanoic acid (1-cyano-cyclopropyl)-amide

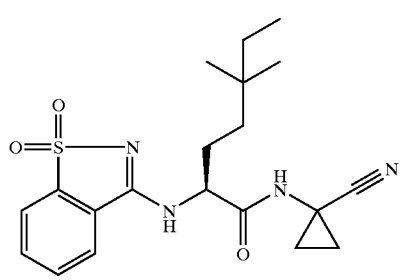
TABLE II
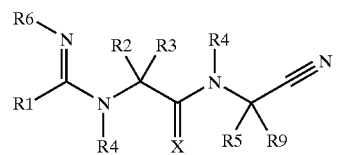 (Ia)
wherein for the Formula (Ia), the components
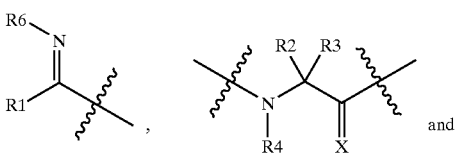, and
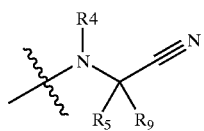
are chosen from any combination of A, B and C as follows:

TABLE II

| A | B | C |
|---|---|---|
| R6\N—⧸⧹R1 | R2 R3\N—C—X\R4 | R4\N—C(CN)R5 R9 |
| A1: 2H-benzo[e][1,3]oxazin-2-one-4-yl | B1: cyclohexylmethyl-CH(NH–)-C(=O)– | C1: –NH–CH₂–C≡N |
| A2: 7-fluoro-2H-benzo[e][1,3]oxazin-2-one-4-yl | B2: isobutyl-CH(NH–)-C(=O)– | C2: –NH–C(cyclopropyl)(C≡N)– |
| A3: 1-methyl-quinazolin-2-one-4-yl | B3: neopentyl-CH(NH–)-C(=O)– | C3: –NH–C(cyclopentyl)(C≡N)– |
| A4: ethoxycarbonyl-N=C(phenyl)– | B4: (4,4-dimethylcyclohexyl)methyl-CH(NH–)-C(=O)– | C4: –NH–C(cyclohexyl)(C≡N)– |

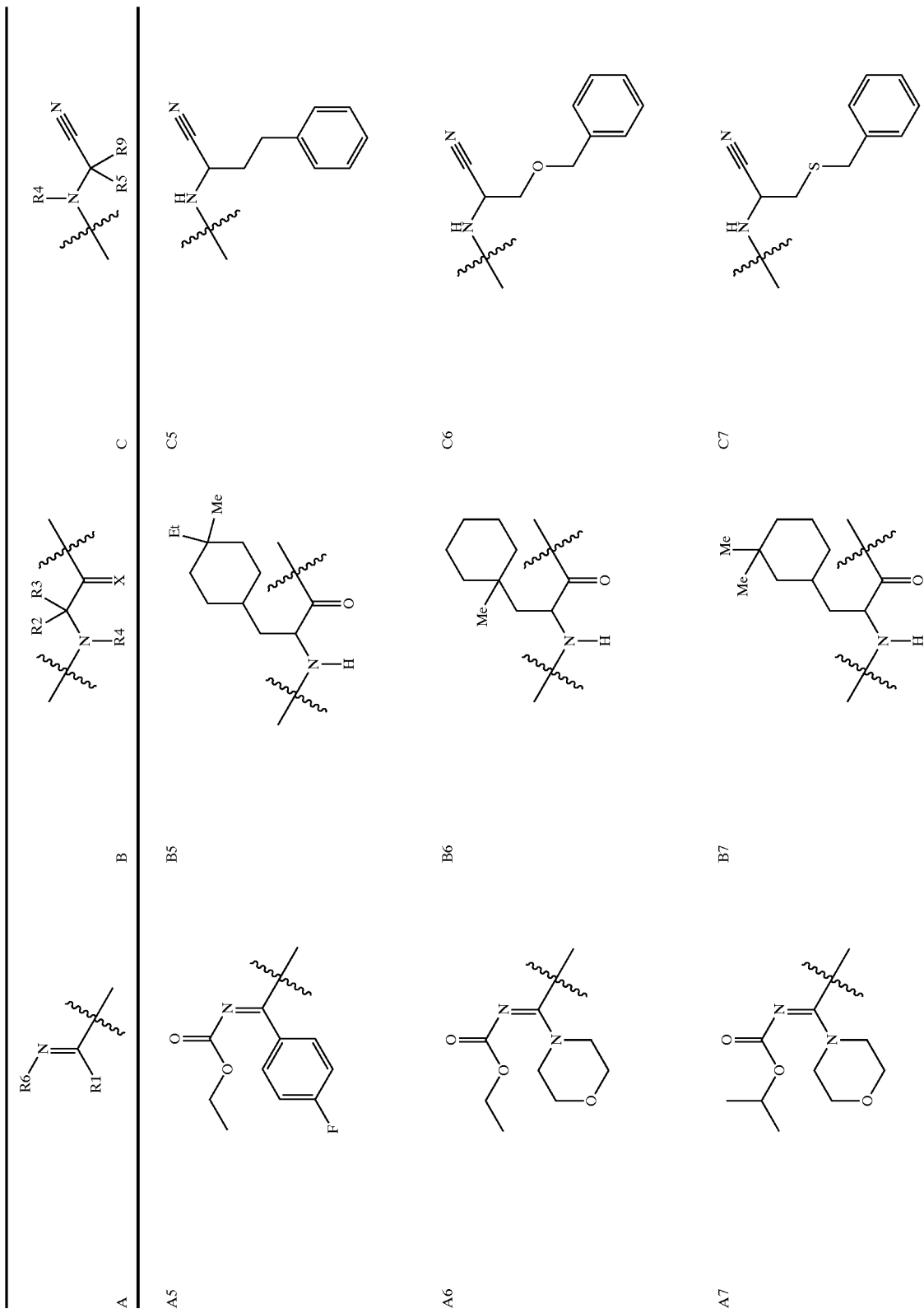

TABLE II-continued
| A | B | C |
|---|---|---|
| A8 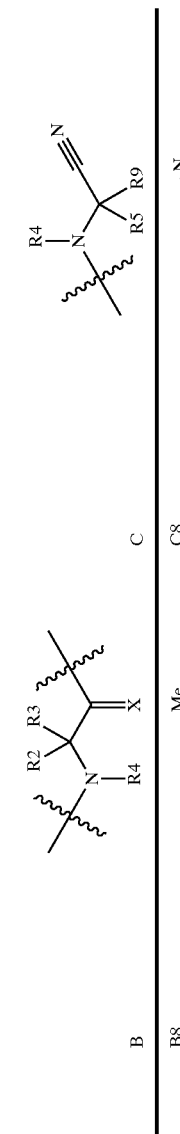 | B8 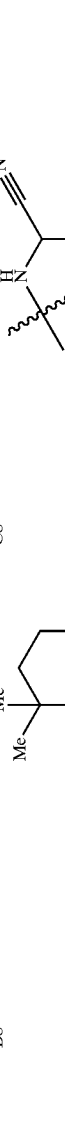 | C8  |
| A9  | B9  | C9  |
| A10  | B10 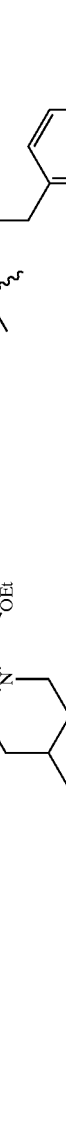 | C10  |

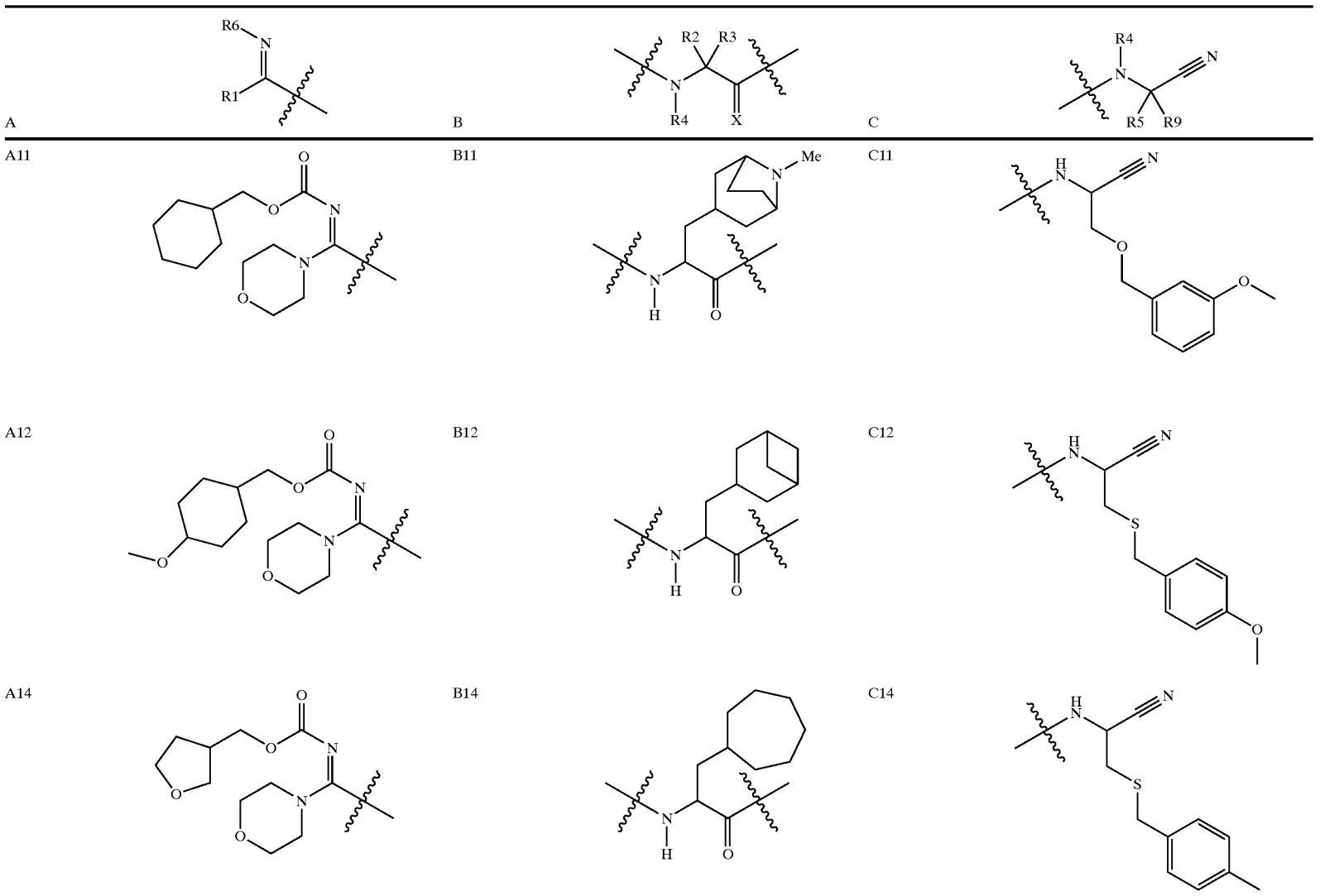

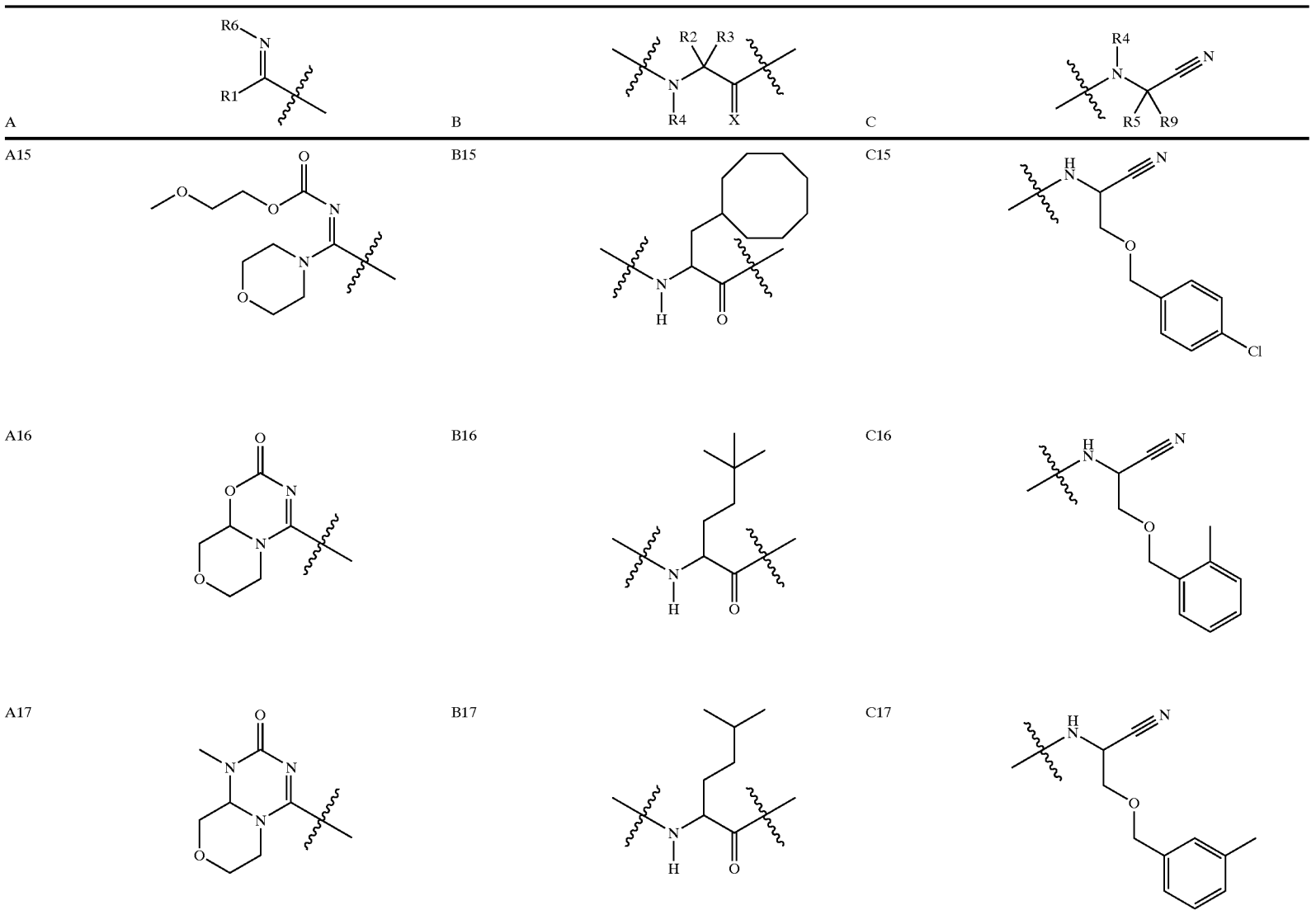

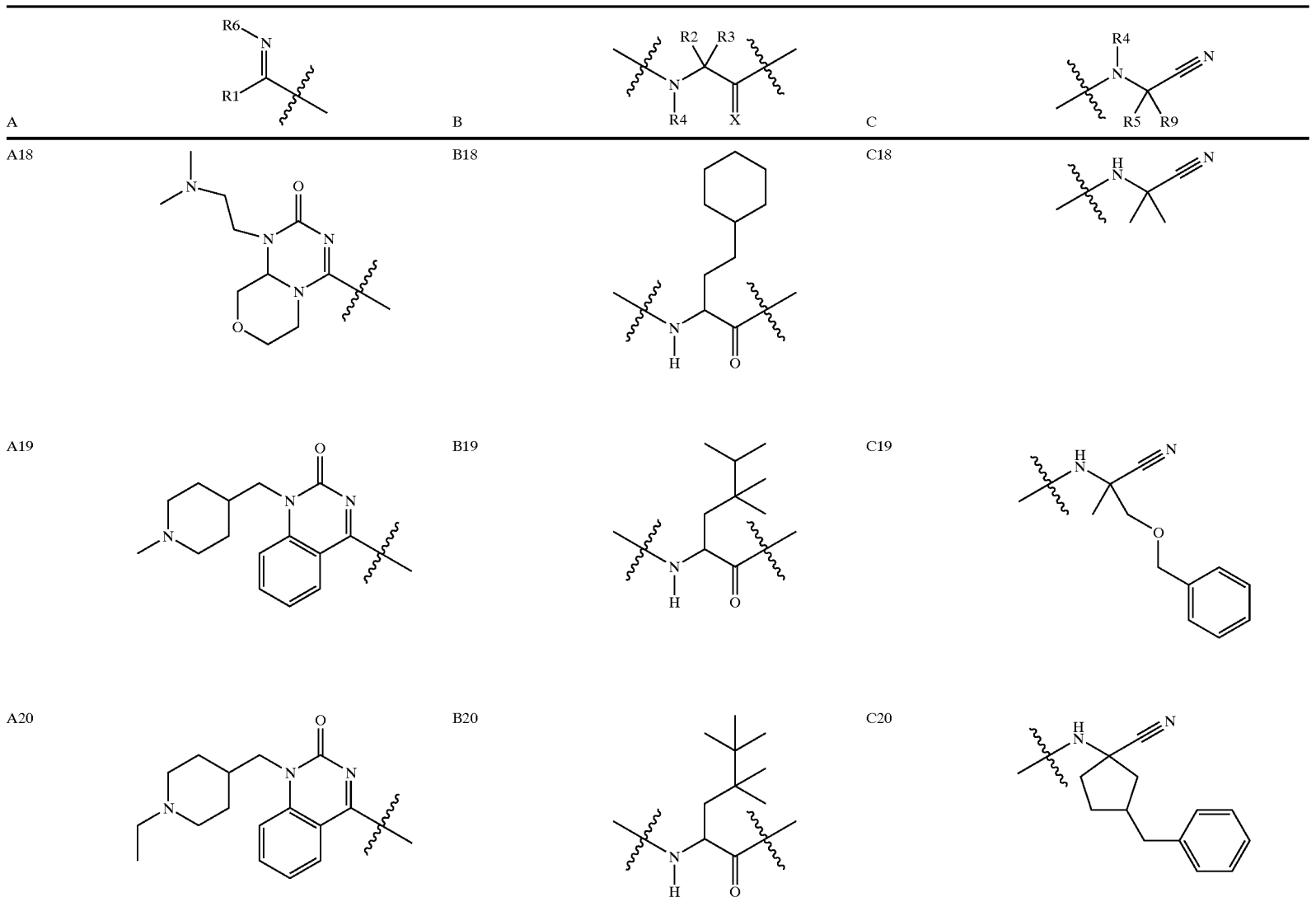

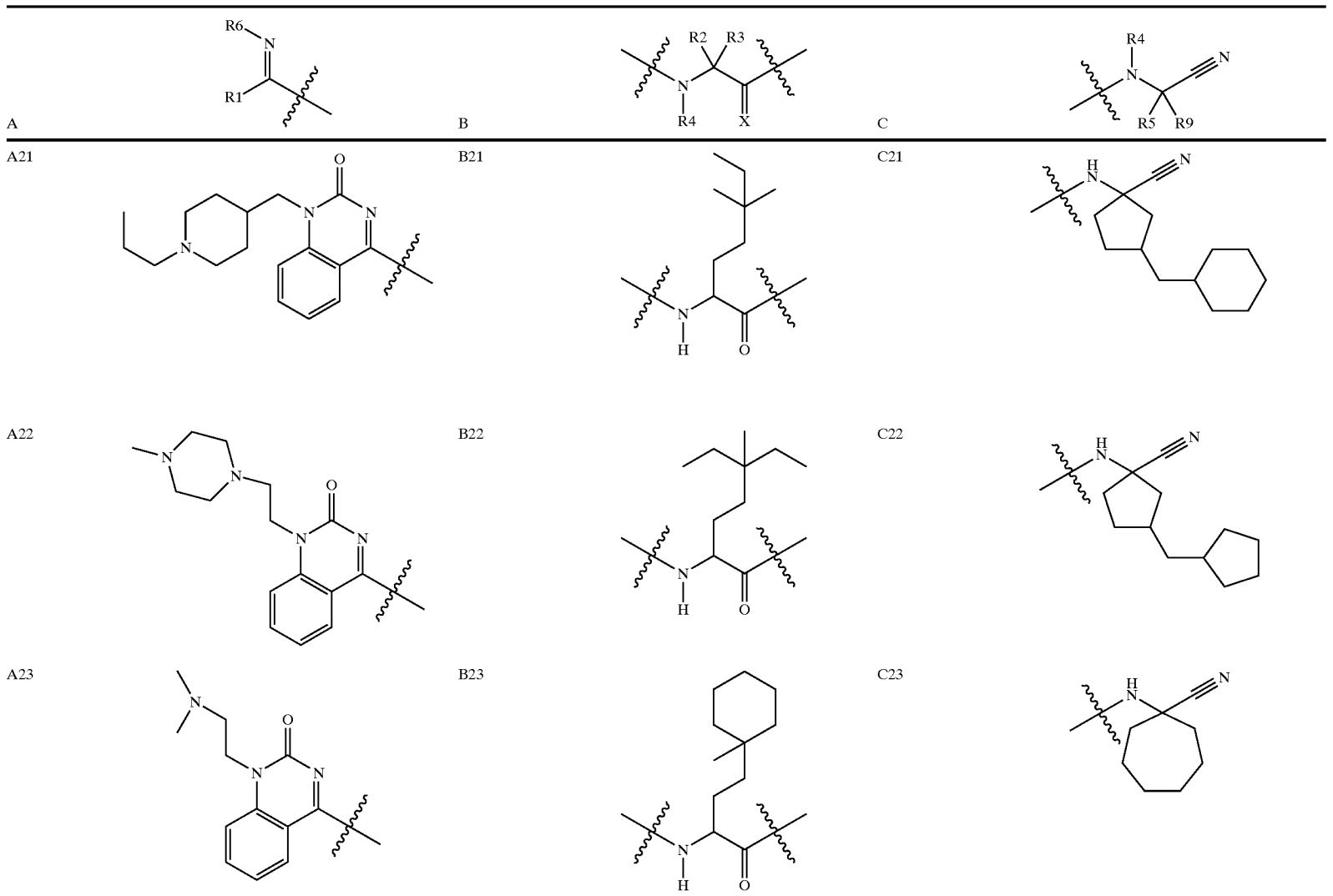

TABLE II-continued
| A | B | C |
|---|---|---|
| A24 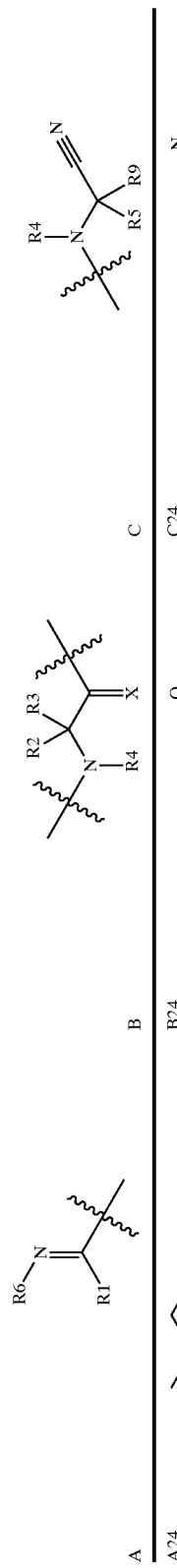 | B24 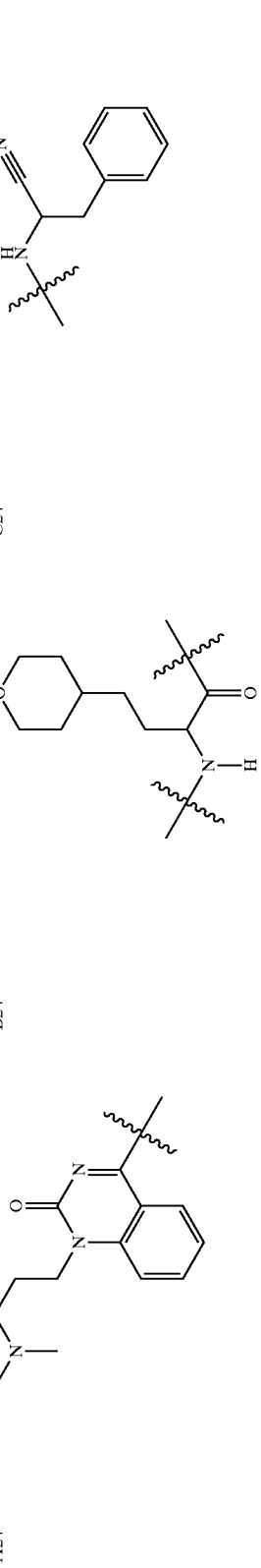 | C24 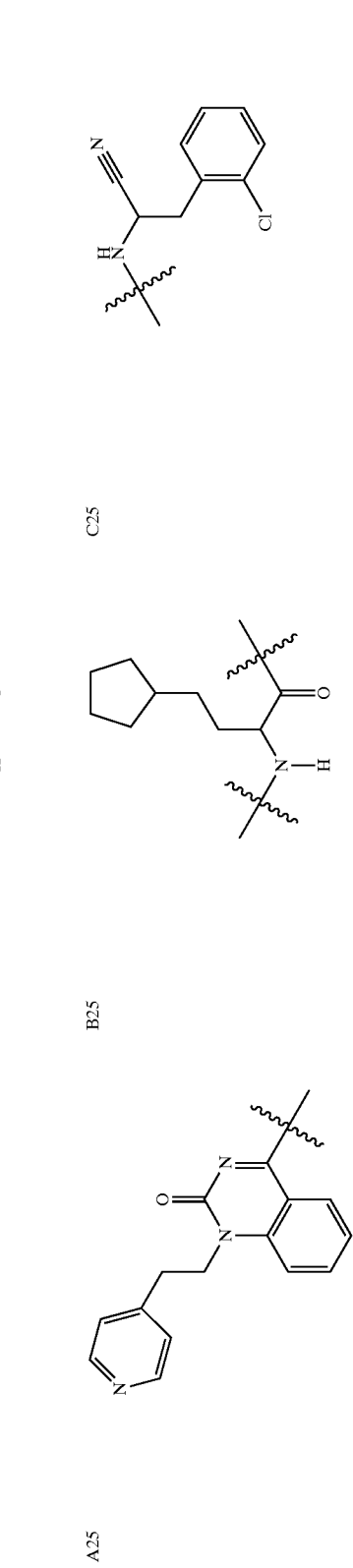 |
| A25 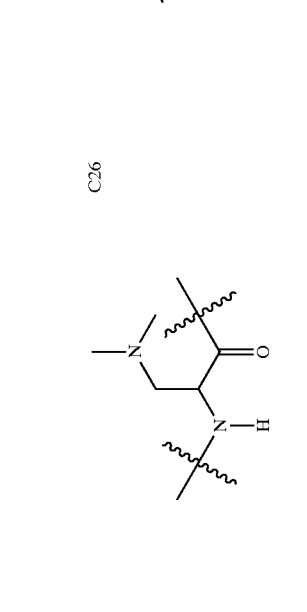 | B25 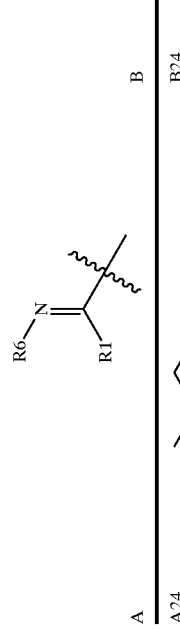 | C25 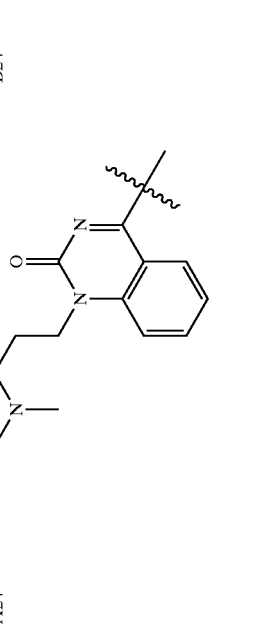 |
| A26 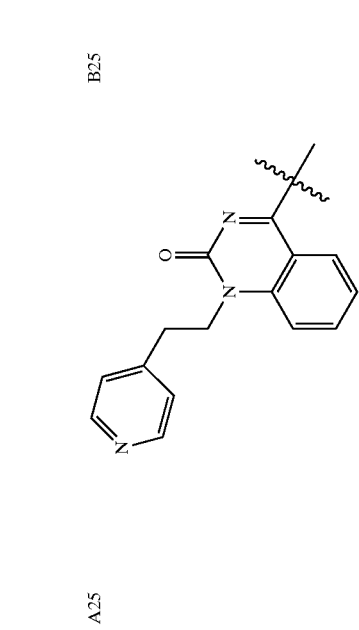 | B26 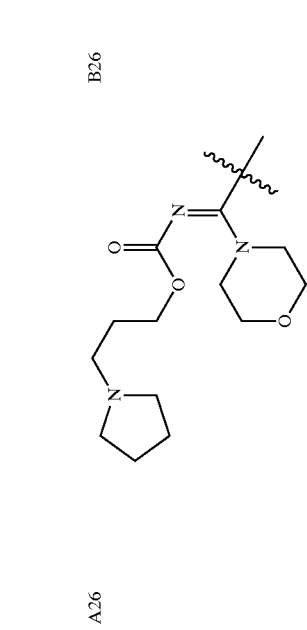 | C26 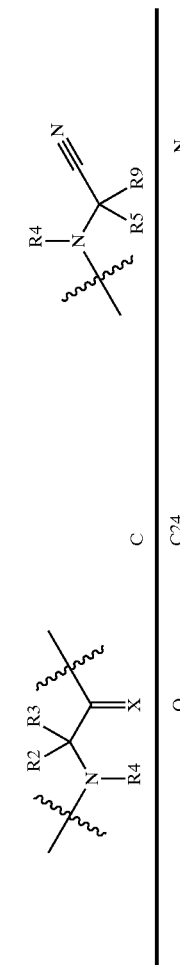 |

TABLE II-continued
| A | B | C |
|---|---|---|
| 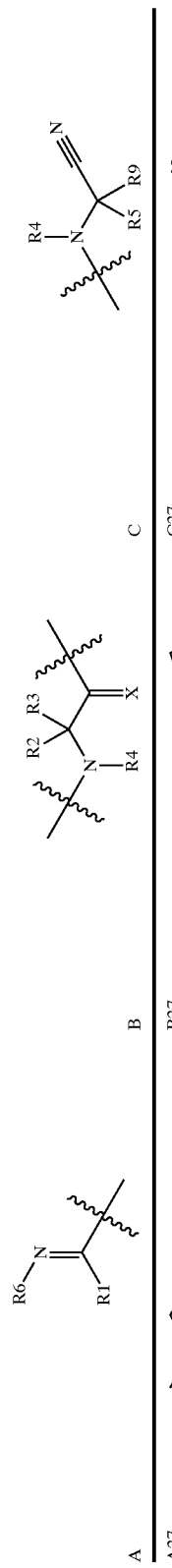 R6—N—R1 | 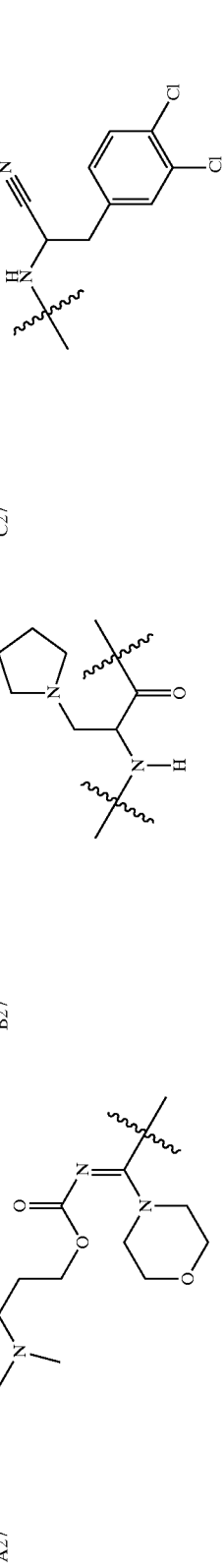 R2 R3 N X R4 | 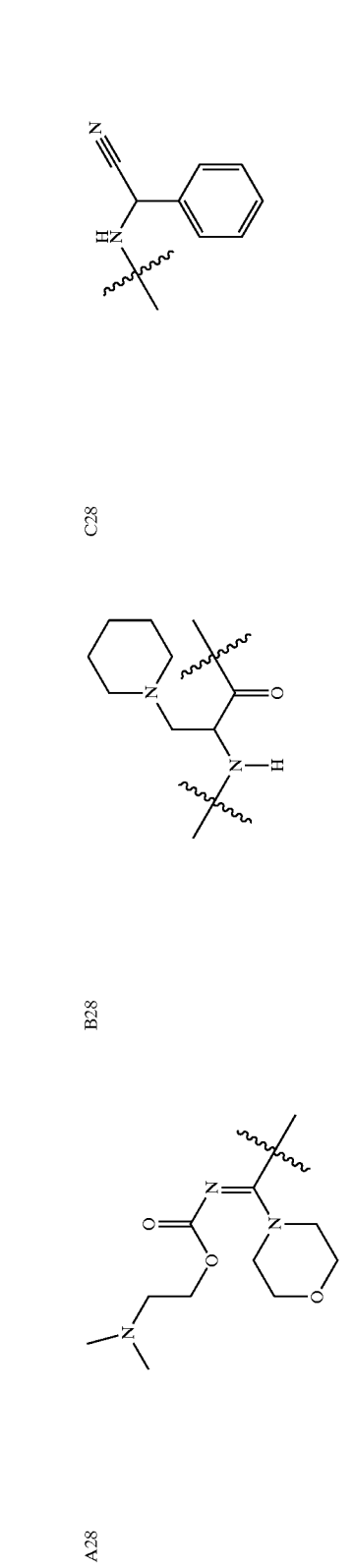 R4 R5 N R9 |
| A27 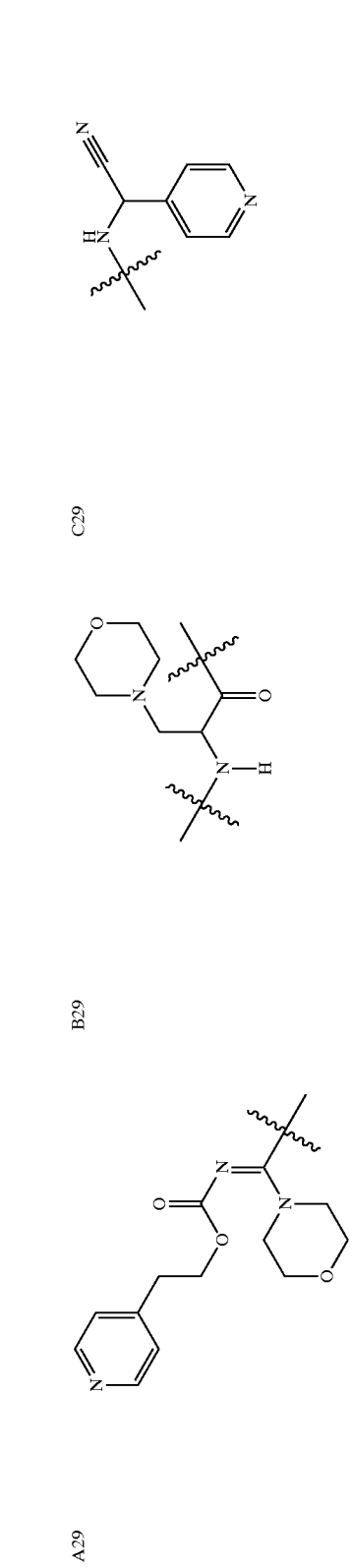 | B27 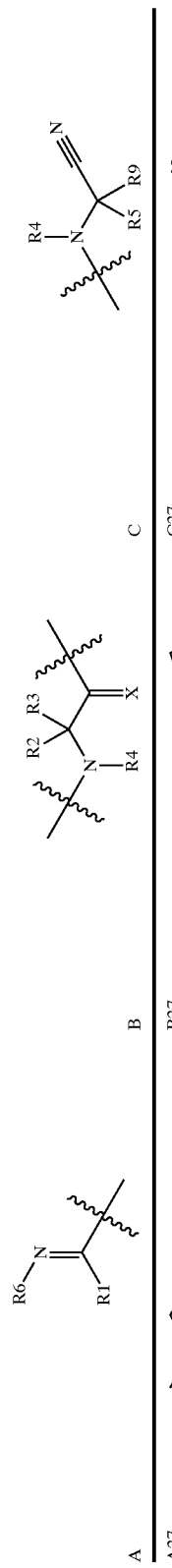 | C27 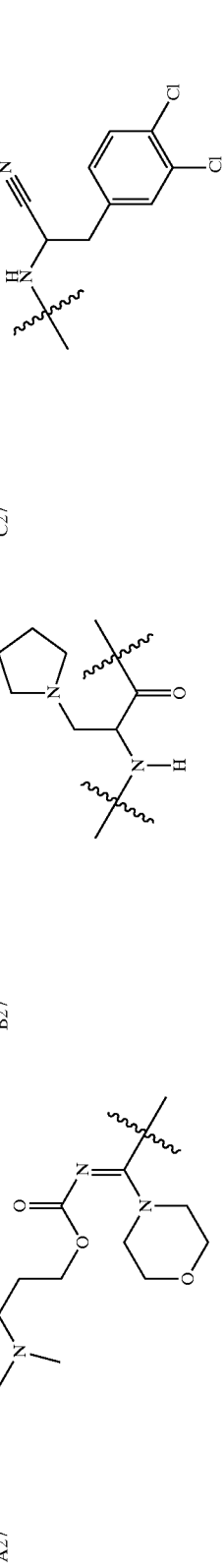 |
| A28 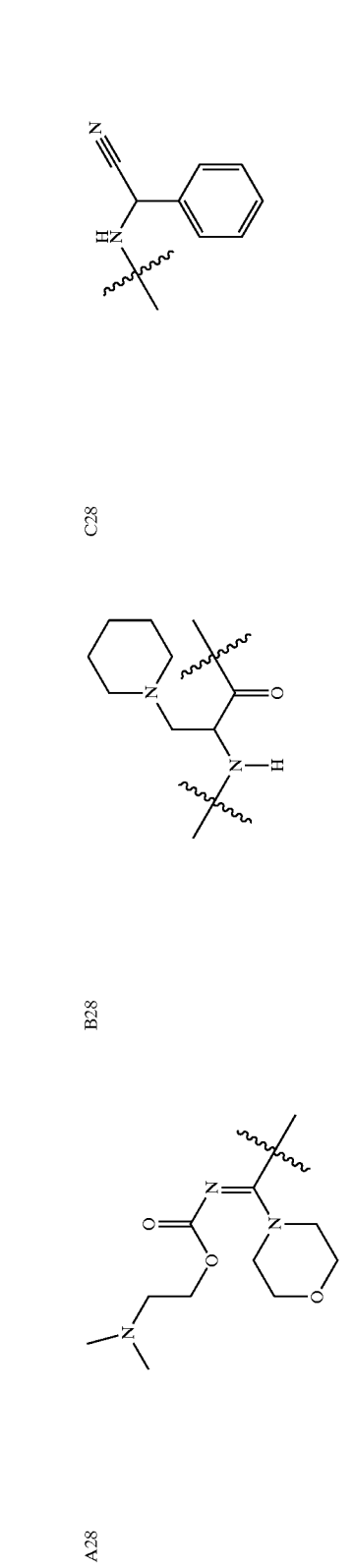 | B28 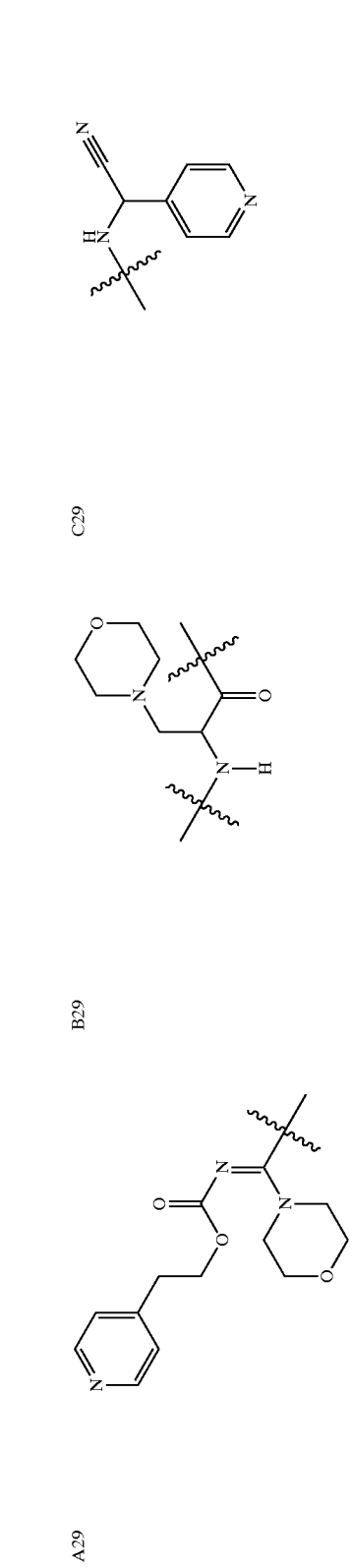 | C28 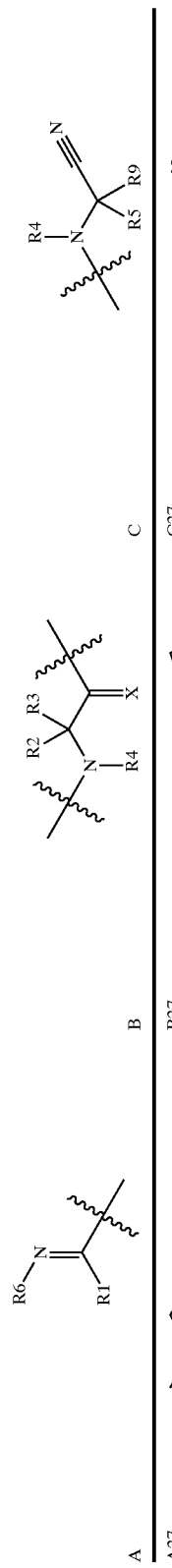 |
| A29 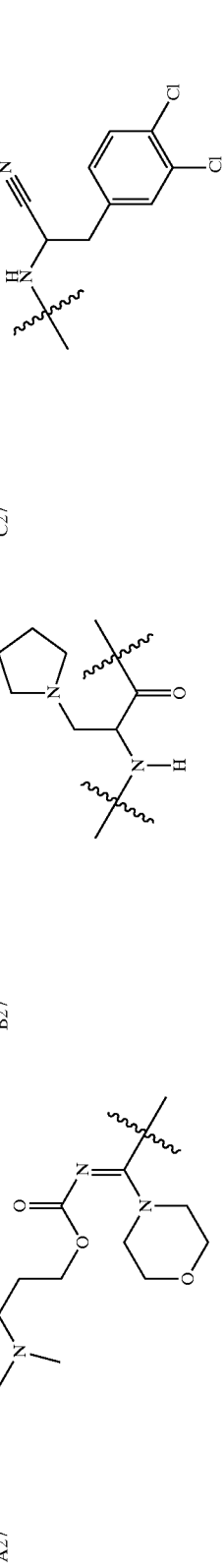 | B29 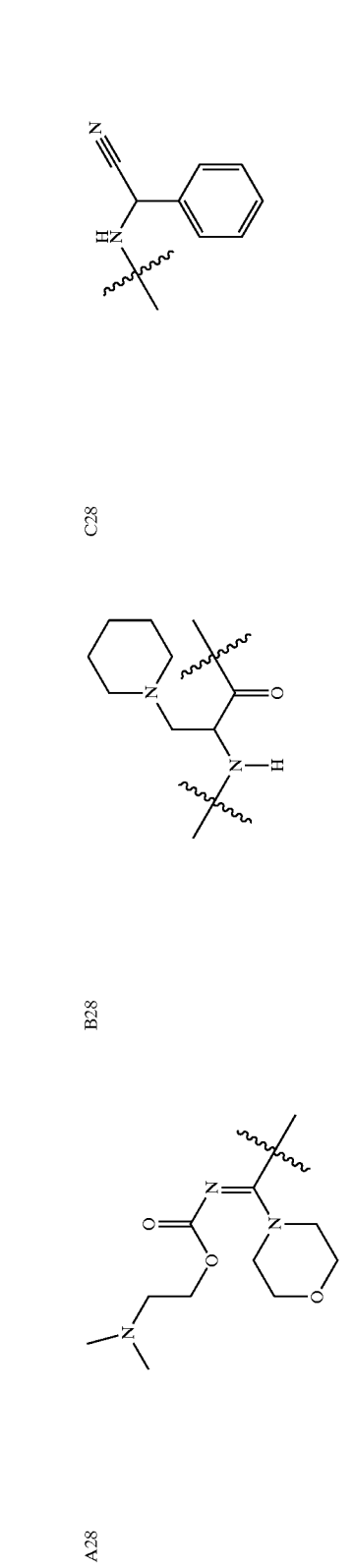 | C29 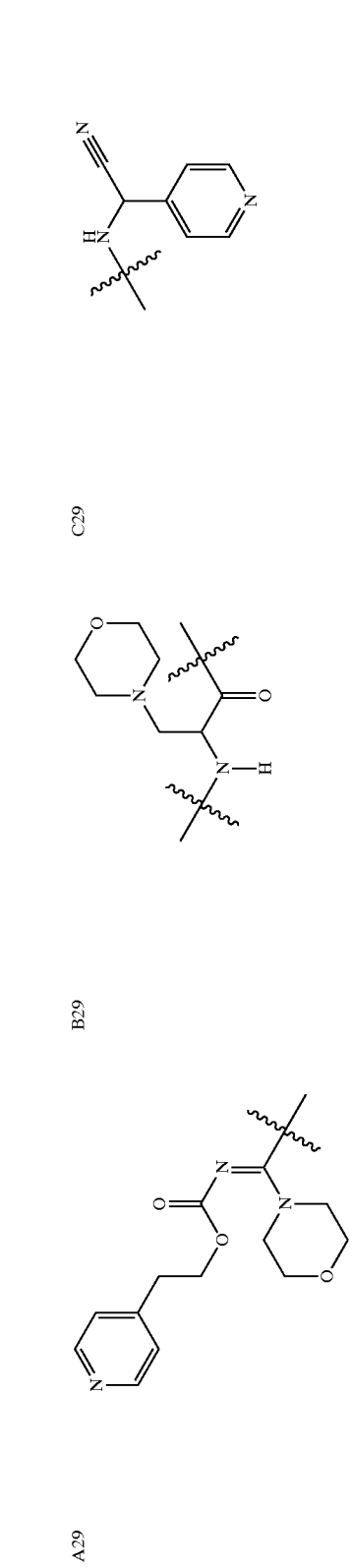 |

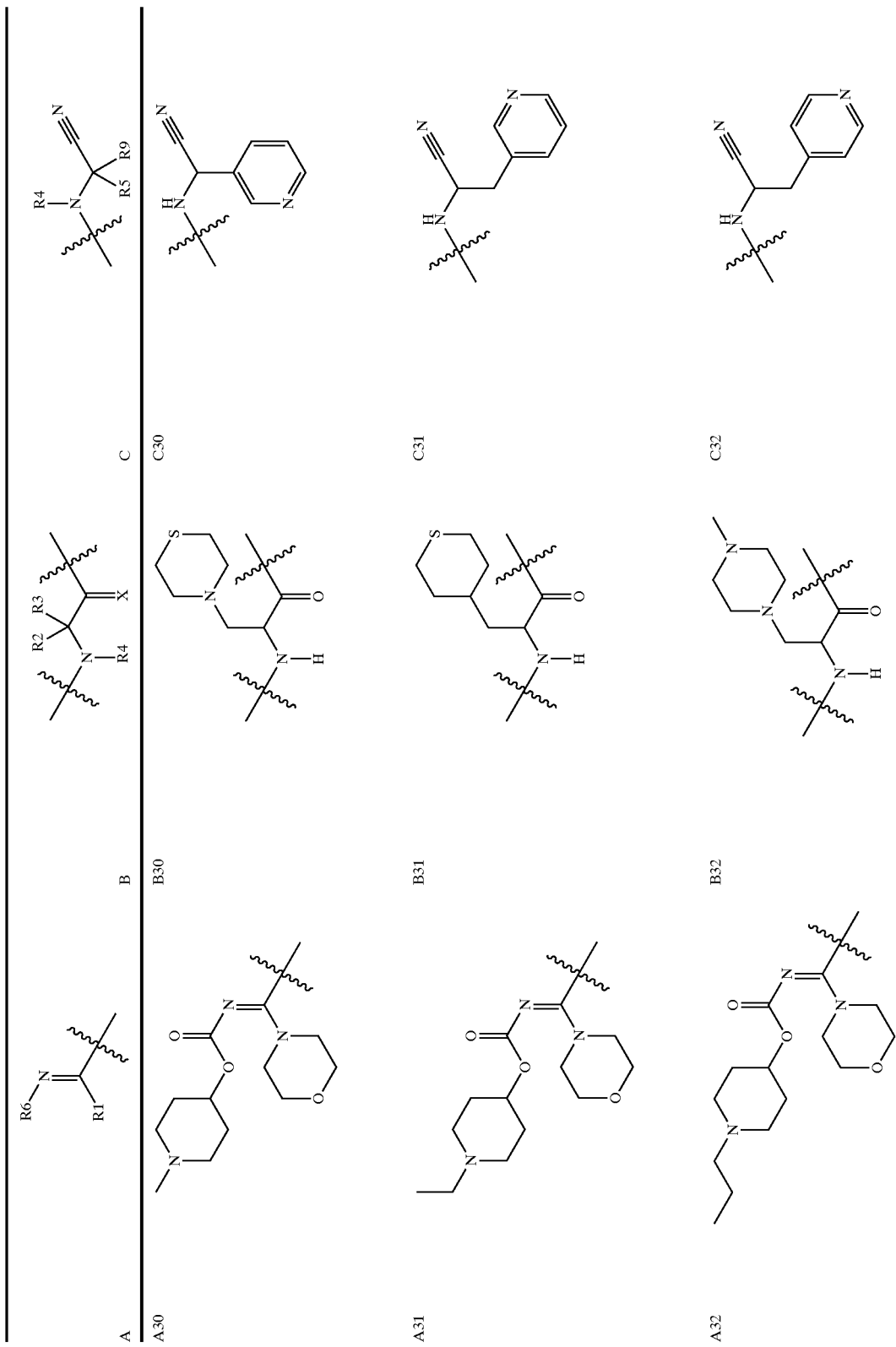

TABLE II-continued
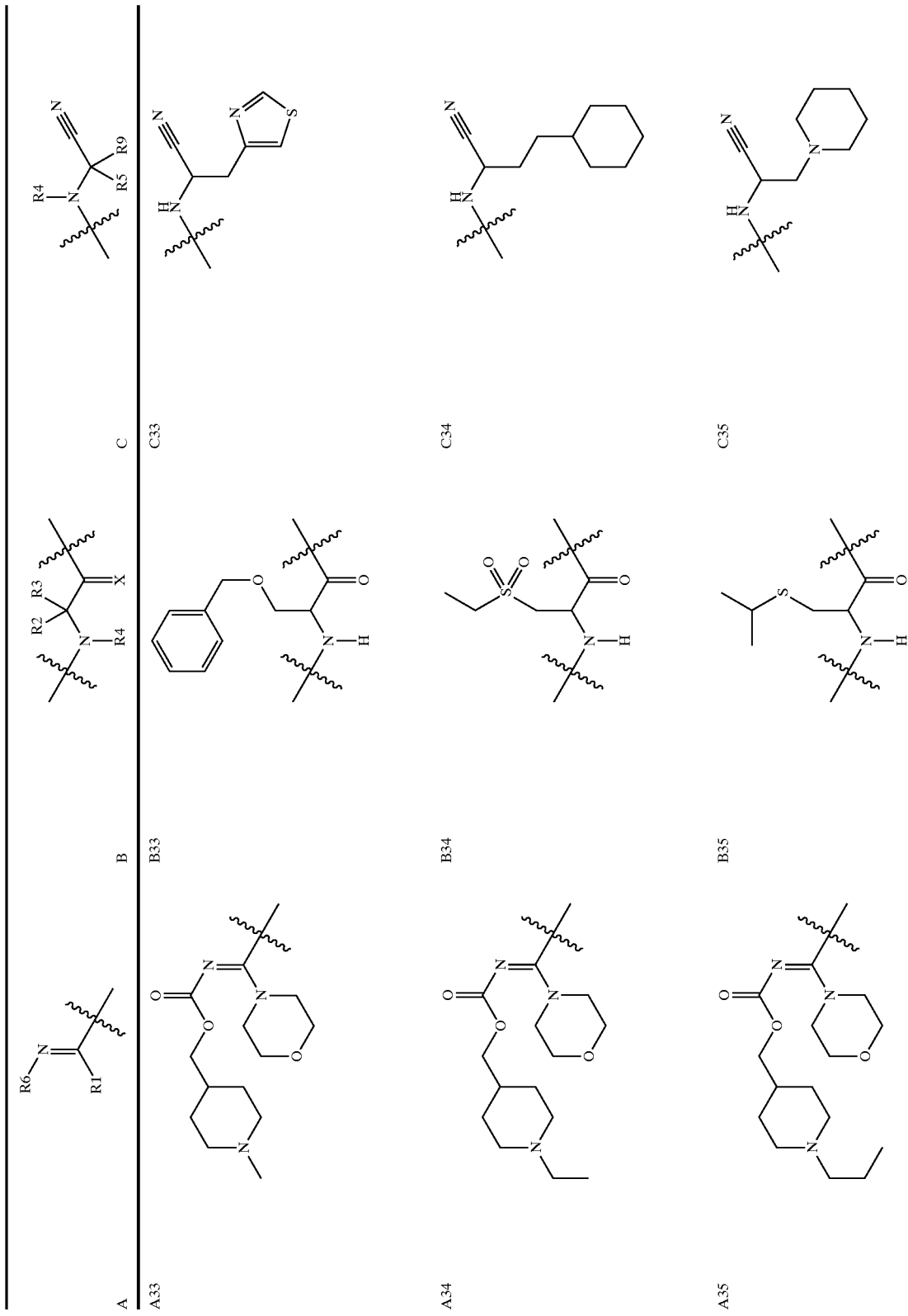

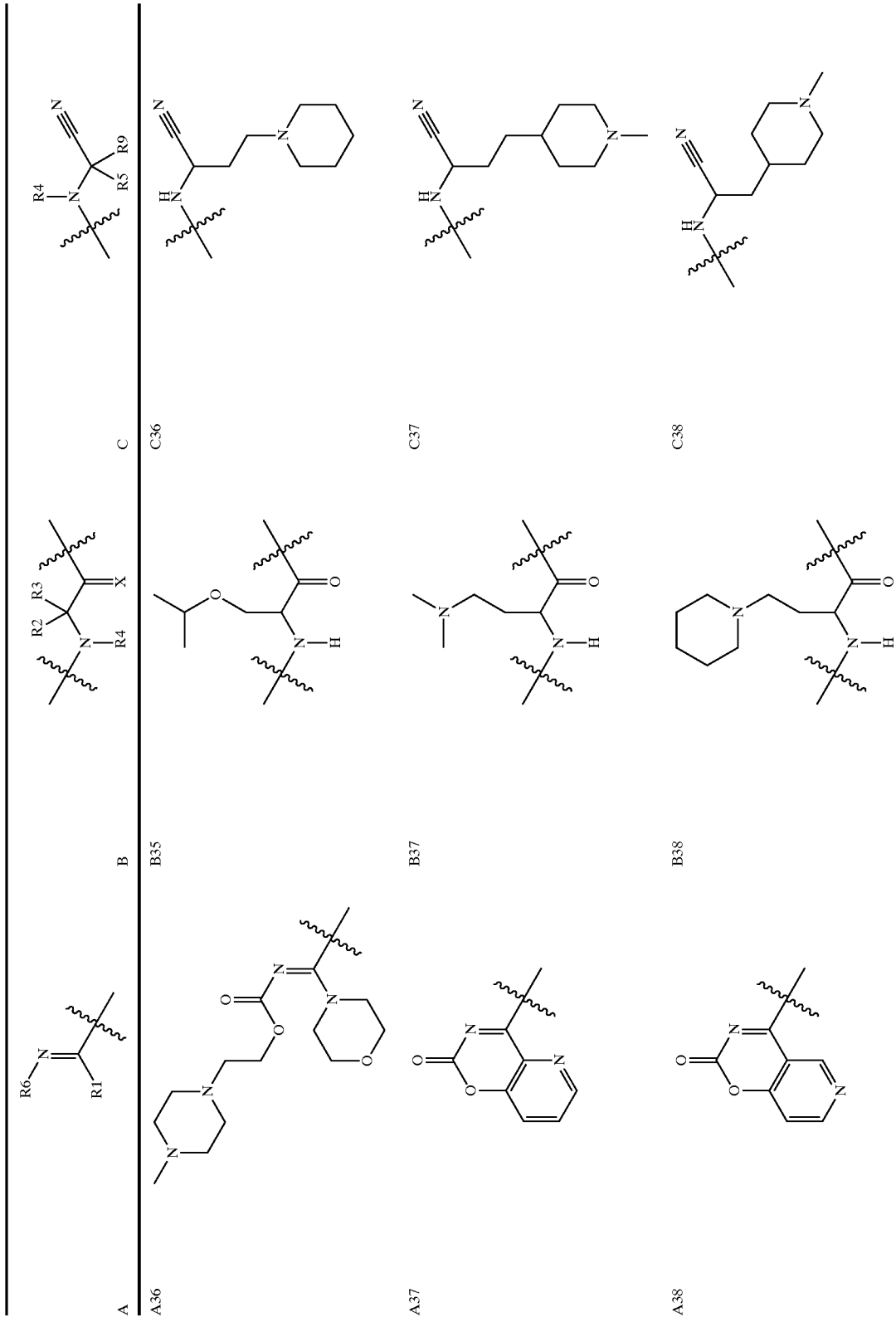

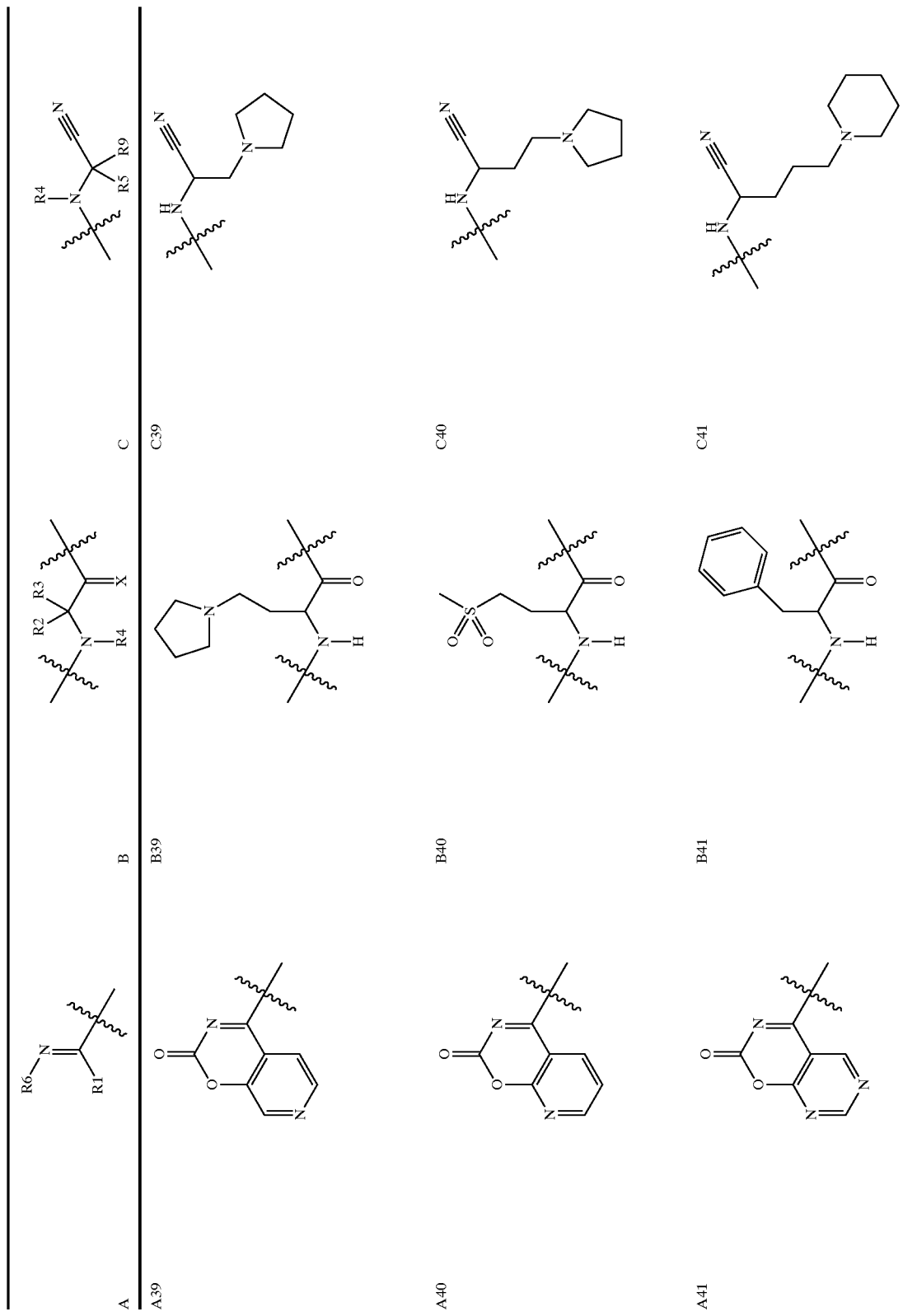

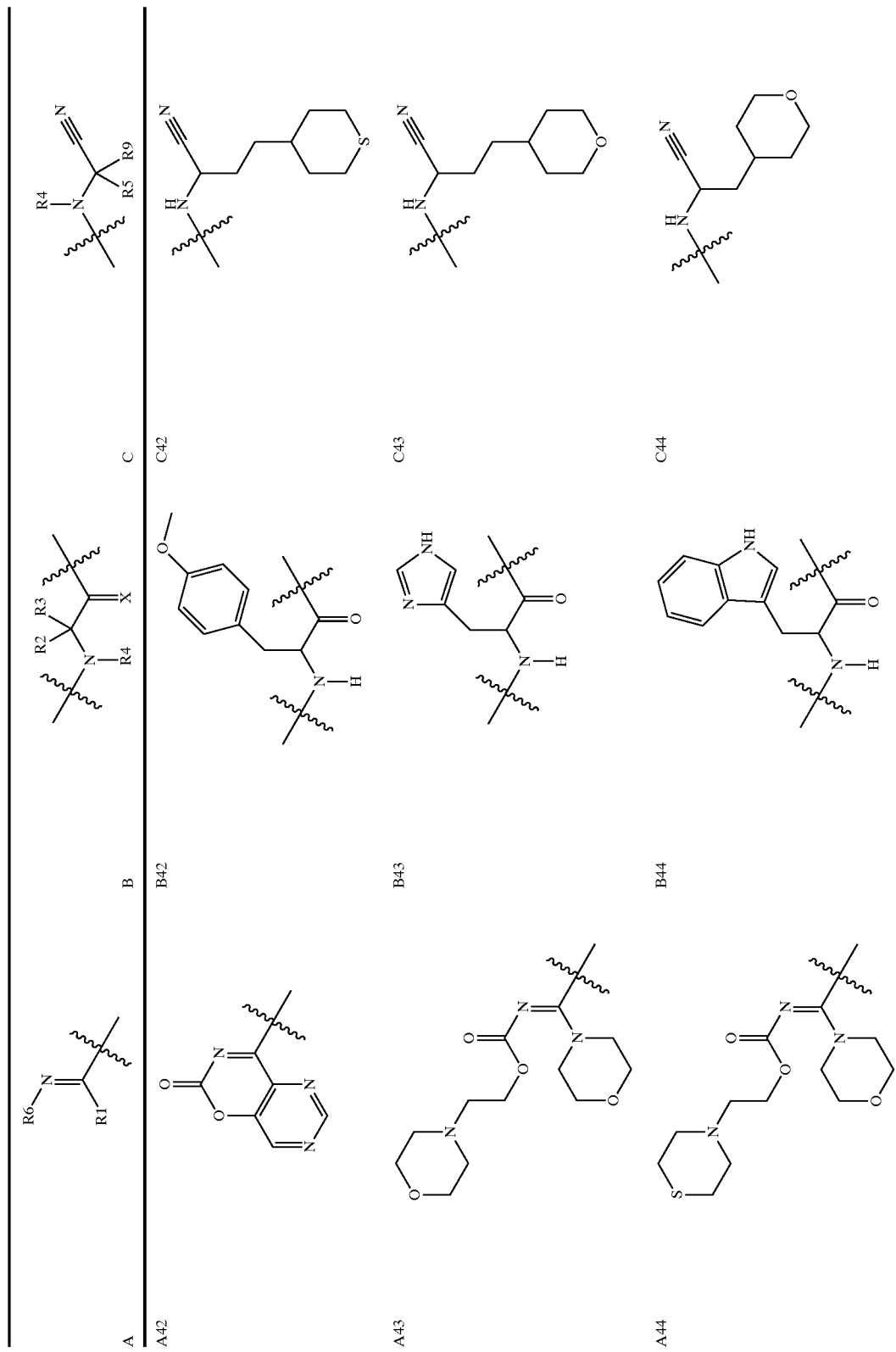

TABLE II-continued
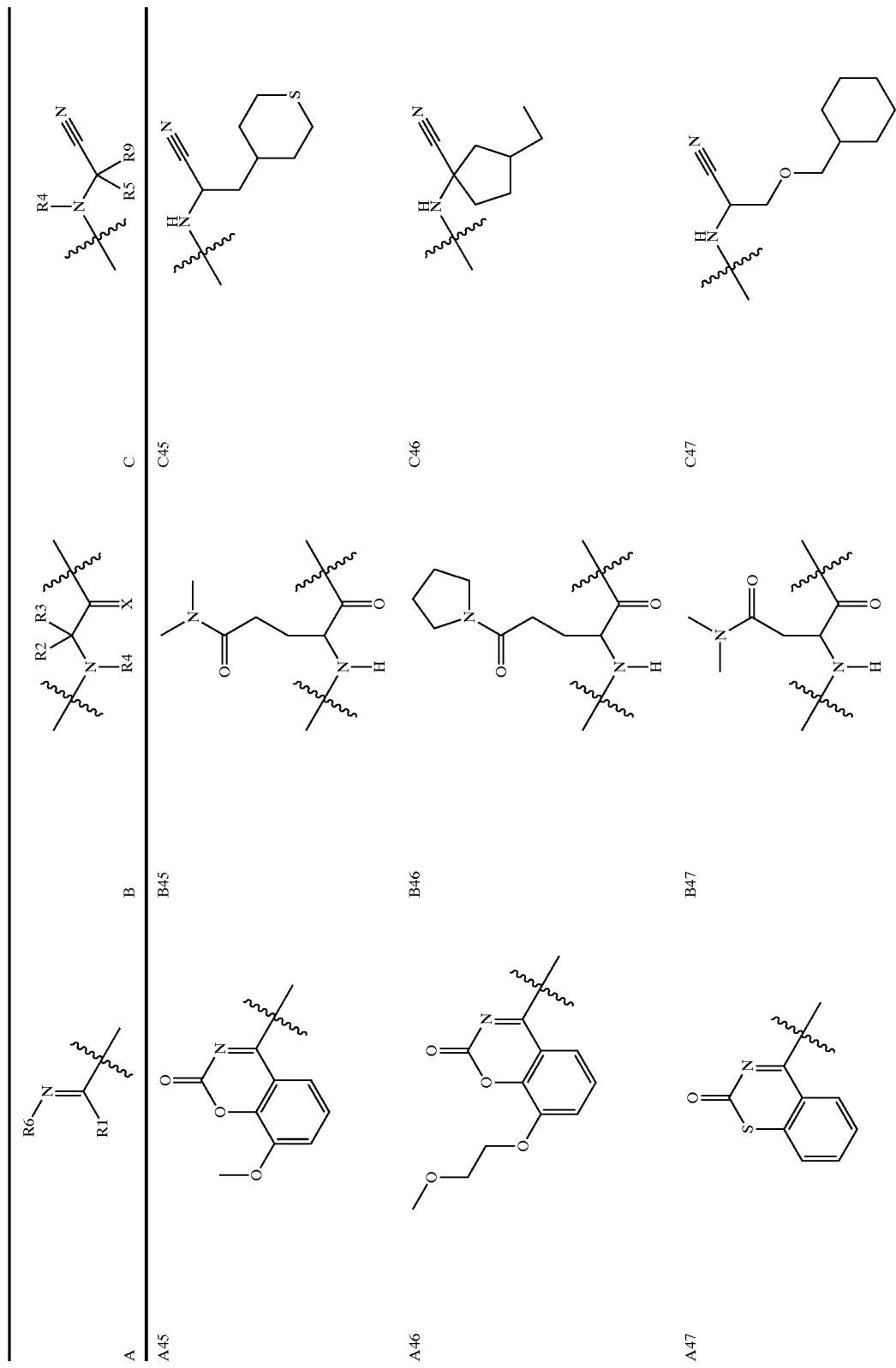

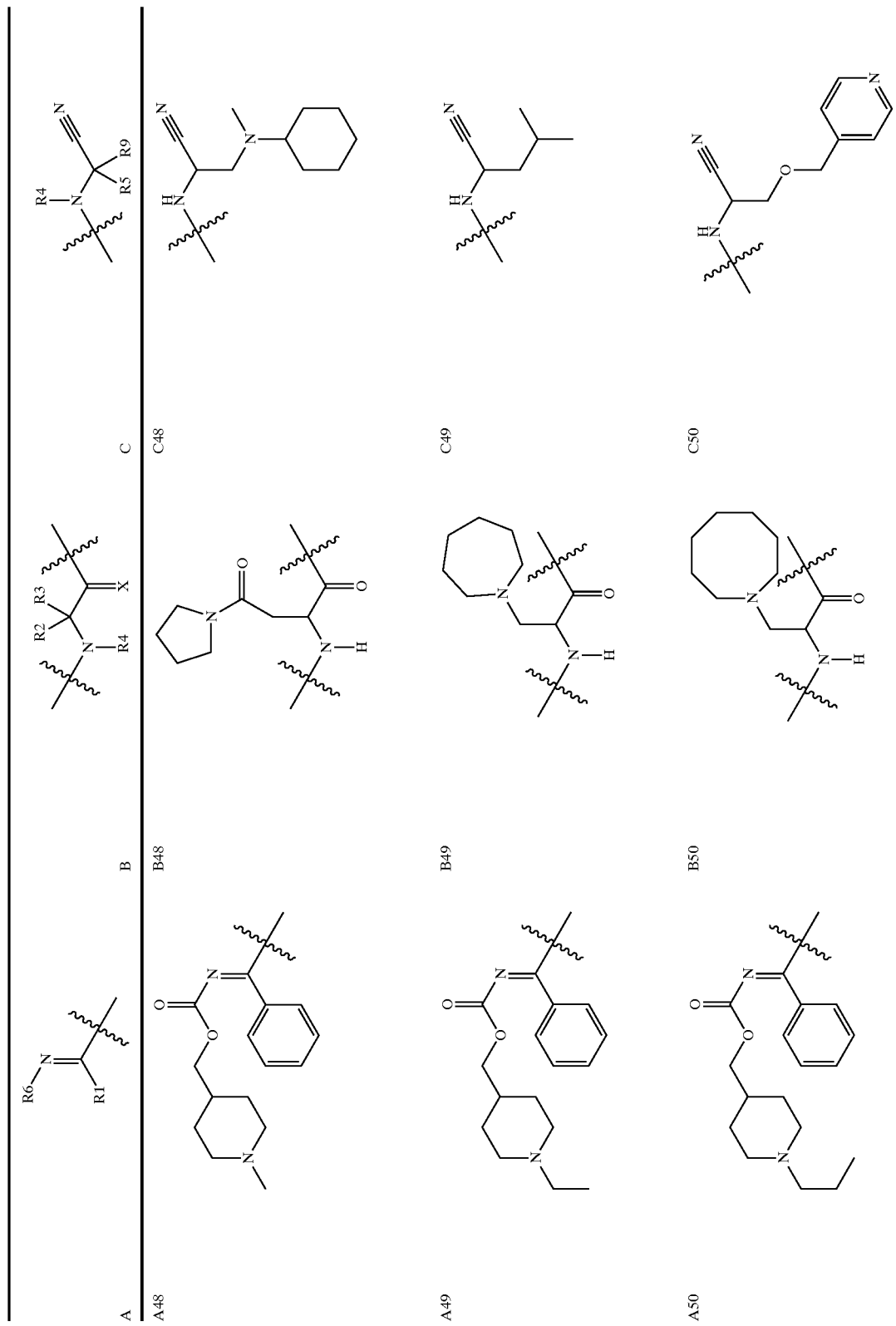

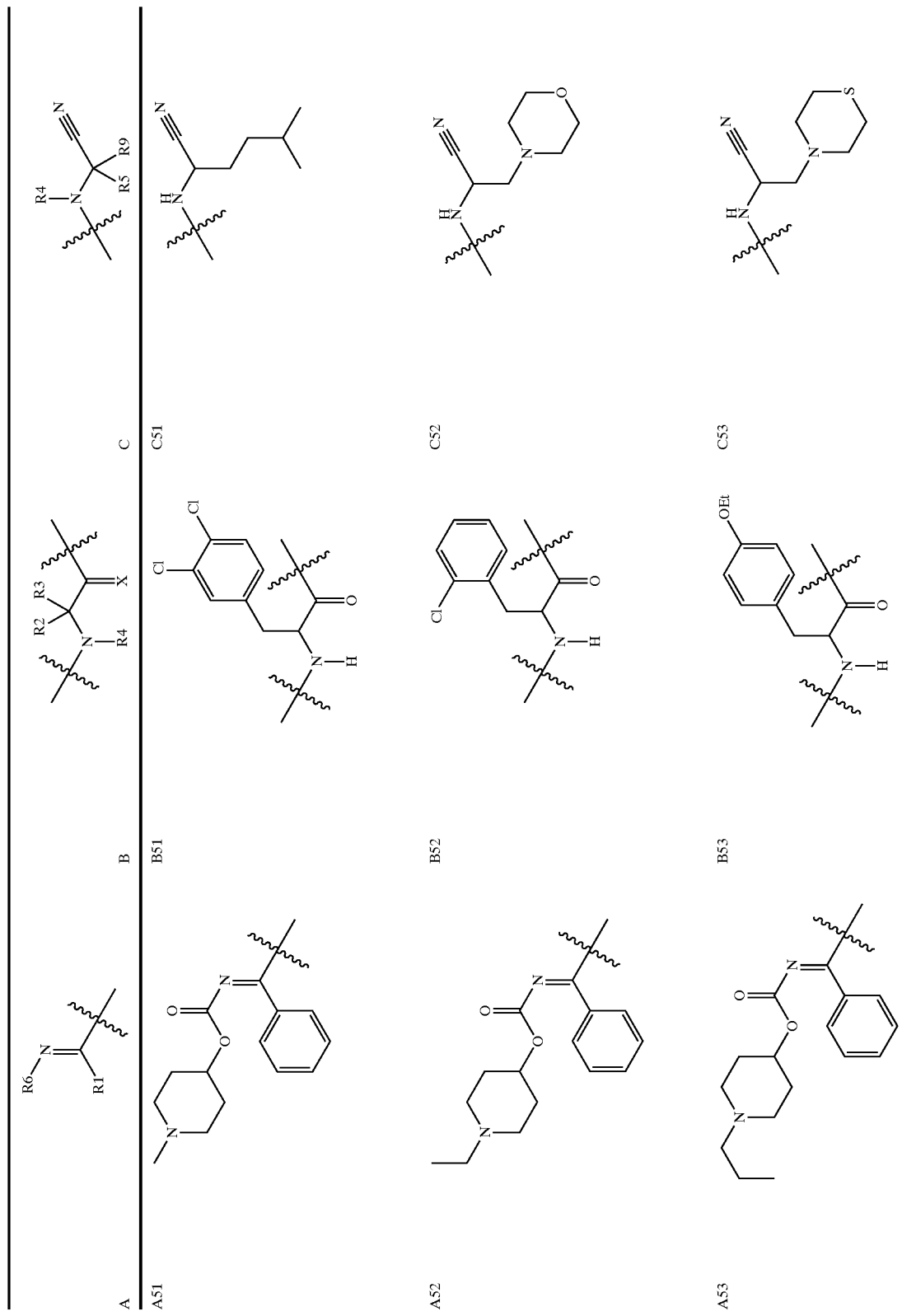

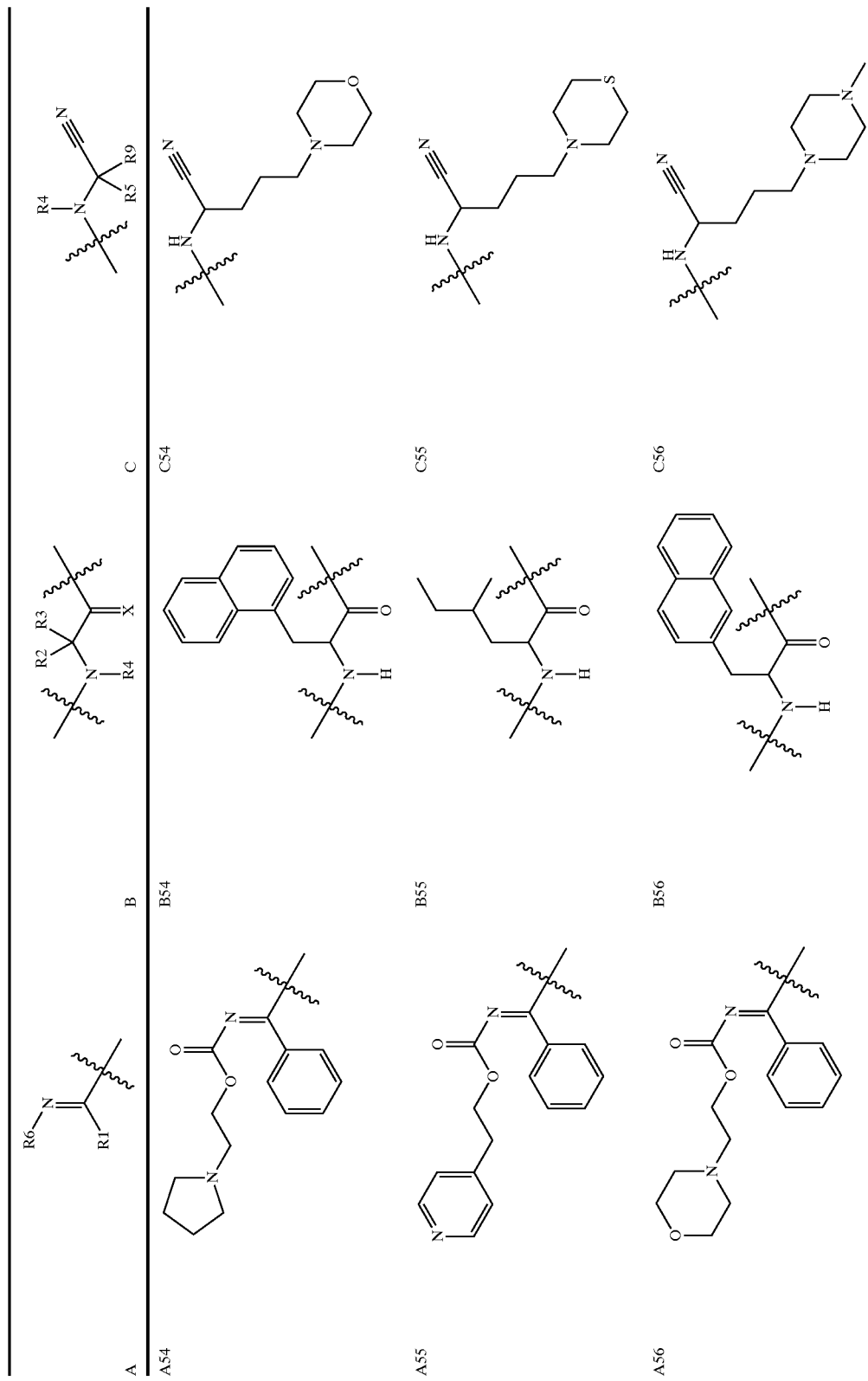

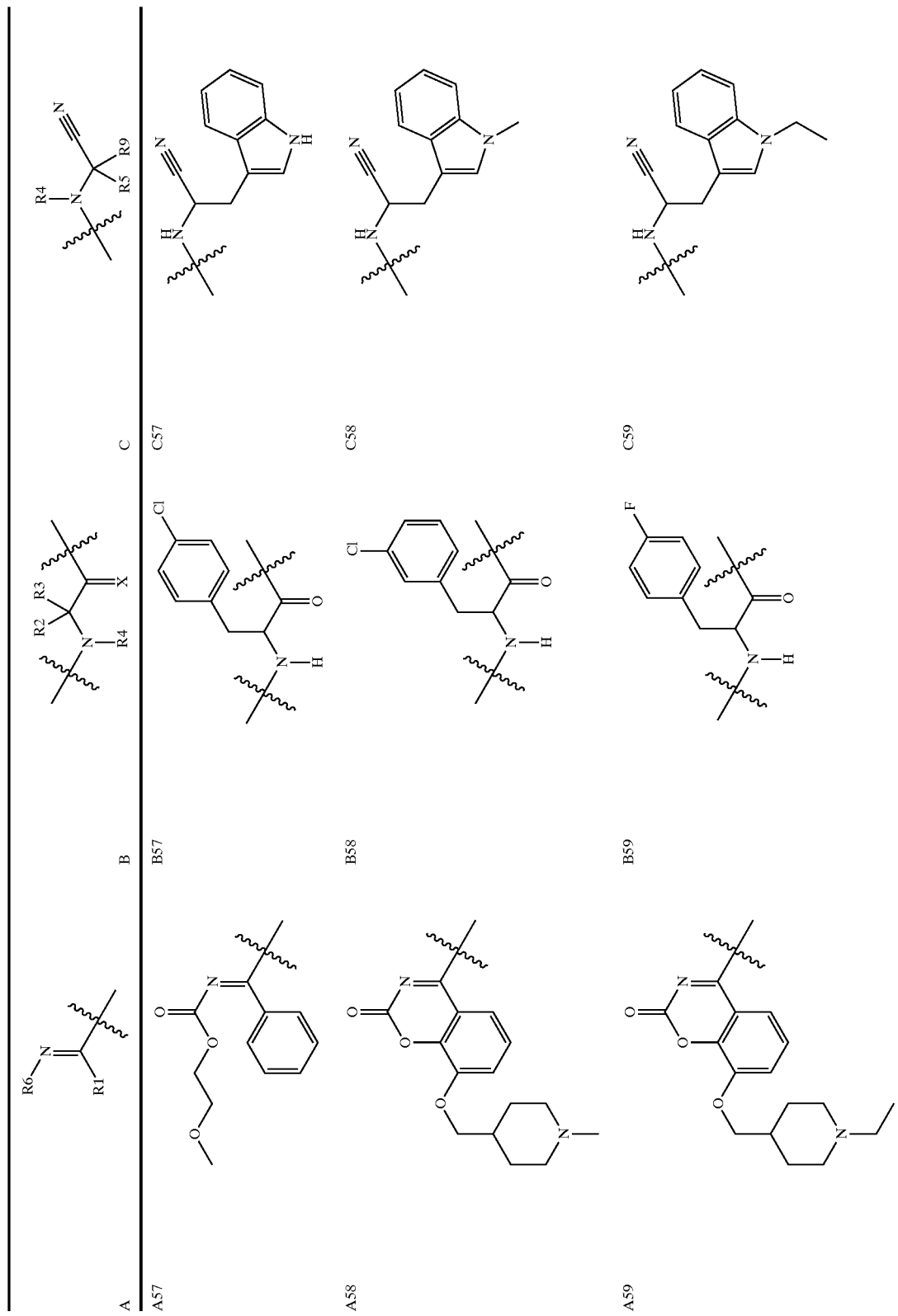

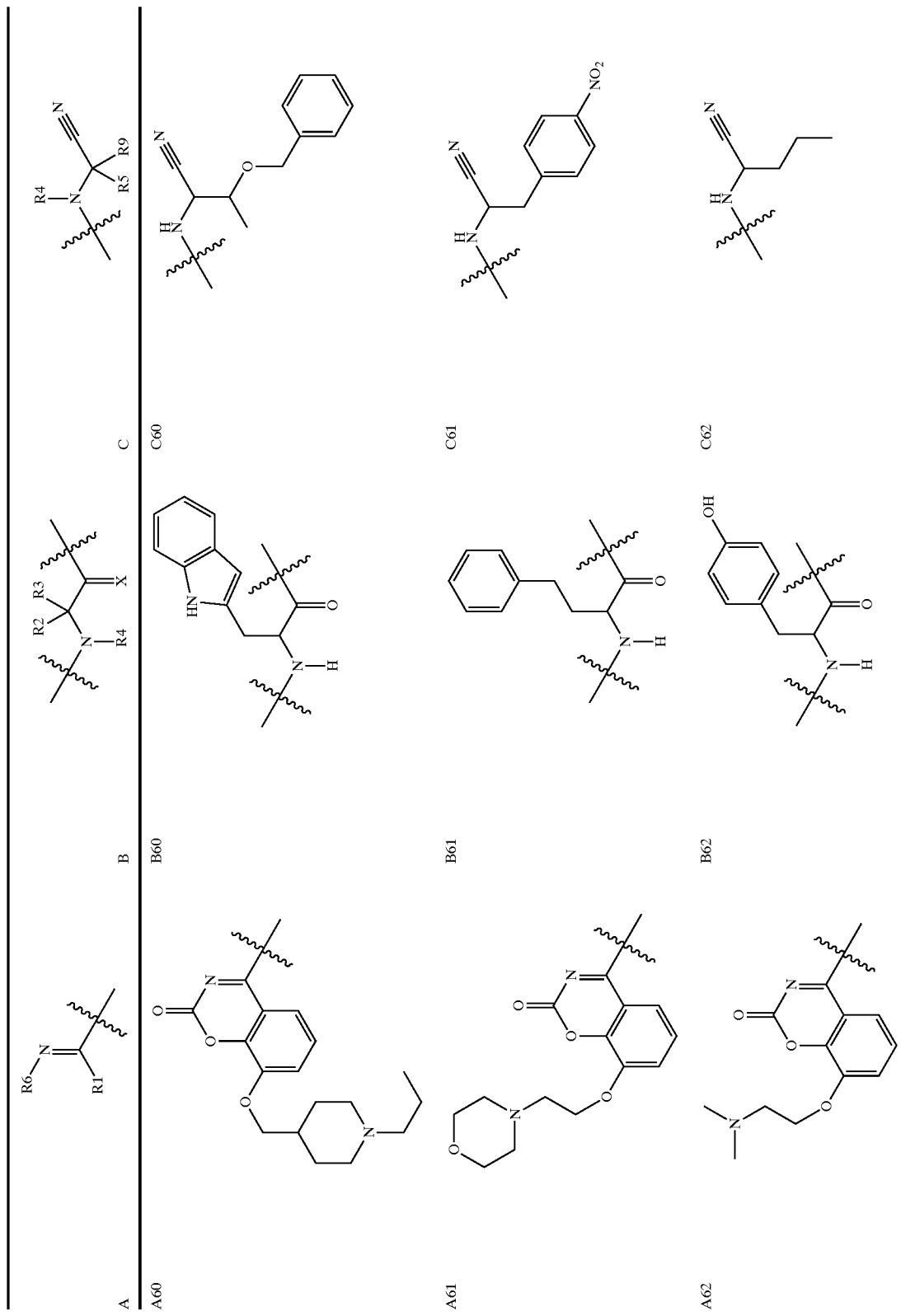

TABLE II-continued

| A | B | C |
|---|---|---|
| A63 | B63 | C63 |
| A64 | B64 | C64 |
| A65 | B65 | C65 |

TABLE II-continued

| A | B | C |
|---|---|---|
| A66 | B66 | C66 |
| A67 | B67 | C67 |
| A68 | B68 | C68 | and the pharmaceutically acceptable derivates thereof.

The following subgeneric aspect of the compounds of the formulas (Ia) or (Ib) is postulated to possess Cathepsin K activity:

The broadest embodiment of the formula (Ia) or (Ib) as described hereinabove and wherein $R_1$ is a bond, C1–4 alkyl, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, C1–2 alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one or more $R_c$;

$R_c$ is methyl, ethyl, cyclohexyl, cyclopentyl, phenyl, naphthyl, bicyclo[3.1.0]hexanyl, bicyclo[1.1.1] pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, or $R_c$ is acetylamino, benzoylamino, methylthio wherein the sulfeur atom may be oxidized to a sulfoxide or sulfone, phenylthio wherein the sulfur atom may be oxidized to a sulfoxide or sulfone, or $R_c$ is phenoxycarbonylamino, phenylcarbamoyloxy, phenylsulfonylamino, phenylaminosulfonyl, amino wherein the nitrogen atom may be independently mono or di-substituted by methyl or phenyl, or $R_c$ is chloro, fluoro, hydroxy, oxo, carboxy or cyano;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is hydrogen or C1–3alkyl;

$R_9$ is hydrogen, C1–12 alkyl wherein one or more carbon atoms are optionally replaced by O, S or N, phenyl or cyano, wherein $R_9$ is optionally substituted by one or more $R_e$;

$R_e$ is selected from C1–3 alkyl, C3–6 cycloalkyl, phenyl, naphthyl, furanyl, thienyl, thiazolyl, imidazolyl, pyridinyl, indolyl, halogen, hydroxy, oxo, carboxy and cyano, $R_e$ may be further optionally substituted by one or more $R_f$;

$R_f$ is selected from C1–3 alkyl, phenyl optionally substituted by one or more groups selected from halogen and methyl, heterocyclyl selected from piperidinyl, morpholinyl and piperazinyl; heteroaryl selected from furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl, halogen, hydroxy, oxo, carboxy and cyano;

or $R_5$ and $R_9$ together with the carbon they are attached form a carbocyclic ring of 3 to 5 carbon atoms, the carbocyclic ring being optionally substituted with one or more $R_g$;

$R_g$ is selected from C1–3 alkyl, phenyl, C1–3 alkoxycarbonyl, benzyloxy, carbamoyl wherein the nitrogen atom may be optionally mono or di-substituted with a group selected from C1–5 alkyl, phenyl and benzyl, halogen, hydroxy, carboxy and cyano.

Preferred cathepsin K inhibitors are those as described immediately above and wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$, is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, or $R_c$ is acetylamino, benzoylamino, methylthio, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is hydrogen or methyl;

$R_9$ is hydrogen, C1–12 alkyl wherein one or more carbon atoms are optionally replaced by O, S or N, phenyl or cyano wherein $R_9$ is optionally substituted by one or more groups of the formula $R_e$;

$R_e$ is selected from methyl, C3–6 cycloalkyl, phenyl, naphthyl, furanyl, thienyl, thiazolyl, imidazolyl, pyridinyl, indolyl, halogen, hydroxy, oxo, carboxy and cyano, $R_e$ may be further optionally substituted by one or more $R_f$;

$R_f$ is selected from C1–3 alkyl, phenyl optionally substituted by one or more groups selected from halogen or methyl, C1–3 alkoxy, aryloxy, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

or $R_5$ and $R_9$ together with the carbon they are attached form a carbocyclic ring of 3 to 5 carbon atoms, the carbocyclic ring being optionally substituted with one or more $R_g$;

$R_g$ is selected from C1–3 alkyl, phenyl, C1–3 alkoxycarbonyl, benzyloxy and carboxy.

Most preferred cathepsin K inhibitors are those as described immediately above and wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl;

$R_9$ is hydrogen, C1–5 alkyl, C1–5 alkylene, C1–5 alkoxyC1–5 alkyl, C1–5 alkoxycarbonylC1–5 alkyl, C1–5 alkylthioC1–5 alkyl, C1–5 alkylthiosulfoneC1–5 alky, C1–5 alkylthiosultonylC1–5 alkyl, aminoC1–5 alkyl, mono or di-C1–5alkylaminoC 1–5 alkyl, mono or di-C1–5 alkylamidoC1–5 alkyl or phenyl, wherein $R_9$ is optionally substituted by one or more Re;

$R_e$ is selected from C3–6 cycloalkyl, phenyl, naphthyl, thienyl, imidazolyl, pyridinyl, indolyl, halogen, hydroxy, carboxy and cyano, $R_e$ may be further optionally substituted by one or more $R_f$;

$R_f$ is selected from methyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

or $R_5$ and $R_9$ together with the carbon they are attached form a carbocyclic ring of 3 to 5 carbon atoms, the carbocyclic ring being optionally substituted with one or more $R_g$;

$R_g$ is selected from phenyl, methoxycarbonyl, benzyloxycarbonyl and carboxy.

Most preferred cathepsin K inhibitors are those as described immediately above and wherein:

$R_1$ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

$R_3$ is n-propyl, i-butyl, propenyl, i-butenyl or 2,2-dimethylpropyl;

$R_2$ and $R_3$ together with the carbon they are attached optionally form a ring selected from cyclopentyl, cyclohexyl, or cycloheptyl;

$R_5$ is hydrogen;

$R_e$ is selected from C5–6 cycloalkyl, phenyl, naphthyl, thienyl, indolyl, halogen, hydroxy, carboxy and cyano, $R_f$ may be further optionally substituted by one or more $R_f$;

$R_f$ is selected from methyl, phenyl optionally substituted by halogen, methoxy, phenoxy, benzyloxy, methoxycarbonyl, halogen, hydroxy and carboxy;

or $R_5$ and $R_9$ together with the carbon they are attached form a carbocyclic ring of 3 carbon atoms, the carbocyclic ring being optionally substituted with one or more $R_g$;

$R_g$ is phenyl.

Even more preferred cathepsin K inhibitors are those as described immediately above and wherein:

$R_e$ is selected from C5–6 cycloalkyl, phenyl, naphthyl, indolyl, halogen and carboxy, $R_f$ may be further optionally substituted by one or more $R_f$;

$R_f$ is selected from methyl, methoxy, methoxycarbonyl, halogen and hydroxy, and $R_5$ and $R_9$ together with the carbon they are attached form a carbocyclic ring of 3 carbon atoms, the carbocyclic ring being optionally substituted with one or more $R_g$.

Further compounds of Formula (Ia), made up of components A, B, and C are provided in Table III below. Any and all combinations of A, B, and C components within the structural limitations of Formula (Ia), comprise a compound of the invention preferably possessing CAT K activity.

FORMULA (Ia)

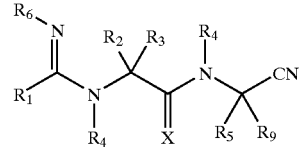

(Ia)

wherein for the Formula (Ia), the components

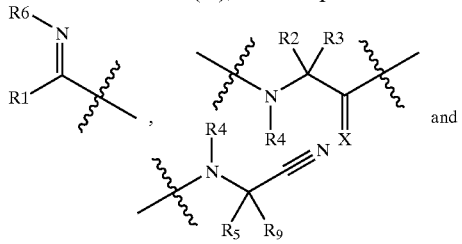

are chosen from any combination of A, B and C as follows:

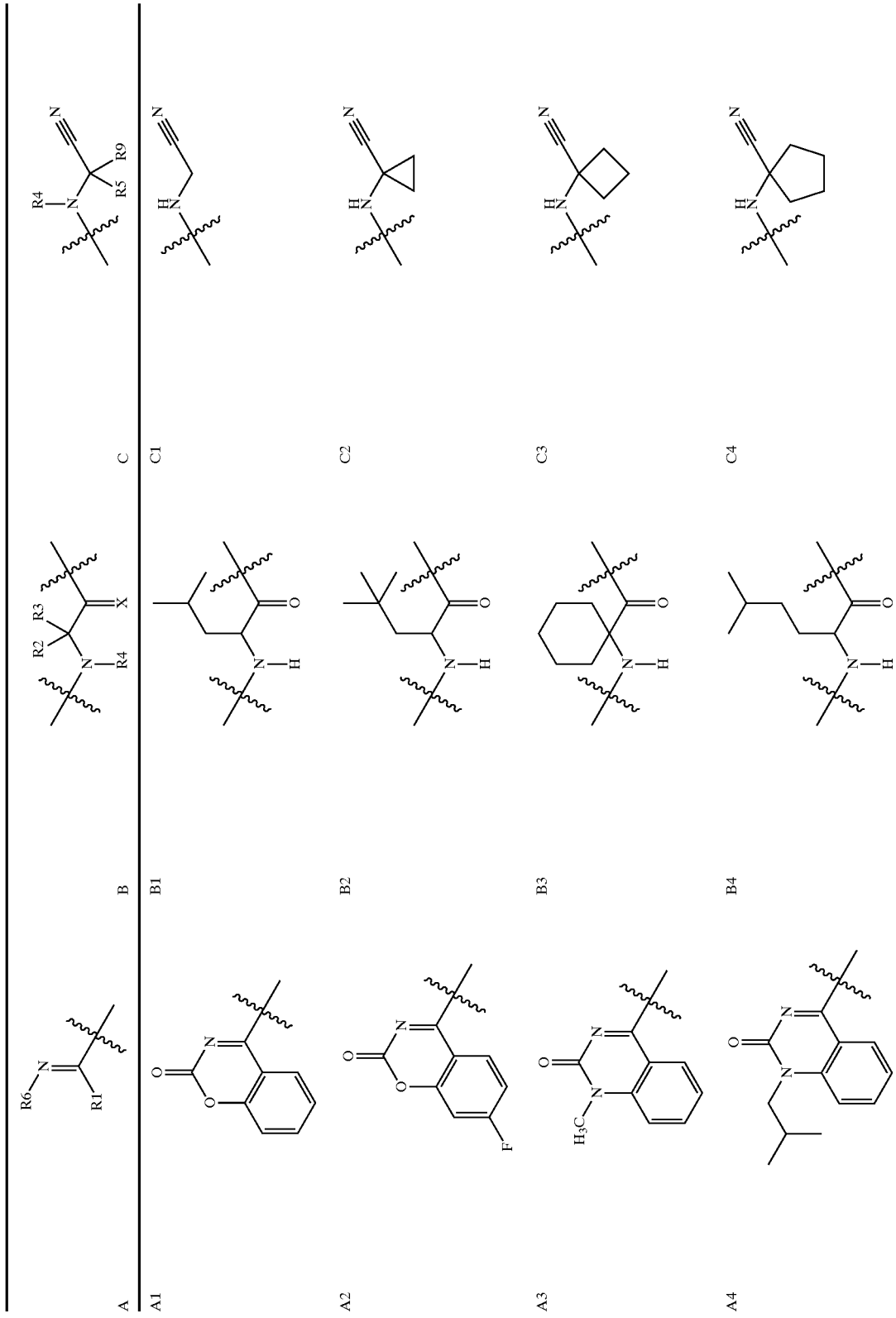
TABLE III

TABLE III-continued

| A | B | C |
|---|---|---|
| A5 | B5 | C5 |
| A6 | B6 | C6 |
| A7 | B7 | C7 |

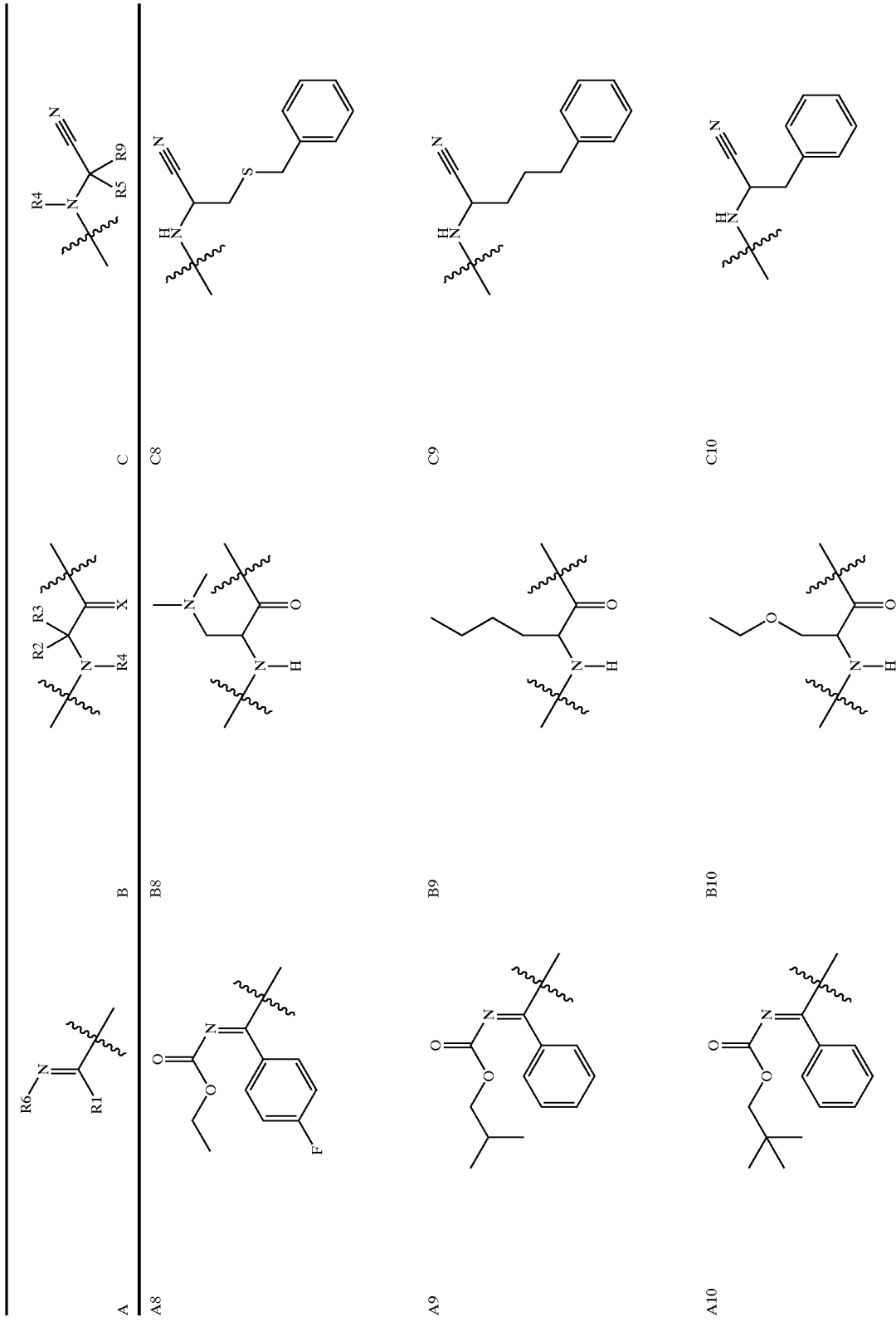

TABLE III-continued

| A | B | C |
|---|---|---|
| A11 | B11 | C11 |
| A12 | B12 | C12 |
| A13 | B13 | C13 |

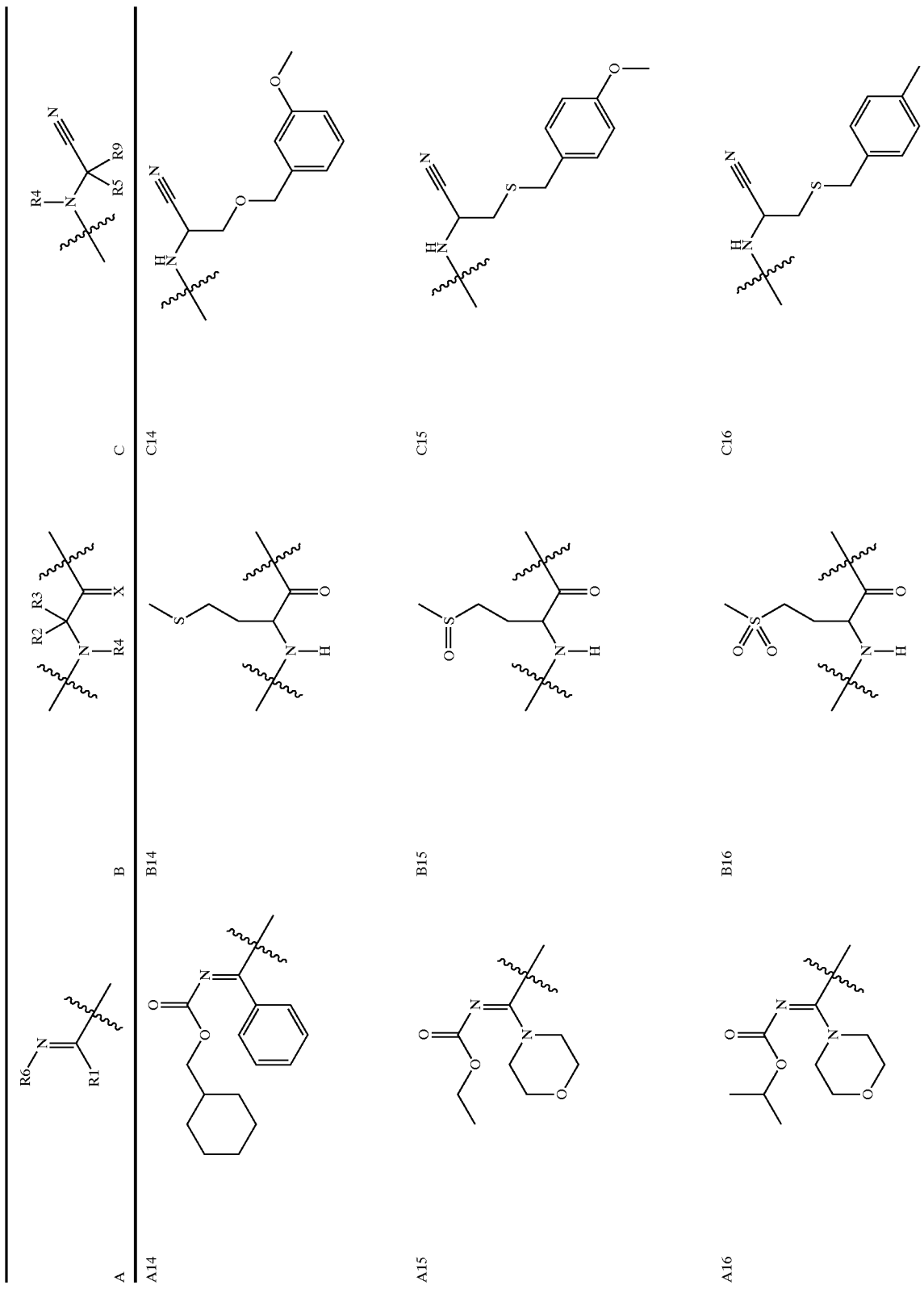

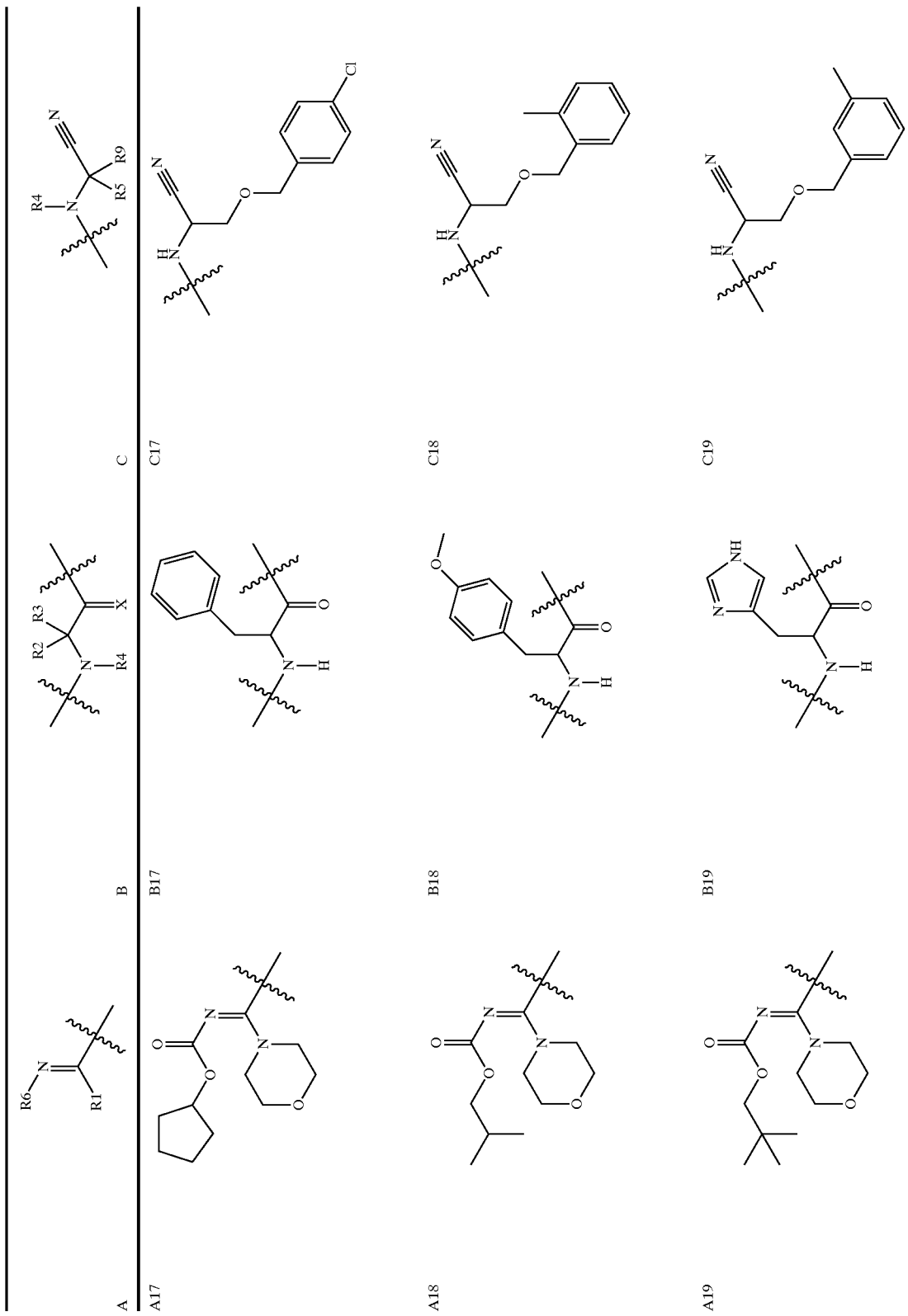

TABLE III-continued
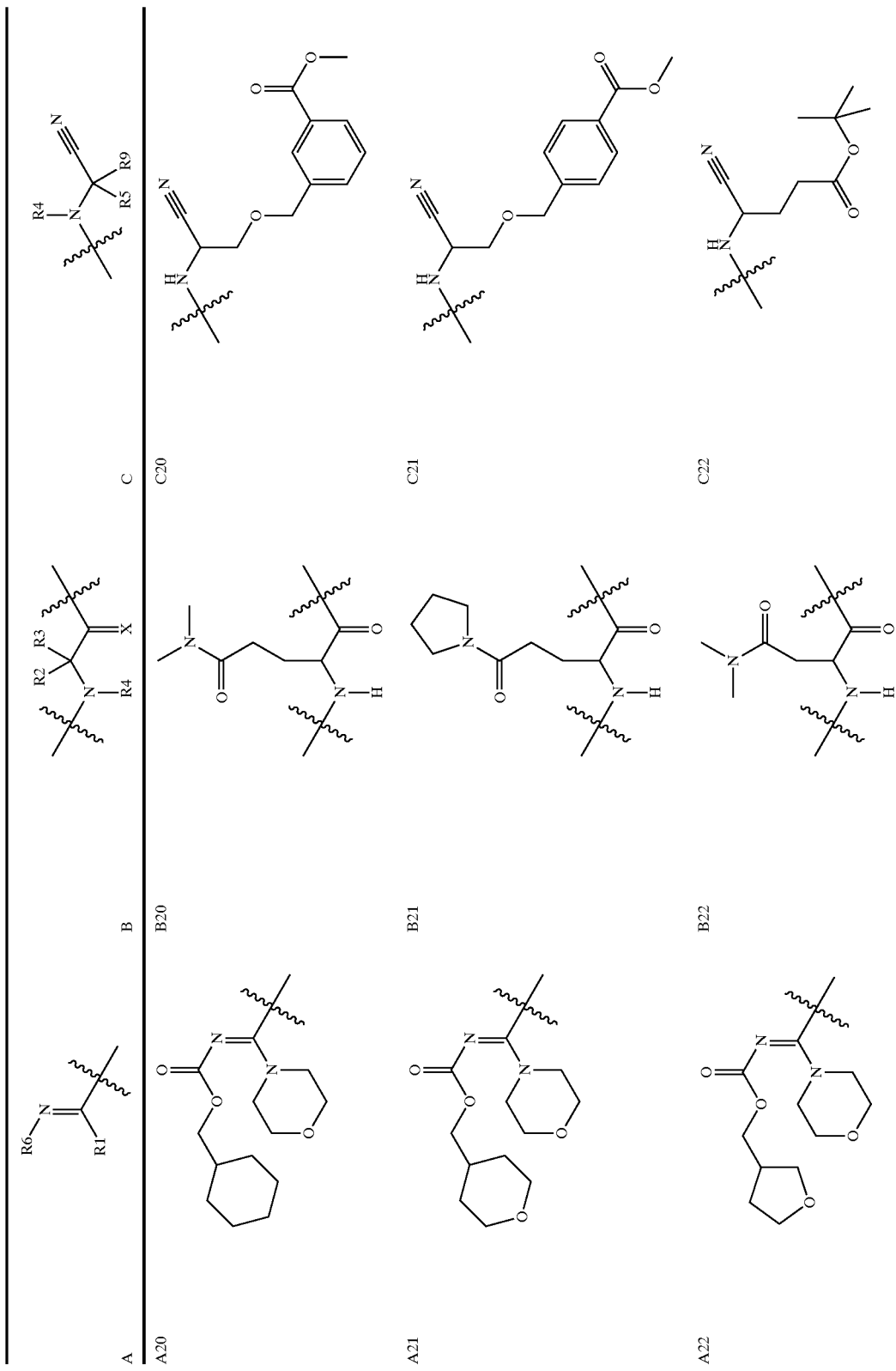

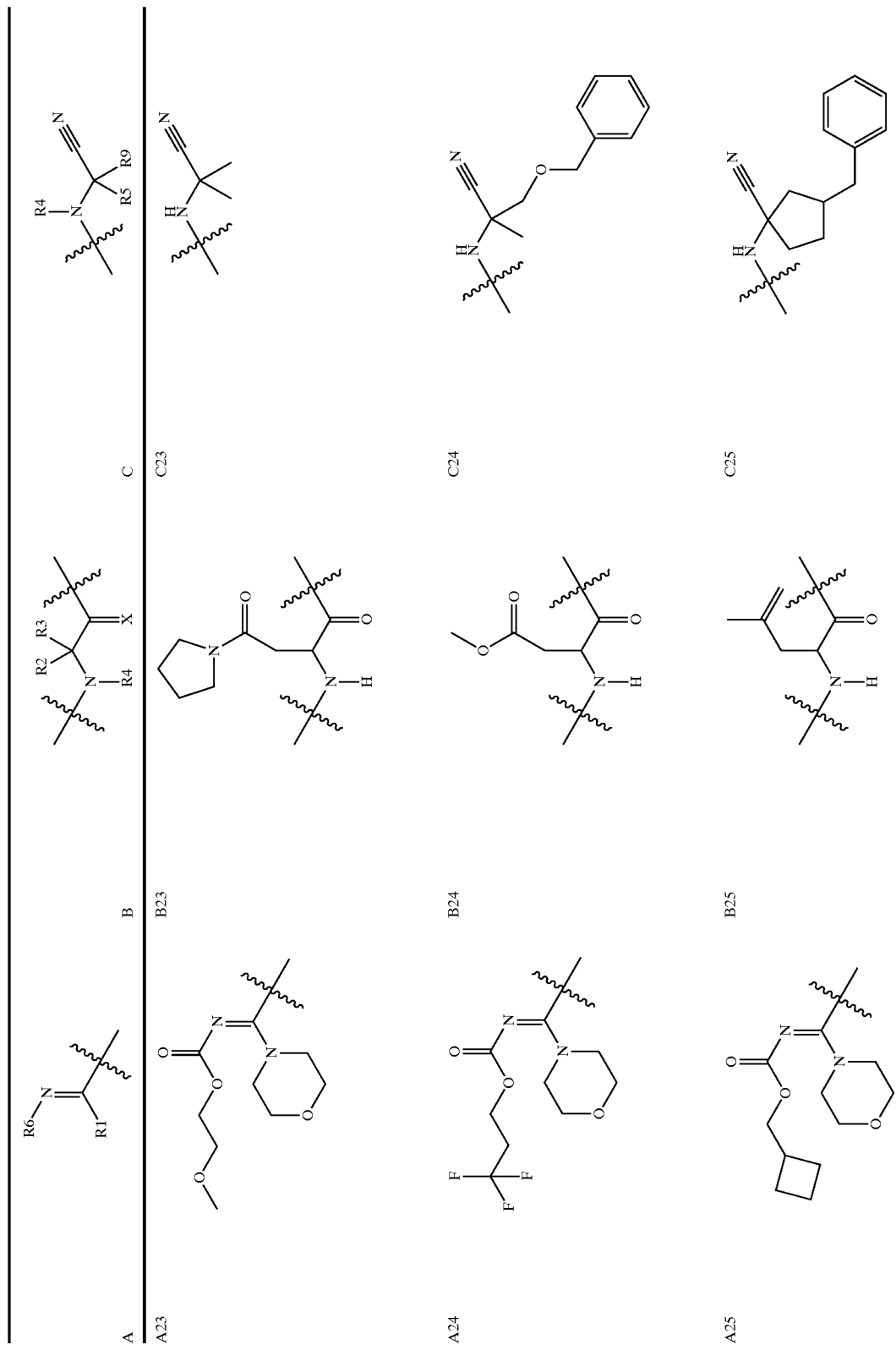

TABLE III-continued

| A | B | C |
|---|---|---|
| A26 | B26 | C26 |
| A27 | B27 | C27 |
| A28 | B28 | C28 |
| A29 | B29 | C29 |

TABLE III-continued

| A | B | C |
|---|---|---|
| A30 | B30 | C30 |
| A31 | B31 | C31 |
| A32 | | C32 |
| A33 | | C33 |

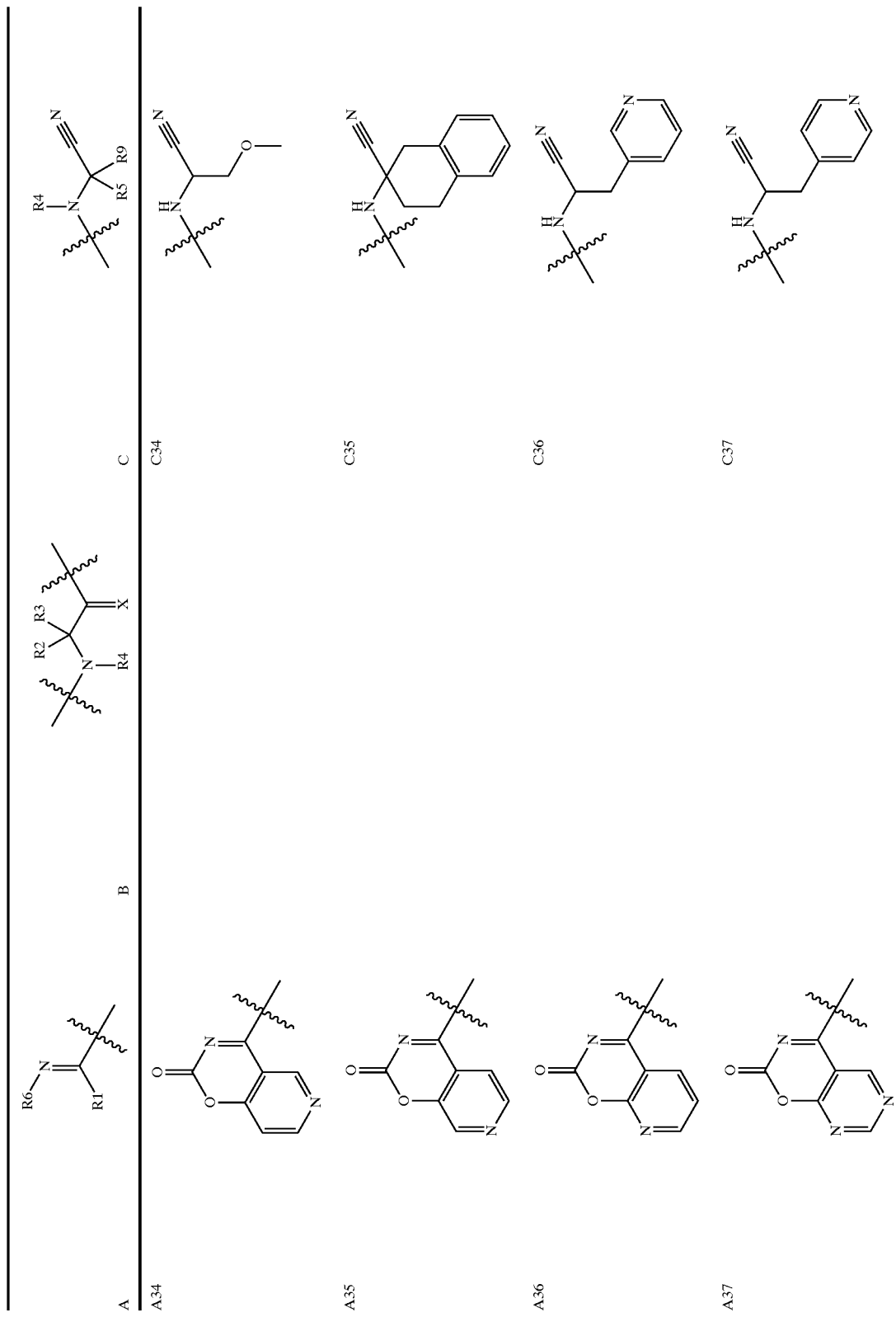

TABLE III-continued

| A | B | C |
|---|---|---|
| A38 | | C38 |
| A39 | | C39 |
| A40 | | C40 |

TABLE III-continued

| A | B | C |
|---|---|---|
| A41 | | C41 |
| A42 | | C42 |
| A43 | | C43 |

TABLE III-continued

| A | B | C |
|---|---|---|
| A44 | | C44 |
| A45 | | C45 |
| A46 | | C46 |
| A47 | | C47 |

TABLE III-continued
| A | B | C |
|---|---|---|
|  A48 | 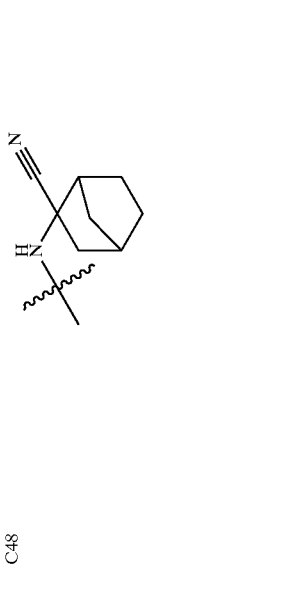 |  C48 |
|  A49 | |  C49 |
|  A50 | |  C50 |

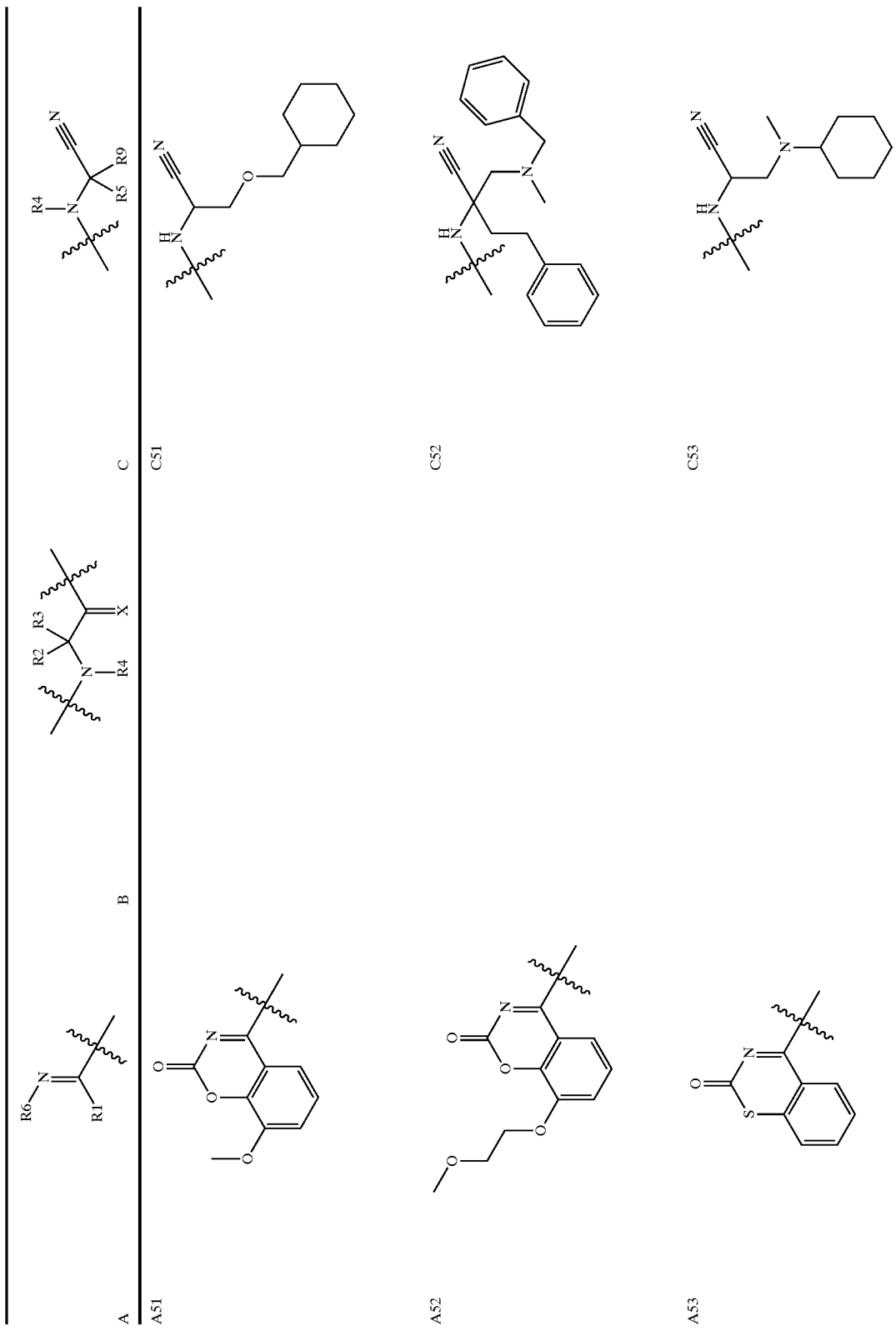

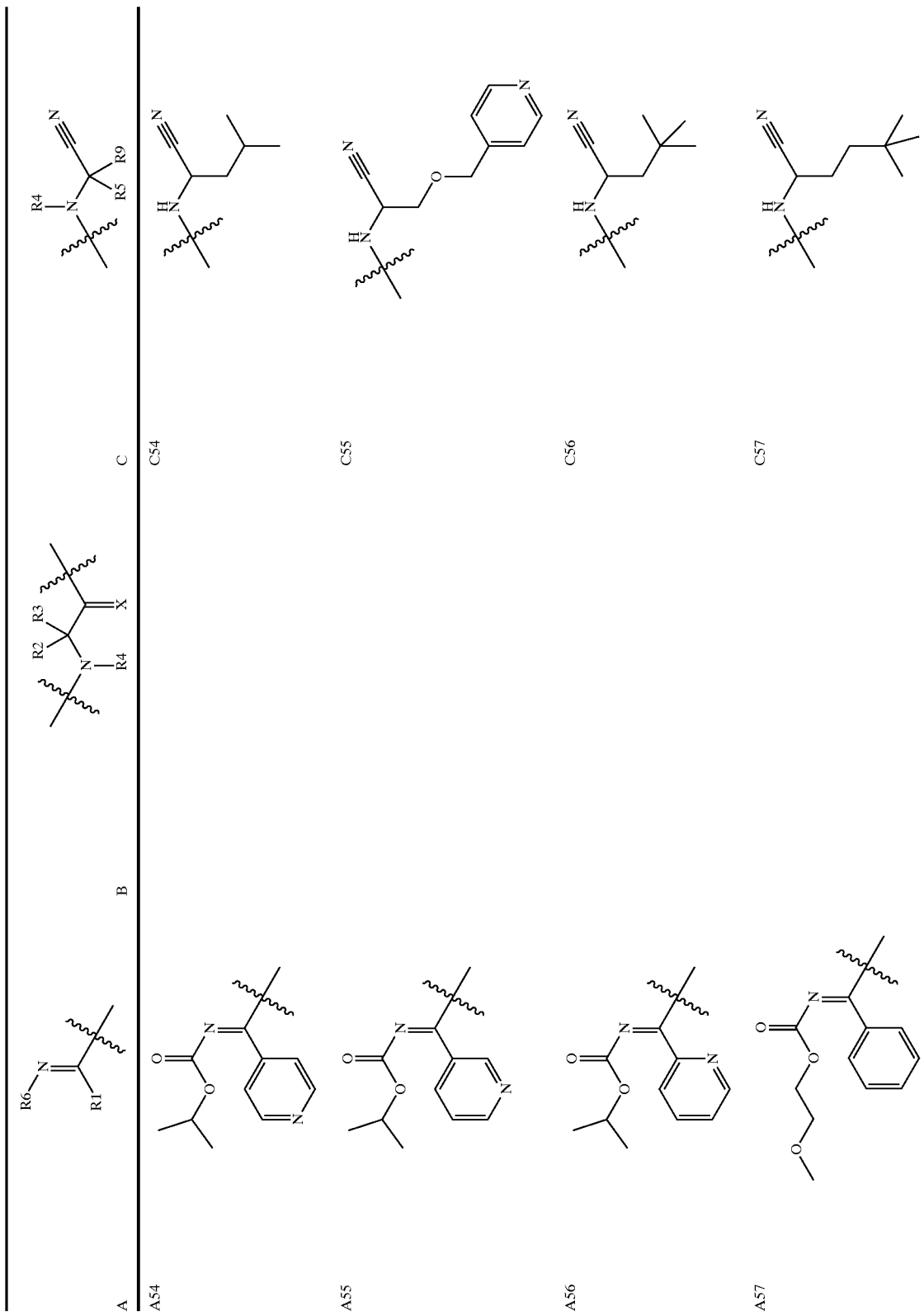

TABLE III-continued

| A | B | C |
|---|---|---|
| A58 | | C58 |
| A59 | | C59 |
| A60 | | C60 |
| A61 | | C61 |

TABLE III-continued

| A | B | C |
|---|---|---|
| A62 | | C62 |
| A63 | | C63 |
| A64 | | C64 |
| A65 | | C65 |

TABLE III-continued

| A | B | C |
|---|---|---|
| A66 | | C66 |
| A67 | | C67 |
| A68 | | C68 |

TABLE III-continued

| A | B | C |
|---|---|---|
| A69 | | C69 |
| A70 | | C70 |
| A71 | | C71 |
| A72 | | C72 |

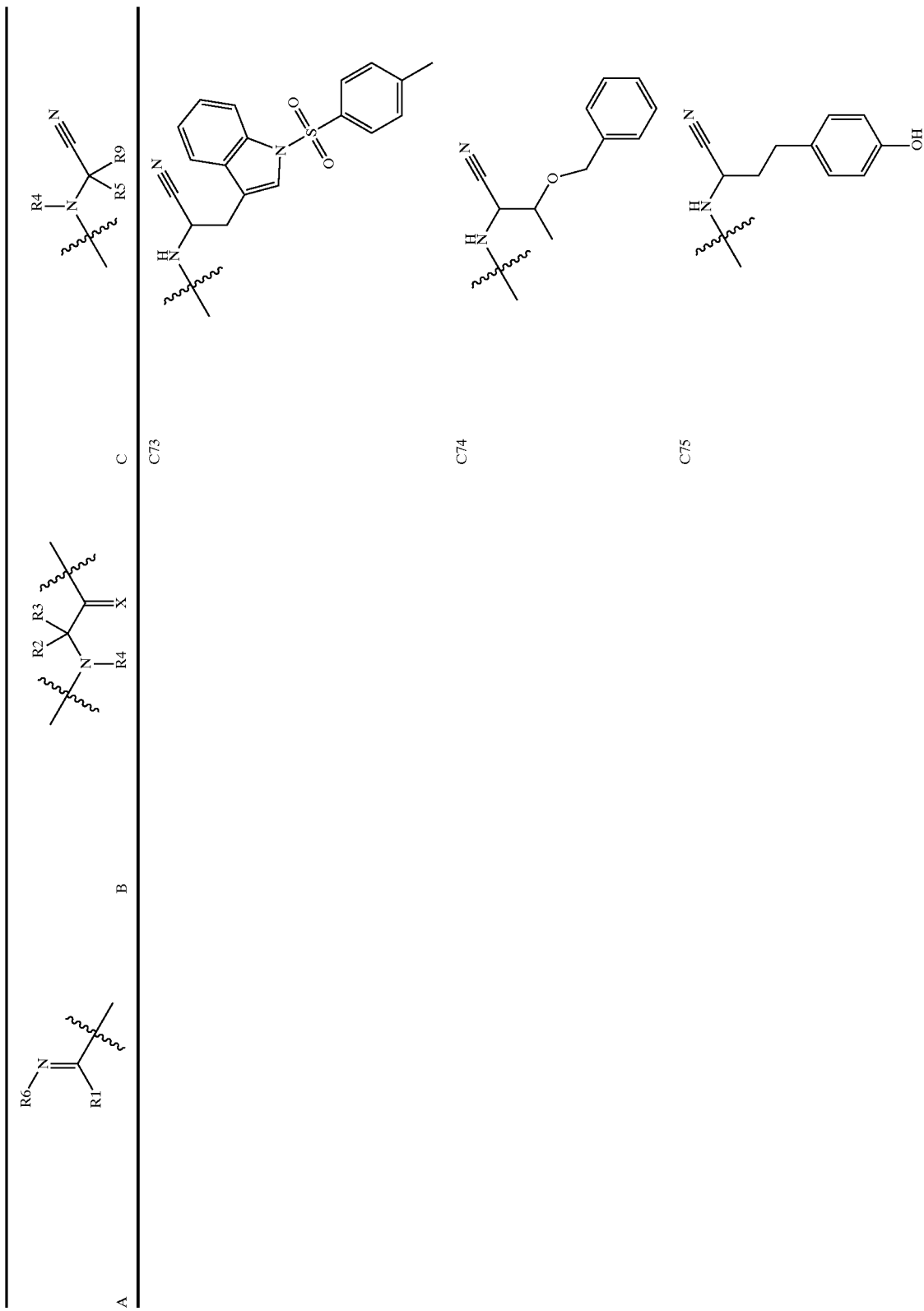

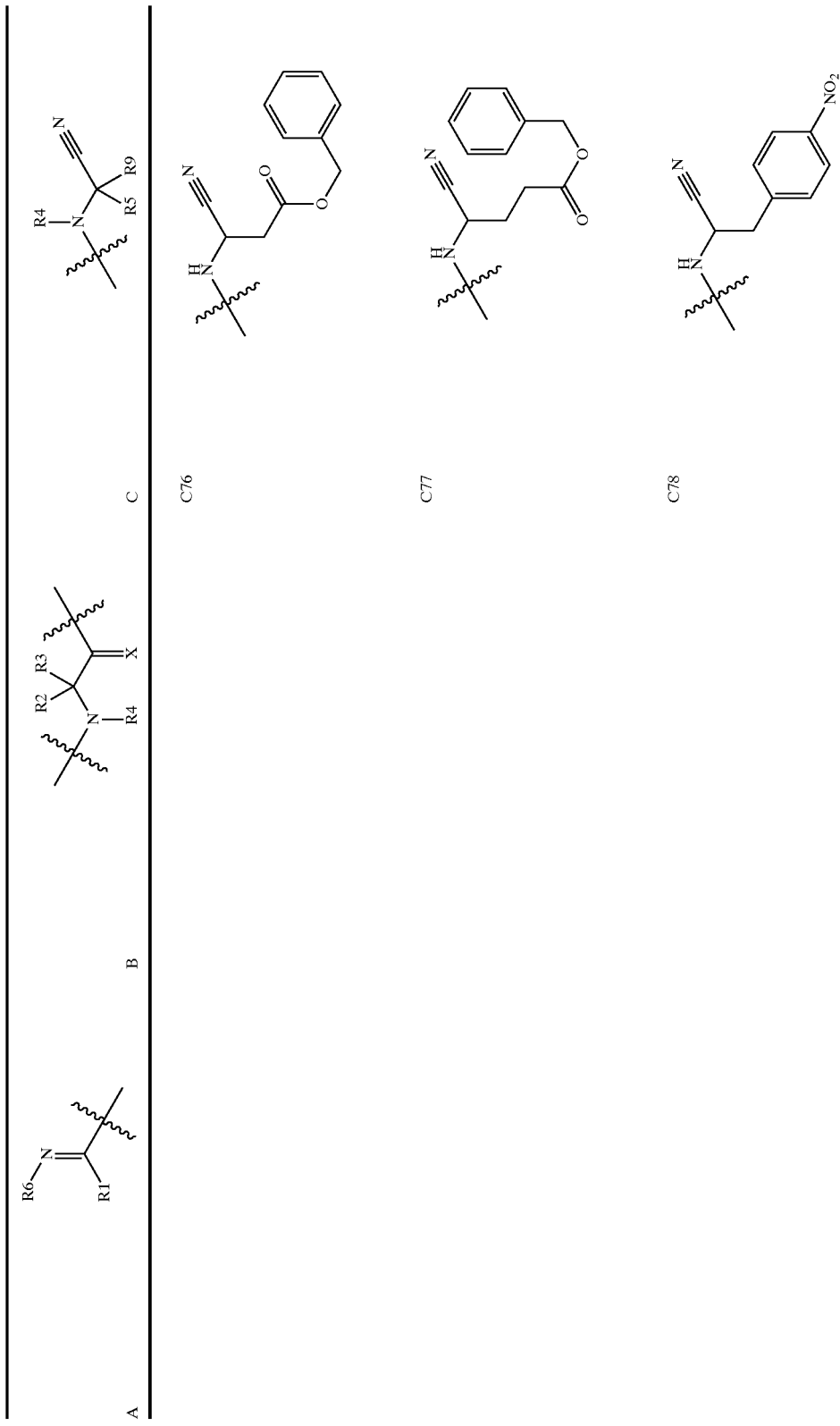

TABLE III-continued
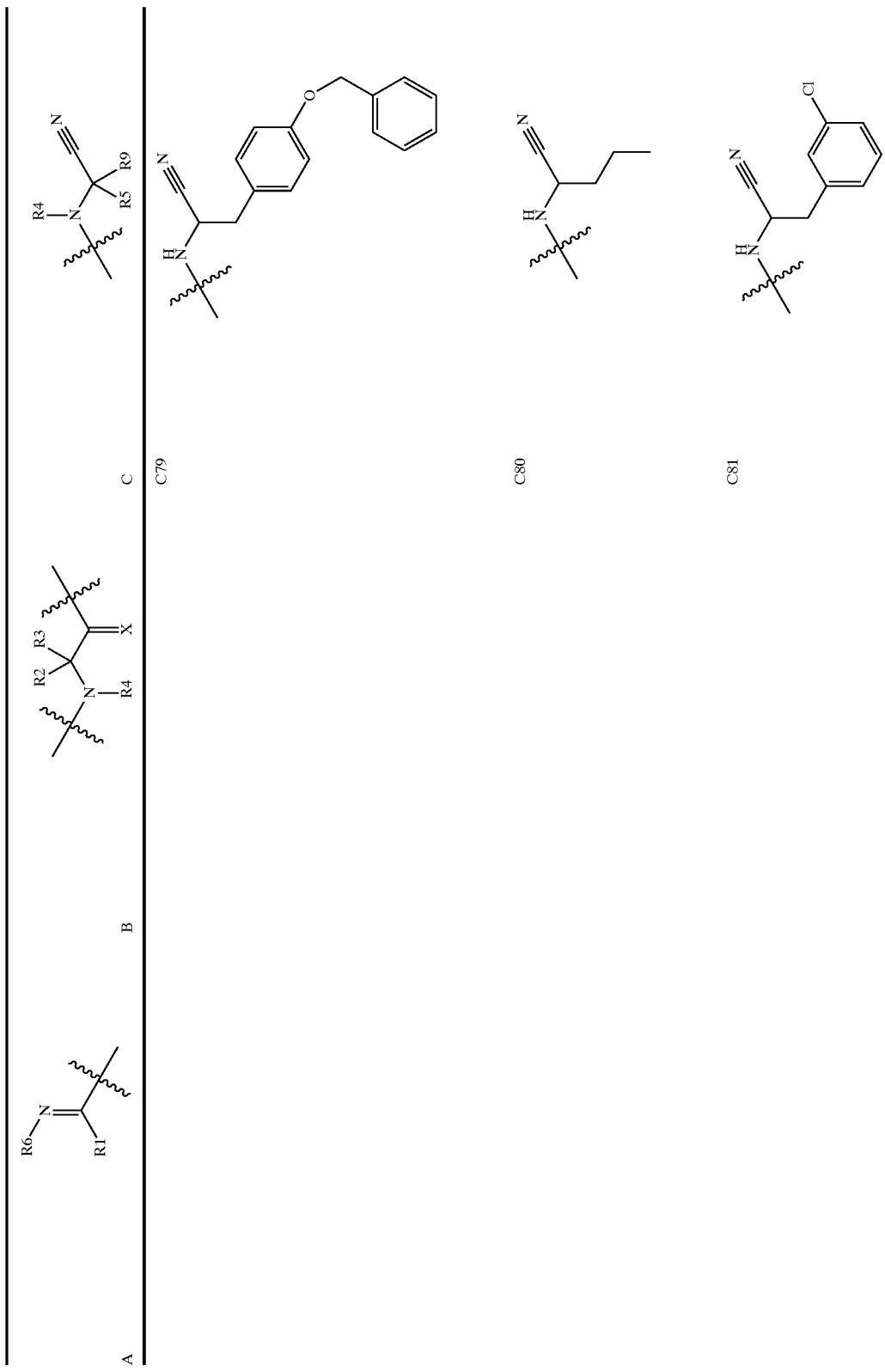

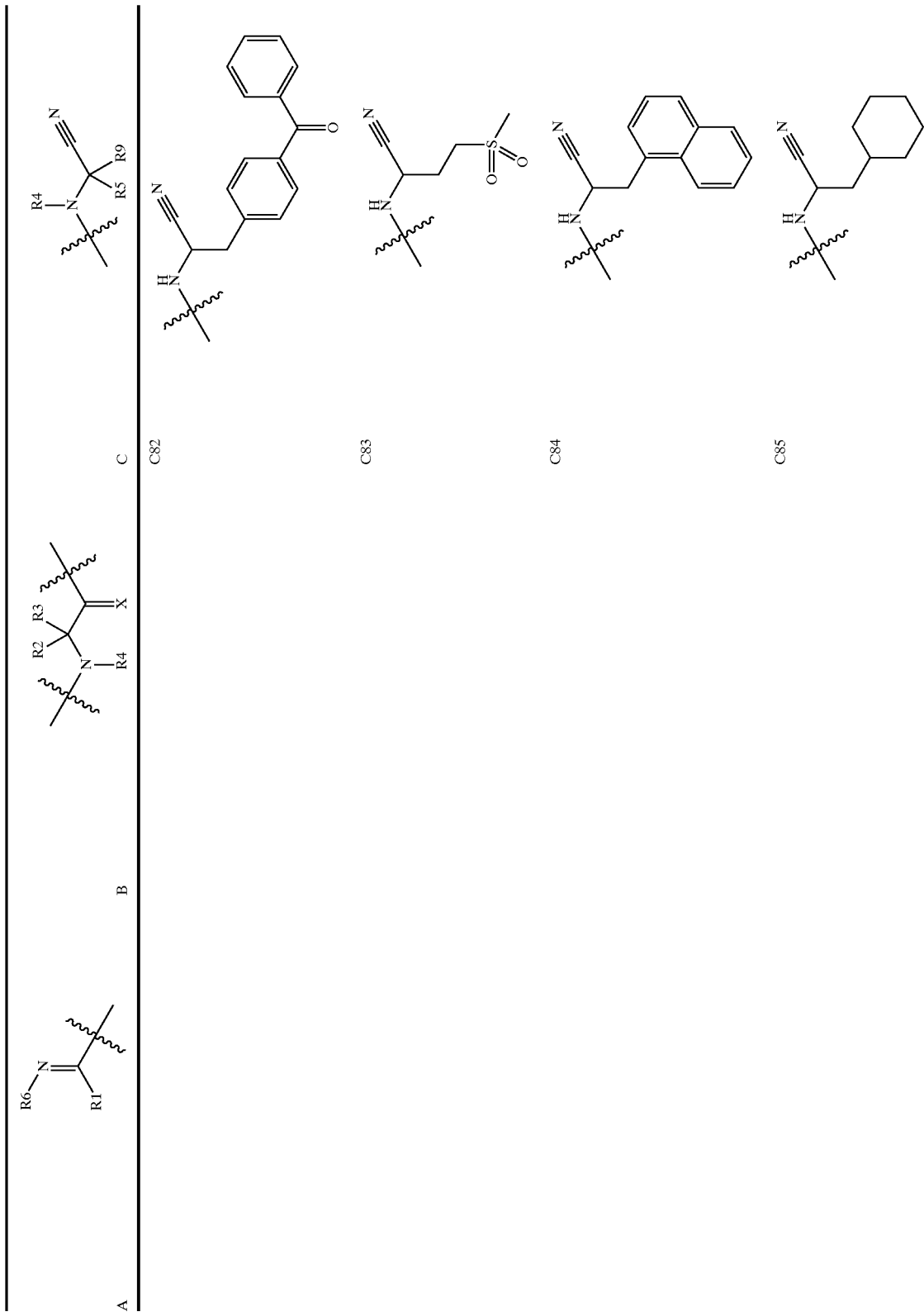

TABLE III-continued

| A | B | C |
|---|---|---|
| | | |
| | | C86 ![structure with CN and NH] |
| | | C87 ![structure with CN, thiophene, NH] |
| | | C88 ![structure with CN, naphthalene, NH] |
| | | C89 ![structure with CN, iodophenol, NH] |

TABLE III-continued
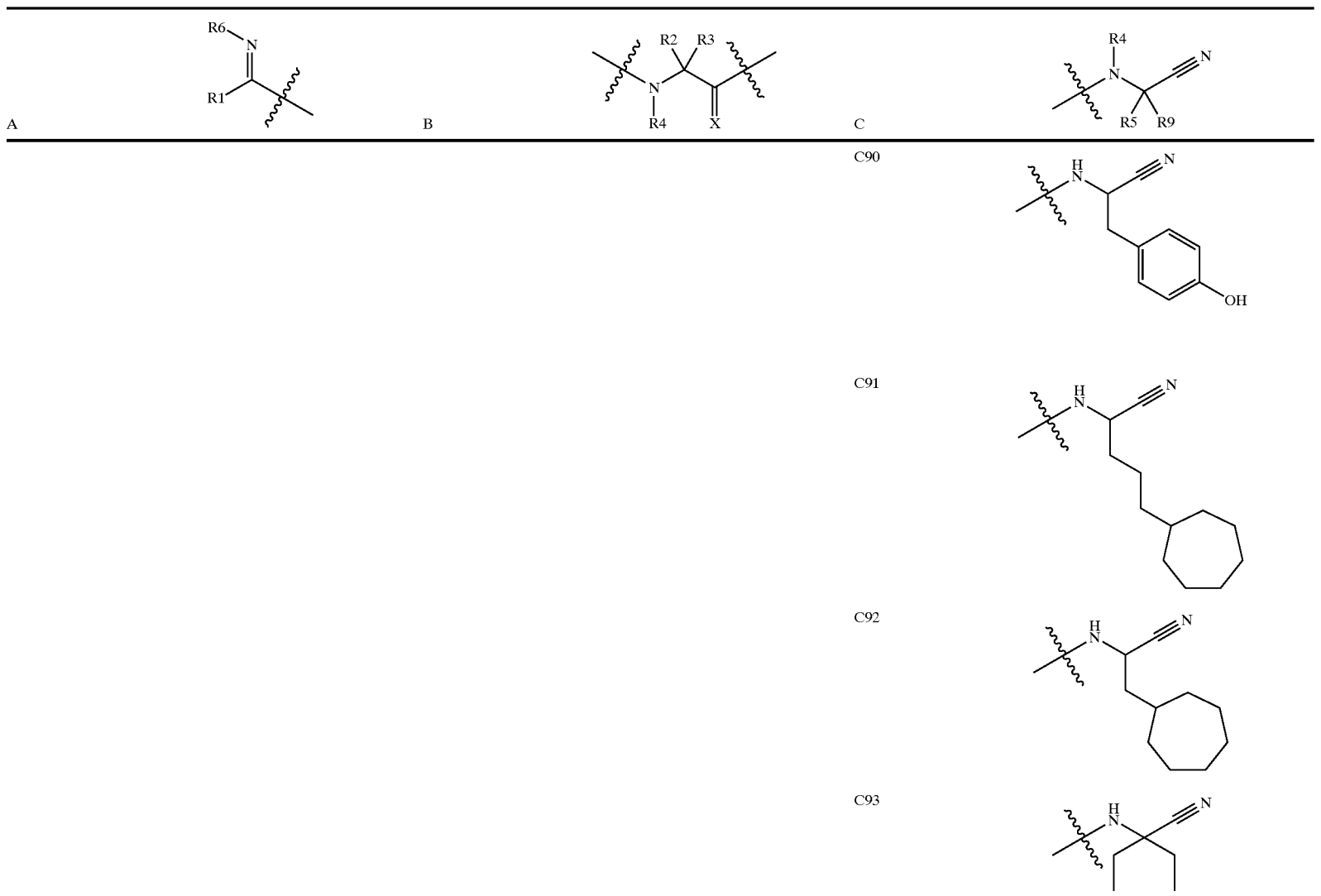

TABLE III-continued
| A | B | C | |
|---|---|---|---|
|  |  | 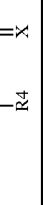 | C94 |
| | | 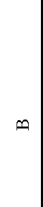 | C95 |
| | |  | C96 |
| | |  | C97 |
| | |  | C98 |

TABLE III-continued
| A | B | C | |
|---|---|---|---|
| 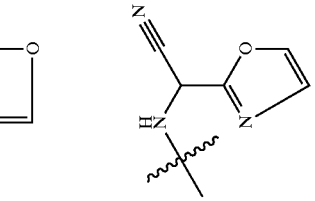 | 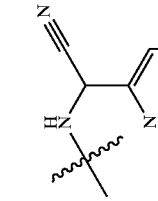 | 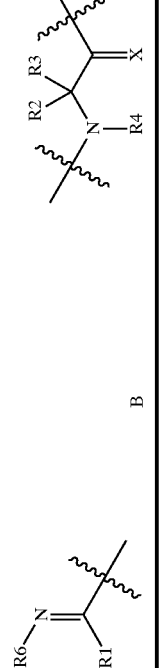 | C99 |
| | |  | C100 |
| | | 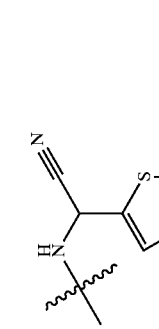 | C101 |
| | | 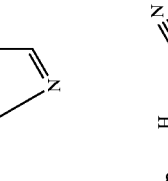 | C102 |

and the pharmaceutically acceptable derivates thereof.

For all the compounds disclosed in this application, in the event the nomenclature is in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

Some of the compounds can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formula (Ia/Ib). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs of compounds of the formula (I/Ib). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (Ia/Ib), thereby imparting the desired pharmacological effect.

In order that the invention herein described may be more fully understood, the following detailed description is set forth. As used herein, the following abbreviations are used:
BOC or t-BOC is tertiary-butoxycarbonyl;
t-Bu is tertiary-butyl;
DMF is dimethylformamide;
EtOAc is ethyl acetate;
THF is tetrahydrofuran;
Ar is argon;
EDC is 1-(3-dimethylaminopropyl)-3-ethylcarbodimide hydrochloride and
HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halo" refers to a halogen radical selected from fluoro, chloro, bromo or iodo.

Representative halo groups of the invention are fluoro, chloro and bromo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, benzoxazinyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The term "heterocycle" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1 dioxide, 1,2,6-thiadiazinanyl-1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless other-wise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

In all alkyl groups or carbon chains where one or more carbon atoms are optionally replaced by heteroatoms: O, S or N, it shall be understood that if N is not substituted then is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkyl, alkylene, alkoxyalkyl, alkoxycarbonylalkyl, alkylthioalkyl, alkylthiosulfonealkyl, alkylthiosulfonylalkyl, amino alkyl, mono or di-alkylaminoalkyl, mono or di-alkylamidoC1–5 alkyl.

As used herein above and throughout this application, "nitrogen" and "sulfur" include any oxidized form of nitrogen and sulfur and the quaternized form of any basic nitrogen.

General Synthetic Methods

The invention also provides processes of making the present novel compounds of formula (Ia) and (Ib). Compounds of the invention may be prepared by methods described below, those found in U.S. application Ser. Nos. 09/434,106, 09/627,869, 09/655,351 and 09/808,439 each incorporated herein in their entirety, and by methods known to those of ordinary skill in the art.

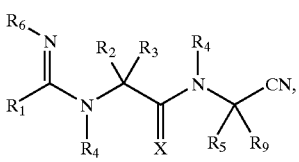
(Ia)

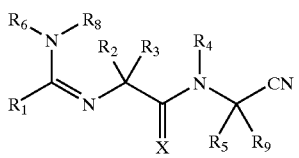
(Ib)

A key intermediate in the preparation of compounds of formula (Ia) and (Ib) is the dipeptide nitrile intermediate (III).

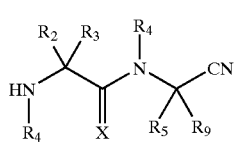
(III)

The synthesis of intermediates of formula (III) may be carried out by methods outlined below in Schemes I and II and methods described in the applications cited above.

Scheme I

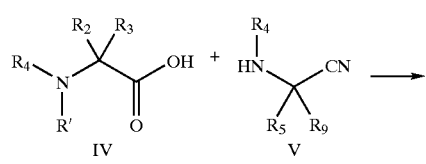

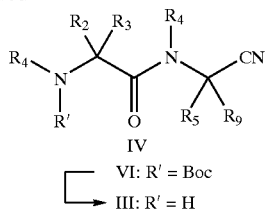
IV
VI: R' = Boc
III: R' = H

As illustrated in Scheme I, an amino acid bearing a suitable protecting group R' (IV), is reacted with an amino nitrile (V) under suitable coupling conditions. An example of a suitable protecting group is the 1-butoxycarbonyl (BOC) group. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. This is followed by deprotection to give amino acid nitrile III.

In a variation of the above method, one may couple IV with an amino amide (Va) and convert the product VIa to nitrile VI by dehydration, for example with cyanuric chloride in DMF

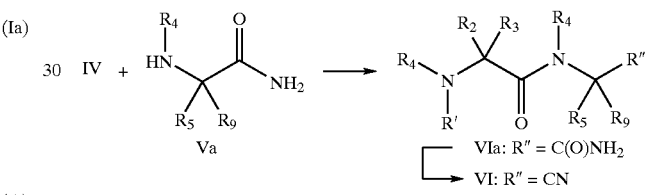
Va
VIa: R'' = C(O)NH$_2$
VI: R'' = CN

The intermediate aminonitrile (V) used in Scheme I above may be prepared as outlined in Scheme II.

Scheme II

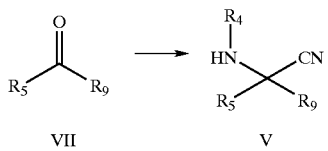
VII    V

In this method, a ketone bearing R$_5$ and R$_9$ (VII) is reacted with an a primary amine or an ammonium salt, such as ammonium chloride, and a cyanide salt, such as potassium cyanide or sodium cyanide, in a suitable solvent, such as water or a solution of ammonia in methanol, at about room temperature to reflux temperature.

Compounds having formula (Ia/Ib) may be prepared by Methods A–D, as illustrated in Schemes III–VI.

Scheme III (Method A)

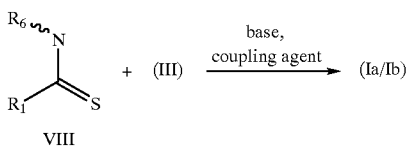

According to Method A, a dipeptide nitrile intermediate (III), or a basic salt thereof, is allowed to react with (VIII)

in the presence of a suitable coupling agent to provide the desired product (Ia/Ib). Suitable reaction conditions are known to those skilled in the art and some examples of suitable coupling agents include 2-chloro-1-methylpyridinium iodide (Yong, Y. F. et al., J. Org. Chem. 1997, 62, 1540), phosgene or triphosgene (Barton, D. H. et al., J. Chem. Soc. Perkin Trans. 1, 1982, 2085), alkyl halides (Brand, E. and Brand, F. C., Org. Synth., 1955, 3, 440) carbodiimides (Poss, M. A. et al., Tetrahedron Lett., 1992, 40, 5933) and mercury salts (Su, W., Synthetic Comm., 1996, 26, 407 and Wiggall, K. J. and Richardson, S. K. J., Heterocyclic Chem., 1995, 32, 867). Compounds having formulas (Ia) and (Ib) may also be prepared by Method B as illustrated in Scheme IV, where R is an alkyl or aryl group.

Scheme IV (Method B)

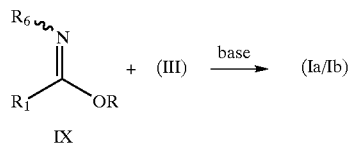

According to Method B a dipeptide nitrile intermediate (III), or a basic salt thereof, is allowed to react with IX, with or without an added base such as triethylamine, to provide the desired product (Ia/Ib). Suitable reaction conditions are known to those skilled in the art and examples of such amine additions may be found in the chemical literature, for example Haake, M. and Schummelfeder, B., Synthesis, 1991, 9, 753; Dauwe, C. and Buddrus, J., Synthesis 1995, 2, 171; Ried, W. and Piechaczek, D., Justus Liebigs Ann. Chem. 1966, 97, 696 and Dean, W. D. and Papadopoulos, E. P., J. Heterocyclic Chem., 1982, 19, 1117.

The intermediate IX is either commercially available or can be synthesized by methods known to those skilled in the art and described in the literature, for example Francesconi, I. et. al., J. Med. Chem. 1999, 42, 2260; Kurzer, F., Lawson, A., Org. Synth. 1963, 645, and Gutman, A. D. US 3984410, 1976.

In a similar reaction, intermediate X having a halogen or other suitable leaving group (X') may be used in place of intermediate IX, as illustrated in Method C, Scheme V.

Scheme V (Method C)

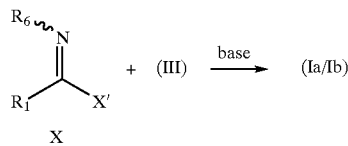

According to Method C, a dipeptide nitrile intermediate, or a basic salt thereof, is allowed to react with intermediate X, with or without an added base such as triethylamine, to provide the desired product (Ia/Ib). Procedures for accomplishing this reaction are known to those skilled in the art and described in the chemical literature (for example, Dunn, A. D., Org. Prep. Proceed. Int., 1998, 30, 709; Lindstroem, S. et al., Heterocycles, 1994, 38, 529; Katritzky, A. R. and Saczewski, F., Synthesis, 1990, 561; Hontz, A. C. and Wagner, E. C., Org Synth., 1963, IV, 383; Stephen, E. and Stephen, H., J. Chem. Soc., 1957, 490).

Compounds having formula (Ia/Ib) in which $R_1$ is an amine may also be prepared by Method D as illustrated in Scheme VI.

Scheme VI (Method D)

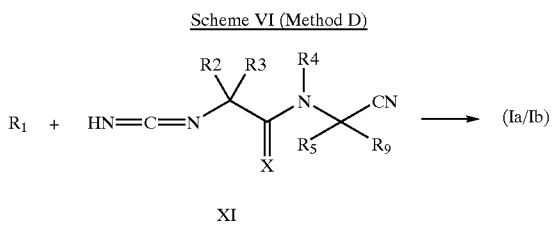

According to Method D, a carbodiimide (XI) derivative of (III) is allowed to react with an amine ($R_1$) to provide the desired guanidine (Ia/Ib) product. The conversion of amines to carbodiimides is known to those in the art and described in the literature (for example, Pri-Bar, I. and Schwartz, J., J. Chem. Soc. Chem. Commun., 1997, 347; Hirao, T. and Saegusa, T., J. Org. Chem., 1975, 40, 298). The reaction of carbodiimides with amine nucleophiles is also described in the literature (for example, Yoshiizumi, K. et al., Chem. Pharm. Bull., 1997, 45, 2005; Thomas, E. W. et al., J. Med. Chem., 1989, 32, 228; Lawson, A. and Tinkler, R. B., J. Chem. Soc. C, 1971, 1429.

In a modification of Method D, one may start with the thiourea XII (formed by reaction of the corresponding amine with an isothiocyanate $R_6N{=}C{=}S$) and then form the corresponding carbodiimide (XI) in situ by reaction with a suitable desulfurizing agent, such as $HgCl_2$, in a suitable solvent such as DMF or acetonitrile.

XII

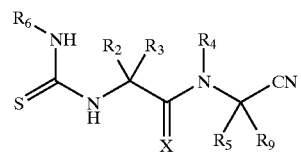

Compounds of formula (Ib), where $R_1$ is an amine may be prepared using a general procedure described by M. Haake and B. Schummfelder (Synthesis, 1991, 753). According to this procedure (Method E, Scheme VII), intermediate XIII bearing two suitable leaving groups Z, such as phenoxy groups, is reacted sequentially with amines $R_1$ and $R_6R_8NH$ in a suitable solvent such as methanol or isopropanol to provide the desired product. Reaction of the first amine may be carried out at about room temperature and reaction of the second amine is preferentially carried out with heating at the reflux temperature of the solvent. If XIII is allowed to react with a bifunctional nucleophile intermediate XIV, where Y is a nucleophilic heteroatom such as N, O or S, one may obtain the product of formula (Ib) where $R_1$ and $R_6$ form a heterocyclic ring. Intermediate XIII may be prepared by reaction of III ($R_4$=H) with dichlorodiphenoxymethane, which in turn, may be prepared by heating diphenyl carbonate with $PCl_5$ (R. L. Webb and C. S. Labow, J. Het. Chem., 1982, 1205).

Scheme VII (Method E)

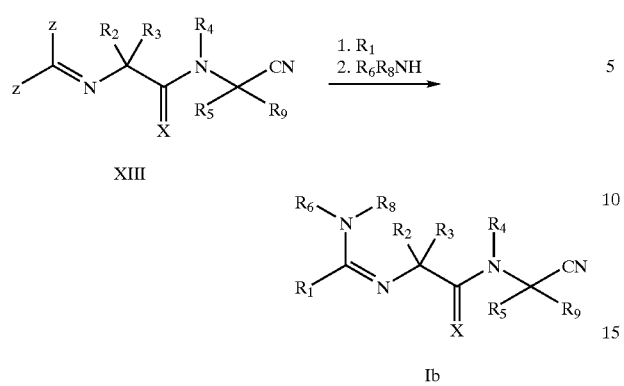

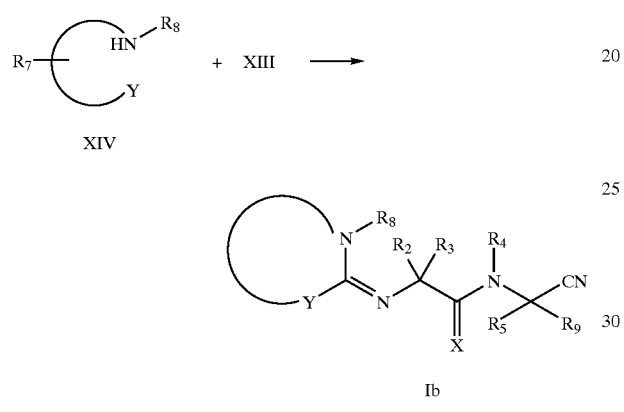

In order that this invention be more fully understood, the following example is set forth. This example is for the purpose of illustrating embodiments of this invention, and is not to be construed as limiting the scope of the invention in any way.

The example which follows is illustrative and, as recognized by one skilled in the art, particular reagents or conditions could be modified as needed for individual compounds. Starting materials used in the scheme below are either commercially available or easily prepared from commercially available materials by those skilled in the art.

EXAMPLE 1
{[1-(1-Cyano-cyclopentylcarbamoyl)-3,3-dimethyl-butylamino]-morpholin-4-yl-methylene}-carbamic acid 1-propyl-piperidin-4-yl Ester

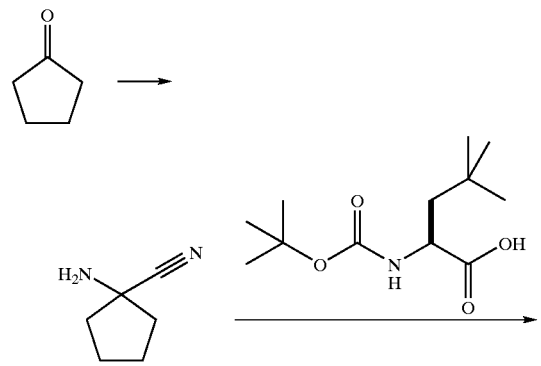

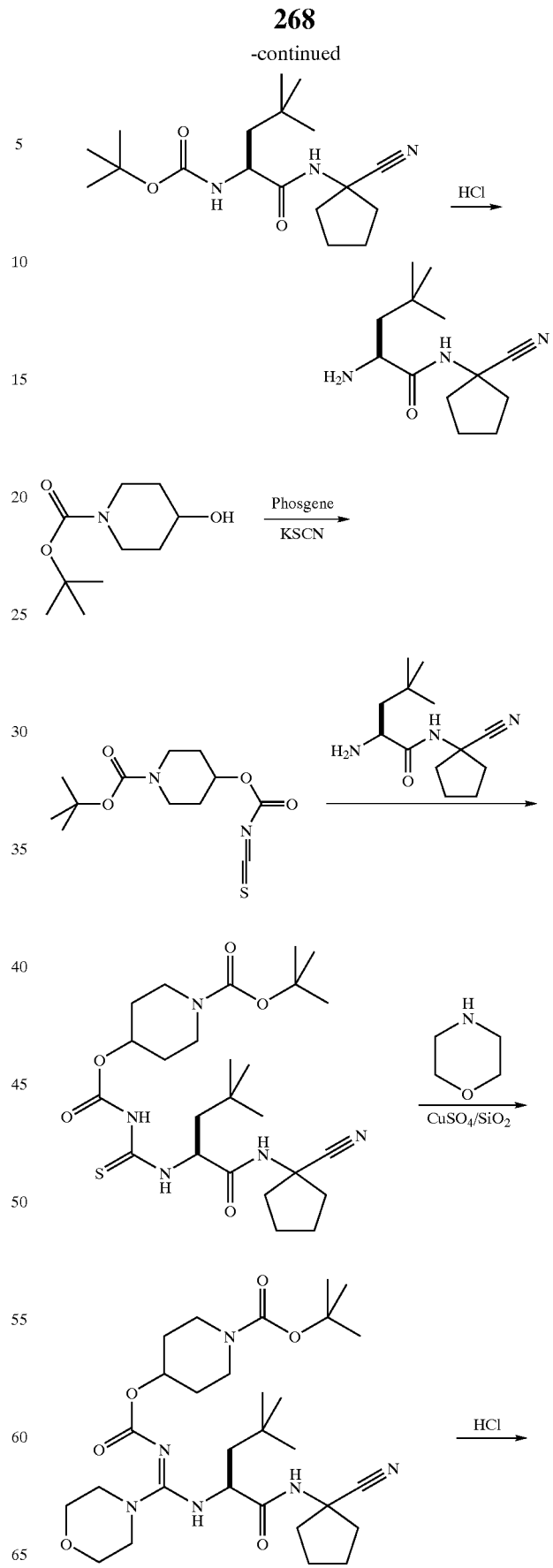

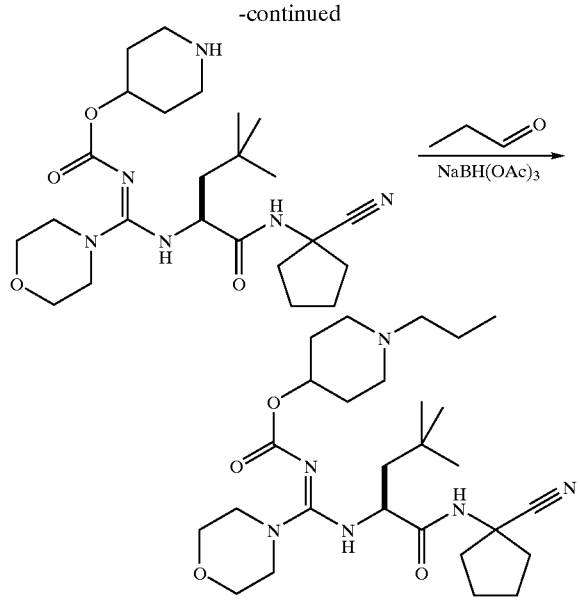

A mixture of cyclopentanone (15.6 mL, 0.176 mol), magnesium sulfate (31.9 g, 0.264 mol), sodium cyanide (9.5 g, 0.194 mol) and ammonium chloride (4.7 g, 0.088 mmol) in 2.0 M NH₃/CH₃OH (300 mL) was heated at 60° C. for 6 h before it was filtered through silica gel. The filtrate was concentrated and stirred with magnesium sulfate in dichloromethane for 6 h. It was filtered, concentrated and dried in vacuo to give 1-amino-cyclopentanecarbonitrile (17 g, 87.7%).

To a stirred solution of 2-tert-butoxycarbonylamino-4,4-dimethyl-pentanoic acid (5 g, 20.3 mmol) and N-methyl morpholine (4.46 mL, 40.6 mmol) in THF (40 mL) at 0° C. was added isobutyl chloroformate (2.64 mL, 20.3 mmol) and, after 10 min, the solution of 1-amino-cyclopentanecarbonitrile (3.35 g, 30.5 mmol) in THF (40 mL). The mixture was allowed to warm to room temperature and stirred overnight. It was diluted with water, extracted with dichloromethane, washed with brine, dried (sodium sulfate) and concentrated to give the crude product. Chromatography on silica gel (dichloromethane:MeOH=30:1) gave [1-(1-cyano-cyclopentylcarbamoyl)-3,3-dimethyl-butyl]-carbamic acid tert-butyl ester (6.15 g, 89.6%).

The above ester (6.15 g, 18.2 mmol) was added to 4N HCl in 1,4-dioxane (40 mL) and stirred for 10 min. It was then diluted with ether. Filtration gave 2-amino-4,4-dimethyl-pentanoic acid (1-cyano-cyclopentyl)-amide hydrochloride salt (5.6 g).

To a cold solution of phosgene (1.89 M in toluene, 47.3 mL, 89.4 mmol) was added a solution of tert-butyl 4-hydroxy-1-piperidinecarboxylate (15 g, 74.5 mmol) in THF (100 mL). The mixture was allowed to warm to room temperature and stirred overnight. The solvent was removed under vacuum and to the residue was added acetonitrile (100 mL) and sodium thiocyanate (7.2 g, 74.5 mmol). This mixture was stirred overnight, the insoluble solid was removed by filtration and the filtrate was used as a stock solution of the isothiocyanatoformate (~0.745 mmol/mL).

2-Amino-4,4-dimethyl-pentanoic acid (1-cyano-cyclopentyl)-amide hydrochloride salt (1.38 g, ~5.0 mmol) was suspended in 10 mL of THF. Triethylamine (1.42 mL, 10 mL) was added. To the flask was next added the above stock solution of isothiocyanatoformate (34 mL). The resulting mixture was stirred at rt for 3 h. The solvent was removed in vacuo. The residue was purified by flash chromatography on silica gel eluting with 10% EtOAc in dichloromethane to give the thiourea (1.02 g, 39%).

The above thiourea (839 mg, 1.6 mmol) and morpholine (0.42 mL, 4.8 mmol) were dissolved in 10 mL of THF. Copper sulfate on silica gel (1.00 g, 2.5 mmol) was added followed by 0.22 mL of triethylamine. This mixture was stirred at 50° C. for 5 h. After cooling to room temperature, the solid was removed by filtration and washed with acetonitrile. The filtrate was concentrated under reduced pressure and then purified by flash chromatography on silica gel, eluting with a mixture of methylene chloride and MeOH (10:1) to give 4-{[1-(1-cyano-cyclopentylcarbamoyl)-3,3-dimethyl-butylamino]-morpholin-4-yl-methylenecarbamoyloxy}-piperidine-1-carboxylic acid tert-butyl ester (653 mg, 70%).

To a stirred solution of the above tert-butyl ester (653 mg, 1.13 mmol) in 1,4-dioxane (10 mL) was added HCl (4N in 1,4-dioxane, 10 mL) and the mixture was stirred for 30 min before the solvent was removed under vacuum. The residue was dried in vacuo to give {[1-(1-cyano-cyclopentylcarbamoyl)-3,3-dimethyl-butylamino]-morpholin-4-yl-methylene}-carbamic acid piperidin-4-yl ester hydrochloride salt (738 mg). Then to a mixture of the hydrochloride salt (246 mg, ~0.37 mmol) in THF (20 mL) was added propionaldehyde (71 µl, 0.96 mmol) and, 20 min later, sodium triacetoxyborohydride (305 mg, 1.44 mmol). The mixture was stirred for 2 h before it was diluted with water, extracted with dichloromethane, washed with brine, dried (sodium sulfate) and concentrated to give the crude product. Chromatography on silica gel (dichloromethane:methanol=10:1) gave the title compound (10 mg, 5%).

EXAMPLE 2

Synthesis of (S)-4,4-Dimethyl-2-[2-oxo-2,3-dihydro-benzo[e][1,3]oxazin-4Z)-ylideneamino]-pentanoic Acid (1-cyano-cyclopropyl)-amide

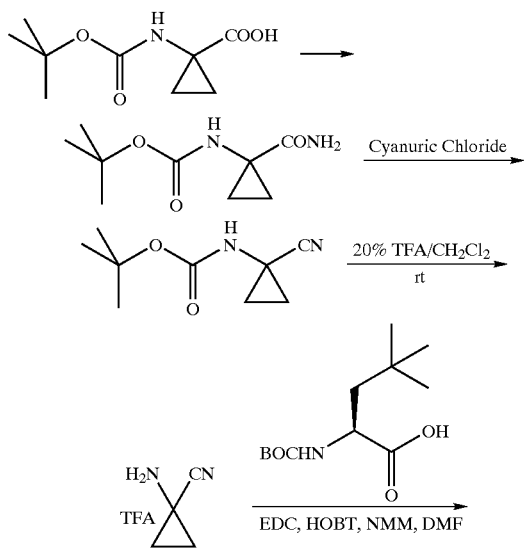

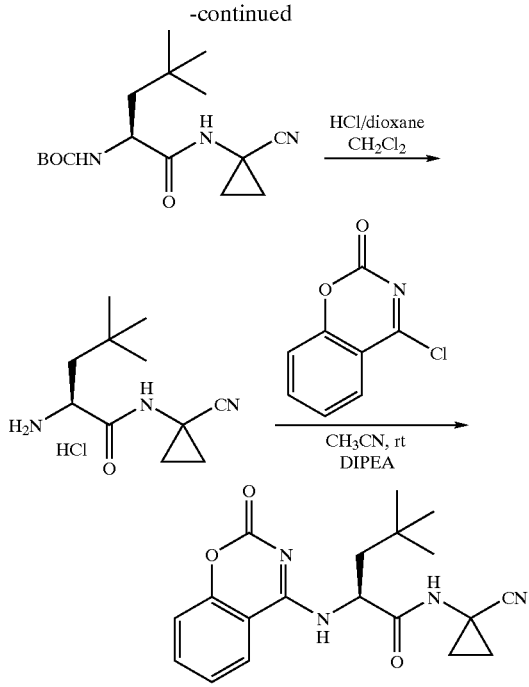

To a stirred solution of Boc-1-aminocyclopropane-1-carboxylic acid (25 g, 124 mmol) and triethylamine (19 mL, 1.1 equivalent) in THF (200 mL) at −10° C. ethylchloroformate (13 mL, 1.1 equivalent) was added slowly. The mixture was stirred at this temperature for 20 min before a solution of ammonia in 1,4-dioxane (0.5 M, 300 mL) was added. It was allowed to warm to room temperature and stirred overnight. It was concentrated, diluted with water, extracted with dichloromethane, washed with brine, dried (sodium sulfate), concentrated again and dried to give (1-carbamoyl-cyclopropyl)-carbamic acid tert-butyl ester (18 g, 72.5%).

To a stirred solution of (1-carbamoyl-cyclopropyl)-carbamic acid tert-butyl ester (5.7 g, 28.4 mmol) in DMF (50 mL) was added cyanuric chloride (2.6 g, 14.2 mmol) and it was stirred at room temperature for 1 h before it was diluted with water (400 mL). The product precipitated and filtration gave (1-cyano-cyclopropyl)-carbamic acid tert-butyl ester (2.79 g, 53.9%).

To (1-cyano-cyclopropyl)-carbamic acid tert-butyl ester (1.0 g, 5.5 mmol) in dichloromethane (5 mL) was added 10 mL of 20% trifluoroacetic acid in dichloromethane. The reaction was stirred for 10 min at room temperature and the solvents removed on an evaporator. Hexane was added to the residue and evaporated. The crude deprotected amine was used for the next step. MS=197 (M+TFA).

To (S)-2-tert-butoxycarbonylamino-4,4-dimethyl-pentanoic acid (1.0 g, 4.08 mmol) in dry DMF (20 mL), at 0° C., was added EDC (1.27 g, 6.6 mmol) and HOBT (0.9 g, 6.6 mmol). The reaction was stirred for 30 min at 0° C. and to this was added the above 1-amino-cyclopropanecarbonitrile-TFA salt (1.0 g, 5.1 mmol) and N-methyl morpholine 2(1 (1.34 g, 13.26 mmol). The reaction was stirred at 0° C. for 1 h and at room temperature overnight. Solvent was removed on an evaporator and the residue was extracted with ethyl acetate. The organic fraction was washed with sat. sodium bicarbonate, water, brine and dried over anhydrous sodium sulfate. Solvent was evaporated and the crude product was purified by flash column chromatography using silica gel and ethyl acetate/hexane 1:1 to afford 700 mg (55%) of the desired product.

To the above [(S)-1-(1-cyano-cyclopropylcarbamoyl)-3,3-dimethyl-butyl]-carbamic acid tert-butyl ester (0.7 g, 2.26 mmol) in dichloromethane (3 mL) at 0° C., was added 4M HCl/dioxane. The reaction was stirred at room temperature for 30 min and the solvent removed. Diethyl ether was added to the residue and the solvent removed on an evaporator to afford 550 mg of the deprotected amine. This was used as is for the next step.

To the above (S)-2-amino-4,4-dimethyl-pentanoic acid (1-cyano-cyclopropyl)-amide hydrochloride (0.28 g, 1.14 mmol) in acetonitrile (10 mL) at 0° C., was added diisopropyl ethylamine (0.46 mL, 2.26 mmol) and the reaction stirred for 20 min. To this was then added 4-chloro-benzo[e][1,3]oxazin-2-one (that was prepared by treating 4a,8a-dihydro-benzo[e][1,3]oxazine-2,4-dione with phosphorus pentachloride in phosphorus oxychloride at reflux for 3 h followed by removing solvent) and the reaction was stirred at room temperature overnight. Evaporation of the solvent, extraction with ethyl acetate, followed by washing with saturated sodium bicarbonate and water gave the crude product. This was purified by flash column chromatography on silica gel using ethyl acetate to give 50 mg (12.45%) of the title compound MS=355 (M+1).

The following examples are illustrative of methods used for preparation of unnatural amino acids used as intermediates in the preparation of compounds of the invention by procedures described in the General Synthetic Methods section.

EXAMPLE 3

2-tert-Butoxycarbonylamino-4,4,5-trimethyl-hexanoic Acid

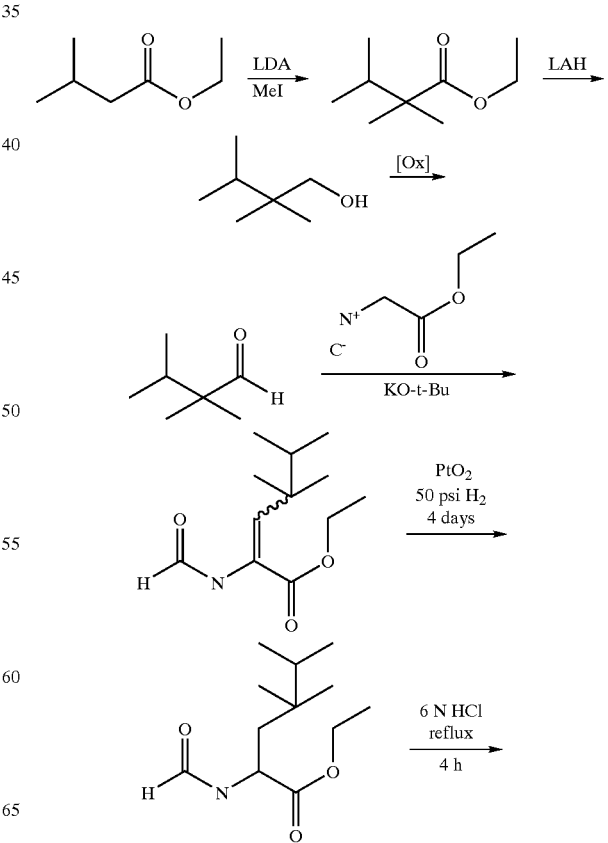

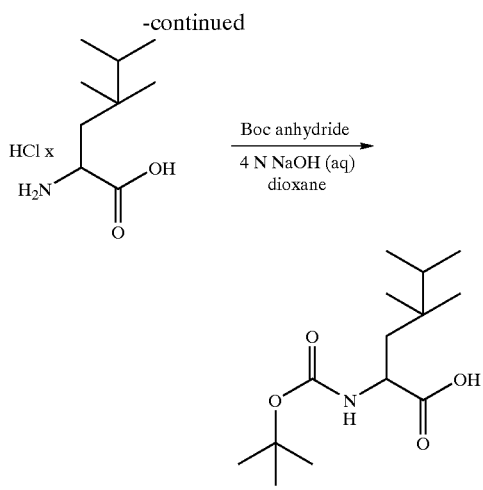

Lithium diisopropylamide (1.5 M solution in cyclohexane/THF/ethylbenzene) (113 mL, 169 mmol, 1.1 equiv) was syringed into a 1000 mL round-bottom flask under a blanket of Ar. Dry THF (150 mL) was added and the mixture was cooled to −78° C. with a dry-ice/acetone bath. 3-Methyl-butanoic acid ethyl ester (20 g, 23 mL, 154 mmol, 1.0 equiv) was added dropwise from a syringe over a 10 min period followed by stirring at −78° C. for 1 h. Methyl iodide (10.5 mL, 169 mmol, 1.1 equiv) was added dropwise from a syringe over a 10 min period and the creamy mixture was stirred for 1 h at −78° C., resulting in a very thick mixture. The dry-ice bath was removed and replaced with an ice bath at 0° C. Another 150 mL of dry THF was added followed by another addition of LDA (I 13 mL, 169 mmol, 1.1 equiv). The resulting mixture was stirred for 10 min and then the flask was re-immersed in a dry-ice/acetone bath. Stirring was continued for another 50 min and then methyl iodide was added dropwise (10.5 mL, 169 mmol, 1.1 equiv) and the dry-ice/acetone bath was removed and the resulting mixture was stirred at ambient temperature for 14 h. The reaction mixture was quenched with 3 mL of conc. HCl and 2 N HCl was added until the pH was adjusted to <1. The mixture was further diluted with 150 mL water and 500 mL Et$_2$O. The layers were separated and the organic layer was washed with 1×100 mL 2 N HCl, 1×100 mL saturated NaHCO$_3$, and 1×200 mL brine. The organic layer was dried over Na$_2$SO$_4$ and then concentrated in vacuo to provide 2,2,3-trimethylbutanoic acid ethyl ester as an orange oil mixed with ethyl benzene (36.4 g of which 22.1 g was product by NMR). The mixture was used without further purification.

A 500 mL round-bottom flask equipped with a stir bar was flushed with Ar and charged with 50 mL dry THF and a 1 M solution of LAH in Et$_2$O (87.5 mL, 87.5 mmol, 0.625 equiv). The solution was cooled to 0° C. with an ice bath and the above ethyl ester (22.1 g, 140 mmol, 1.0 equiv) (approximately a 50% solution in ethylbenzene) was added dropwise at such a rate that the solution did not reflux (required 50 min). After addition of the ester, the reaction was stirred at 0° C. for 2 h and then at ambient temperature for 14 h. The reaction solution was re-cooled to 0° C. and carefully quenched by addition of EtOAc. 1 N NaOH was added until a granular precipitate formed (7.5 mL). The mixture was filtered on a pad of diatomaceous earth which was then washed 3×100 mL Et$_2$O. The organics were combined and dried over Na$_2$SO$_4$. The solution was decanted and concentrated in vacuo to yield 2,2,3-trimethylbutanol as a nearly colorless oil (11.7 g of alcohol in 15.4 g of a mix with ethylbenzene). The crude product was used without further purification.

A 1000 mL round-bottom-flask was equipped with a stir bar, flushed with Ar and charged with 300 mL dry CH$_2$Cl$_2$ and oxalyl chloride (13.2 mL, 151 mmol, 1.5 equiv). The solution was cooled to −78° C. with a dry-ice/acetone bath. Dry DMSO (21.5 mL, 302 mmol, 3.0 equiv) was added dropwise over a 30 min period (vigorous gas evolution). The above alcohol (11.7 g, 100 mmol, 1.0 equiv) was added (with residual ethylbenzene) over a 10 min period. The resulting solution was stirred for 90 min. Triethylamine (56 mL, 403 mmol, 4.0 equiv) was added over 5 min and the cold-bath was removed. The resulting creamy white mixture was stirred at room temperature over 1.5 h. The reaction mixture was carefully diluted with 200 mL water (more gas evolution). Layers were separated and the organic phase was washed with 2 N HCl (1×100 mL) and brine (1×100 mL). The organic layer was dried over Na$_2$SO$_4$, decanted and concentrated in vacuo. The crude aldehyde was fractionally distilled through a 4 inch Vigoreux column at 57–67° C. at 15 mm Hg to provide the 2,2,3-trimethyl-butanal (9.1 g) as a colorless oil.

A clean and dry 250 mL round-bottom flask was equipped with a stir bar and flushed with Ar. Dry THF was added (40 mL) followed by addition of a 1.0 M solution of KO-t-Bu (32.2 mL, 32.2 mmol, 1.05 equiv). The solution was cooled to −78° C. in a dry-ice/acetone bath. Ethyl isocyanoacetate (3.35 mL, 30.7 mmol, 1.0 equiv) was added dropwise over a 10 min period. The resulting mixture was stirred an additional 5 min followed by addition, via syringe, of 2,2,3-trimethyl-butanal (3.5 g, 30.7 mmol, 1.0 equiv). The cold-bath was removed and resulting mixture was stirred at room temperature for 1 h. The reaction mixture was diluted by addition of a mix of 125 mL Et$_2$O, 20 g ice, 2 mL AcOH. After the ice melted, 50 mL of water was added and the layers were mixed and separated. The organic layer was washed with 1×50 mL sat. NaHCO$_3$ and dried over Na$_2$SO$_4$. The organic layer was decanted and concentrated. The crude enamide was purified by flash chromatography on silica gel using CH$_2$Cl$_2$ to 4% MeOH in CH$_2$Cl$_2$ to provide 2-formylamino-4,4,5-trimethyl-hex-2-enoic acid ethyl ester as a thick oil (4.54 g); MS: 228 (M+1).

The above ethyl ester (4.54 g, 20 mmol, 1.0 equiv) was dissolved in 35 mL of MeOH in a Parr bottle followed by addition of PtO$_2$ (1 g, 4.4 mmol, 0.22 equiv). The mixture was shaken on a Parr hydrogenation apparatus for 4 days at which time MS showed consumption of the starting material; MS: 230 (M+1), 216 (M+1 of methyl ester). The liquid was carefully decanted and the Pt was washed three times with 20 mL MeOH followed each time by decantation, being careful not to allow the Pt to dry (if allowed to dry, the Pt may ignite). The MeOH solutions were combined and concentrated to a thick oil that was suspended in 25 mL of 6 N HCl and the mixture was refluxed for 4 h during which time 5 mL of conc. HCl was added at the end of each of the first 3 h. The mixture was cooled and the water and excess HCl were removed on a rotovap at a bath temperature of 70° C. After about 50% concentration, a flaky crystalline solid formed. The mixture was cooled to 0° C. and the precipitate was collected by filtration. The filtrate was again concentrated by about 50% and cooled again to 0° C. to provide a second crop of crystals. The crystals were combined and dried under high vacuum to provide 2-amino-4,4,5-trimethyl-hexanoic acid hydrochloride as an off-white crystalline solid (2.32 g); MS: 174 (M-Cl+1).

The above amino acid salt (2.32 g, 11.1 mmol, 1.0 equiv) was dissolved in 100 mL of 50/50 dioxane/4 N NaOH. The solution was cooled to 0° C. and Boc anhydride (3.6 g, 16.6 mmol, 1.5 equiv) was added. The cold-bath was removed and the reaction stirred at ambient temperature for 16 h. The pH was carefully adjusted to 2 with conc. HCl, and the product was extracted with 3×100 mL CH$_2$Cl$_2$. The organic layers were combined and dried over Na$_2$SO$_4$. The solution was decanted and concentrated using 100 mL of hexane as a chaser to provide a thick glass, which was triturated with 100 mL of hexane. After vigorous stirring for 4 h, a waxy solid resulted which was filtered and dried in air to provide the title compound (1.42 g); MS: 272 (M−H).

The following Boc-protected amino acids were prepared in a manner identical to this method from the commercially available esters:

2-tert-Butoxycarbonylamino-4,4-dimethyl-hexanoic acid

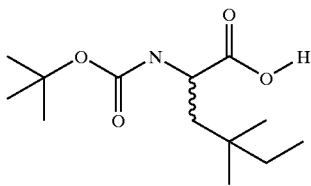

2-tert-Butoxycarbonylamino-4,4,5,5-tetramethyl-hexanoic acid

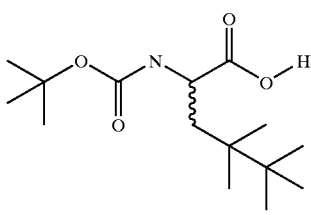

2-tert-Butoxycarbonylamino-4-cyclohexyl-4-methyl-pentanoic acid

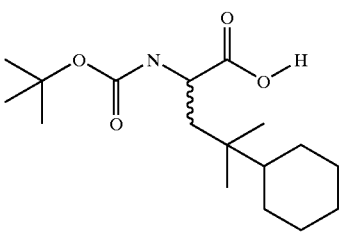

In addition, the following Boc-protected amino acids may be prepared by an appripriate modification of this procedure:

2-tert-Butoxycarbonylamino-4-methyl-4-phenyl-pentanoic acid

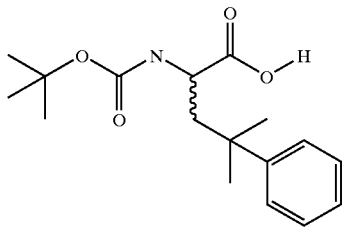

2-tert-Butoxycarbonylamino-4-cyclopropyl-4-methyl-pentanoic acid

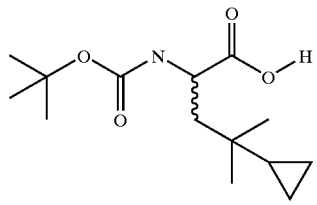

2-tert-Butoxycarbonylamino-4,4,5,5-tetramethyl-heptanoic acid

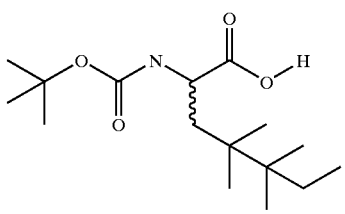

2-tert-Butoxycarbonylamino-4-cyclobutyl-4-methyl-pentanoic acid

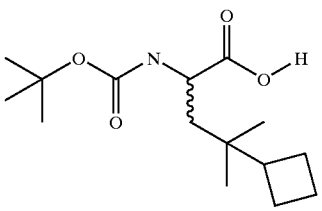

EXAMPLE 4

2-tert-Butoxycarbonylamino-5,5-dimethyl-hexanoic Acid

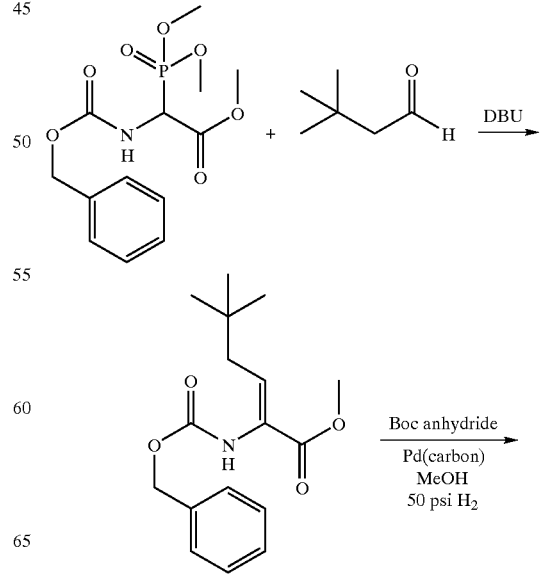

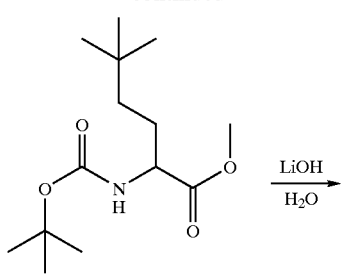

N-(Benzyloxycarbonyl)-α-phosphonoglycine trimethyl ester (2 g, 6.0 mmol, 1.0 equiv) was dissolved in dry THF (20 mL). tert-Butylacetaldehyde (0.758 mL, 6.0 mmol, 1.0 equiv) and DBU (0.903 mL, 6.0 mmol, 1.0 equiv) were added and the reaction mixture was stirred for 16 h. The solution was diluted with 100 mL of $CH_2Cl_2$ and washed with water (1×50 mL), and brine (1×50 mL). The organic layer was dried over $Na_2SO_4$, decanted and concentrated in vacuo to provide 2-benzyloxycarbonylamino-5,5-dimethyl-hex-2-enoic acid methyl ester as a thick oil (1.73 g, 94%) which was used without further purification; MS: 306 (M+1).

The above ester (1.73 g, 5.67 mmol, 1.0 equiv) was dissolved in a Parr bottle with Boc anhydride (1.36 g, 6.23 mmol, 1.0 equiv) and MeOH (35 mL). Pd on carbon (Degussa type) (0.5 g) was added. The mixture was shaken under 50 psi $H_2$ for 16 h. The mixture was filtered through diatomaceous earth followed by washing of the diatomaceous earth with 3×50 mL MeOH. The organics were combined and concentrated to provide 2-tert-butoxycarbonylamino-5,5-dimethyl-hexanoic acid methyl ester as a very thick oil which was used without further purification.

The above ester (1.31 g, 4.79 mmol, 1.0 equiv) was dissolved in 50 mL of MeOH. 1 N LiOH (50 mL) was added and the mixture was stirred 16 h. Concentrated HCl was added carefully until the pH approached 2 at which time a bright white solid precipitated. The solid was collected by filtration and washed 2×20 mL water and dried under vacuum to provide the title compound (1.05 g, 85%); MS: 258 (M−1).

The procedure described in this example may be used with any commercially available aldehyde to prepare the corresponding Boc-protected amino acid as outlined below.

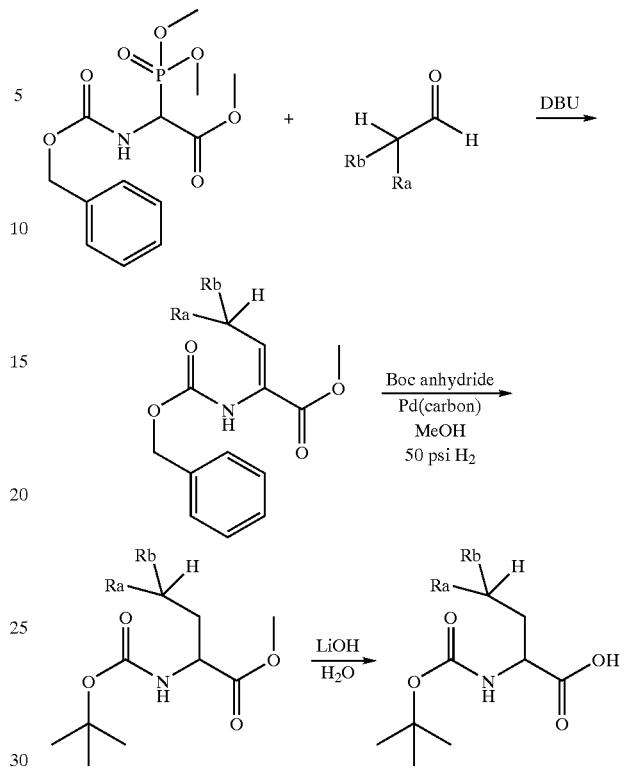

Additionally, many aldehydes may be prepared from the corresponding commercially available esters using the procedure described in Example 5.

EXAMPLE 5
4-Formyl-piperidine-1-carboxylic Acid Ethyl Ester

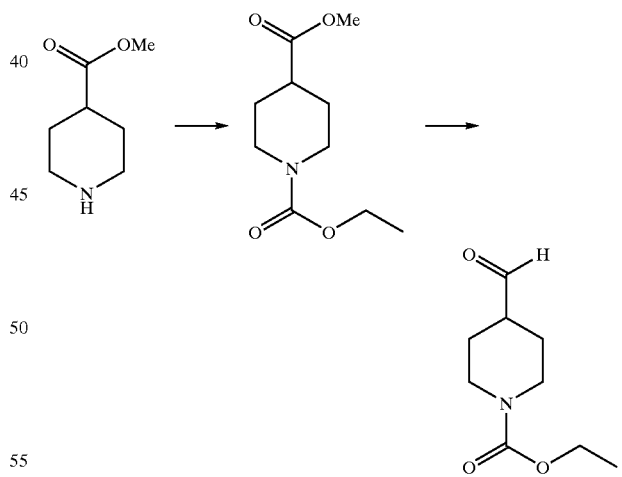

Methyl isonipecotate (10 g, 69.9 mmol, 1.0 equiv) was dissolved in 50 mL of THF and 250 mL of saturated aqueous bicarbonate. Ethyl choloformate (9.1 g, 83.9 mmol, 1.2 equiv) was added dropwise and the resulting solution was stirred for 2 h. The reaction mixture was diluted with 250 mL diethyl ether and the layers were separated. The organic layer was washed with brine and dried over $Na_2SO_4$. The liquid was decanted and concentrated in vacuo to yield piperidine-1,4-dicarboxylic acid 1-ethyl ester 4-methyl ester as a pink liquid (12.8 g) which was used without further purification.

The above ester (12.8 g, 59.5 mmol, 1.0 equiv) was dissolved in 50 mL of dry CH$_2$Cl$_2$ under Ar and cooled to −78° C. A 1 Molar solution of DIBAL-H in CH$_2$Cl$_2$ (149 mL, 149 mmol, 2.5 equiv) was added dropwise over a 30 min period. The cold bath was removed and the reaction solution allowed to warm to ambient temperature. At this time EtOAc (10 mL) was added dropwise to quench the excess DIBAL-H. 100 mL of 1H HCl (aq) was added dropwise over a 30 min period with rapid stirring. The resulting mixture was filtered on a pad of diatomaceous earth and the filtrate was dried over Na$_2$SO$_4$, decanted and concentrated to yield 4-hydroxymethyl-piperidine-1-carboxylic acid ethyl ester as a nearly colorless oil that was used without further purification.

The above alcohol (7.5 g, 40.0 mmol, 1.0 equiv) was dissolved in 500 mL of CH$_2$Cl$_2$. Pyridinium chlorochromate (12.96 g, 60.1 mmol, 1.5 equiv) was added and resulting mixture was stirred for 16 h. The dark liquid was decanted and the solvent was removed in vacuo. The residue was triturated with 500 mL of diethyl ether and the mixture was filtered. The filtrate was washed with 150 mL of 1 N HCl and dried over Na$_2$SO$_4$. The liquid was decanted and concentrated by rotary evaporation to yield 4-formyl-piperidine-1-carboxylic acid ethyl ester as a light brown oil (6.1 g).

The following example illustrates how this aldehyde may be used in a manner analogous to that described in Example 4.

EXAMPLE 6
4-(2-tert-Butoxycarbonylamino-2-carboxy-ethyl)-piperidine-1-carboxylic Acid Ethyl Ester.

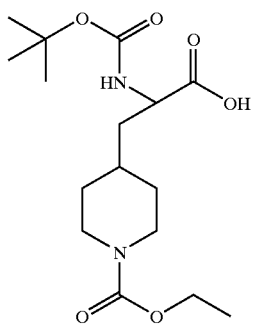

N-(Benzyloxycarbonyl)-α-phosphonoglycine trimethyl ester (1.0 equiv) is dissolved in dry THF. The above aldehyde (1.0 equiv) and DBU (1.0 equiv) are added and the reaction mixture is stirred for 16 h. The solution is diluted with CH$_2$Cl$_2$ and washed with water and brine. The organic layer is dried over Na$_2$SO$_4$, decanted and concentrated in vacuo to provide 4-(benzyloxycarbonylamino-2-carbomethoxy-ethyl)-piperidine-1-carboxylic acid ethyl ester.

The above ester (1.0 equiv) is dissolved in a Parr bottle with Boc anhydride (1.0 equiv) and MeOH. Pd on carbon (Degussa type) (0.1 equiv) is added. The mixture is shaken under 50 psi H$_2$. The mixture is filtered on diatomaceous earth followed by washing of the diatomaceous earth with MeOH. The organics are combined and concentrated to provide 4-(2-tert-Butoxycarbonylamino-2-carbomethoxy-ethyl)-piperidine-1-carboxylic acid ethyl ester.

The above ester (1.0 equiv) is dissolved in a minimum amount of MeOH. 1 N LiOH (3.0 equiv hydroxide) is added and the mixture is stirred. The aqueous layer is washed with diethyl ether and then acidified to pH=2. The product is extracted with 2 washes of diethyl ether and the organics are combined and concentrated after drying over Na$_2$SO$_4$.

EXAMPLE 7
(2S)-2-(tert-Butoxyoxycarbonylamino)-5,5-dimethyl-heptanoic Acid.

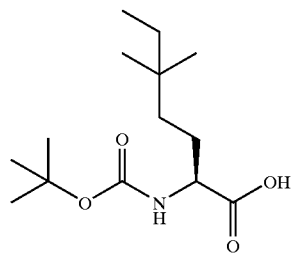

Lithium aluminum hydride (8.0 g, 211 mmol, 1.0 equiv) was placed in a 500 mL round-bottom flask under Ar. Dry THF (200 mL) was added and the mixture was cooled to −78° C. 3,3-Dimethyl-pent-4-en-oic acid methyl ester (30 g, 211 mmol, 1.0 equiv) was added dropwise over a 30 min period via a syringe. The cold bath was removed and replaced with an ice-water bath at 0° C. Stirring was continued for 2 h. The excess LAH was quenched by addition of EtOAc dropwise. 1 N NaOH was added dropwise until a granular precipitate formed (approximately 15 mL). The reaction mixture was filtered on a pad of diatomaceous earth. The filtrate was dried over MgSO$_4$, filtered and concentrated by rotary evaporation to yield 3,3-dimethyl-pent-4-en-ol as a colorless oil (20.2 g, 85%) which was used without further purification.

3,3-Dimethyl-pent-4-en-ol (20.2 g, 177 mmol, 1.0 equiv) was dissolved in 500 mL of CH$_2$Cl$_2$. Solid pyridinium chlorochromate (57.2 g, 266 mmol, 1.5 equiv) was added and the resulting mixture was stirred 16 h. The liquid was decanted into a 1000 mL RBF and the black tar was washed with CH$_2$Cl$_2$ (2×100 mL). The combined liquids were concentrated on the rotovap at a bath temperature <20° C. (the aldehyde is quite volatile). The resulting paste was triturated with 500 mL of hexane and the mixture filtered on a frit. The filtrate was diluted with 150 mL Et$_2$O, washed with 200 mL of 1 N aqueous HCl, dried over Na$_2$SO$_4$, decanted and concentrated to yield 3,3-dimethyl-pent-4-en-al as a light beige liquid (11.6 g, 56%) that was used without further purification.

N-(Benzyloxycarbonyl)-α-phosphonoglycine trimethyl ester (34.3 g, 103 mmol, 1.0 equiv) was dissolved in dry THF (250 mL) and the solution was cooled to 0° C. 3,3-Dimethyl-pent-4-en-al (11.6 g, 103 mmol, 1.0 equiv) and DBU (15.5 mL, 103 mmol, 1.0 equiv) were added and the reaction mixture was stirred for 16 h. The solution was diluted with 500 mL of CH$_2$Cl$_2$ and washed with 1×150 mL water, and 1×150 mL brine. The organic layer was dried over Na$_2$SO$_4$, decanted and concentrated in vacuo to provide 2-benzyloxycarbonylamino-5,5-dimethyl-hept-2,6-dienoic acid methyl ester as a thick oil (31 g, 95% crude). The enamide is purified by flash chromatography on silica using hexanes/EtOAc as mobile phase to yield 2-benzyloxyearbonylamino-5,5-dimethyl-hept-2,6-dienoic acid methyl ester as a thick oil that solidifies on standing.

The above ester may be converted to the title compound by catalytic reduction followed by hydrolysis as described in Example 4.

Additionally, Boc-protected amino acids of the formula below may be prepared as outlined for in the following scheme:

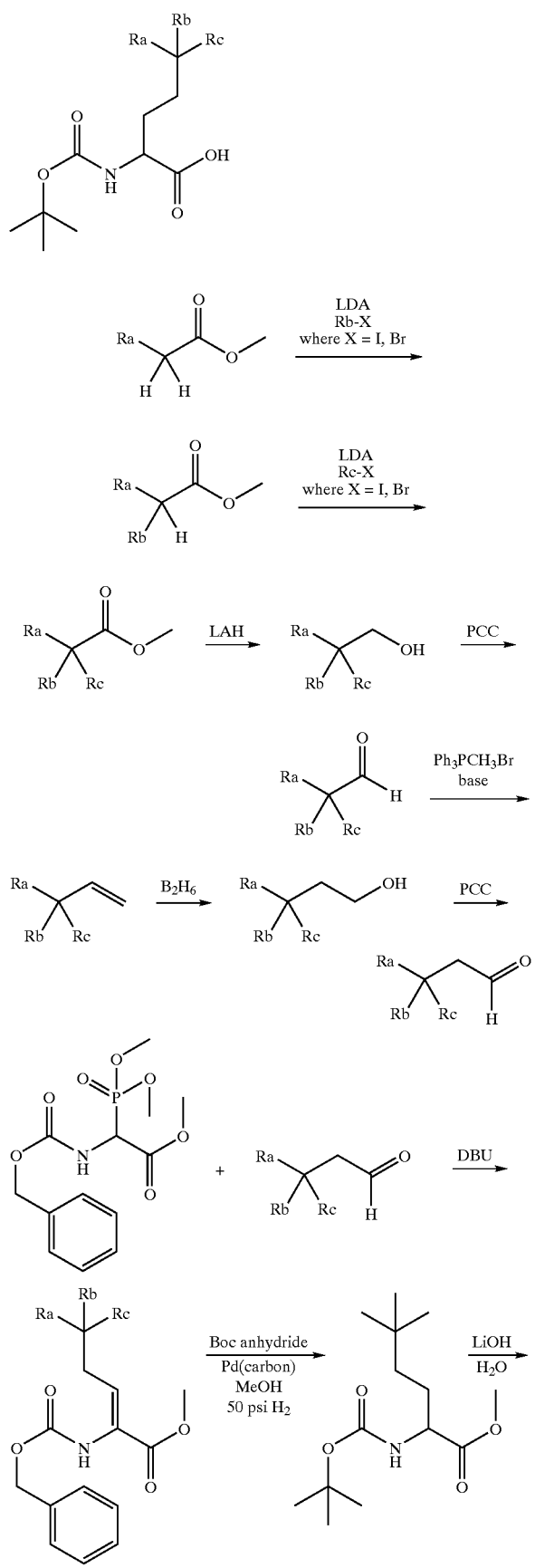

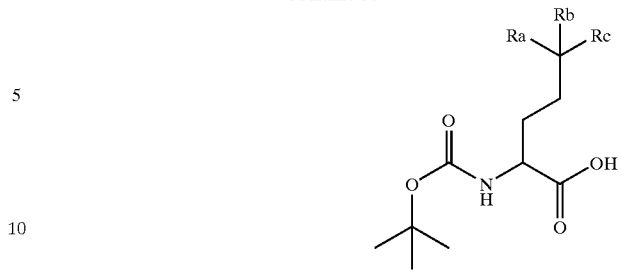

EXAMPLE 8

2,2,3-Trimethyl-butanal

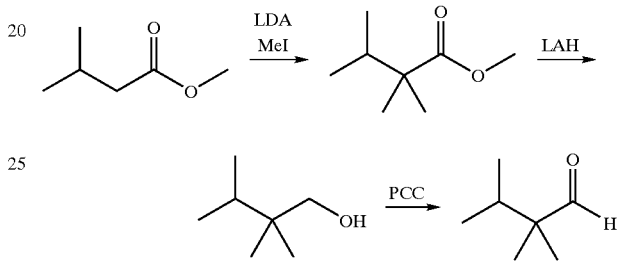

Lithium diisopropylamide (1.5 M solution in cyclohexane/THF/ethylbenzene) (113 mL, 169 mmol, 1.1 equiv) was syringed into a 1000 mL round-bottom flask under a blanket of Ar. Dry THF (150 mL) was added and the mixture was cooled to −78° C. with a dry-ice/acetone bath. 3-Methyl-butanoic acid ethyl ester (20 g, 23 mL, 154 mmol, 1.0 equiv) was added dropwise from a syringe over a 10 min period followed by stirring at −78° C. for 1 h. Methyl iodide (10.5 mL, 169 mmol, 1.1 equiv) was added dropwise from a syringe over a 10 min period and the creamy mixture was stirred for 1 h at −78° C., resulting in a very thick mixture. The dry-ice bath was removed and replaced with an ice bath at 0° C. Another 150 mL of dry THF was added followed by another addition of LDA (113 mL, 169 mmol, 1.1 equiv). The resulting mixture was stirred for 10 min and then the flask was re-immersed in a dry-ice/acetone bath. Stirring was continued for another 50 min and then methyl iodide was added dropwise (10.5 mL, 169 mmol, 1.1 equiv) and the dry-ice/acetone bath was removed and the resulting mixture was stirred at ambient temperature for 14 h. The reaction mixture was quenched with 3 mL of conc. HCl and 2 N HCl was added until the pH was adjusted to <1. The mixture was further diluted with 150 mL water and 500 mL Et$_2$O. The layers were separated and the organic layer was washed with 2 N HCl (1×100 mL), saturated NaHCO$_3$ (1×100 mL), and brine (1×200 nL). The organic layer was dried over Na$_2$SO$_4$ and then concentrated in vacuo to provide 2,2,3-trimethylbutanoic acid ethyl ester as an orange oil mixed with ethyl benzene (36.4 g of which 22.1 g was product by NMR). The mixture was used without further purification.

A 500 mL round-bottom-flask equipped with a stir bar was flushed with Ar and charged with 50 mL dry THF and a 1 M solution of LAH in Et$_2$O (87.5 mL, 87.5 mmol, 0.625 equiv). The solution was cooled to 0° C. with an ice bath and the above ethyl ester (22.1 g, 140 mmol, 1.0 equiv) (approximately a 50% solution in ethylbenzene) was added dropwise at such a rate that the solution did not reflux (required 50 min). After addition of the ester, the reaction was stirred at 0° C. for 2 h and then at ambient temperature for 14 h. The reaction solution was re-cooled to 0° C. and carefully quenched by addition of EtOAc. 1 N NaOH was added until a granular precipitate formed (7.5 mL). The mixture was filtered on a pad of diatomaceous earth which was then washed 3×100 mL Et$_2$O. The organics were combined and dried over Na$_2$SO$_4$. The solution was decanted and concentrated in vacuo to yield 2,2,3-trimethyl-butanol as a nearly colorless oil (1.7 g of alcohol in 15.4 g of a mix with ethylbenzene). The crude product was used without further purification.

A 1000 mL round-bottom-flask was equipped with a stir bar, flushed with Ar and charged with 300 mL dry CH$_2$Cl$_2$ and oxalyl chloride (13.2 mL, 151 mmol, 1.5 equiv). The solution was cooled to −78° C. with a dry-ice/acetone bath. Dry DMSO (21.5 mL, 302 mmol, 3.0 equiv) was added dropwise over a 30 min period (vigorous gas evolution). The above alcohol (11.7 g, 100 mmol, 1.0 equiv) was added (with residual ethylbenzene) over a 10 min period. The resulting solution was stirred for 90 min. Triethylamine (56 mL, 403 mmol, 4.0 equiv) was added over 5 min and the cold-bath was removed. The resulting creamy white mixture was stirred at room temperature over 1.5 h. The reaction mixture was carefully diluted with 200 mL water (more gas evolution). Layers were separated and the organic phase was washed with 1×100 mL 2 N HCl and 1×100 mL brine. The organic layer was dried over Na$_2$SO$_4$, decanted and concentrated in vacuo. The crude aldehyde was distilled fractionally through a 4 inch Vigoreux column at 57–67° C. at 15 mm Hg to provide the 2,2,3-trimethyl-butanal (9.1 g) as a colorless oil.

EXAMPLE 9
2-Benzyloxycarbonylamino-5,5,6-trimethyl-heptanoic Acid

The title compound may be prepared from 2,2,3-trimethyl-butanal by the following procedure

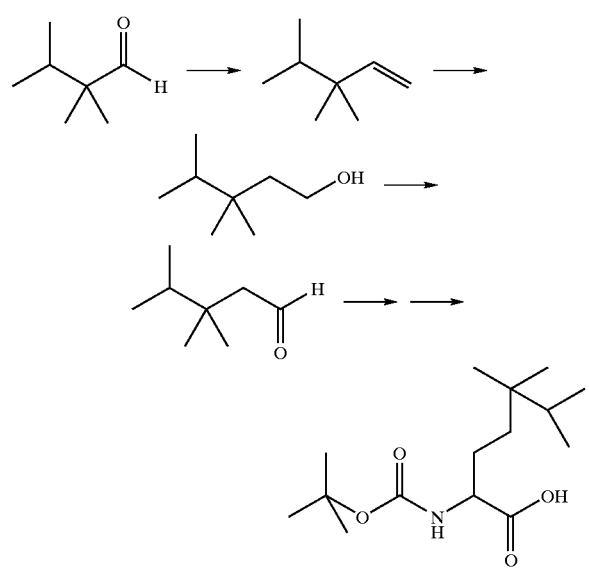

Methyltriphenylphosphonium bromide (1.0 equiv) is dissolved under Ar in dry THF. The solution is cooled to −78° C. at which time n-BuLi in hexanes (1.05 equiv) is added dropwise. 2,2,3-Trimethyl-butanal (1.0 equiv) is added dropwise to the stirred solution and the cold bath is removed and the reaction mixture is allowed to warm to ambient temperature. The reaction mixture is quenched by addition of saturated ammonium chloride solution. The mixture is diluted with ether and water and the layers are separated. The organic is dried over Na$_2$SO$_4$, decanted and the solution is fractionally distilled through a vigoreux column to give 3,3,4-trimethylpentene.

3,3,4-Trimethylpentene (1 equiv) is dissolved in dry THF under Ar. The reaction mixture is cooled to −78° C. at which time a 1 M solution of borane/dimethylsulfide complex in THF (0.4 equiv) is added dropwise. The cold bath is removed and the reaction mixture is allowed to warm to ambient temperature. The reaction mixture is carefully diluted with a solution of sodium acetate in aqueous hydrogen peroxide (large exess). The reaction mixture is stirred at ambient temperature and then diluted with diethyl ether and the layers are separated. The organic layer is dried over Na$_2$SO$_4$, decanted and concentrated. The crude material is purified by fractional distillation to yield 3,3,4-trimethylpentanol.

3,3,4-Trimethylpentanol (1 equiv) is dissolved in CH$_2$Cl$_2$. Pyridinium chlorochromate (1.5 equiv) is added and the resulting mixture is stirred at ambient temperature. The liquid is decanted and concentrated by rotary evaporation. The residue is triturated with 1 to 1 diethyl ether/hexane and mixture is filtered and the filtrate is washed with 1 N HCl. The organic layer is dried over Na$_2$SO$_4$, decanted and concentrated. The aldehyde is purified by fractional distillation to yield 3,3,4-trimethylpentanal.

This aldehyde may be converted to the title compound by reaction with N-(Benzyloxycarbonyl)-α-phosphonoglycine trimethyl ester, followed by catalytic reduction and hydrolysis by the procedures described in Example 4.

EXAMPLE 10

Preparation of 2-tert-Butoxycarbonylamino-3-(4,4-dimethyl-cyclohexyl)-propionic Acid.

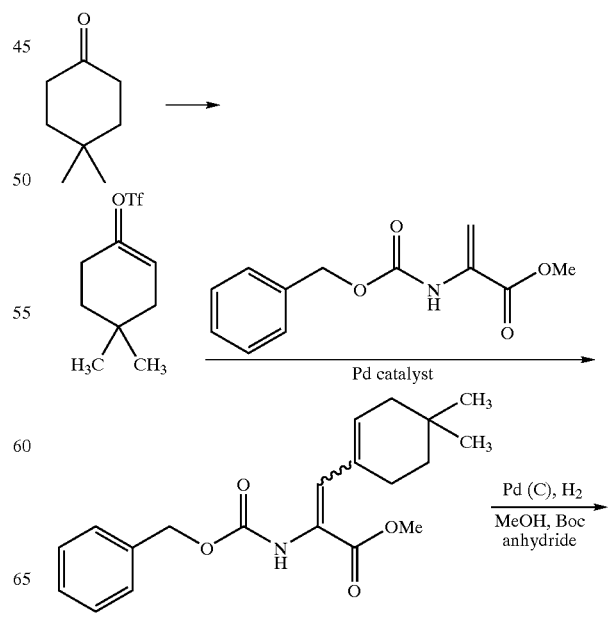

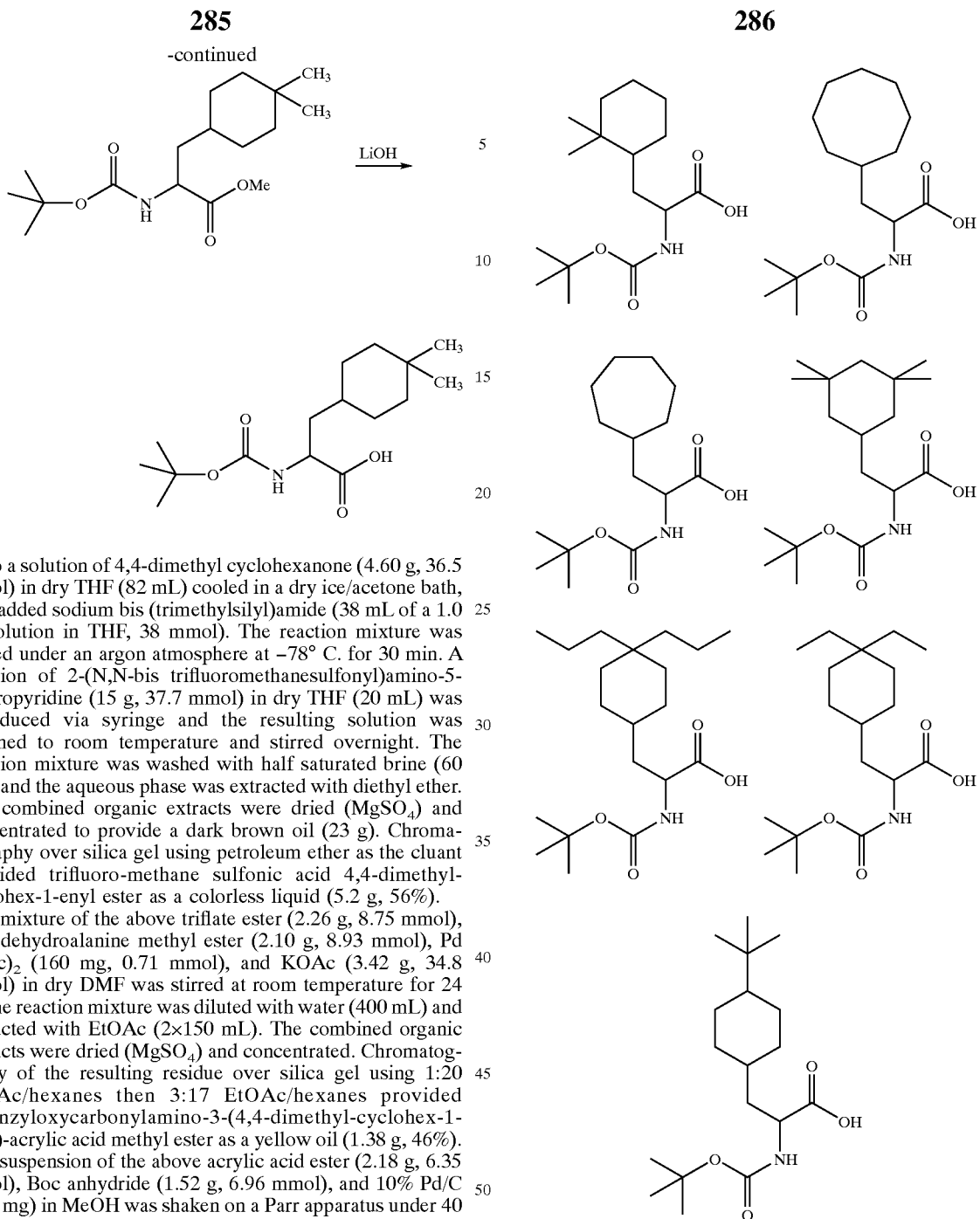

To a solution of 4,4-dimethyl cyclohexanone (4.60 g, 36.5 mmol) in dry THF (82 mL) cooled in a dry ice/acetone bath, was added sodium bis (trimethylsilyl)amide (38 mL of a 1.0 M solution in THF, 38 mmol). The reaction mixture was stirred under an argon atmosphere at −78° C. for 30 min. A solution of 2-(N,N-bis trifluoromethanesulfonyl)amino-5-chloropyridine (15 g, 37.7 mmol) in dry THF (20 mL) was introduced via syringe and the resulting solution was warmed to room temperature and stirred overnight. The reaction mixture was washed with half saturated brine (60 mL) and the aqueous phase was extracted with diethyl ether. The combined organic extracts were dried (MgSO$_4$) and concentrated to provide a dark brown oil (23 g). Chromatography over silica gel using petroleum ether as the eluant provided trifluoro-methane sulfonic acid 4,4-dimethyl-cyclohex-1-enyl ester as a colorless liquid (5.2 g, 56%).

A mixture of the above triflate ester (2.26 g, 8.75 mmol), Cbz dehydroalanine methyl ester (2.10 g, 8.93 mmol), Pd (OAc)$_2$ (160 mg, 0.71 mmol), and KOAc (3.42 g, 34.8 mmol) in dry DMF was stirred at room temperature for 24 h. The reaction mixture was diluted with water (400 mL) and extracted with EtOAc (2×150 mL). The combined organic extracts were dried (MgSO$_4$) and concentrated. Chromatography of the resulting residue over silica gel using 1:20 EtOAc/hexanes then 3:17 EtOAc/hexanes provided 2-benzyloxycarbonylamino-3-(4,4-dimethyl-cyclohex-1-enyl)-acrylic acid methyl ester as a yellow oil (1.38 g, 46%).

A suspension of the above acrylic acid ester (2.18 g, 6.35 mmol), Boc anhydride (1.52 g, 6.96 mmol), and 10% Pd/C (300 mg) in MeOH was shaken on a Parr apparatus under 40 psi of hydrogen gas for 17 h. The reaction mixture was filtered through a pad of diatomaceous earth and concentrated to provide 2-tert-butoxycarbonylamino-3-(4,4-dimethyl-cyclohexyl)-propionic acid methyl ester as a yellow oil (1.87 g, 94%).

A suspension of the above methyl ester (1.87 g, 5.97 mmol) and lithium hydroxide monohydrate (1.76 g, 41.9 mmol) in THF (18 mL), MeOH (6 mL), and water (6 mL) was stirred at room temperature for 4 h. The reaction mixture was acidified with 10% citric acid (aqueous) and extracted with diethyl ether (3×100 mL). The combined organic layers were dried (MgSO$_4$) and concentrated to provide a the corresponding carboxylic acid as a white foam (1.21 g, 68%).

The following Boc-protected amino acids were prepared using the above procedure starting from the commercially available ketones:

Additionally the following cyclic ketones may be synthesized according to methods described in the literature and converted by the above procedure, into Boc-protected amino acids:

Sauers, R. R.; Tucker, R. J.; *J Org Chem,* 1963, 28, 876.

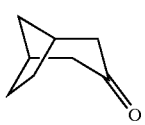

Burgstahler, A. W.; Sticker, R. E.; *Tetrahedron*, 1968, 2435.

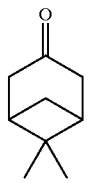

The following examples illustrate procedures that may be used to prepare amino nitrite intermediates that may be used to prepare compounds of the invention.

EXAMPLE 11

1-Amino-1-cyano-cyclopentane

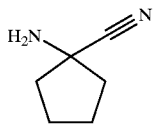

Cyclopentanone (1 equiv), NaCN (1.1 equiv) and NH₄Cl (1.1 equiv) are mixed together in 2 Molar NH₃/MeOH (4 equiv NH₃). The flask is fitted with a reflux condenser and the mixture is refluxed. At the end of each of the first 3 h an additional equivalent of NH₃ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica with EtOAc/hexanes as an eluent to yield the titled compound.

EXAMPLE 12

1-Amino-1-cyano-3-phenyl-cyclopentane

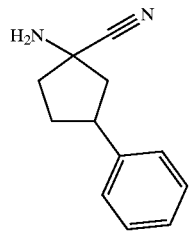

Cyclopent-2-enone (1 equiv) is dissolved in dry THF under Ar. CuI (1.5 equiv) is added and the mixture is cooled to −78° C. A 1 Molar solution of PhMgBr (1 equiv) is added dropwise. The resulting mixture is slowly warmed to ambient temperature over a 4 h period. The reaction is quenched by the addition of saturated ammonium chloride solution (aq). The product is extracted with diethyl ether. The organic layer is dried over Na₂SO₄, decanted and concentrated. The product ketone is purified by flash chromatography on silica using EtOAc and hexanes as mobile phase.

The above ketone (1 equiv), NaCN (1.1 equiv) and NH₄Cl (1.1 equiv) are mixed together in 2 Molar NH₃/MeOH (4 equiv NH₃). The flask is fitted with a reflux condenser and the mixture is refluxed. At the end of each of the first 3 h an additional equivalent of NH₃ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica with EtOAc/hexanes as an eluent to yield the titled compound.

EXAMPLE 13

1-Amino-1-cyano-3-piperid-1-yl)-propane.

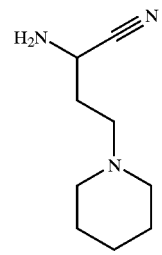

Acrolyl chloride (1 equiv) is dissolved in dry methylene chloride and the solution is cooled to −20° C. in a methanol/ice bath. Solid N,O-dimethylhydroxylamine hydrochloride (1 equiv) is added followed by dropwise addition of Et₃N (2.2 equiv). The reaction is stirred and then poured into ice-water. The mixture is diluted with methylene chloride and the layers separated. The organic layer is dried over Na₂SO₄, decanted and concentrated to yield N-methoxy-N-melhyl-propenamide.

The above amide (1 equiv) is dissolved in THF. Piperidine (1.1 equiv) is added and the reaction solution is stirred at ambient temperature for 48 h. The reaction mixture is concentrated and the product is purified by flash chromatography on silica using MeOH/CH₂Cl₂ as mobile phase to yield N-methoxy-N-methyl-3-(piperid-1-yl)-propanamide.

The above amide (1 equiv) is dissolved in dry THF and the solution is cooled to −78° C. Solid LAH (0.5 equiv) is carefully added. The reaction mixture is then immersed in an ice-bath at 0° C. and stirred 30 min. The reaction is quenched by the addition of EtOAc followed by water. The mixture is diluted with Et₂O and the layers are separated. The organic is washed with brine, dried over Na₂SO₄, decanted and concentrated to yield 3-(piperid-1-yl)-propanal which is used immediately in the next step.

The above aldehyde (1 equiv) is mixed with NaCN (1.1 equiv), NH₄Cl (1.1 equiv) are mixed together in 2 Molar NH₃/MeOH (4 equiv NH₃). The flask is fitted with a reflux condenser and the mixture is refluxed. At the end of each of the first 3 h an additional equivalent of NH₃ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica with EtOAc/hexanes as an eluent to yield 1-amino-1-cyano-3-(piperid-1-yl)-propane.

EXAMPLE 14
Amino-1-cyan-2-(piperid-1-yl)-ethane.

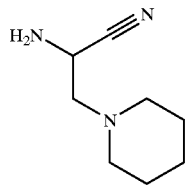

Bromoacetylchloride (1.0 equiv) is dissolved in dry methylene chloride and the solution is cooled to −20° C. in a methanol/ice bath. Solid N,O-dimethylhydroxylamine hydrochloride (1 equiv) is added followed by dropwise addition of $Et_3N$ (2.2 equiv). The reaction is stirred for 1 h and then poured into ice-water. The mixture is diluted with methylene chloride and the layers separated. The organic layer is dried over $Na_2SO_4$, decanted and concentrated to yield N-methoxy-N-methyl-2-bromo-ethanamide.

The above amide (1 equiv) is dissolved in THF. Piperidine (1.1 equiv) is added and the reaction solution is stirred at ambient temperature for 48 h. The reaction mixture is concentrated and the product is purified by flash chromatography on silica using $MeOH/CH_2Cl_2$ as the mobile phase to yield N-methoxy-N-methyl-2-(piperid-1-yl)-ethanamide.

The above amide (1 equiv) is dissolved in dry THF and the solution is cooled to −78° C. Solid LAH (0.5 equiv) is carefully added. The reaction mixture is then immersed in an ice-bath at 0° C. and stirred 30 min. The reaction is quenched by the addition of EtOAc followed by water. The mixture is diluted with $Et_2O$ and the layers are separated. The organic is washed with brine, dried over $Na_2SO_4$, decanted and concentrated to yield 3-(piperid-1-yl)-ethanal which is used immediately in the next step.

The above aldehyde (1 equiv) is mixed with NaCN (1.1 equiv) and $NH_4Cl$ (1.1 equiv) in 2 Molar $NH_3$/MeOH (4 equiv $NH_3$). The flask is fitted with a reflux condenser and mixture is refluxed for 4 h. At the end of each of the first 3 h an additional equivalent of $NH_3$ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica gel with EtOAc/hexanes as eluent to yield 1-amino-1-cyano-2-(piperid-1-yl)-ethane.

EXAMPLE 15
1-Amino-cyano-2-(1-methyl-piperid-4-yl)-ethane.

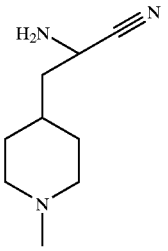

2-(1-Methyl-piperid-4-yl)-ethanoic acid ethyl ester is prepared from 1-methyl-piperid4-one (1 equiv), triethyl phosphono acetate (1 equiv) and NaH (1.1 equiv) in benzene followed by reduction of the alkene bond according to the procedure of Cignarella etc. (*J Heterocyclic Chem* 1993, 30 (5), 1337–1340).

The above ester (1 equiv) is dissolved in MeOH and 1 N LiOH (3 equiv of hydroxide) is added. The mixture is stirred until the starting material is consumed. Concentrated HCl is added until the pH=2 (as judged by pH paper). The mixture is then concentrated by lyophilization to yield 2-(1-methyl-piperid-yl)-ethanoic acid hydrochloride as a mix with LiCl.

The above mixture (about 1 equiv of carboxylic acid) is suspended in DMF. EDC (1.1 equiv) is added followed by N-methylmorpholine (3.0 equiv). After 20 min, solid N,O-dimethylhydroxylamine hydrochloride is added and the resulting mixture is stirred for 16 h. The mixture is diluted with saturated aqueous bicarbonate solution and the product extracted twice with EtOAc. The organic layer is washed with brine, dried over $Na_2SO_4$, decanted and concentrated. The product is purified by flash chromatography on silica using $MeOH/CH_2Cl_2$ as eluent to yield N,O-dimethyl-2-(1-methyl-piperid-4-yl)-ethanamide.

The above amide (1 equiv) is dissolved in dry THF and the solution is cooled to −78° C. Solid LAH (0.5 equiv) is carefully added. The reaction mixture is then immersed in an ice-bath at 0° C. and stirred. The reaction is quenched by the addition of EtOAc followed by water. The mixture is diluted with $Et_2O$ and the layers are separated. The organic layer is washed with brine, dried over $Na_2SO_4$, decanted and concentrated to yield 2-(1-methyl-piperid-4-yl)-ethanal which is used immediately in the next step.

The above aldehyde (1 equiv) is mixed with NaCN (1.1 equiv) and $NH_4Cl$ (1.1 cquiv) in 2 Molar $NH_3$/MeOH (4 equiv $NH_3$). The flask is fitted with a reflux condenser and the mixture is refluxed. At the end of each of the first 3 h an additional equivalent of $NH_3$ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica with EtOAc/hexanes as an eluent to yield 1-amino-1-cyano-2-(1-methyl-piperid-4-yl)-ethane.

EXAMPLE 16
Amino-cyano-(furan-2-yl)-methane.

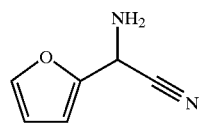

Furfural (1.0 equiv) is mixed with NaCN (1.1 equiv) and $NH_4Cl$ (1.1 equiv) in 2 Molar $NH_3$/MeOH (4 equiv $NH_3$). The flask is fitted with a reflux condenser and mixture is refluxed. At the end of each of the first 3 h an additional equivalent of $NH_3$ in MeOH is added. The reaction mixture is cooled and the excess solids are filtered away on a frit. The filtrate is concentrated by rotary evaporation and the residue is triturated with diethyl ether and the mixture is filtered again. The filtrate is concentrated on a rotovap. The product is purified, if necessary, by flash chromatography on silica gel with EtOAc/hexanes as an eluent to yield amino-cyano-(furan-2-yl)methane.

In addition, the following amino-nitriles may be prepared from the commercially available aldehydes in a manner identical to that for amino-cyano-(furan-2-yl)-methane.
Amino-cyano-(furan-3-yl)-methane
Amino-cyano-(thiophen-2-yl)-methane
Amino-cyano-(thiophen-3-yl)-methane
Amino-cyano-(thiazol-2-yl)-methane
Amino-cyano-(thiazol-4-yl)-methane Amino-cyano-(thiazol-5-yl)-methane
Amino-cyano-(oxazol-2-yl)-methane
Amino-cyano-(oxazol-4-yl)-methane
Amino-cyano-(oxazol-5-yl)-methane
Amino-cyano-(pyrid-2-yl)-methane
Amino-cyano-(pyrid-3-yl)-methane
Amino-cyano-(pyrid-4-yl)-methane Methods of Therapeutic use The compounds of the invention are useful in inhibiting the activity of cathepsin S, K, F, L and B. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis including contact and atopic dermatitis, insulin-dependent diabetes mellitus, endometriosis and asthma including allergic asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also inhibit cathepsin K. In doing so, they may block inappropriate degradation of bone collagen and other bone matrix proteases. Thus, there is provided a method for treating diseases where these processes play a role such as osteoporosis. Inhibition of cathepsins F, L, and B are also within the scope of the invention due to similarity of the active sites in cysteine proteases as described above.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (11990)). Dosage levels and requirements are well-recognized in the art and may be selected by those of ordinary skill in the art from available methods and techniques suitable for a particular patient. In some 2.5 embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties
Expression and Purification of recombinant human Cathepsin S
Cloning of Human Cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBacl donor plasmid (GibcoBRL, 8717 Grovemont Cr., Gaithersburg, Md. 20884) which had been cut with restriction enzyme BamHI and blunt-ended and then cut with restriction enzyme SalI. The ligation mixture was used to transform DH5a competent cells (GibcoBRL) and plated on LB plates containing 100 ug/mL ampicillin. Colonies were grown in overnight cultures of LB media containing 50 ug/mL Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/mL kanamycin, 7 ug/mL gentamicin, 10 ug/mL tetracycline, 100 ug/mL Bluo-gal, and 40 ug/mL IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science*, 1996, 5:789–791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na acetate, pH 6.5, 2.5 mM EDTA, 2.5 mM TCEP. Enzyme is incubated with either compound or DMSO for 10 min at 37° C. Substrate 7-amino-4-methylcoumarin, CBZ-L-valyl-L-valyl-L-arginineamide (custom synthesis by Molecular Probes) is diluted to 20 uM in water (final concentration of 5 M), added to assay and incubated for additional 10 minutes at 37° C. Compound activity is measured by diminished fluorescence compared to DMSO control when read at 360 nm excitation and 460 nm emission.

Examples listed above were evaluated for inhibition of cathepsin S in the above assay. All had $IC_{50}$ values of 100 micromolar or below.

Inhibition of Cathepsin K, F, L and B:

Inhibition of these enzymes by particular compounds of the invention may be determined without undue experimentation by using art recognized methods as provided hereinbelow each of which is incorporated herein by reference:

Cathepsin B, and L Assays are to be found in the Following References:

1. Methods in Enzymology, Vol.244, Proteolytic Enzymes: Serine and Cysteine Peptidases, Alan J. Barrett, ed.

Cathepsin K Assay is to be Found in the Following Reference:

2. Bromme, D., Okamoto, K., Wang, B. B., and Biroc, S. (1996) *J. Biol. Chem.* 271, 2126–2132.

Cathepsin F Assays are to be Found in the Following References:

3. Wang, B., Shi, G. P., Yao, P. M., Li, Z., Chapman, H. A., and Bromme, D. (1998)*J. Biol. Chem.* 273, 32000–32008.
4. Santamaria, I., Velasco, G., Pendas, A. M., Paz, A., and Lopez-Otin, C (1999) *J. Biol. Chem.* 274, 13800–13809.

Preferred compounds to be evaluated for inhibition of Cathepsin K, F, L and B in the above assays desirably have $IC_{50}$ values of 100 micromolar or below.

What is claimed is:

1. A compound of the formula (Ia) or (Ib):

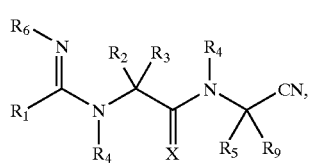

(Ia)

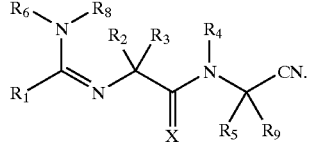

(Ib)

wherein:

$R_2$ is hydrogen or C1–3 alkyl;

$R_3$ is a bond, hydrogen, alkyl wherein one or more carbon atoms are optionally replaced by O, S or N wherein it shall be understood if N is not substituted by $R_c$ then it is NH, or $R_3$ is C2–10alkylene, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl and quinoxalinyl, C3–8 cycloalkyl, arylC1–5alkyl or aryl wherein $R_3$ is optionally substituted by one or more $R_c$;

$R_c$ is C3–8 cycloalkyl, aryl, indanyl, indenyl, bicyclo [2.2.1]heptanyl, bicyclo[2.2.2]octanyl, bicyclo [4.1.0]heptanyl, bicyclo[3.1.0]hexanyl, bicyclo [1.1.1]pentanyl, spiroC8–12 cycloalkyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, aryloxy, aroyl, aryloxycarbonyl, aroyloxy, or $R_c$ is aroylamino, alkylthio, arylthio, aryloxycarbonylamino, arylcarbamoyloxy, arylsulfonylamino, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

each $R_4$ is independently hydrogen, hydroxy or C1–3 alkyl;

$R_5$ is hydrogen, alkyl, alkoxy, alkoxyalkyl or arylalkyl;

$R_9$ is hydrogen, alkyl wherein one or more carbon atoms are optionally replaced by O, S or N wherein it shall be understood if N is not substituted by $R_c$ then it is NH, or $R_9$ is cycloalkyl, aryl, heterocyclyl, aryl, heteroaryl or cyano, wherein $R_9$ is optionally substituted by one or more $R_e$;

$R_e$ is selected from alkyl, cycloalkyl, aryl, aroyl, heterocyclyl, heteroaryl, halogen, hydroxy, oxo, carboxy, cyano, nitro, amidino and guanidino, $R_e$ may be further optionally substituted by one or more $R_f$;

$R_f$ is selected from alkyl, cycloalkyl, aryl optionally substituted by one or more groups selected from halogen, methyl or methoxy, heterocyclyl, heteroaryl, alkoxy, aryloxy, aroyl, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl, heteroaryl, halogen, hydroxy, carboxy and cyano;

$R_6$ is hydrogen, hydroxy, nitrile or a C1–6 saturated or unsaturated branched or unbranched alkyl optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C1–4 alkyl, C3–7 cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formula (Ia) form the bicyclic ring selected from:

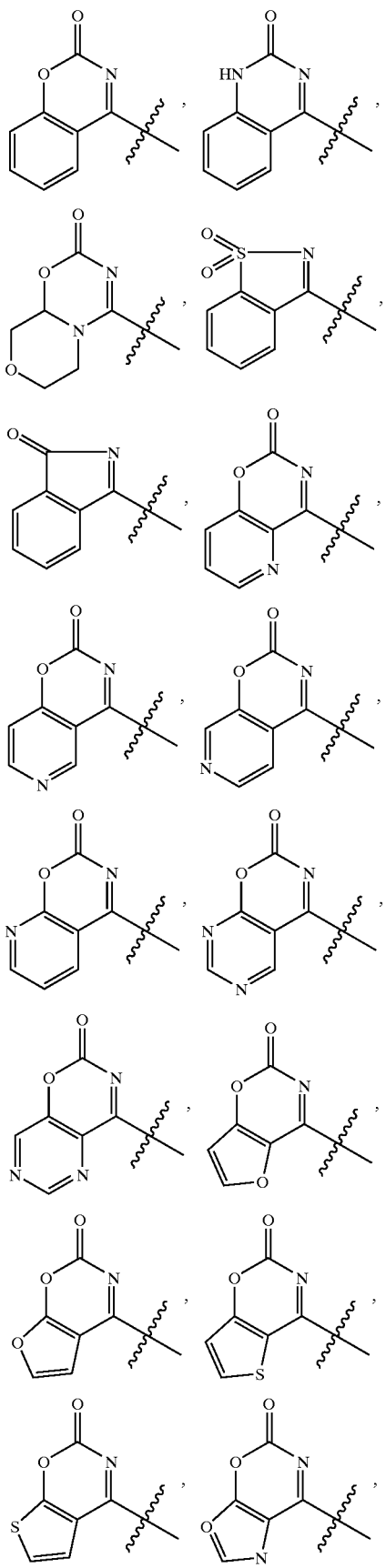

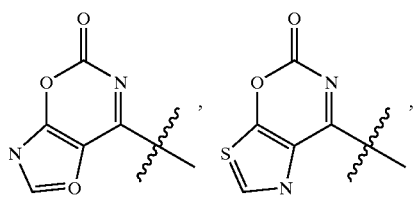

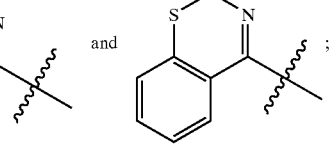

or R₁ and R₆ of the formula (Ia) form the tricyclic ring selected from:

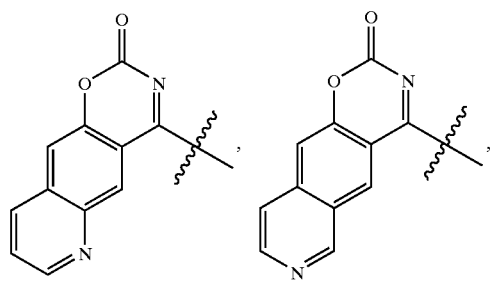

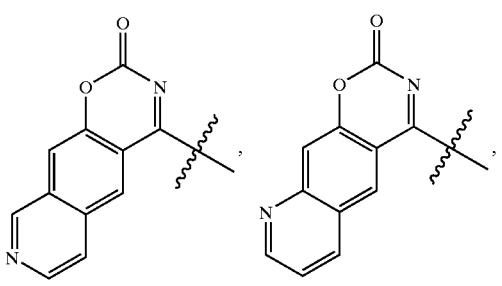

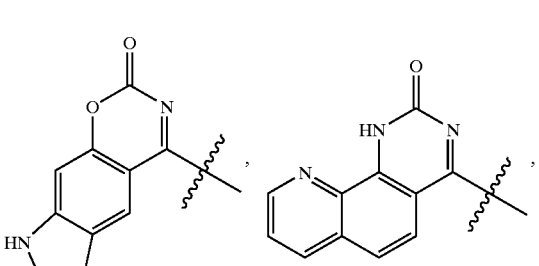

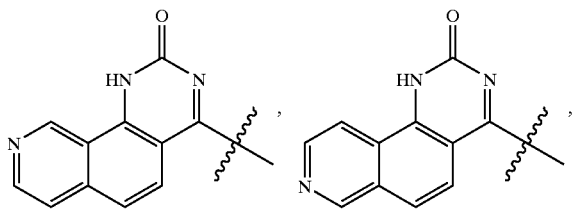

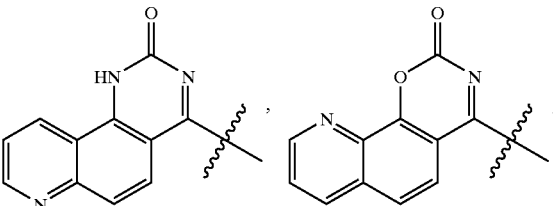

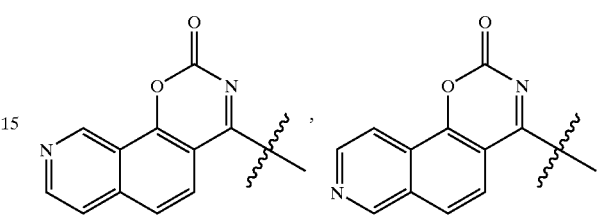

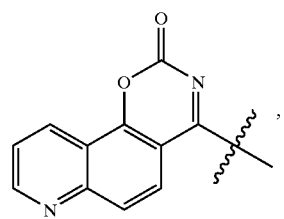

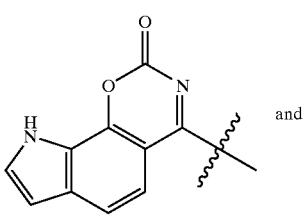

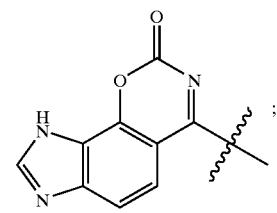

wherein each ring is optionally independently substituted by one or two $R_7$; and wherein $R_1$ and $R_6$ in the formula (Ib) optionally form a 4 to 8 membered mono- or 7–14 membered polycyclo heteroring system, each aromatic or nonaromatic, wherein each ring is optionally substituted by one or more $R_7$;

each $R_7$ and $R_8$ are independently:

hydrogen, C1–5 alkyl chain optionally interrupted by one or two N, O or $S(O)_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated, halogen, hydroxy, oxo, carboxy, nitrile, nitro or $NH_2C(O)$—;

m is 0, 1 or 2;

and

X is =O, =S or =N—$R_6$ wherein $R_6$ is as defined above, or the pharmaceutically acceptable salts, esters and tautomers thereof.

2. The compound according claim 1 wherein:

$R_1$ and $R_6$ of the formula (Ia) form the bicyclic ring selected from:

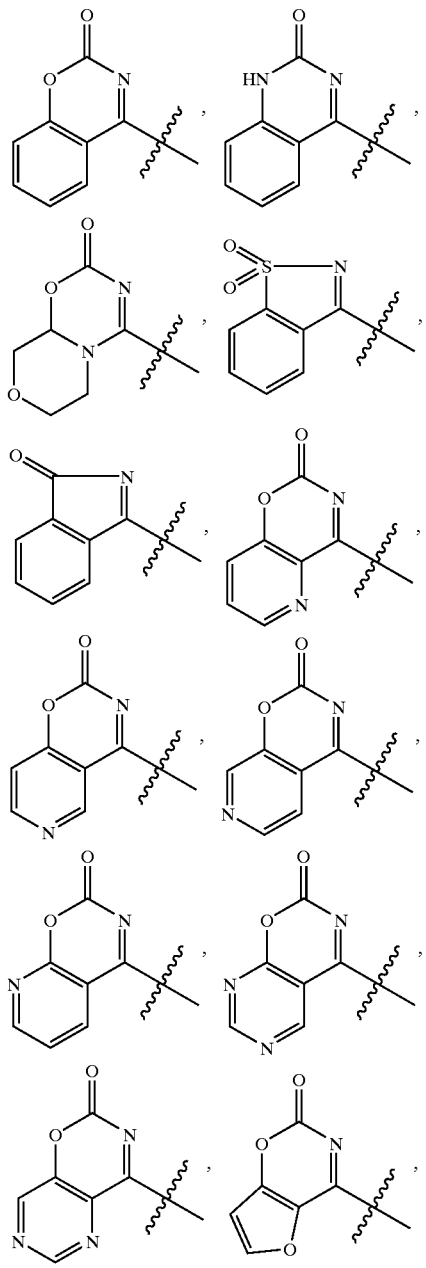

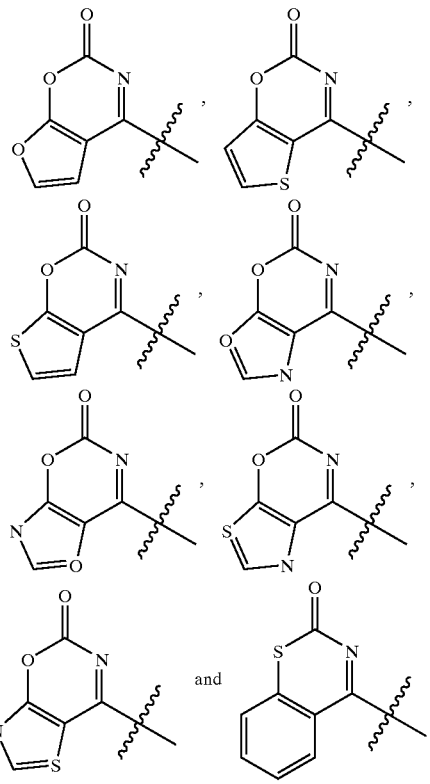

or $R_1$ and $R_6$ of the formula (Ia) form the tricyclic ring selected from:

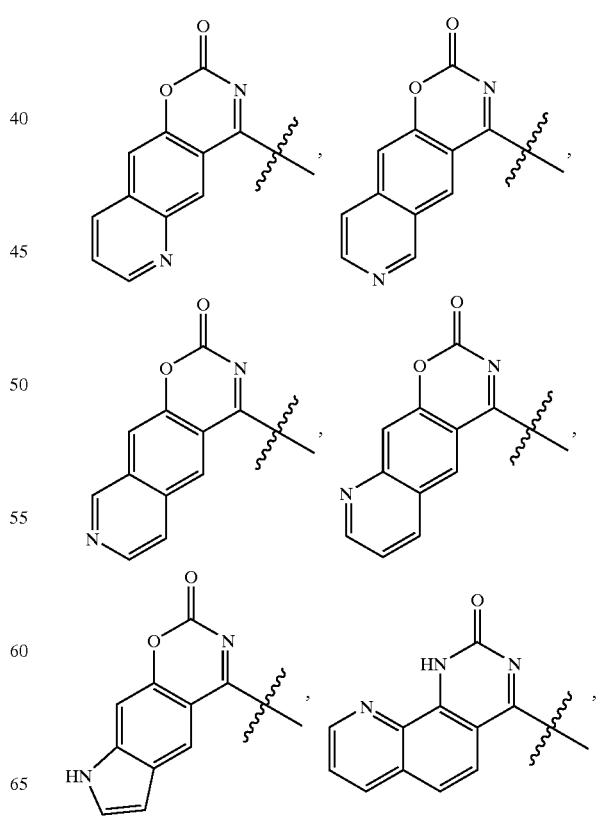

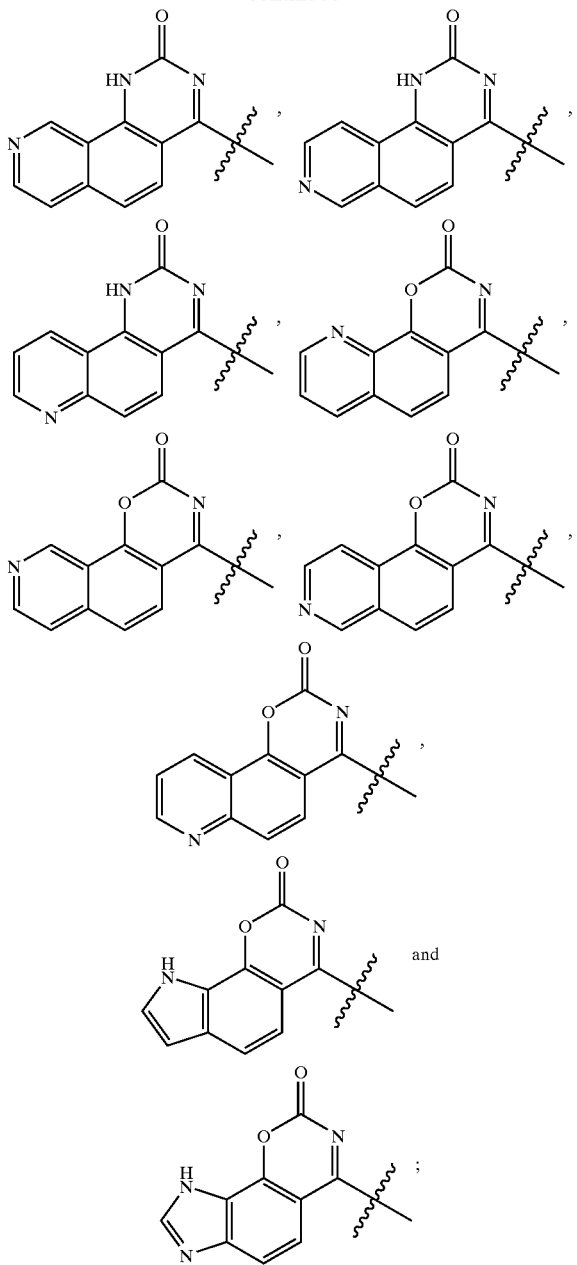

wherein each ring is optionally independently substituted by one or two $R_7$; and wherein $R_1$ and $R_6$ in the formula (Ib) form a monocyclic 5, 6 or 7 membered aromatic or non aromatic heterocyclic ring optionally substituted by $R_7$;

a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

or a tricyclic ring wherein the abovementioned bicyclic ring is further fused to a third 5–7 membered aromatic or nonaromatic heterocyclic or carbocyclic ring wherein each ring is optionally independently substituted by one or more $R_7$;

$R_2$ is hydrogen or methyl or ethyl;

$R_3$ is a bond, hydrogen, C1–10 alkyl wherein one or more carbon atoms are optionally replaced by O, S or N, or $R_3$ is C2–5alkylene, C3–7 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, pyridinyl, pyrimidinyl, pyrazinyl and indolyl, arylC1–3alkyl or aryl wherein $R_3$ is optionally substituted by one or more $R_c$;

$R_c$ is C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, aryloxy, aroyl, aryloxycarbonyl, aroyloxy, or $R_c$ is aroylamino, arylthio, aryloxycarbonylamino, arylcarbamoyloxy, arylsulfonylamino, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, aryl or cyano, wherein $R_9$ is optionally substituted by one or more $R_e$;

$R_e$ is selected from C1–8 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_e$ may be further optionally substituted by one or more $R_f$;

$R_f$ is selected from C1–8 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, aroyl, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_8$;

$R_g$ is selected from C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, carboxy and cyano;

$R_7$ and $R_8$ are independently hydrogen, C1–5 alkyl, C3–6 cycloalkyl, aryl, C1–5 alkoxy, aryloxy, benzyloxy each of the aforementioned are optionally halogenated, halogen, hydroxy, oxo, carboxy, nitrile, nitro or $NH_2C(O)-$;

m is 0, 1 or 2 and

X is O or S.

3. The compound according claim 2 wherein:

$R_1$ and $R_6$ of the formula (Ia) form the bicyclic ring selected from:

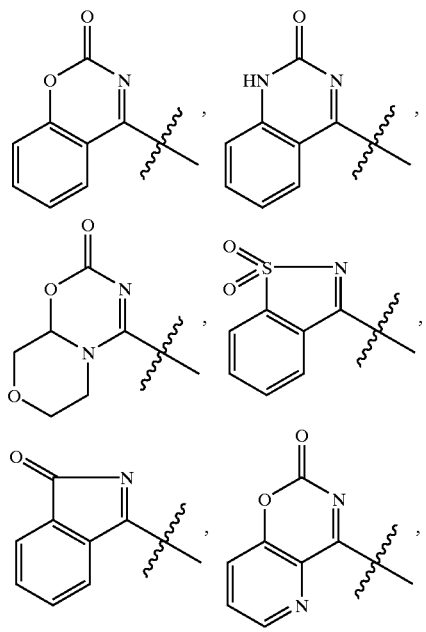

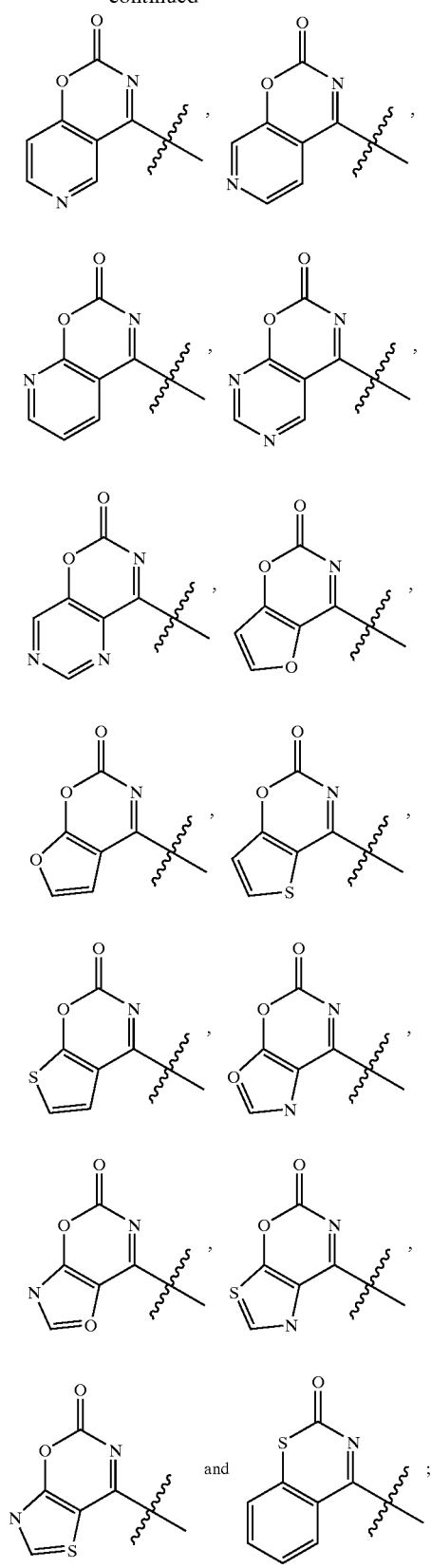
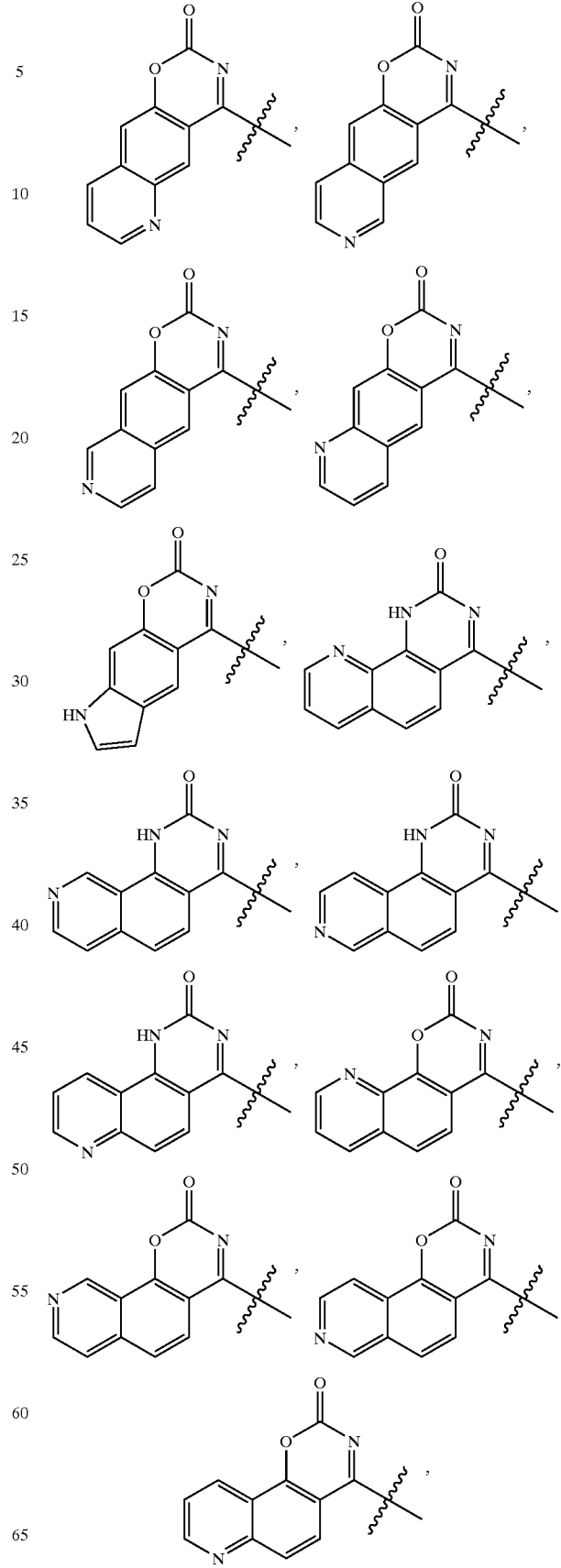
or $R_1$ and $R_6$ of the formula (Ia) form the tricyclic ring selected from:

-continued

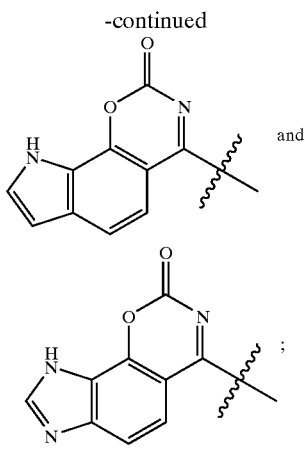
and

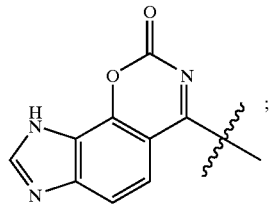
;

wherein each ring is optionally independently substituted by one or two $R_7$; and wherein $R_1$ and $R_6$ in the formula (Ib) form a monocyclic 5 or 6 membered aromatic or nonaromatic heterocyclic ring optionally substituted by $R_7$;

a bicyclic ring having one 5, 6 or 7 membered aromatic or nonaromatic heterocyclic ring fused to a second 5–6 membered aromatic or nonaromatic heterocyclic or carbocyclic ring wherein each ring is optionally independently substituted by one or more $R_7$;

or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring;

$R_2$ is hydrogen or methyl;

$R_3$ is a bond, hydrogen, C1–10 alkyl wherein one or more carbon atoms are optionally replaced by O, S or N, or $R_3$ is C2–5alkylene, C4–6 cycloalkyl, heterocyclylC1–5 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolinyl, or arylC1–2alkyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, phenoxy, naphthyloxy, benzoyl, phenoxycarbonyl, benzoyloxy, benzoylamino, phenylthio, aryloxycarbonylamino, arylcarbamoyloxy, arylsulfonylamino, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is hydrogen, C1–8 alkyl, C1–3 alkoxyC1–3 alkyl, C1–8 alkoxy, phenylC1–5 alkyl or naphthylC1–5 alkyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, aryl or cyano, wherein $R_9$ is optionally substituted by one or more $R_e$;

$R_e$ is selected from C1–5 alkyl, C3–7 cycloalkyl, aryl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_e$ may be further optionally substituted by one or more $R_f$;

$R_f$ is selected from C1–5 alkyl, C3–7 cycloalkyl, aryl optionally substituted by one or more groups selected from halogen, methyl or methoxy, heterocyclyl selected from pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from pyrrolidinyl, piperidinyl, morpholinyl, thiomorpholinyl, piperazinyl and indolinyl, or heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, carboxy and cyano;

$R_7$ and $R_8$ are independently hydrogen, C1–4 alkyl, C5–6 cycloalkyl, C1–4 alkoxy, halogen, hydroxy, oxo, carboxy, nitrile, nitro or $NH_2C(O)$—;

and

X is O.

4. The compound according claim 3 wherein:

$R_1$ and $R_6$ of the formula (Ia) form the bicyclic ring selected from:

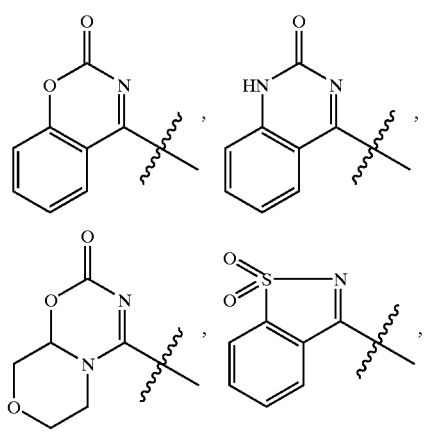

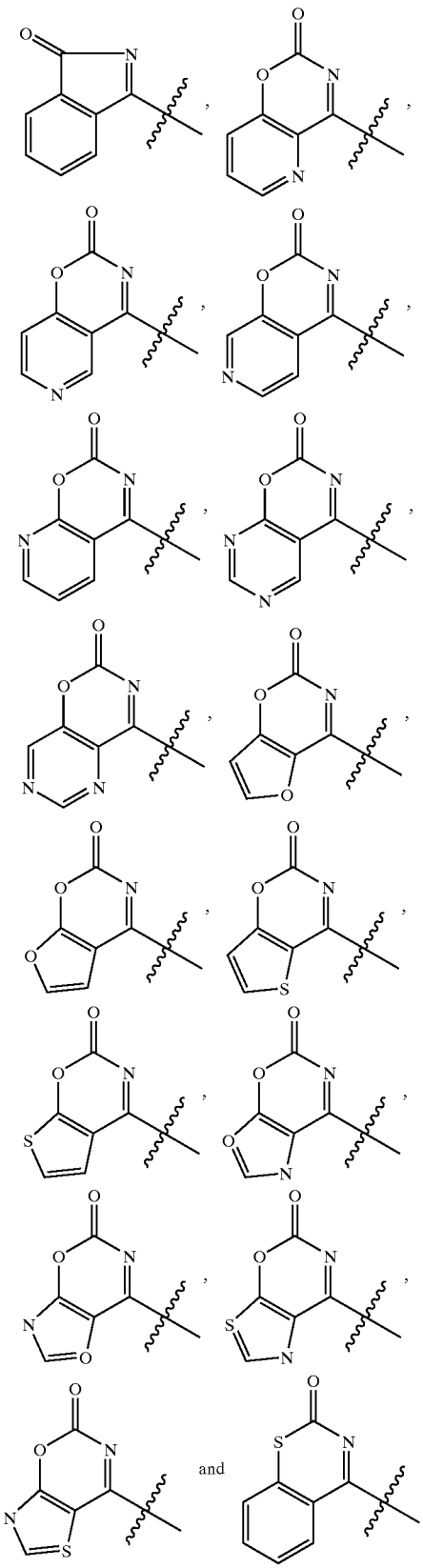

or $R_1$ and $R_6$ of the formula (Ia) form the tricyclic ring selected from:

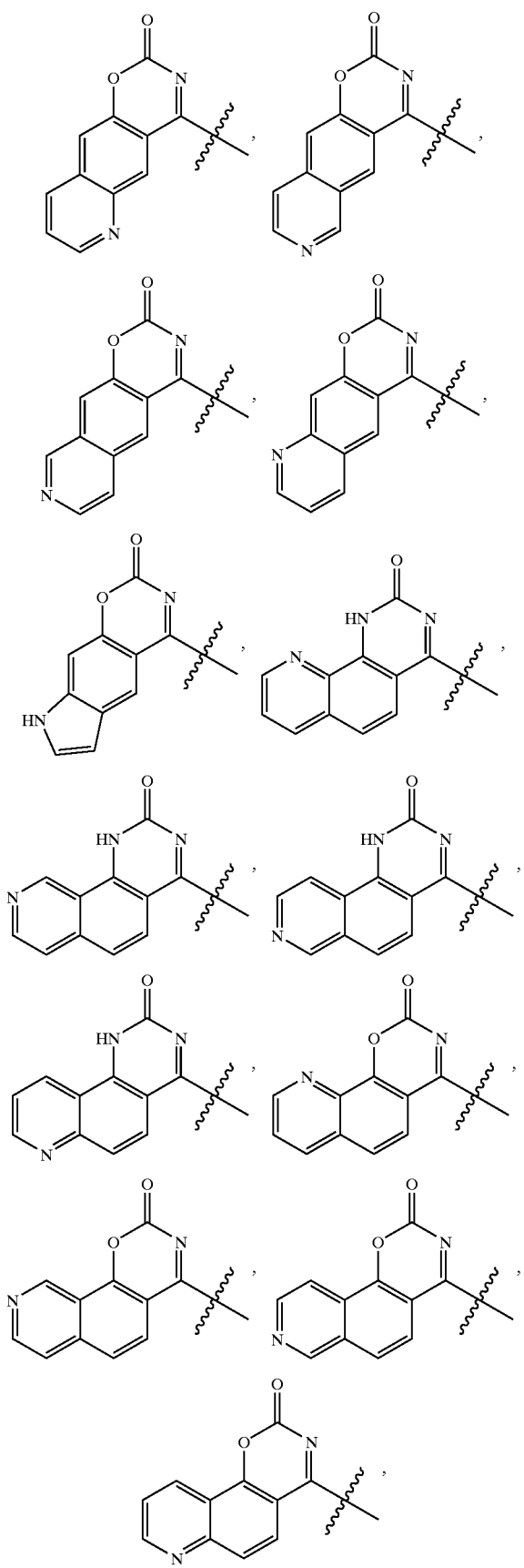

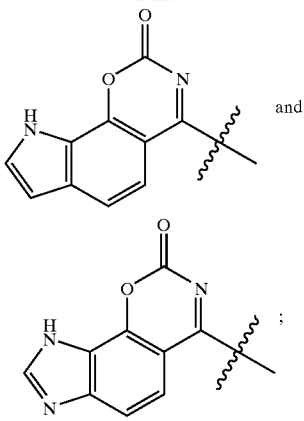

wherein each ring is optionally independently substituted by one or two $R_7$; and wherein $R_1$ and $R_6$ in the formula (Ib) form
a bicyclic ring having one 5 or 6 membered aromatic or nonaromatic heterocyclic ring fused to a second 5–6 membered heteroaryl, heterocycle or phenyl ring;
or a tricyclic ring having one 5, 6 or 7 membered aromatic or nonaromatic heterocyclic ring fused to a 5–6-membered aromatic or nonaromatic carbocyclic ring which in turn is fused to a 5, 6 or 7 membered aromatic or nonaromatic heterocyclic ring; wherein each ring is optionally independently substituted by one or two $R_7$ $R_2$ is hydrogen;

$R_3$ is a bond, C1–10 alkyl wherein one or more carbon atoms are optionally replaced by O, S or N, or $R_3$ is C2–4alkylene, C5–6 cycloalkyl, heterocyclylC1–3 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, phenoxy, naphthyloxy, benzoyl, phenoxycarbonyl, benzoyloxy, benzoylamino, phenylthio, phenoxycarbonylamino, arylcarbamoyloxy, phenylsulfonylamino, phenylaminosulfonyl, amino wherein the nitrogen atom may be independently mono or di-substituted by C1–3 alkyl or phenyl,
or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_5$ is hydrogen, C1–5 alkyl, C1–3 alkoxyC1–3 alkyl, benzyl or phenethyl;

$R_9$ is hydrogen, C1–12 alkyl wherein one or more carbon atoms are optionally replaced by O, S or N, C3–7 cycloalkyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, phenyl, naphthyl or cyano, wherein $R_9$ is optionally substituted by one or more $R_e$;

$R_e$ is selected from C1–5 alkyl, C3–7 cycloalkyl, phenyl, naphthyl, aroyl, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, aroyl, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, nitro, carboxy and cyano, $R_e$ may be further optionally substituted by one or more $R_f$;

$R_f$ is selected from C1–5 alkyl, C3–7 cycloalkyl, phenyl optionally substituted by one or more groups selected from halogen, methyl or methoxy, naphthyl optionally substituted by one or more groups selected from halogen, methyl or methoxy, heterocyclyl selected from pyrrolidinyl, piperidinyl, morpholinyl, thiomorpholinyl, piperazinyl and indolinyl; heteroaryl selected from furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano;

or $R_5$ and $R_9$ together with the carbon they are attached form a 3 to 7-membered monocyclic carbocycle or a 7 to 14-membered bicyclic carbocycle optionally bridged, wherein either carbocycle is optionally benzofused and optionally substituted with one or more $R_g$;

$R_g$ is selected from C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl, naphthyl, arylC1–3alkyl, heterocyclyl selected from pyrrolidinyl, piperidinyl, morpholinyl and piperazinyl or heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, carboxy and cyano.

5. The compound according claim 4 wherein:

$R_1$ and $R_6$ of the formula (Ia) form the bicyclic ring selected from:

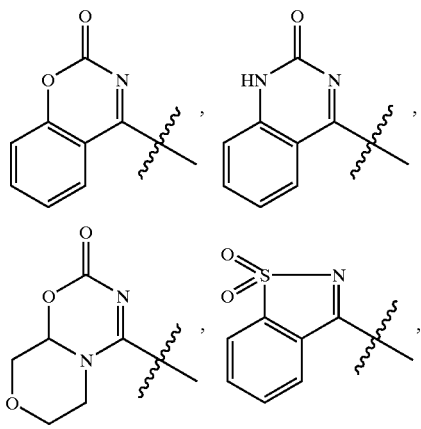

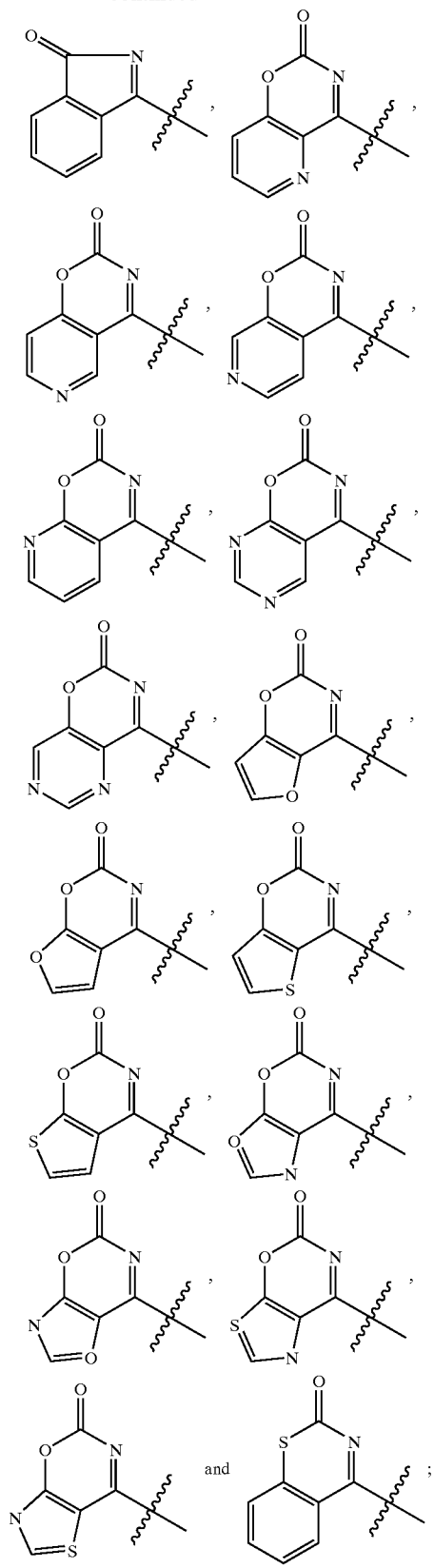
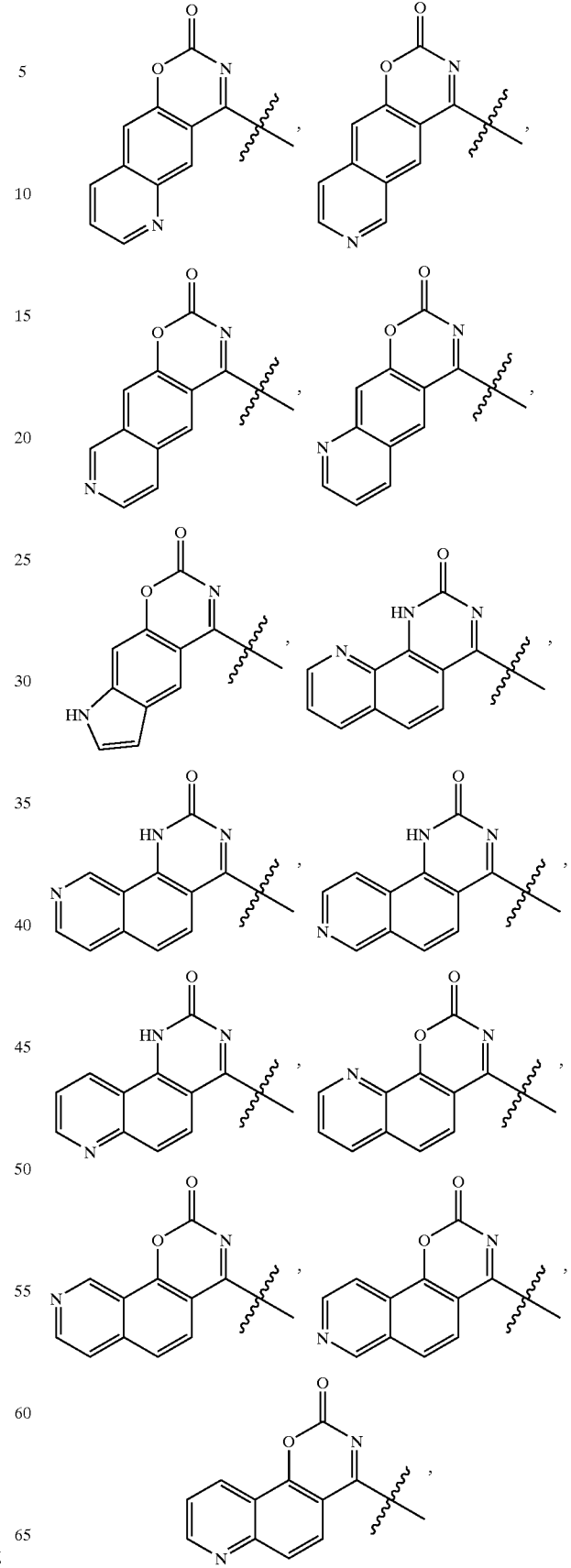
or $R_1$ and $R_6$ of the formula (Ia) form the tricyclic ring selected from:

-continued

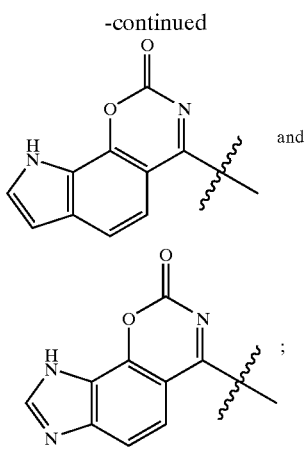

wherein each ring is optionally independently substituted by one or two $R_7$; and wherein $R_1$ and $R_6$ in the formula (Ib) form a bicyclic ring having one 5–6 membered aromatic or nonaromatic heterocyclic ring fused to a phenyl or 5–6 membered aromatic or nonaromatic heterocyclic ring;

a tricyclic ring having one 5–6 membered aromatic or nonaromatic heterocyclic ring fused to a 6-membered aromatic or nonaromatic carbocyclic ring which in turn is fused to a 5–6 membered aromatic or nonaromatic heterocyclic ring;

wherein each ring is optionally independently substituted by one or two $R_7$;

$R_3$ is a bond, C1–10 alkyl wherein one or more carbon atoms are optionally replaced by O, S or N, or $R_3$ is C2–4alkylene, C5–6 cycloalkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one or more $R_c$;

$R_c$ is C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiroC8–10 cycloalkyl, cubanyl, 1,2,3,4-tetrahydronaphthyl, thienyl, oxazolyl, thiazolyl, indolyl, benzofuranyl, benzothienyl, benzthiazolyl, phenoxy, benzoyl, phenoxycarbonyl, benzoyloxy, benzoylamino, phenylthio, phenoxycarbonylamino, phenylcarbamoyloxy, phenylsulfonylamino, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_9$ is hydrogen, C1–12 alkyl wherein one or more carbon atoms are optionally replaced by O, S or N, C3–6 cycloalkyl, phenyl or cyano, wherein $R_9$ is optionally substituted by one or more $R_e$;

$R_e$ is selected from C1–3 alkyl, C3–6 cycloalkyl, phenyl, naphthyl, aroyl, heterocyclyl selected from pyrrolidinyl, piperidinyl, morpholinyl, thio morpholinyl and piperazinyl; heteroaryl selected from furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from piperidinyl, morpholinyl and piperazinyl or heteroaryl selected from furanyl, thienyl, pyrrolyl, oxazolyl, thiazolyl, imidazolyl, pyridinyl, indolyl, halogen, hydroxy, oxo, nitro, carboxy and cyano, $R_e$ may be further optionally substituted by one or more $R_f$;

$R_f$ is selected from C1–3 alkyl, C5–6 cycloalkyl, phenyl optionally substituted by one or more groups selected from halogen or methyl, heterocyclyl selected from pyrrolidinyl, piperidinyl, morpholinyl and piperazinyl, heteroaryl selected from furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano;

or $R_5$ and $R_9$ together with the carbon they are attached form a carbocyclic ring selected from:

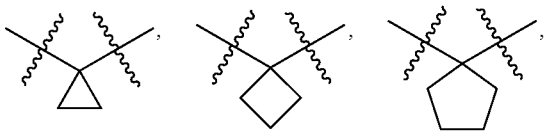

-continued

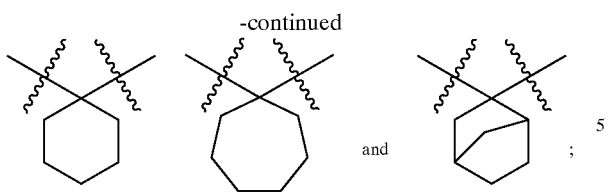

and ;

each carbocyclic ring being optionally benzofused and optionally substituted with one or more $R_g$;

$R_g$ is selected from C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl or arylC1–3alkyl; halogen, hydroxy, carboxy and cyano.

6. The compound according claim 5 wherein:

$R_1$ and $R_6$ of the formula (Ia) form the bicyclic ring selected from:

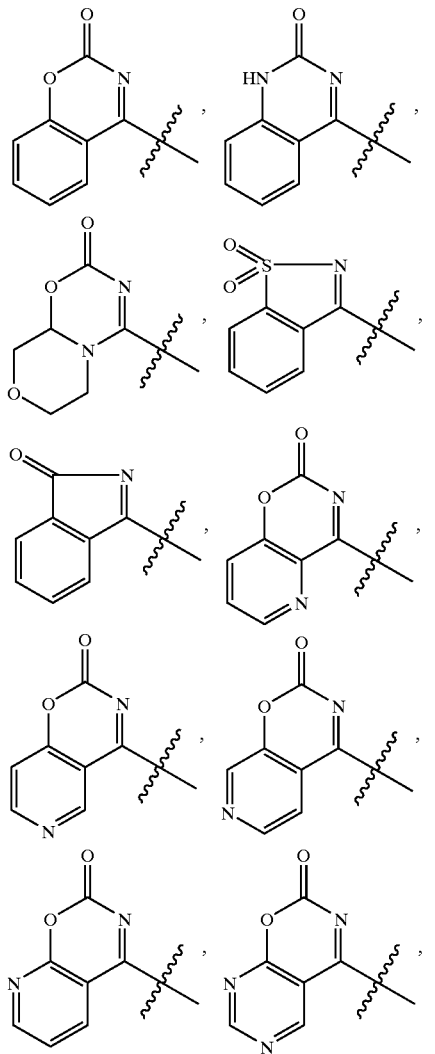

-continued

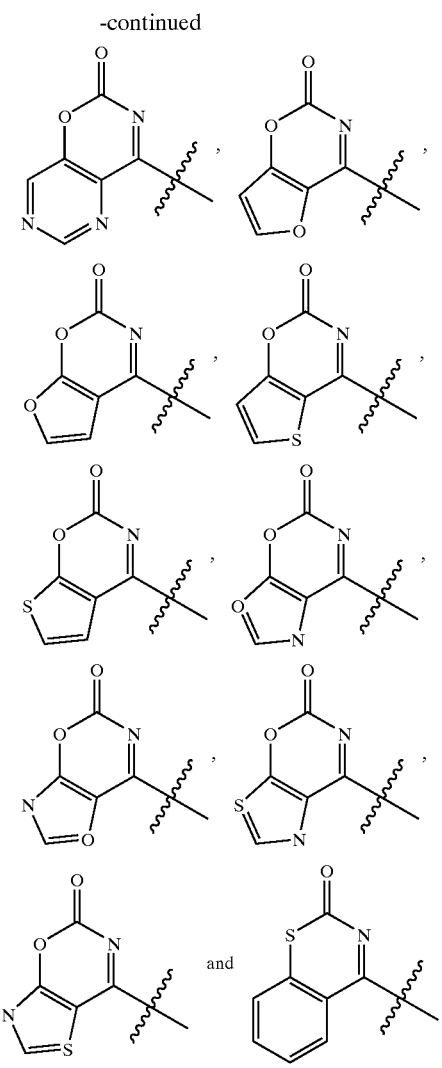

or $R_1$ and $R_6$ of the formula (Ia) form the tricyclic ring selected from:

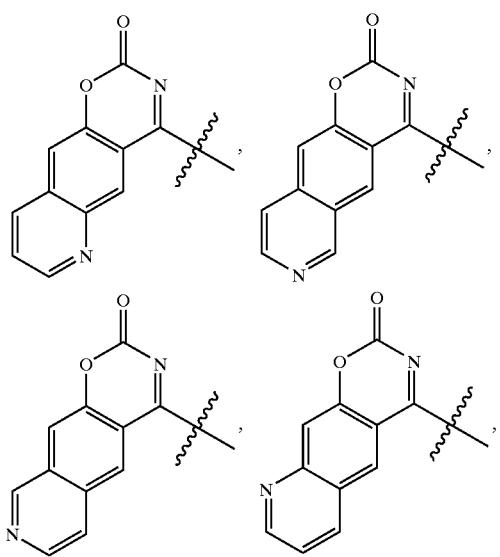

-continued

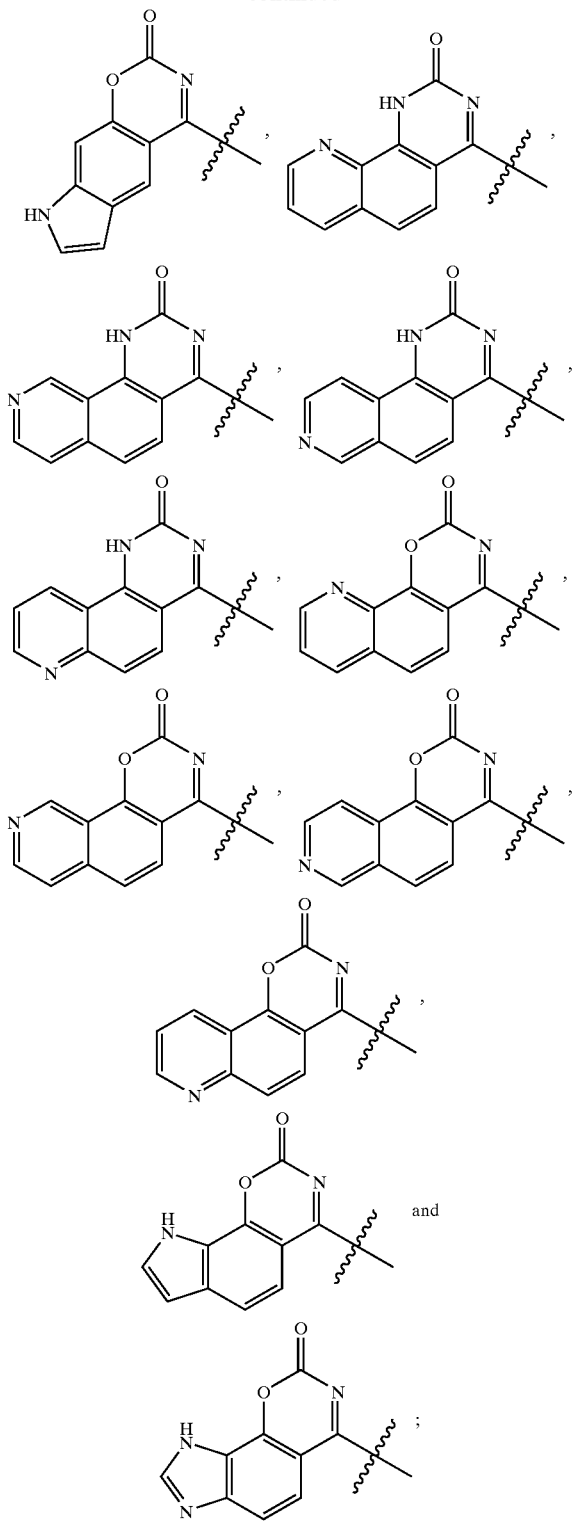

wherein each ring is optionally independently substituted by one or two $R_7$;

$R_3$ is methyl, ethyl, n-propyl, propenyl, butenyl, i-butenyl, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminocC1–3 alkyl, mono or di-C1–3 alkylaminoC1–3 alkyl, mono or di-C1–3 alkylamidoC1–3 alkyl, heterocyclylC1–2 alkyl wherein the heterocyclic moiety is selected from pyrrolidinyl, piperidinyl, morpholinyl, thiomorpholinyl, 8-aza-bicyclo[3.2.1]octane, silinane, piperazinyl, tetrahydrofuranyl, tetrahydropyranyl, tetrahydrothiopyranyl and indolyl, benzyl or naphthylmethyl wherein $R_3$ is optionally substituted by one to two $R_c$;

$R_c$ is methyl, cyclohexyl, cyclopentyl, indanyl, 1,2,3,4-tetrahydronaphthyl, spiro[2.5] octanyl, spiro[3.5] nonyl, spiro[4.5] decanyl, fluoro or chloro;

$R_9$ is hydrogen, C1–4 alkyl, C1–5 alkylene, C1–3 alkoxyC1–3 alkyl, C1–3 alkoxycarbonylC1–3 alkyl, C1–3 alkylthioC1–3 alkyl, C1–3 alkylsulfinylC1–3 alkyl, C1–3 alkylsulfonylC1–3 alkyl, aminoC1–3 alkyl, mono or di-C1–3 alkylaminoC1–3 alkyl, mono or di-C1–3 alkylamidoC1–3 alkyl, phenyl, furanyl, thienyl, thiazolyl, imidazolyl, pyridinyl, indolyl or cyano wherein $R_5$ is optionally substituted by one to two groups of the formula $R_e$;

$R_e$ is selected from methyl, C3–6 cycloalkyl, phenyl, benzoyl, naphthyl, furanyl, thienyl, thiazolyl, imidazolyl, pyridinyl, piperidinyl, piperazinyl, morpholinyl, thiomorpholinyl, indolyl, halogen, hydroxy, carboxy and cyano, $R_e$ may be further optionally substituted by one or more $R_f$.

$R_f$ is selected from C1–3 alkyl, phenyl or phenylsulfonyl each optionally substituted by one or more groups selected from halogen or methyl, C1–3 alkoxy, aryloxy, benzoyl, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, nitro, carboxy and cyano;

and $R_g$ is selected from C1–3 alkyl, phenyl, C1–3 alkoxycarbonyl, benzyloxy and carboxy.

7. A compound formula (Ia)

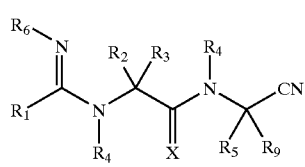

(Ia)

wherein for the formula (Ia), the components

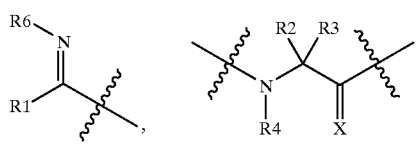

and

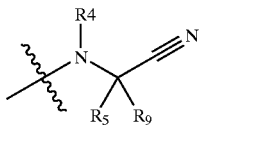

are chosen from any combination of A, B and C as follows:

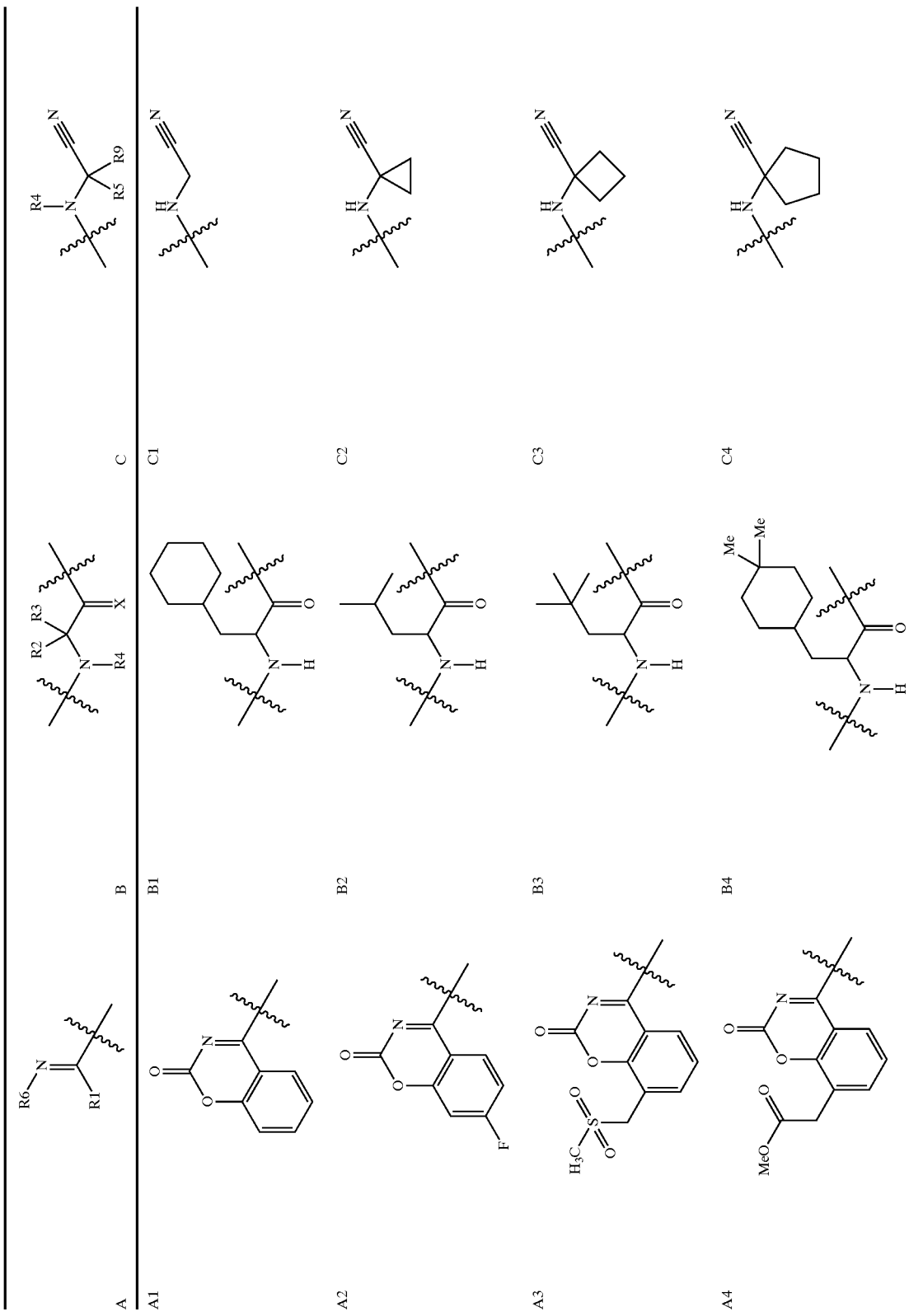

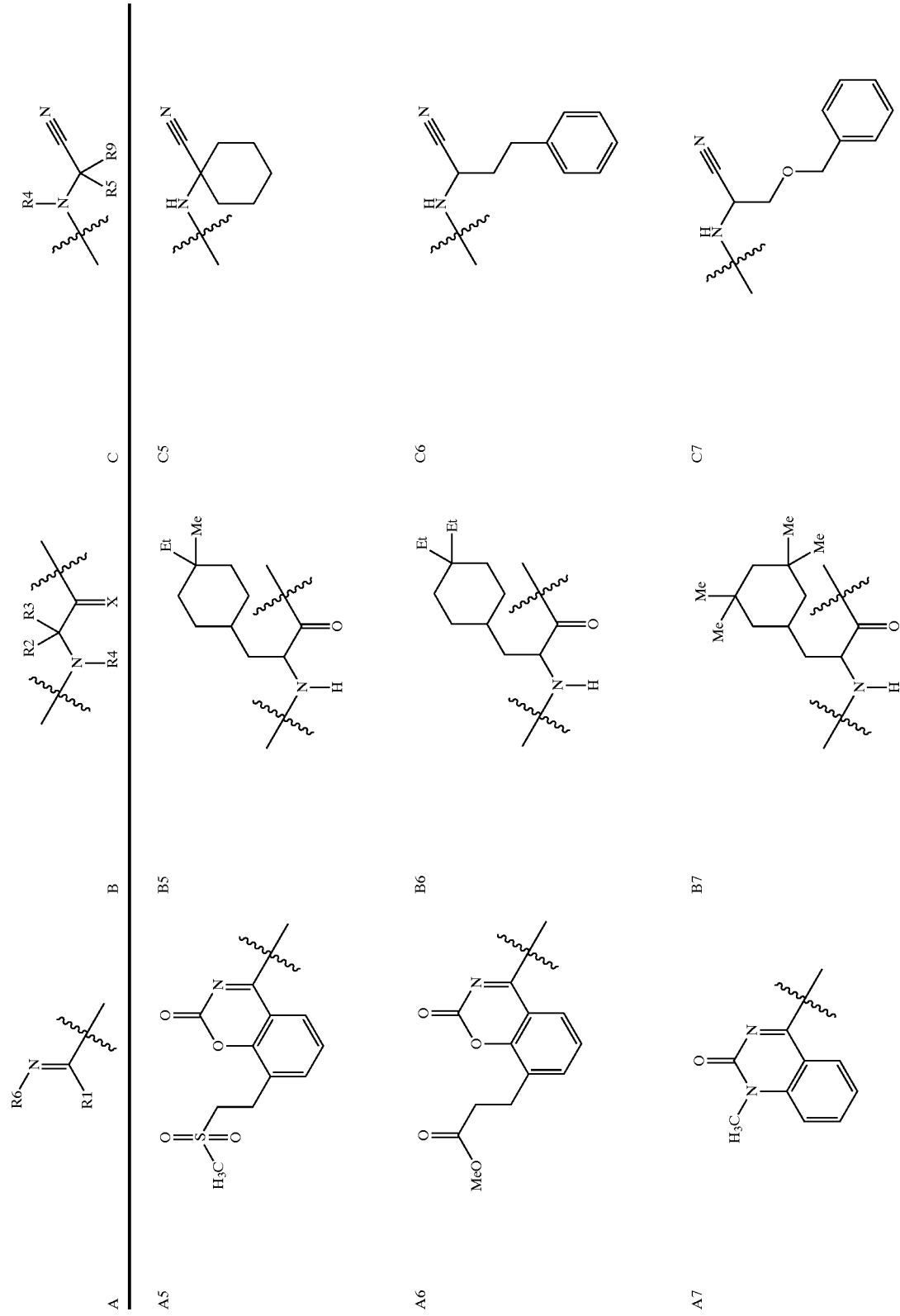

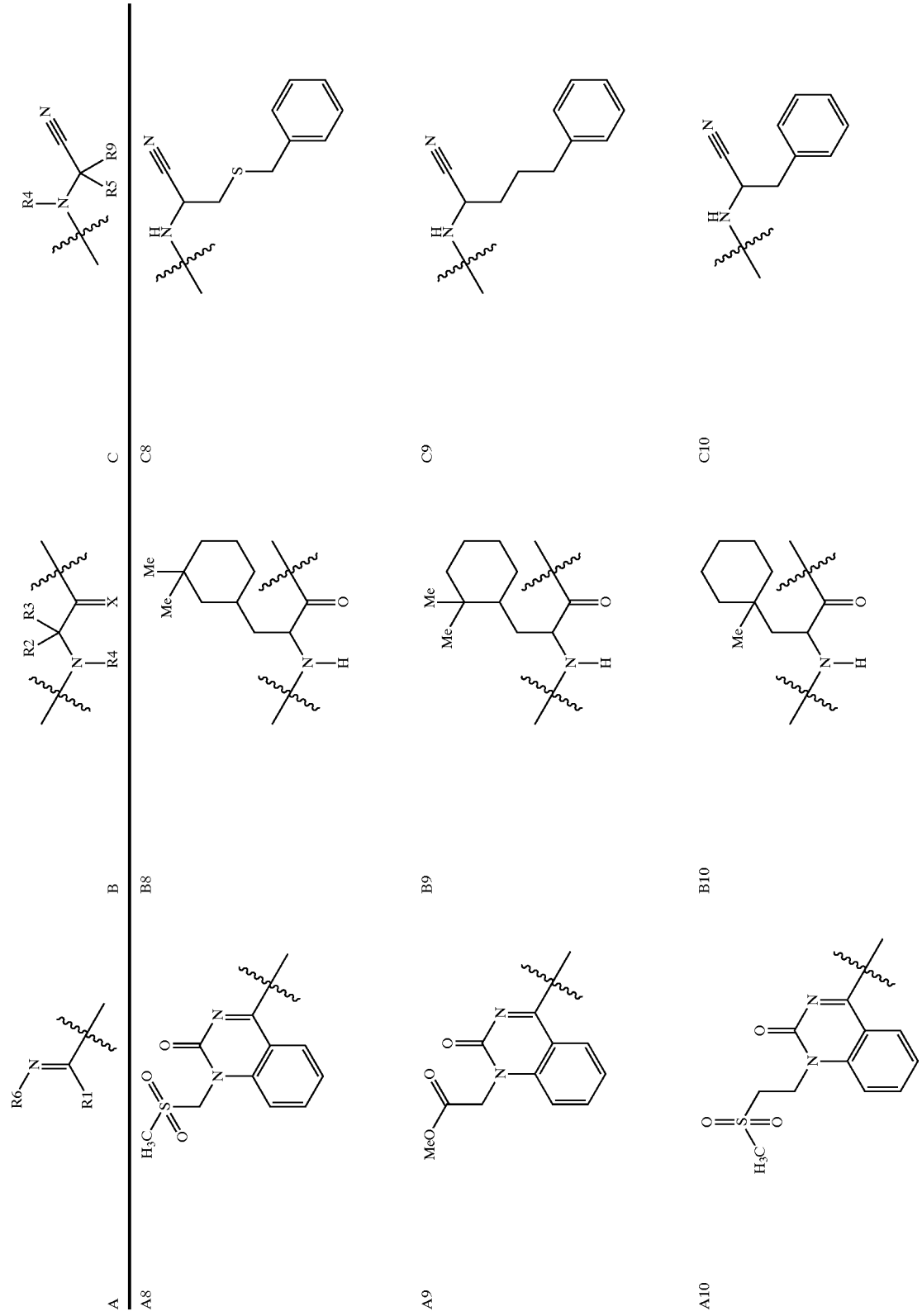

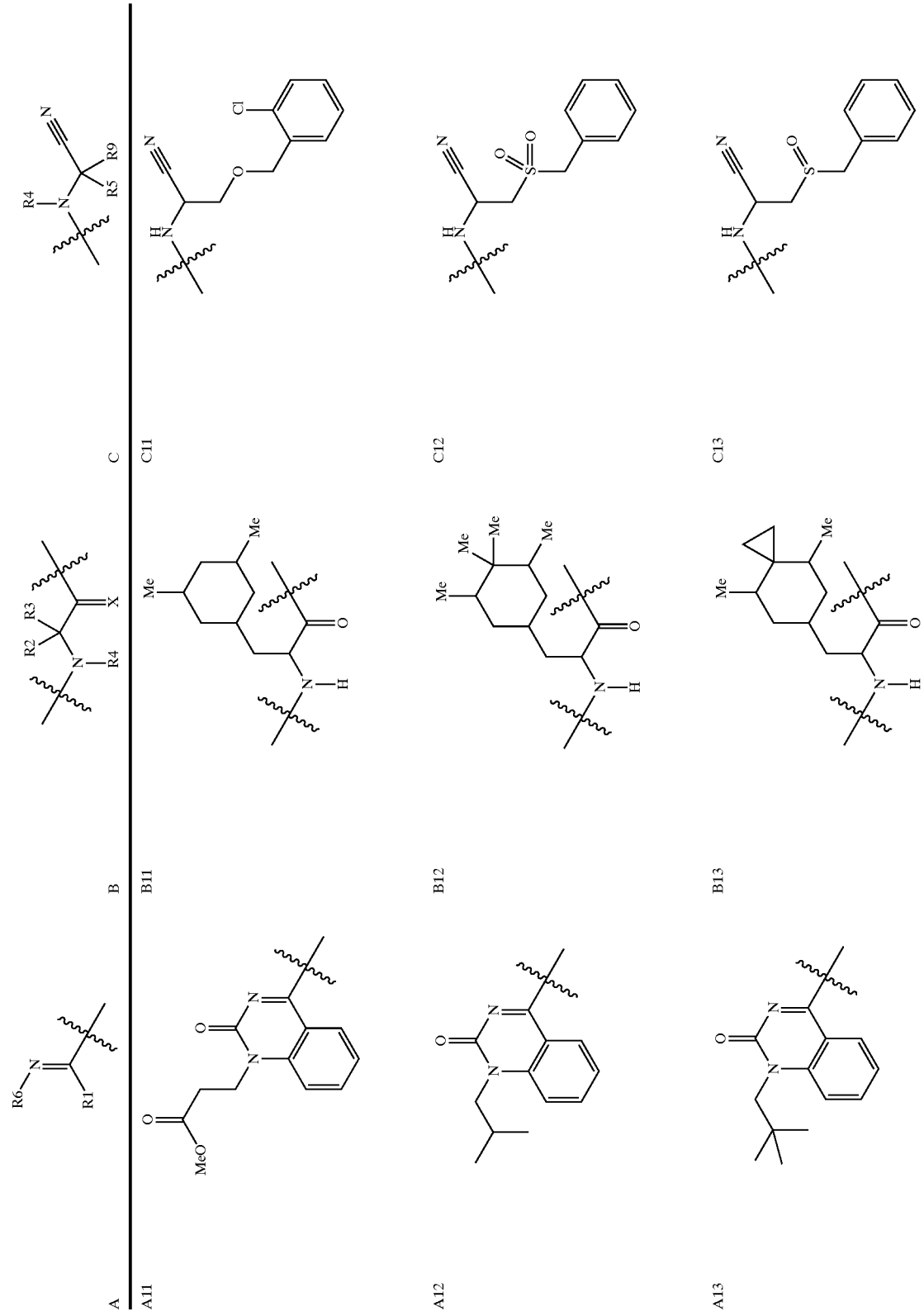

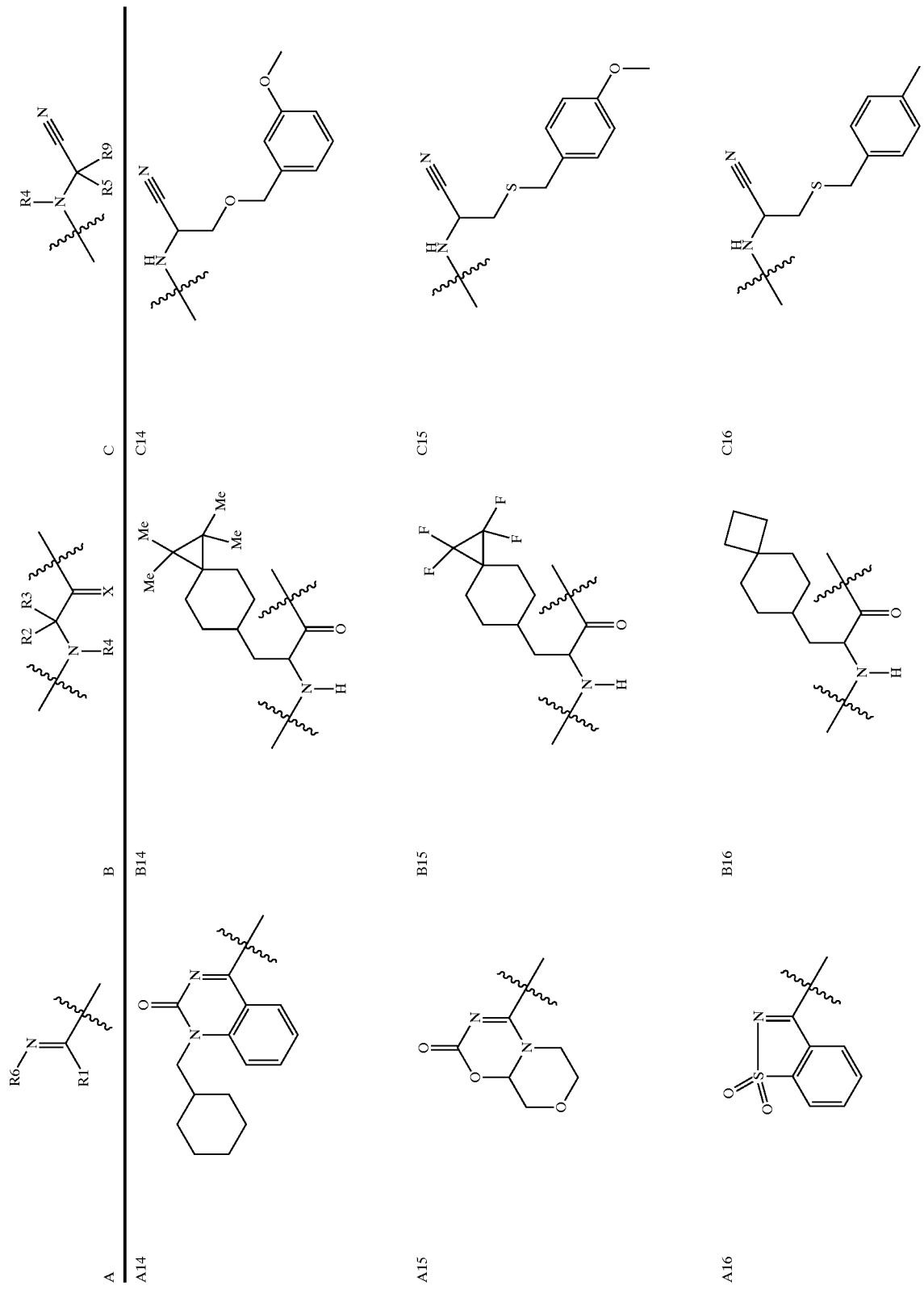

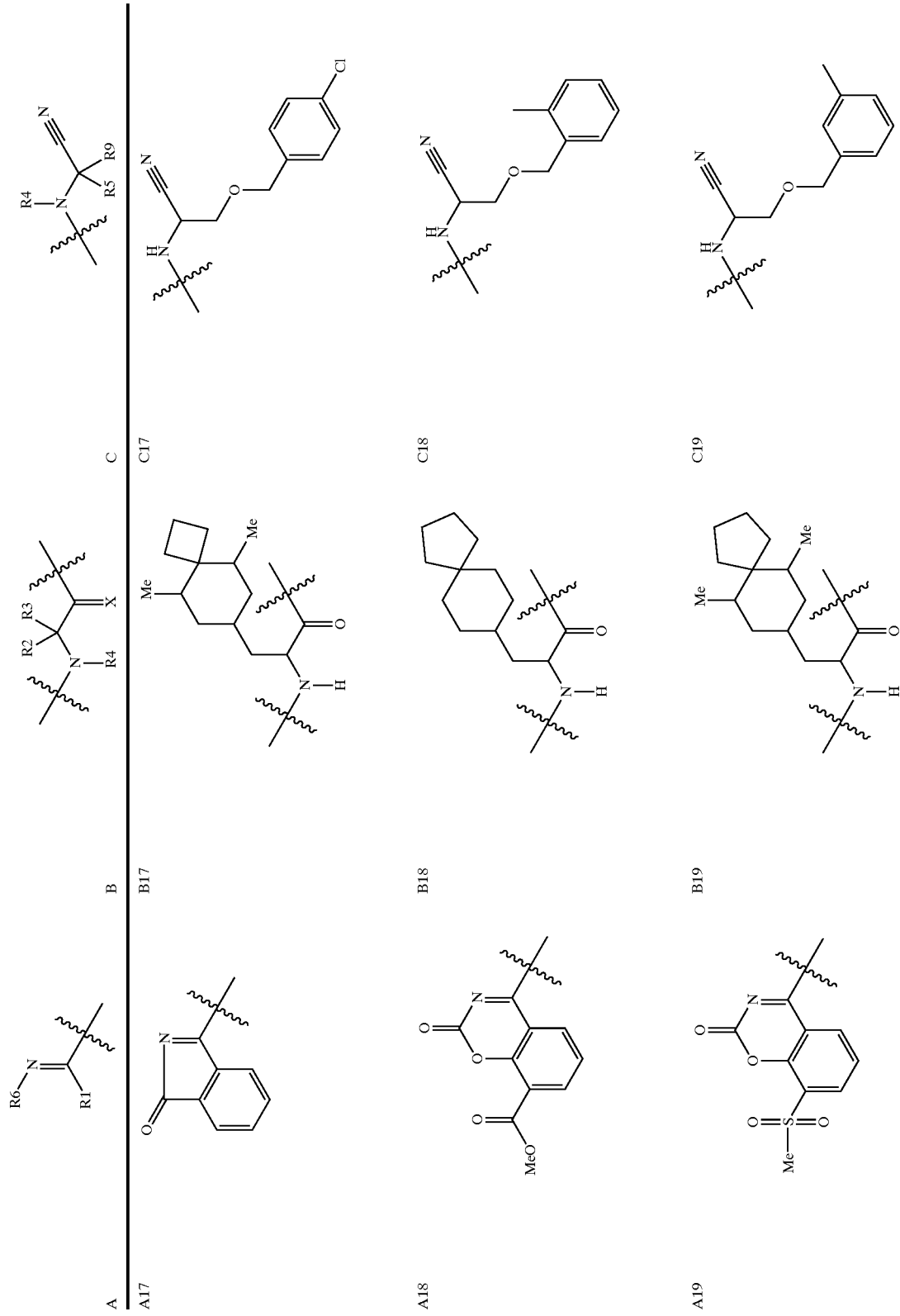

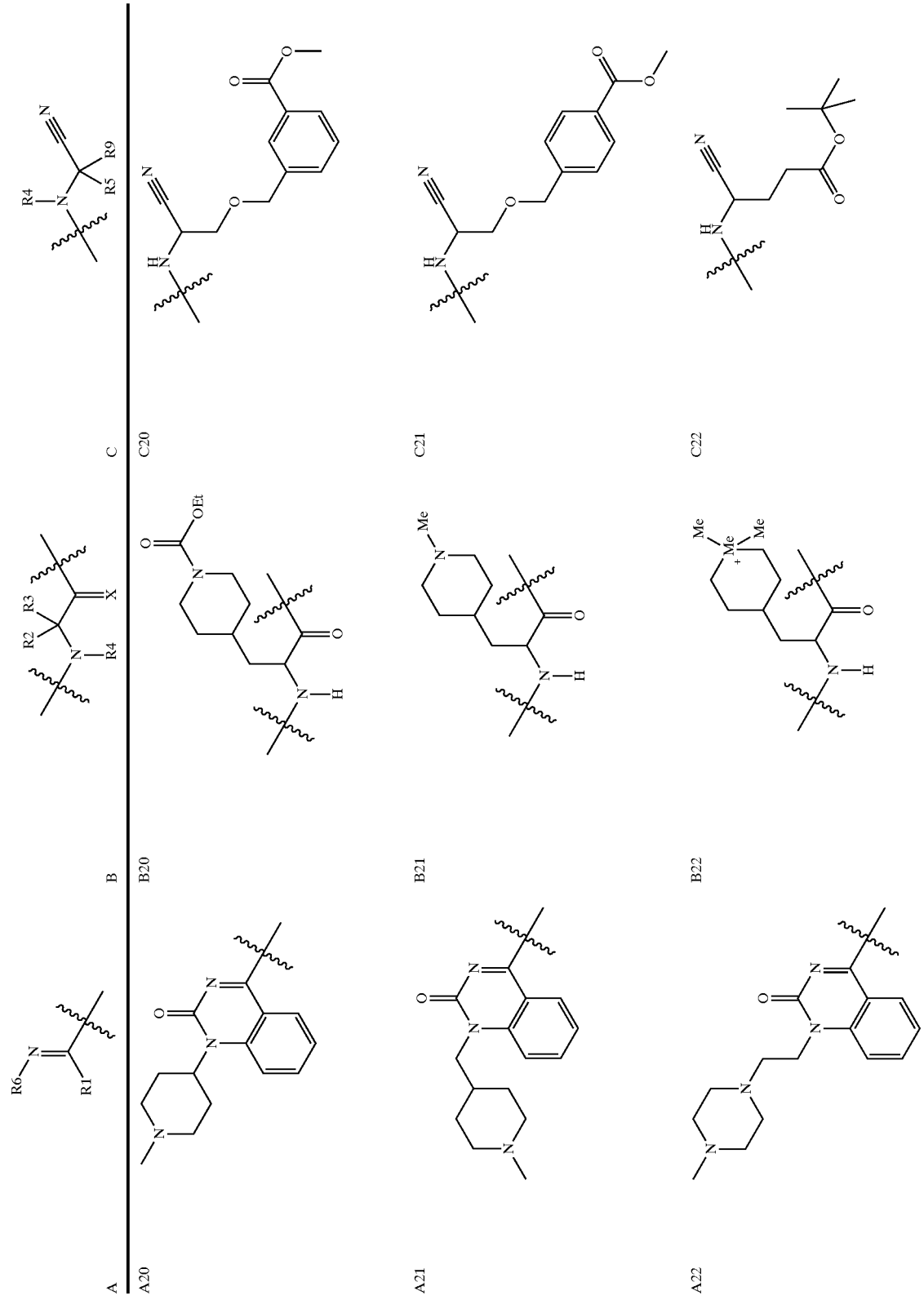

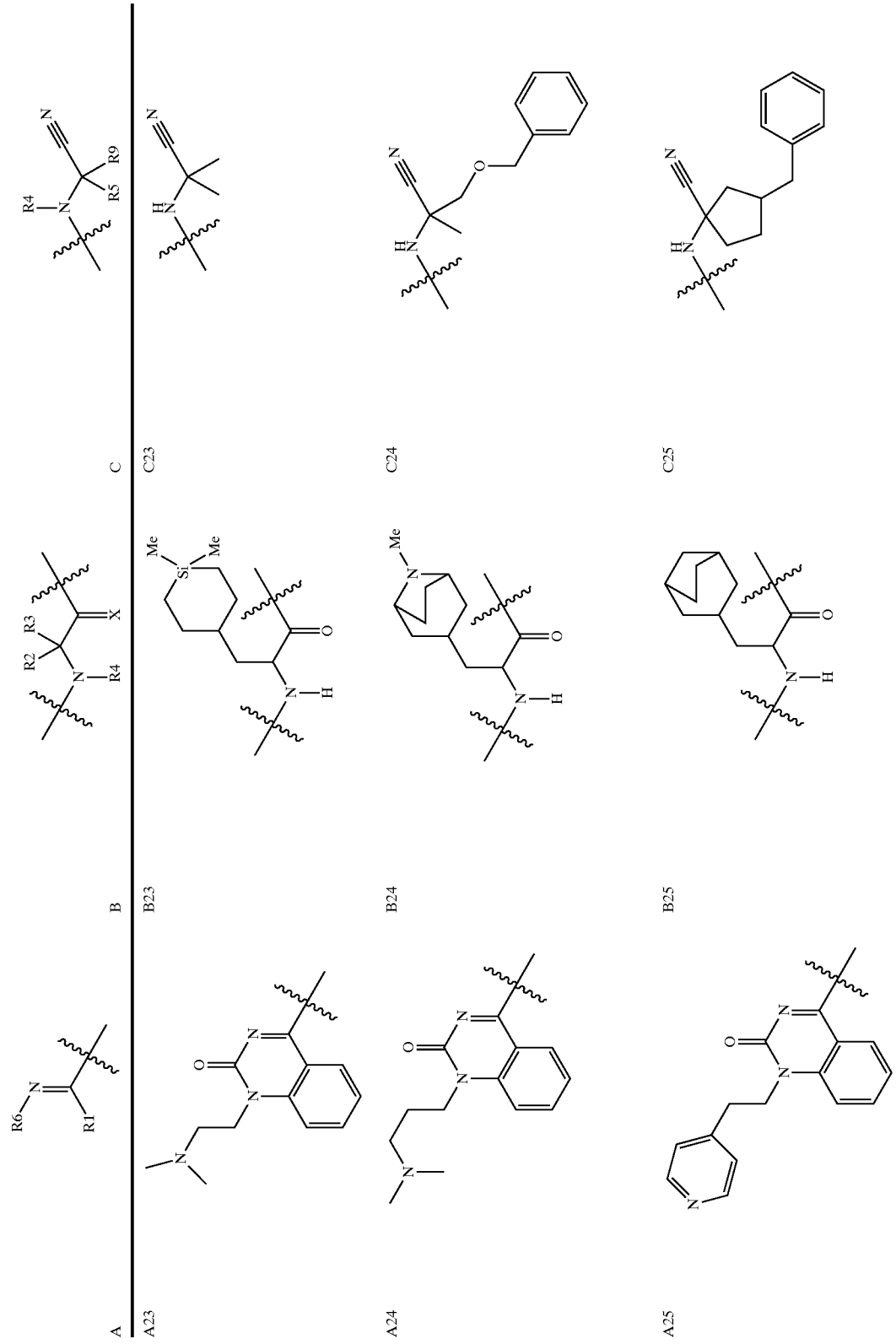

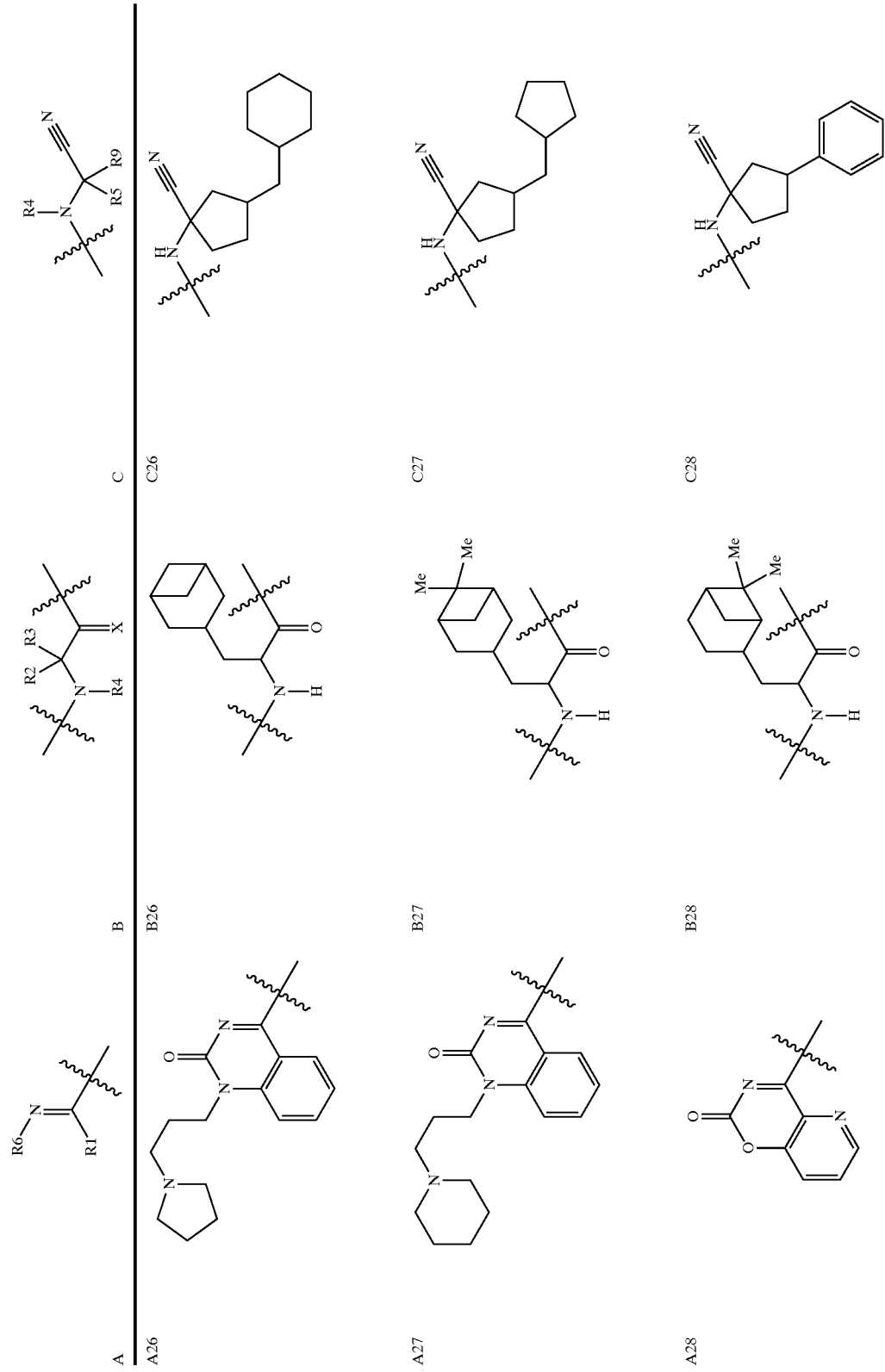

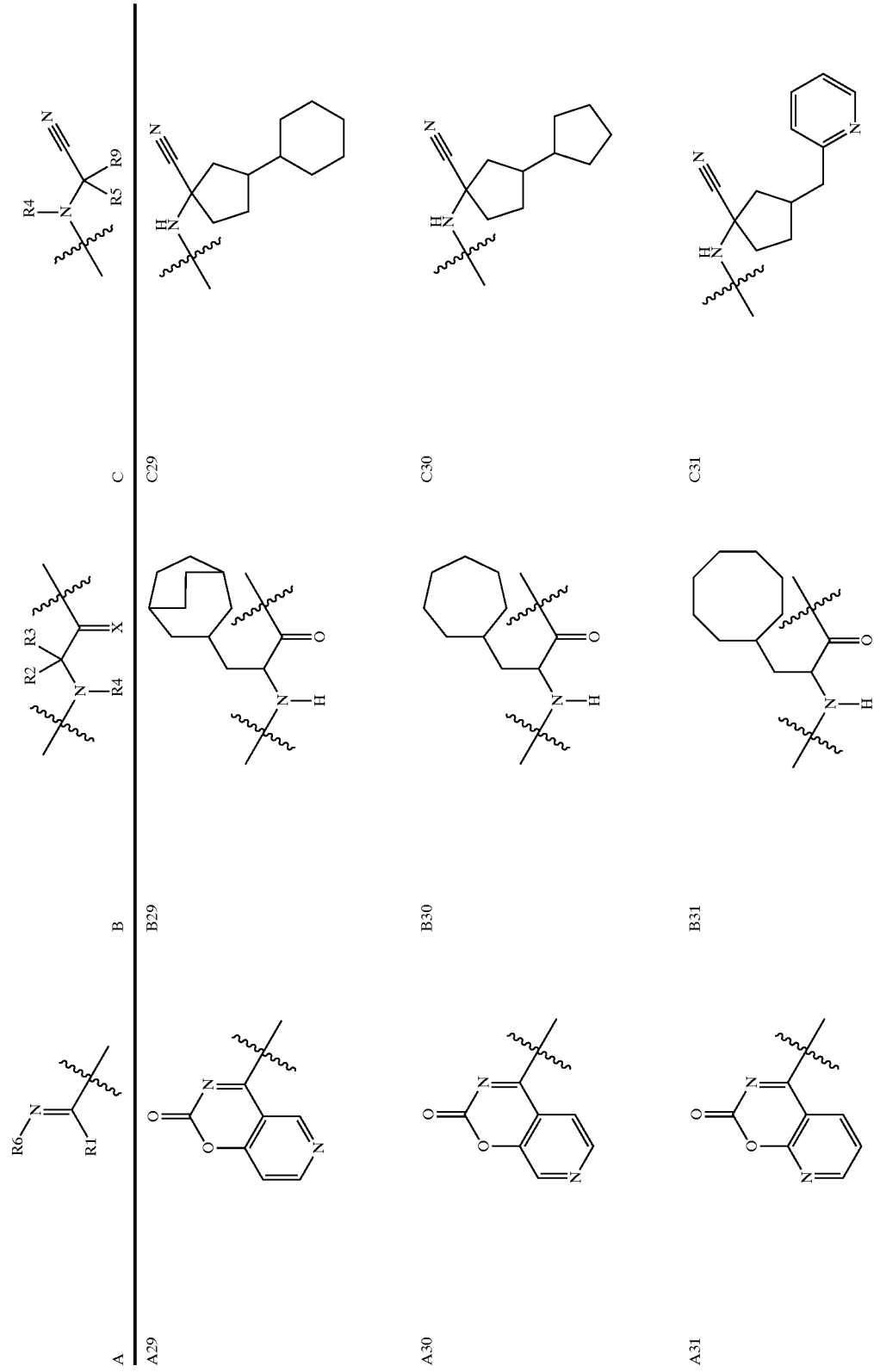

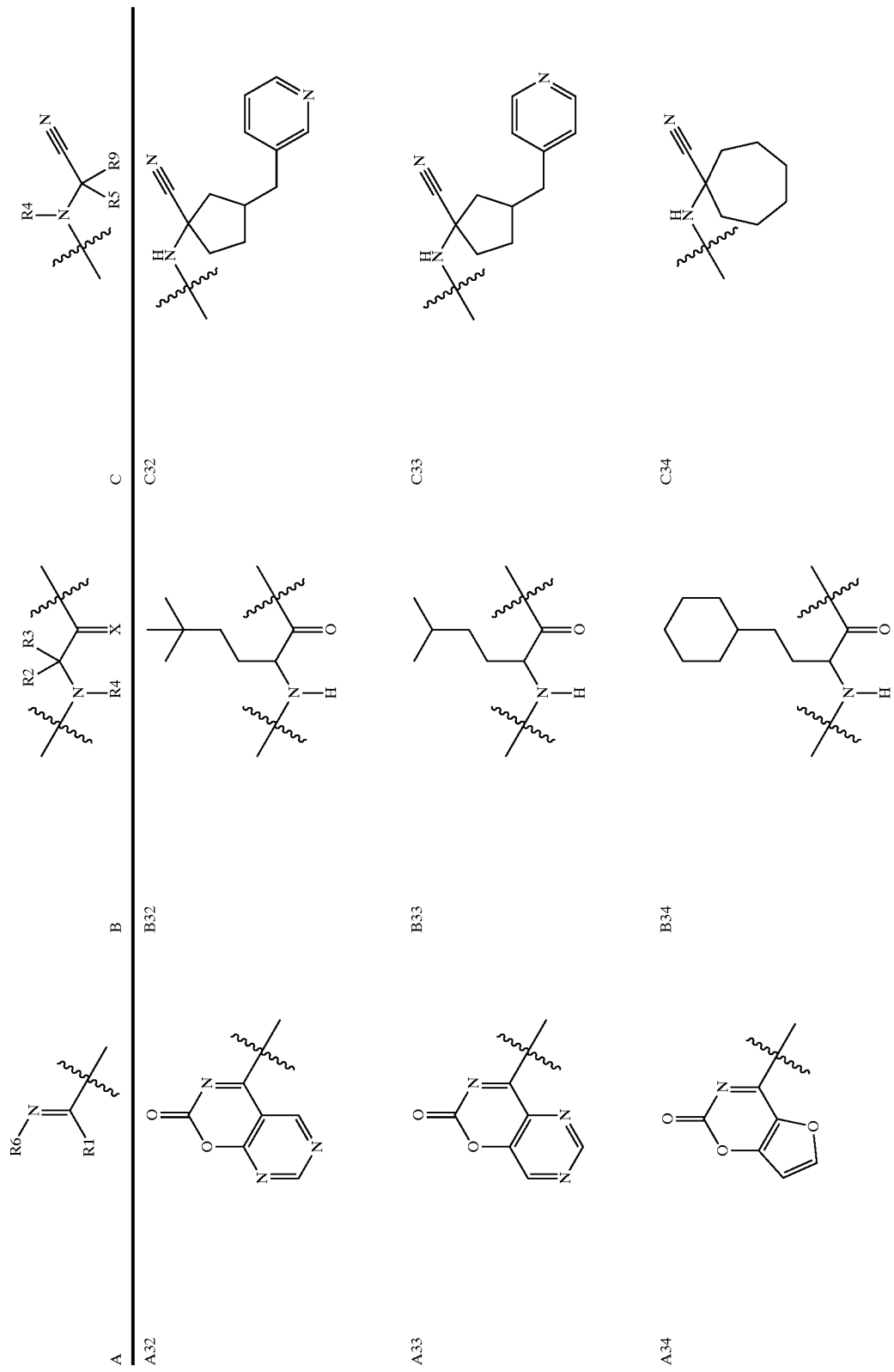

-continued
| A | B | C |
|---|---|---|
| A35 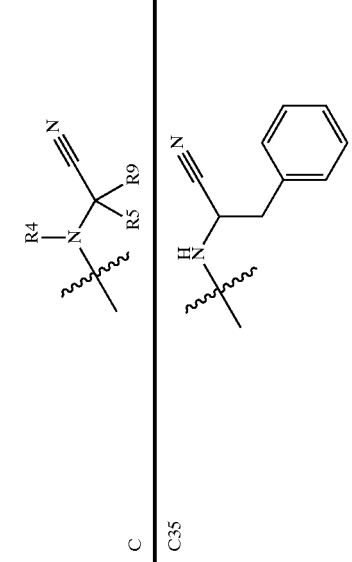 | B35 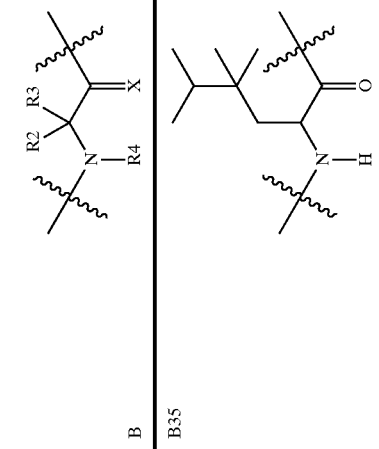 | C35 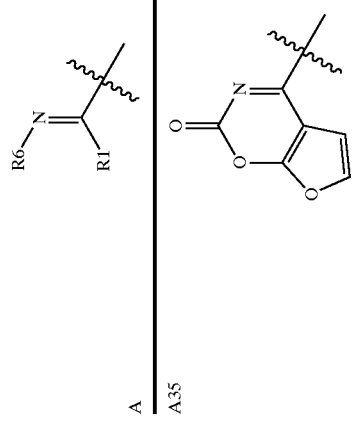 |
| A36 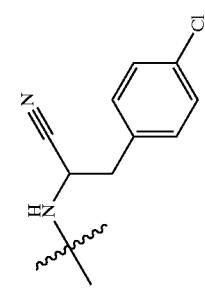 | B36 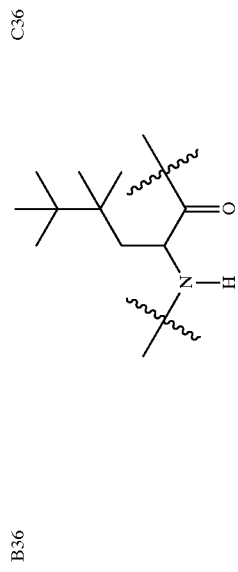 | C36 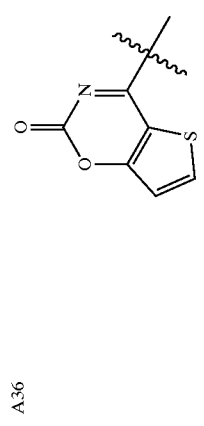 |
| A37 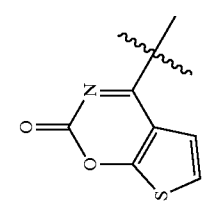 | B37 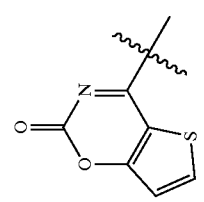 | C37 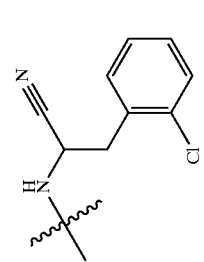 |

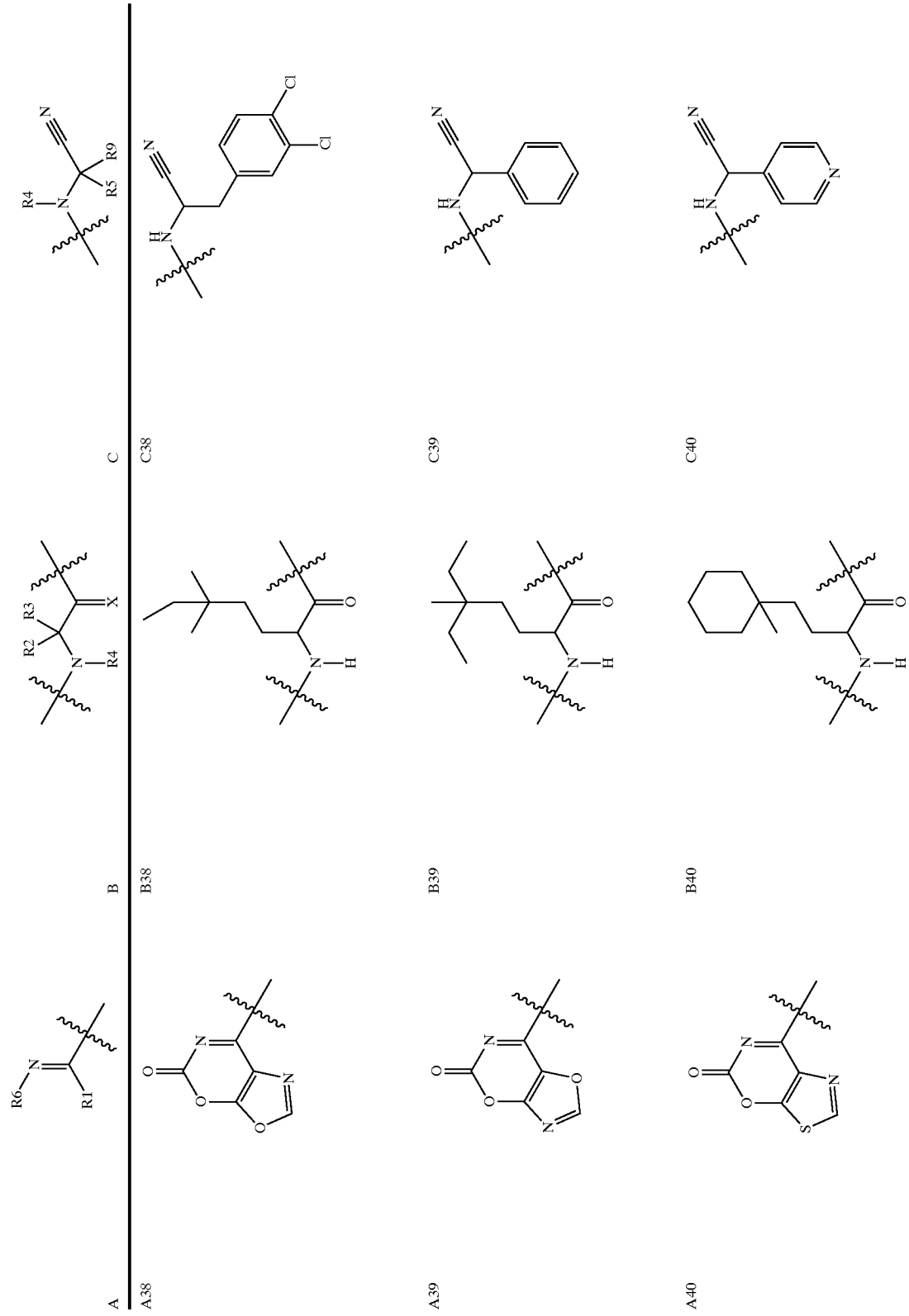

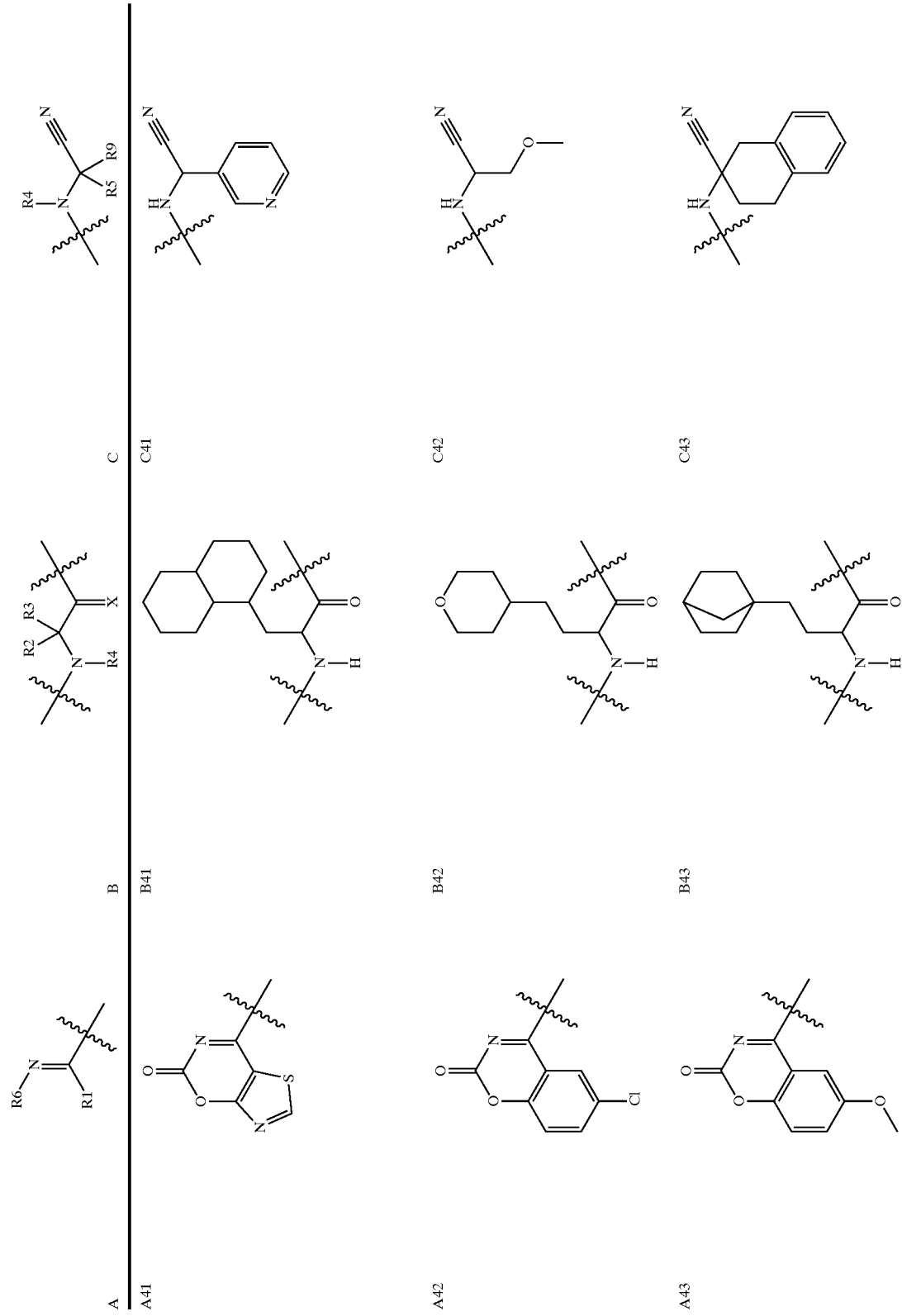

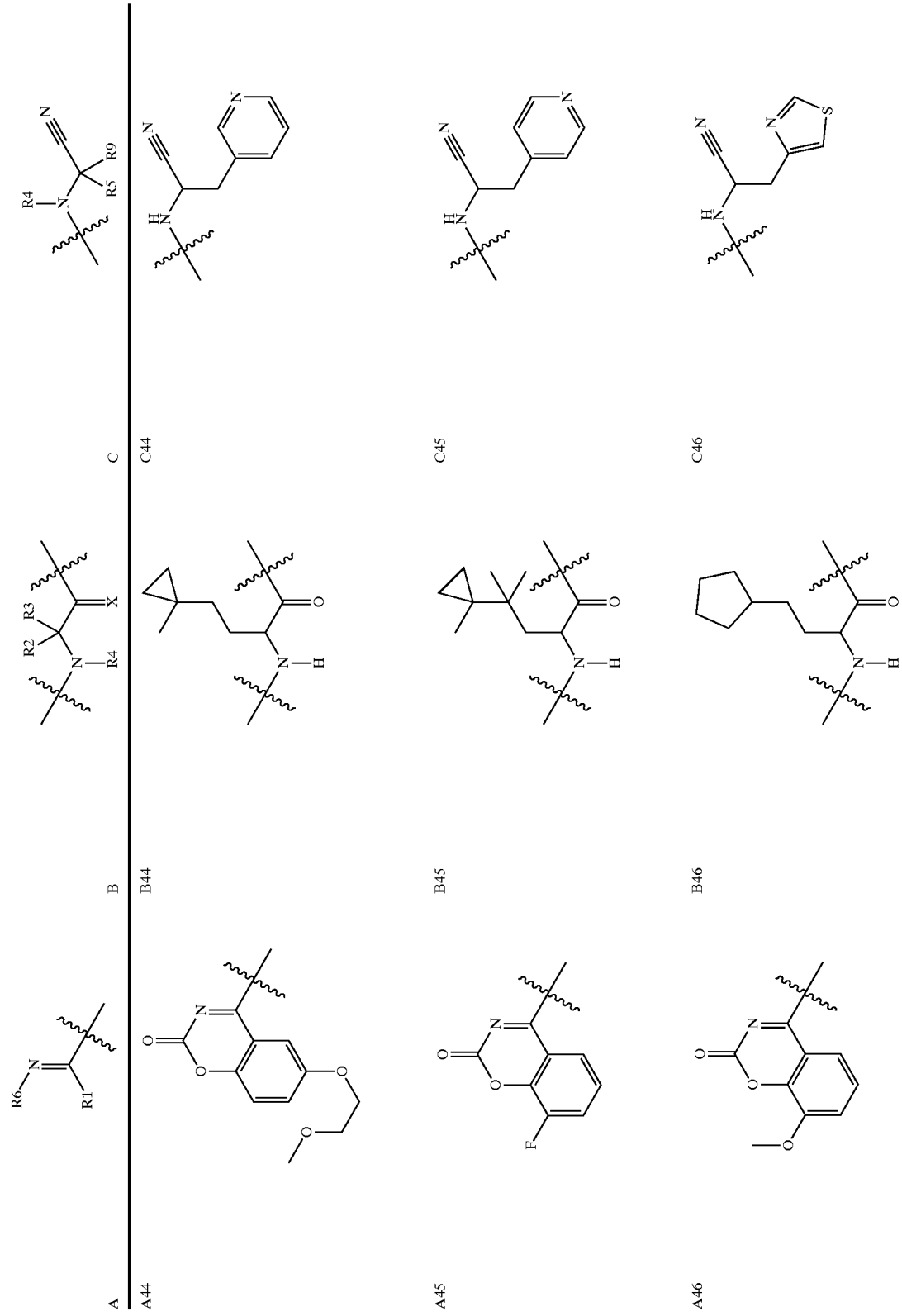

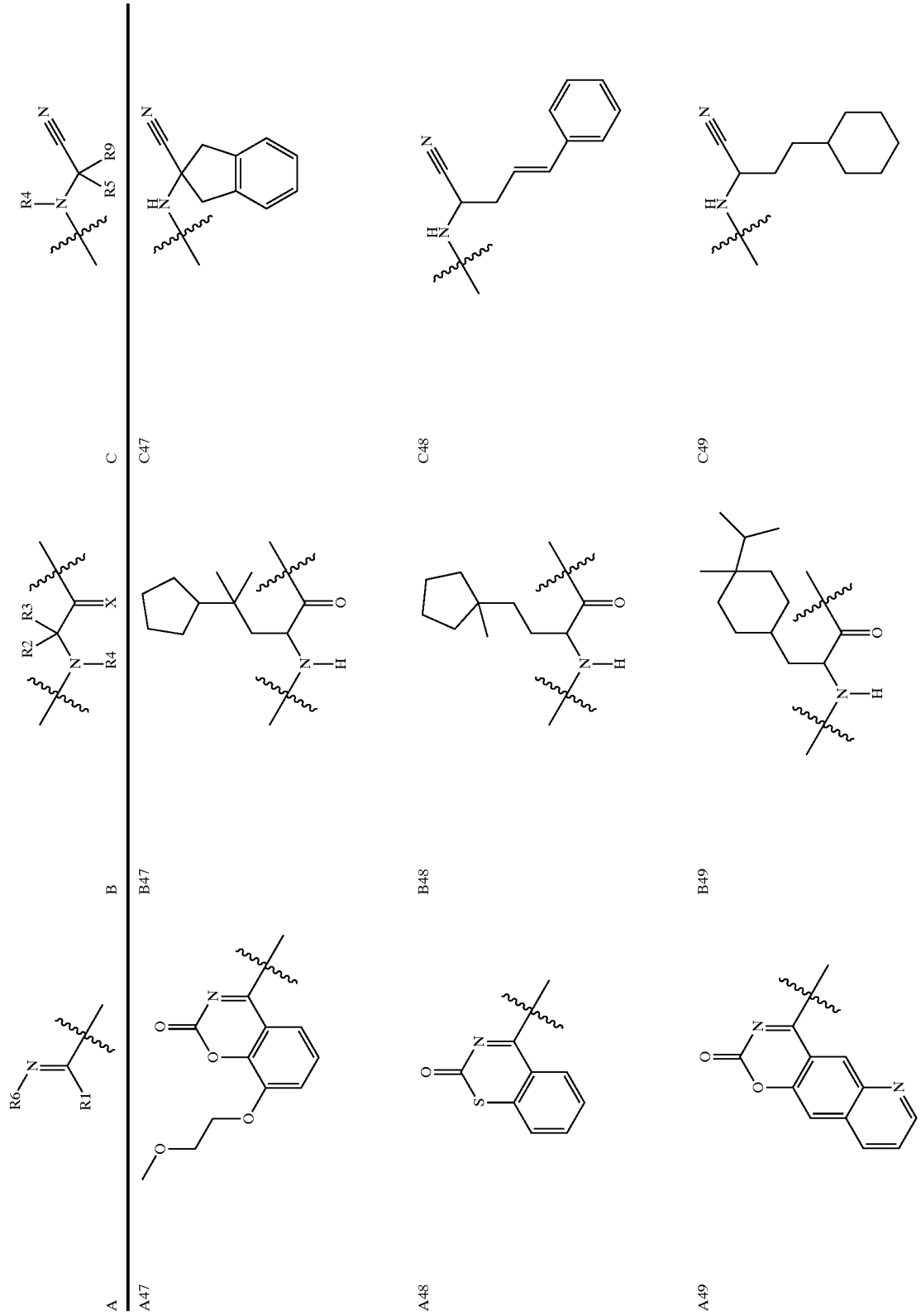

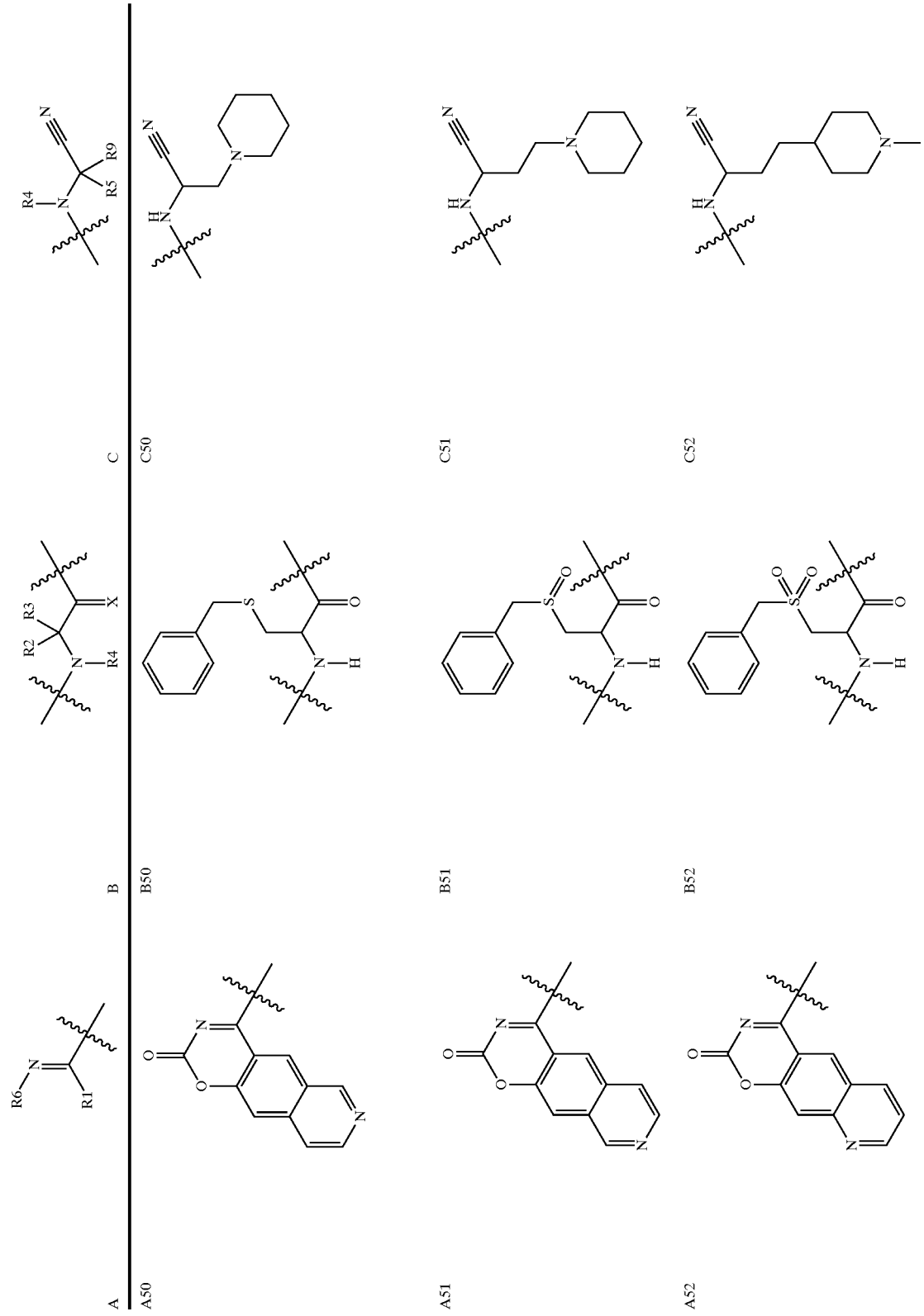

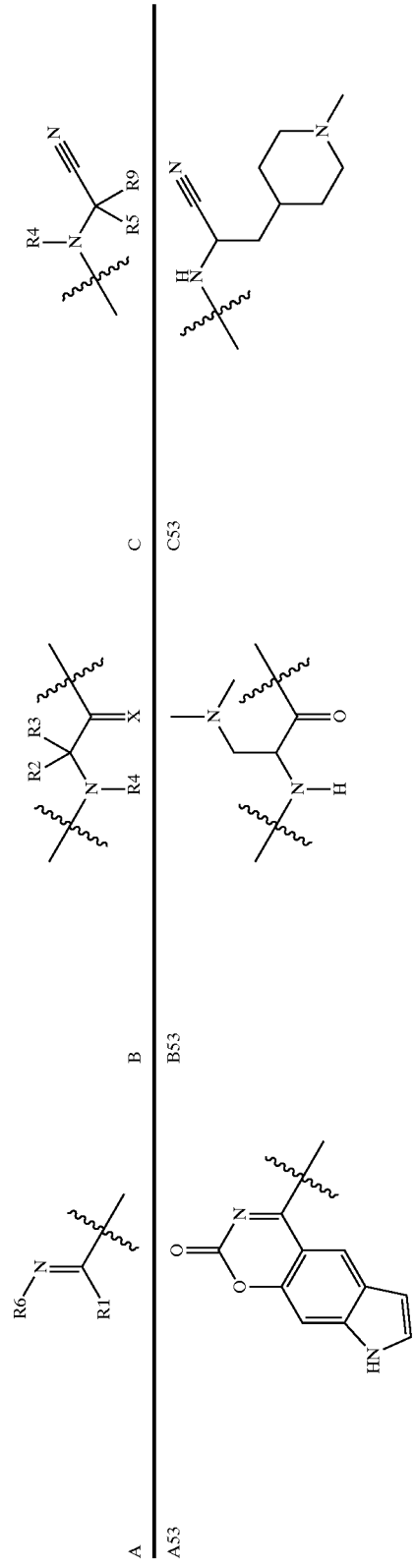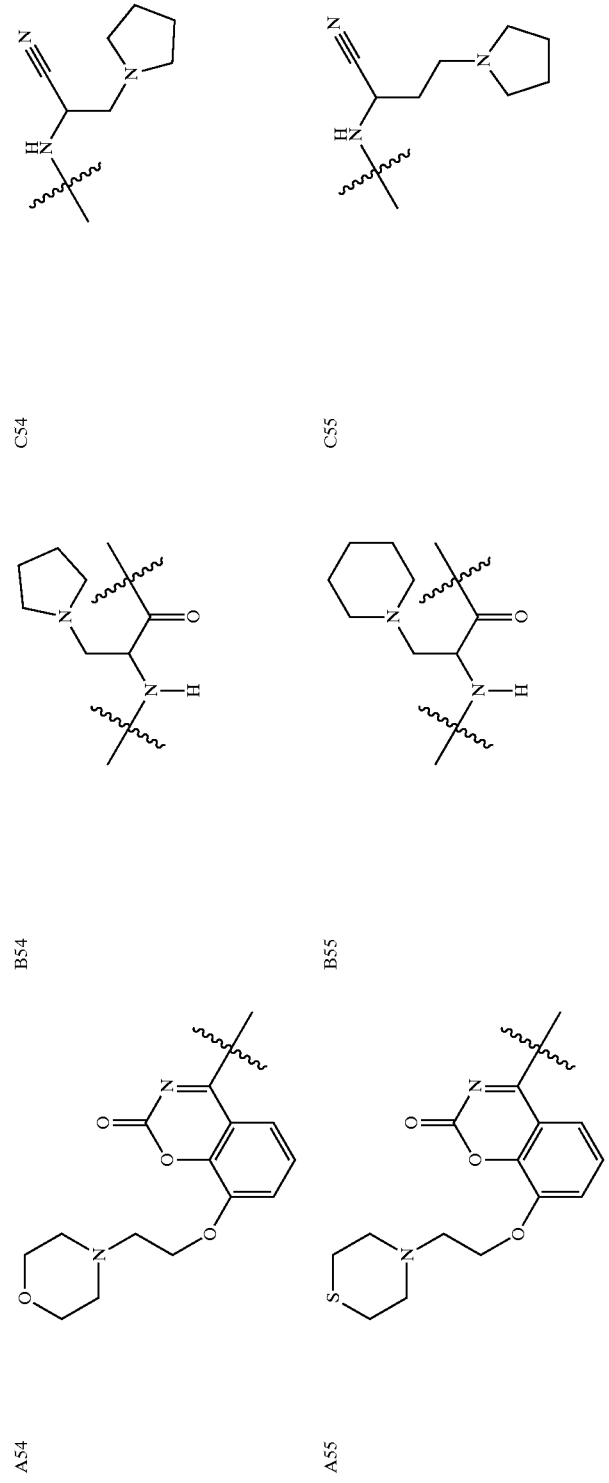

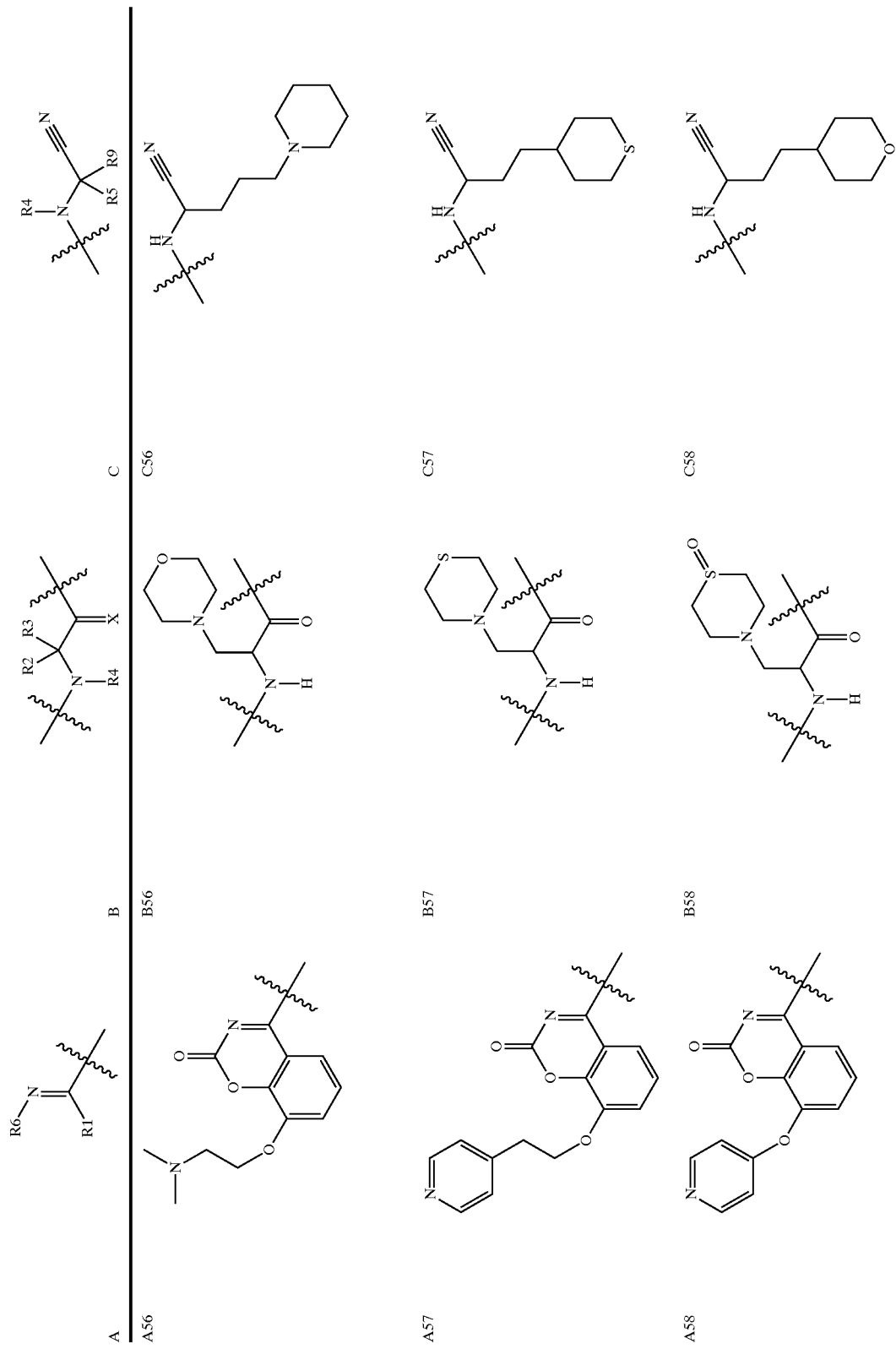

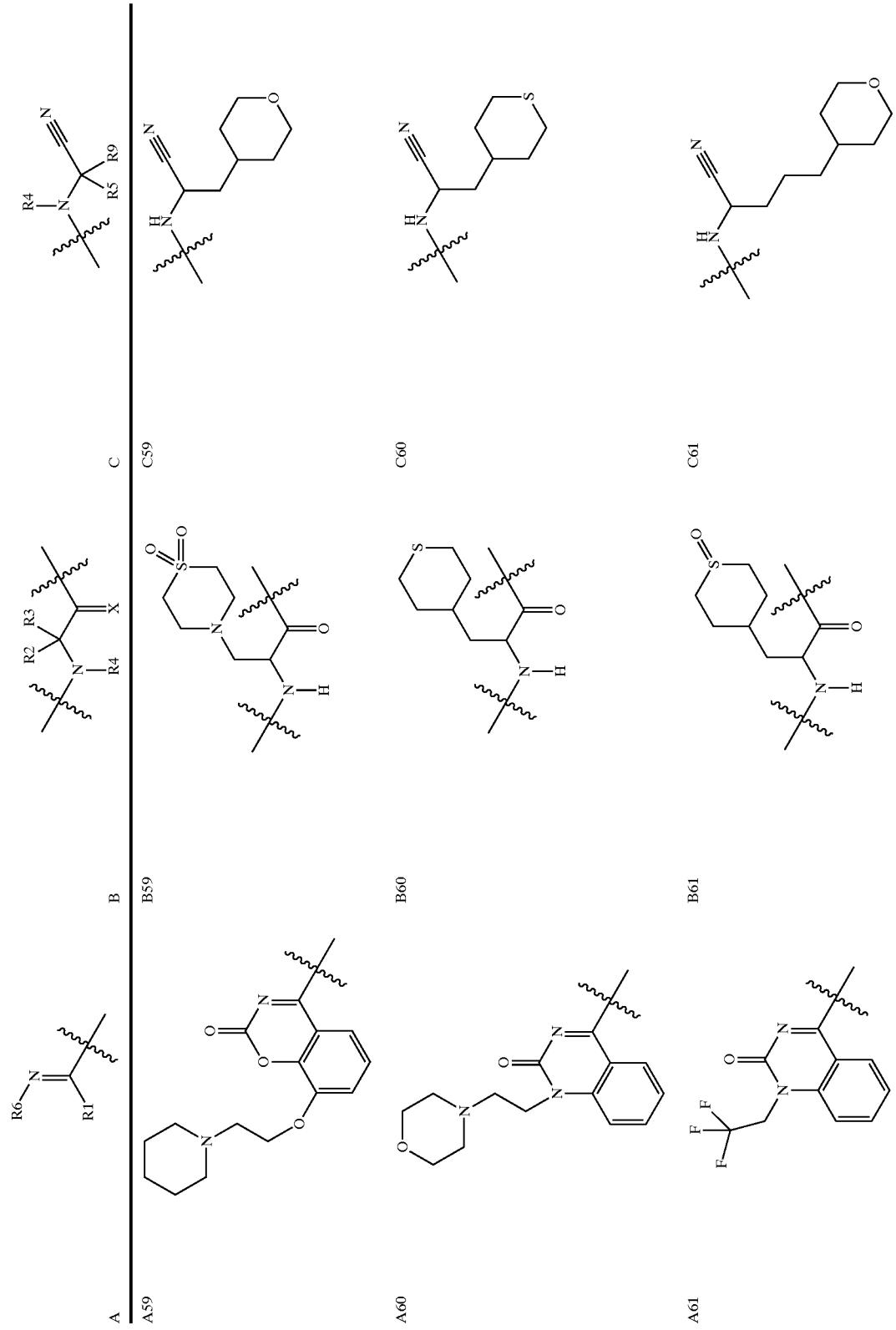

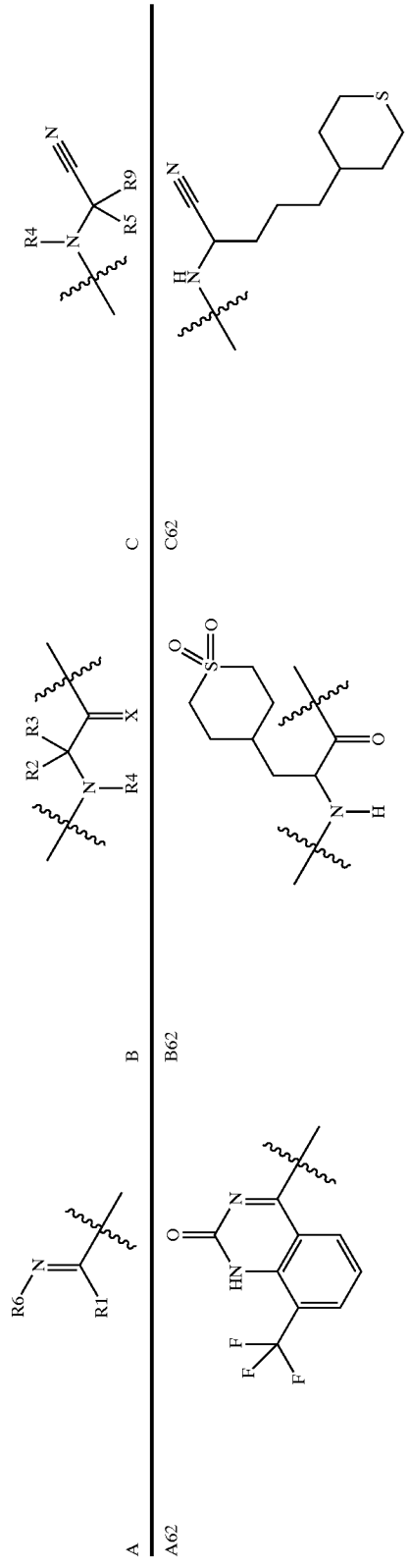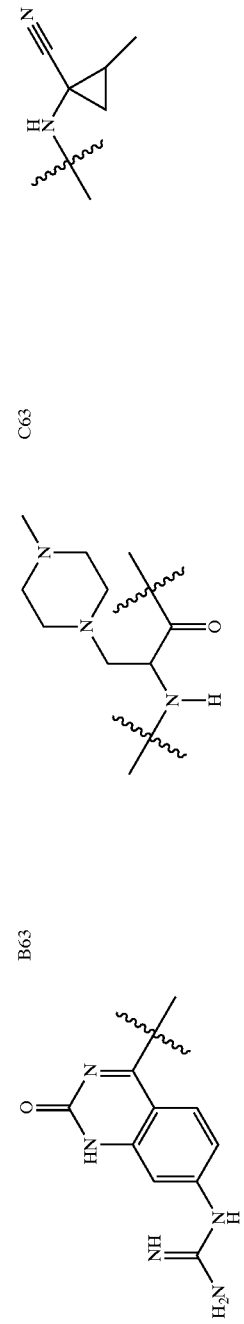

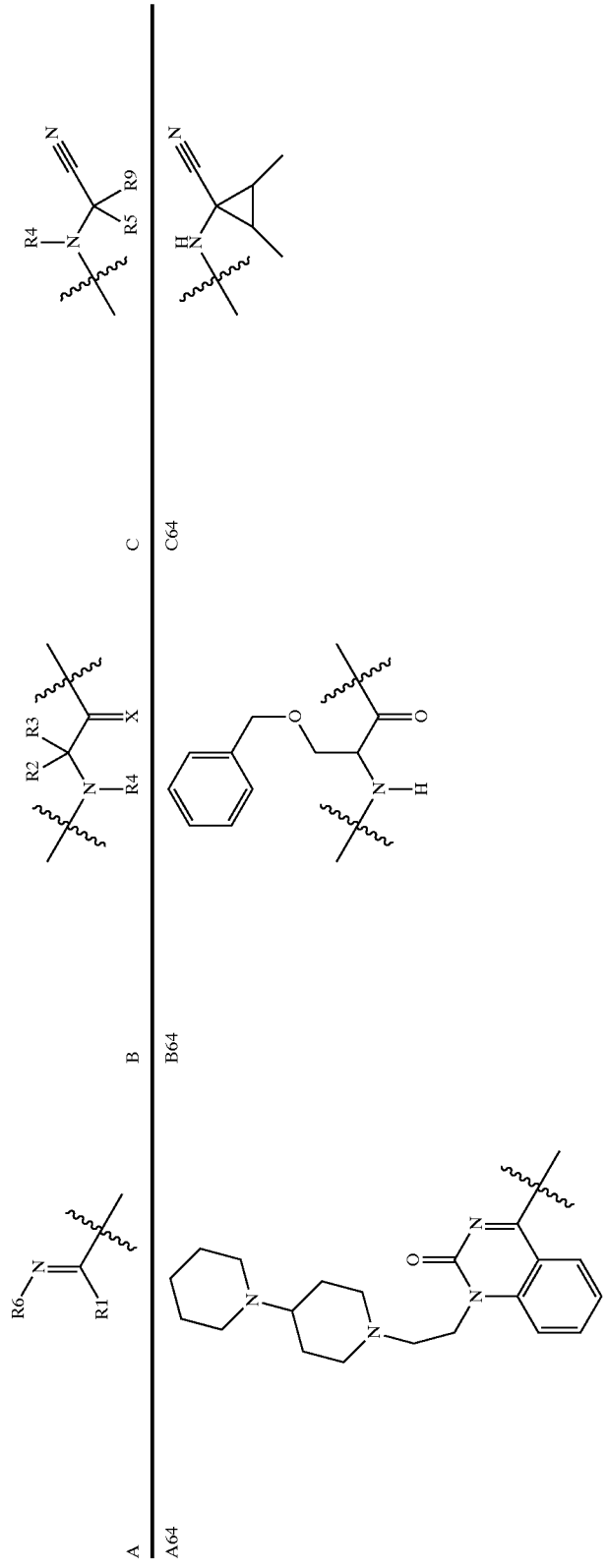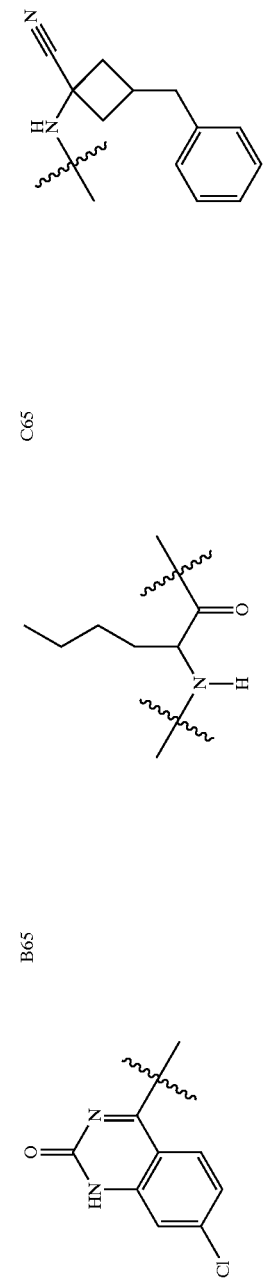

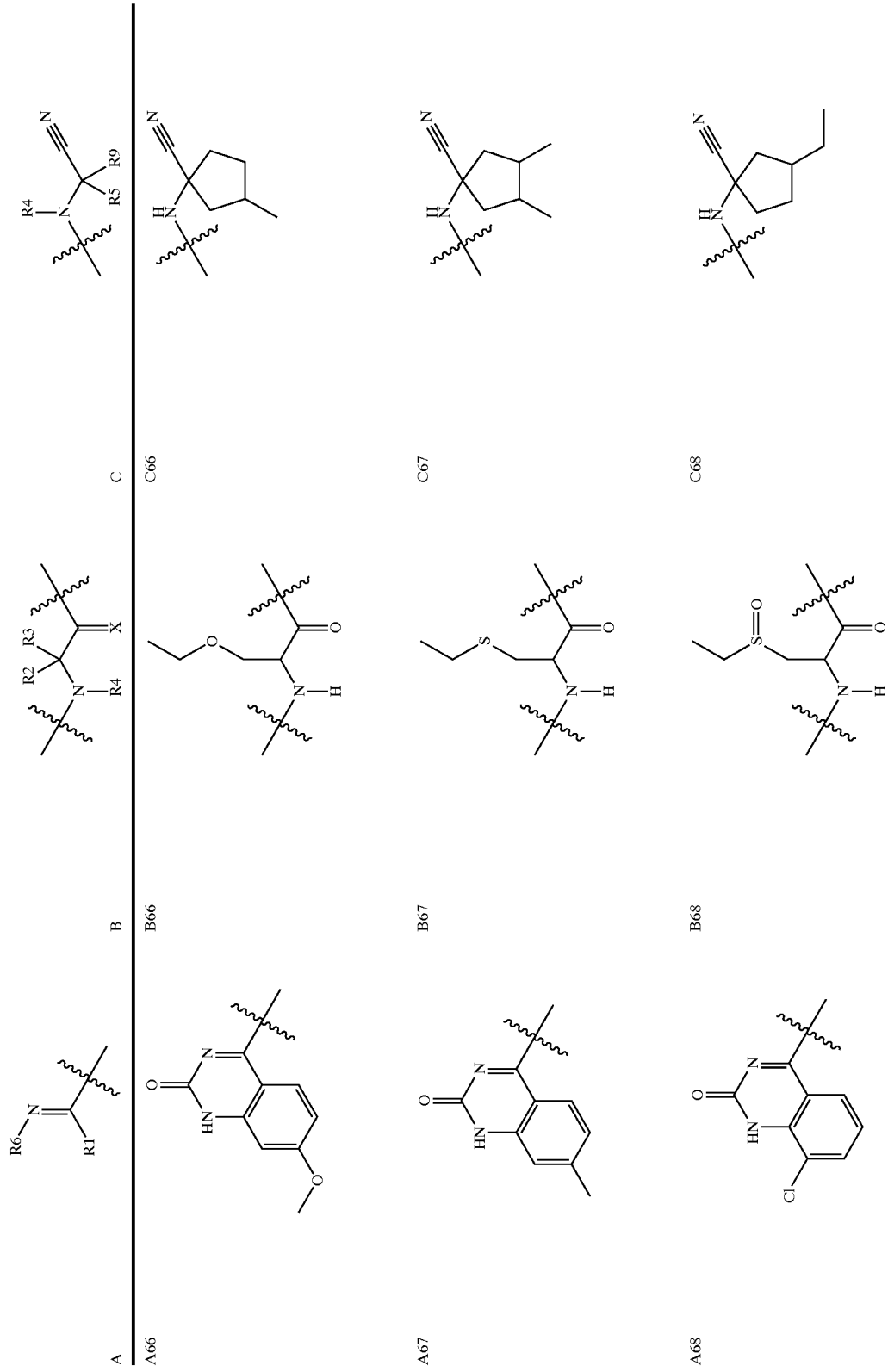

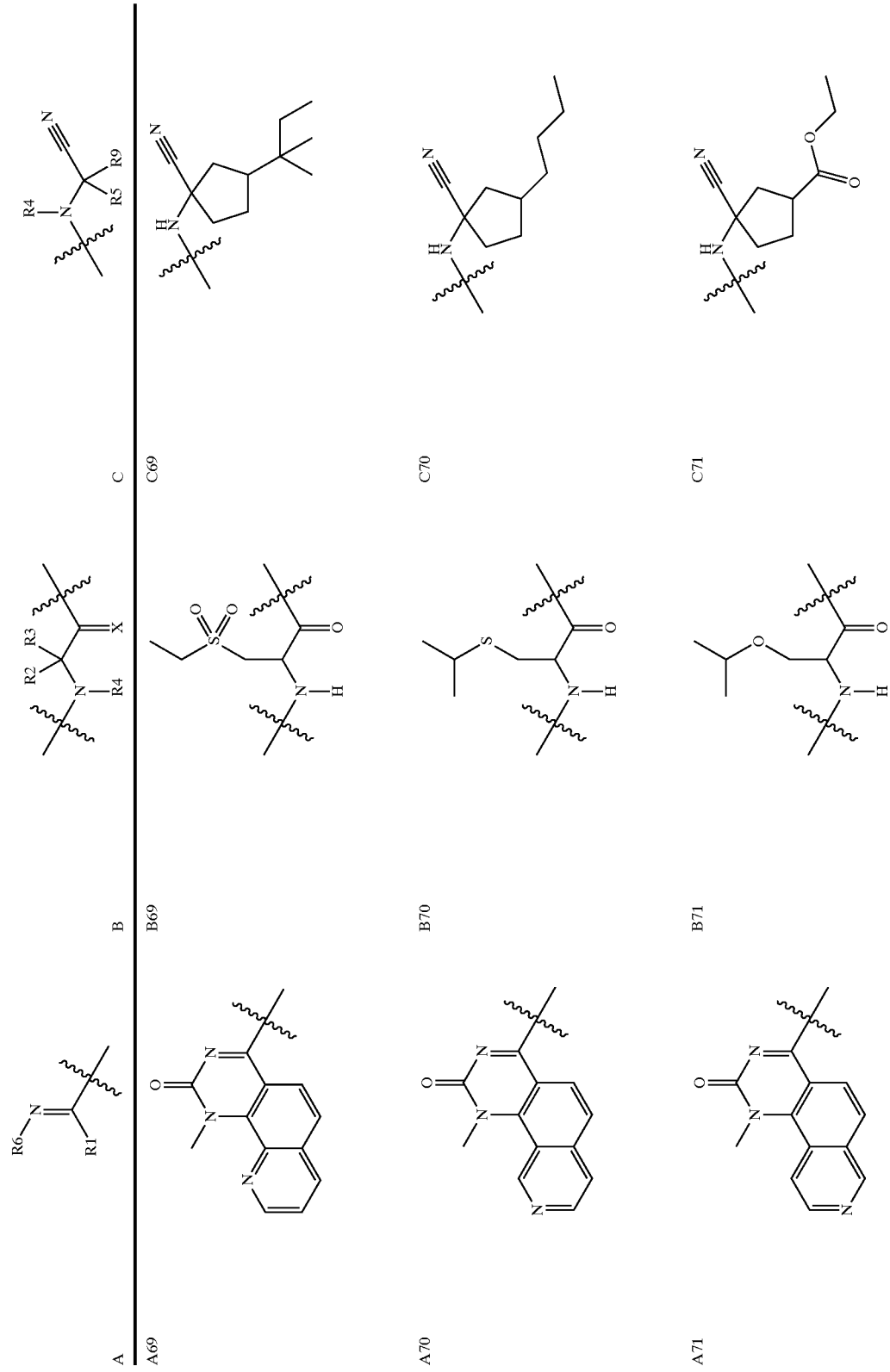

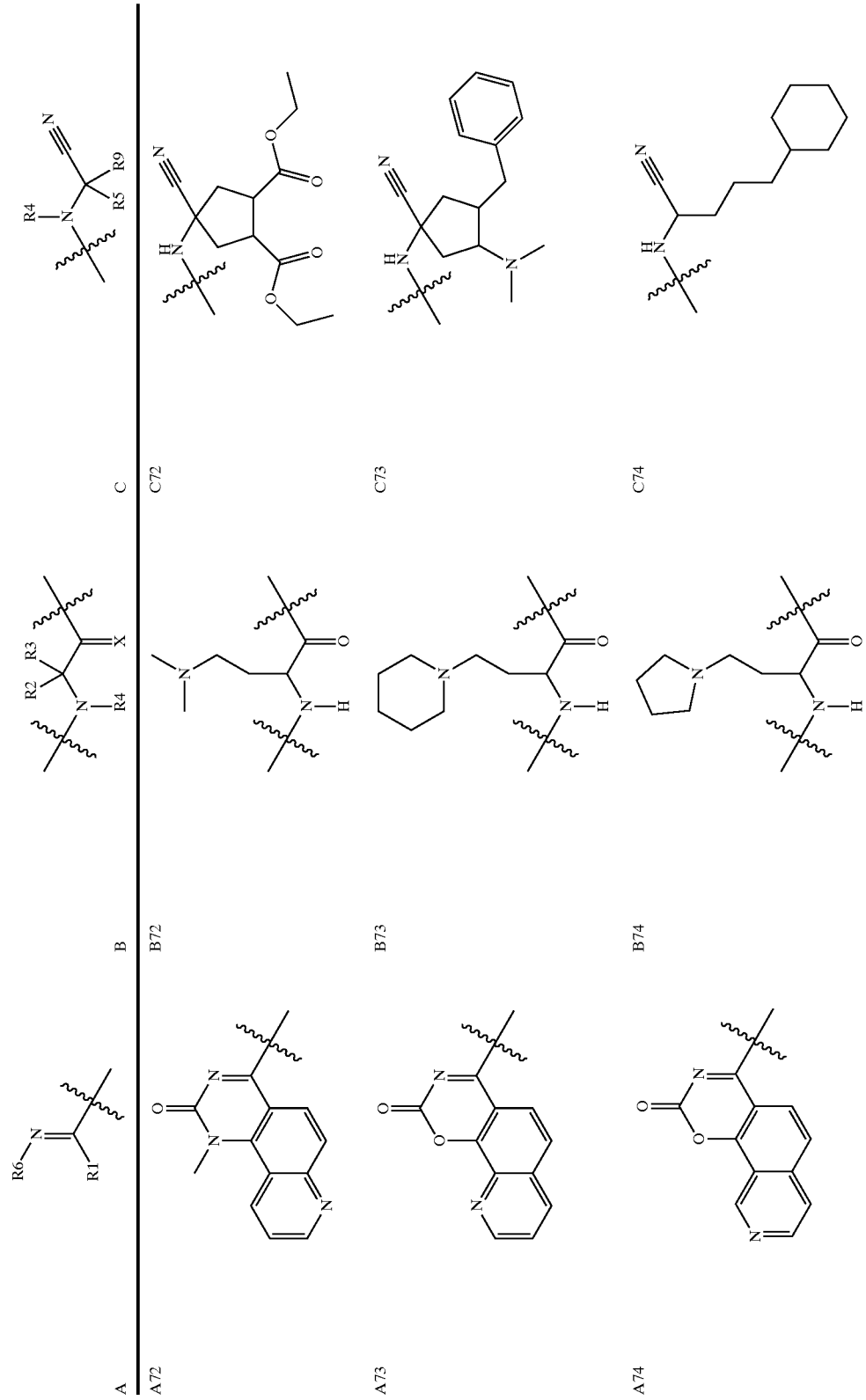

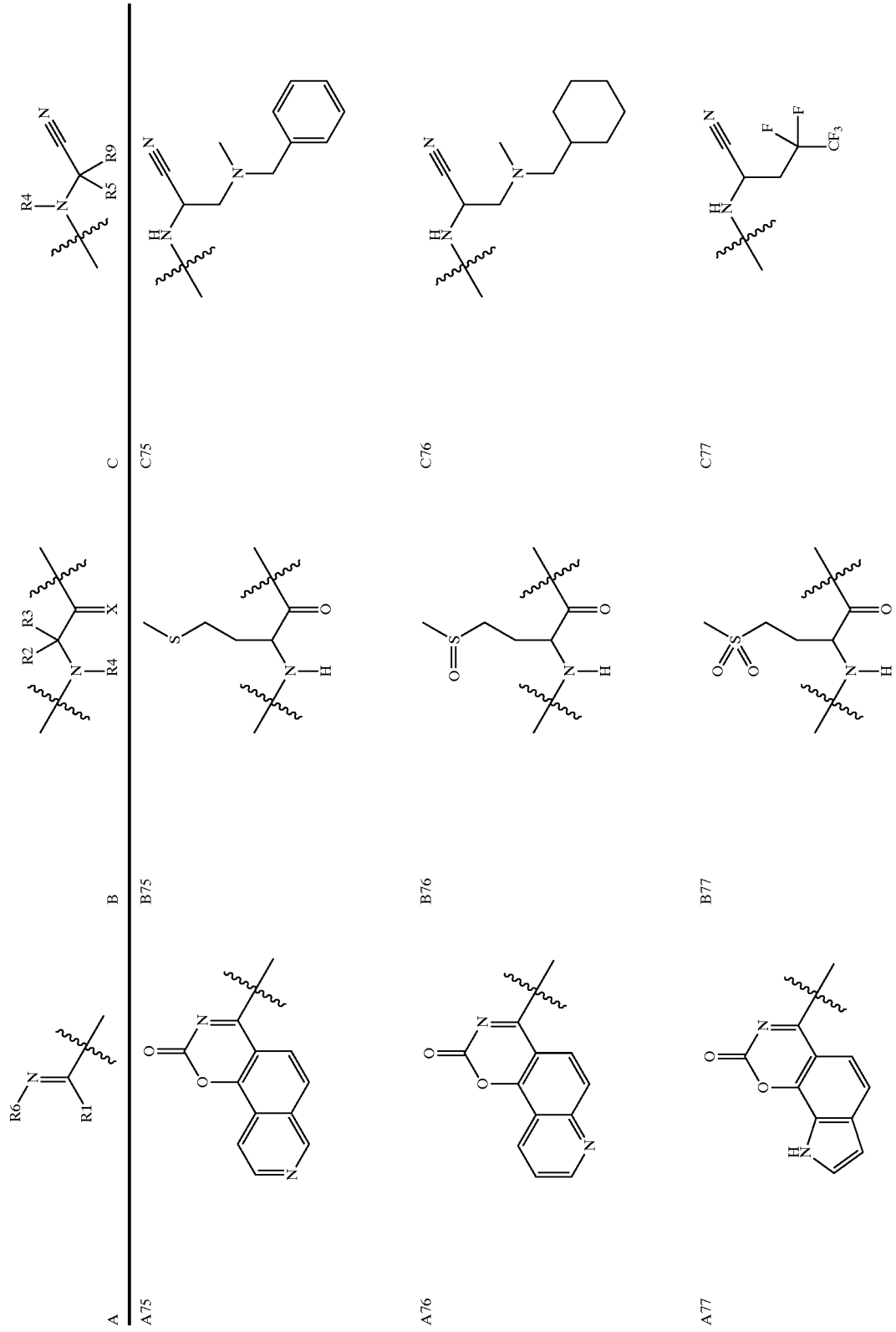

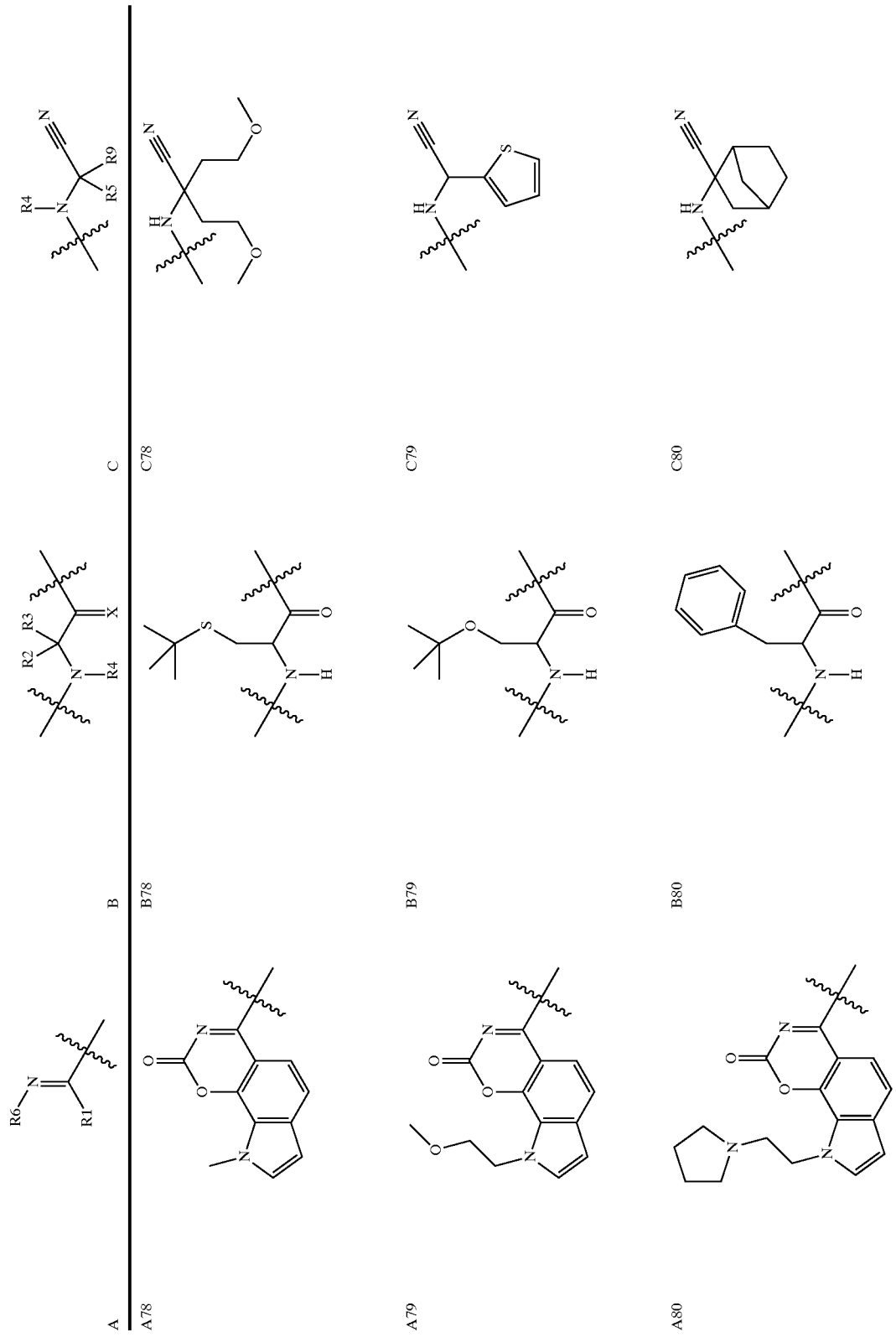

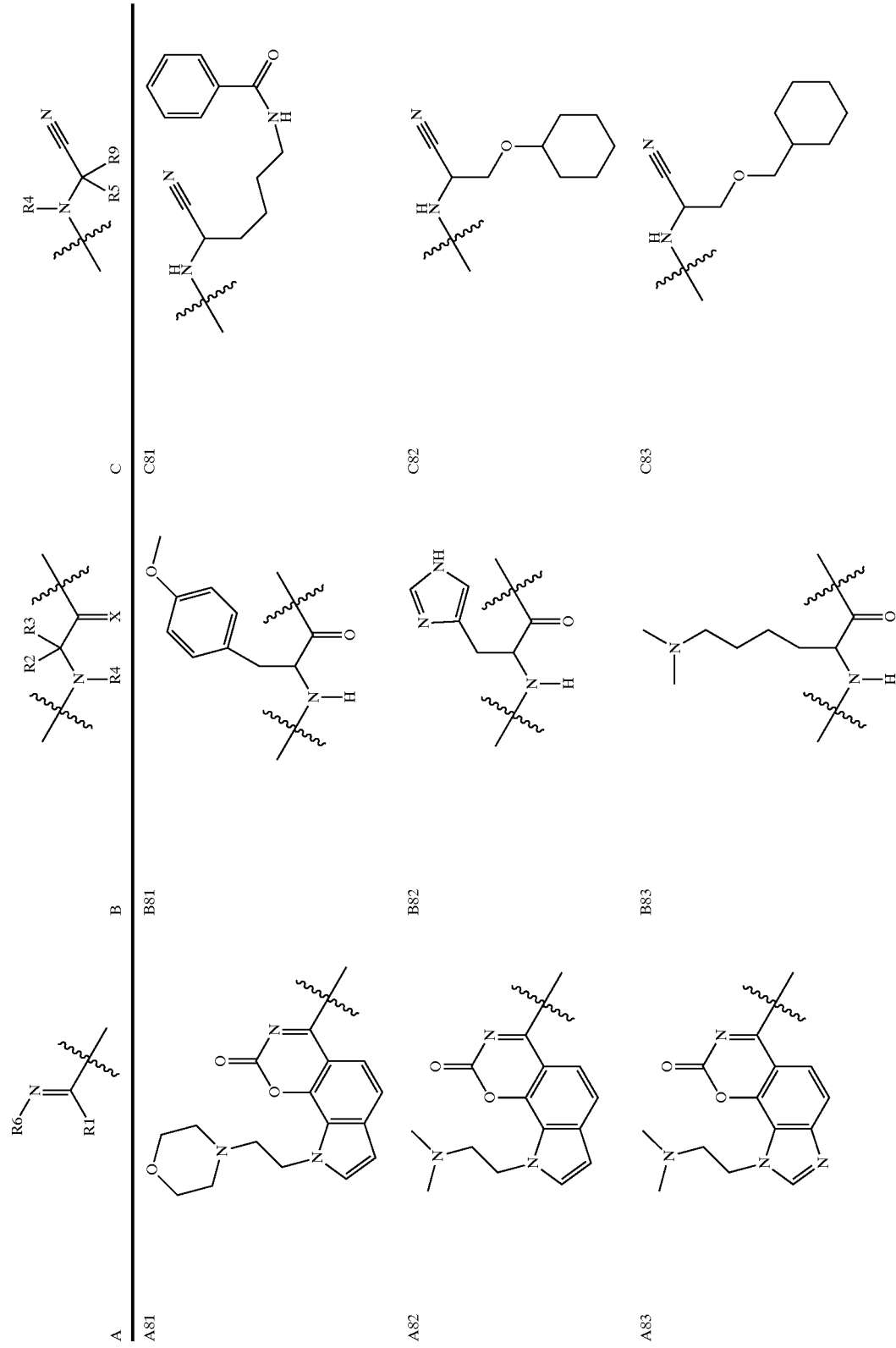

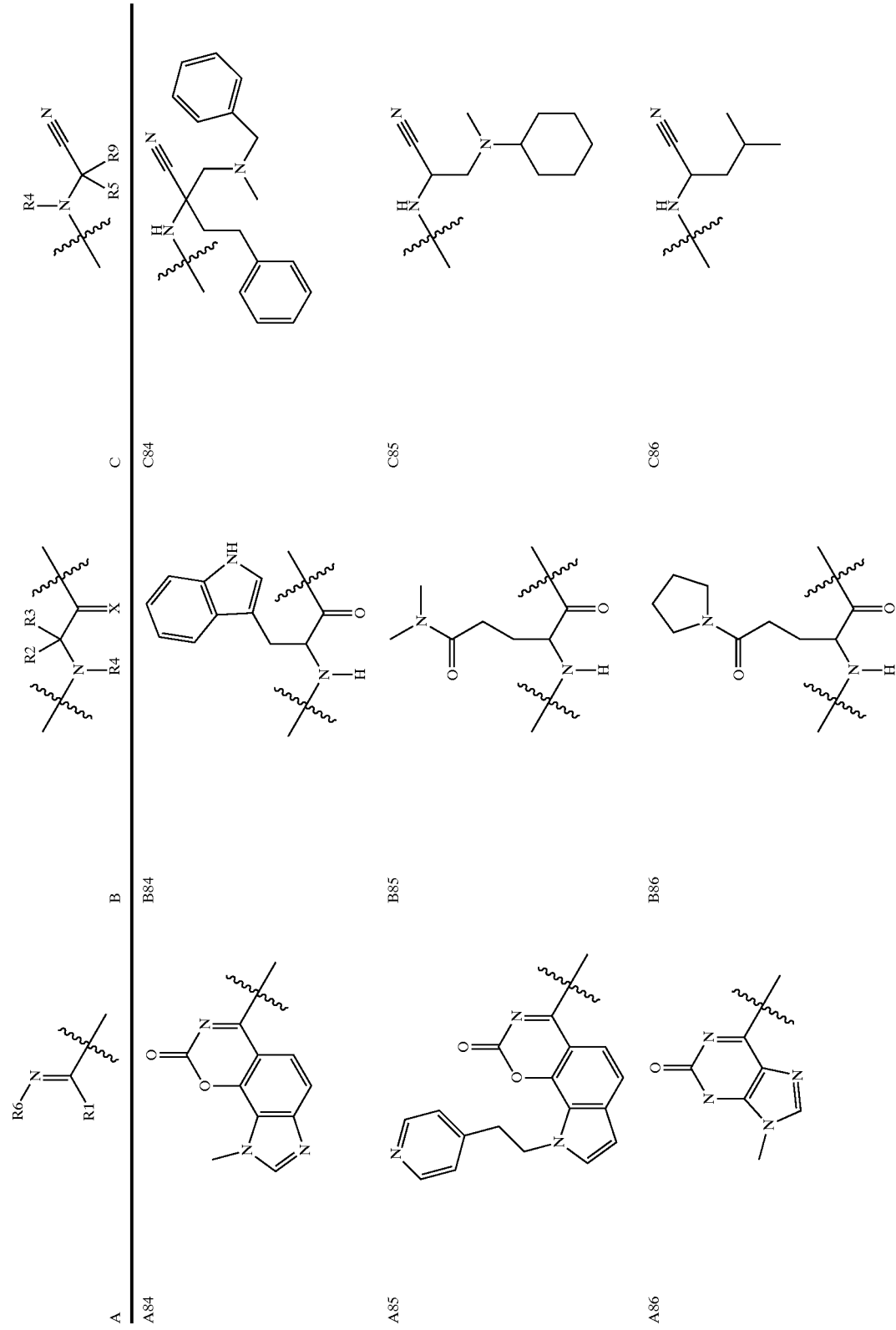

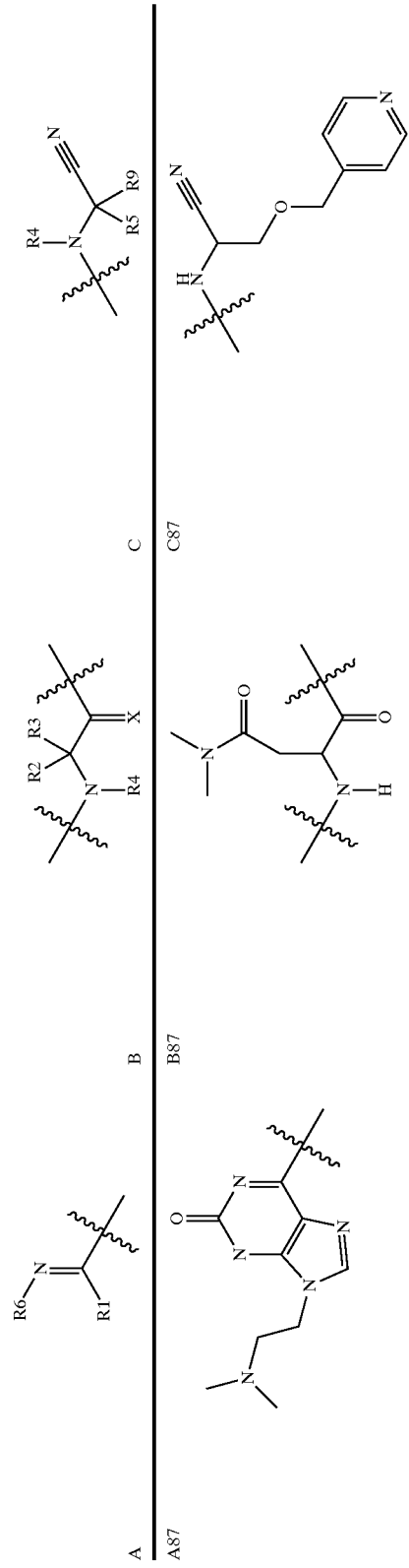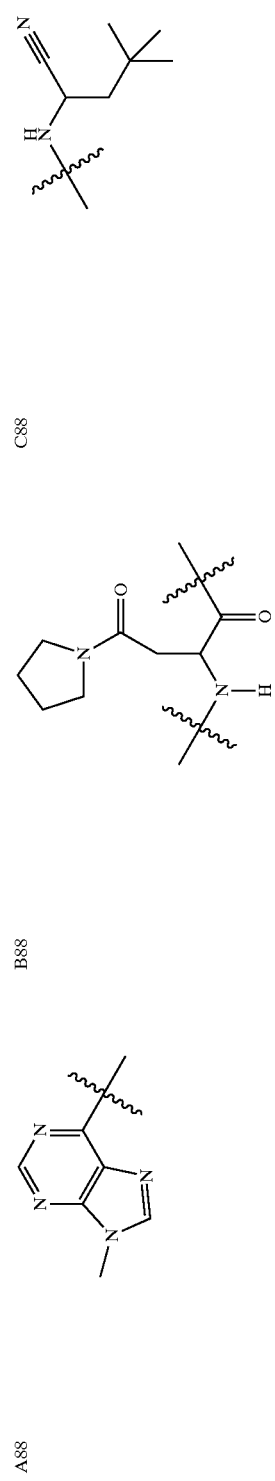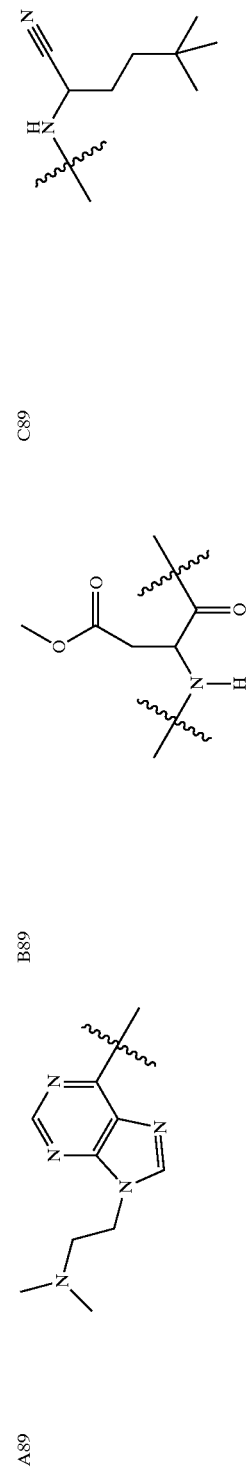

-continued
| A | B | C |
|---|---|---|
| 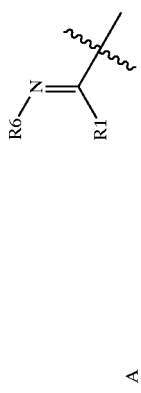 | | |
| | B90 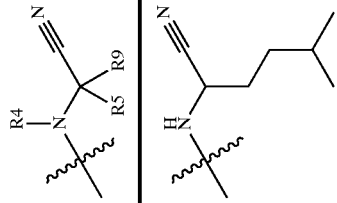 | C90 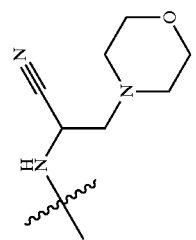 |
| | B91 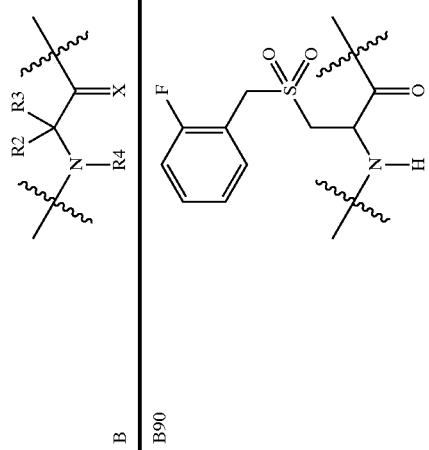 | C91 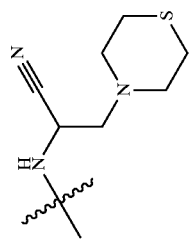 |
| | B92 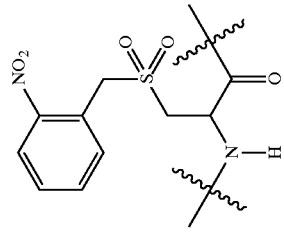 | C92 |

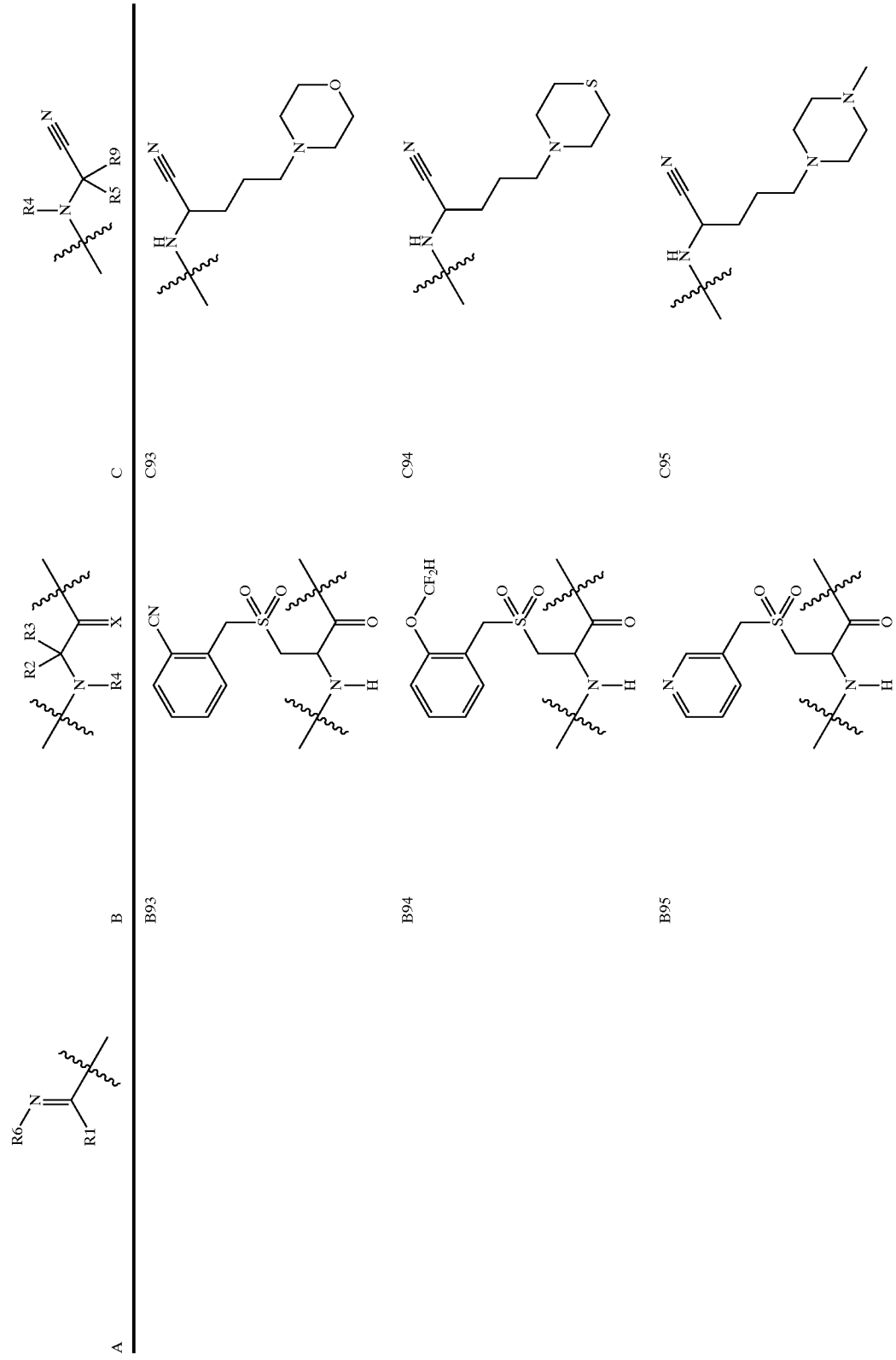

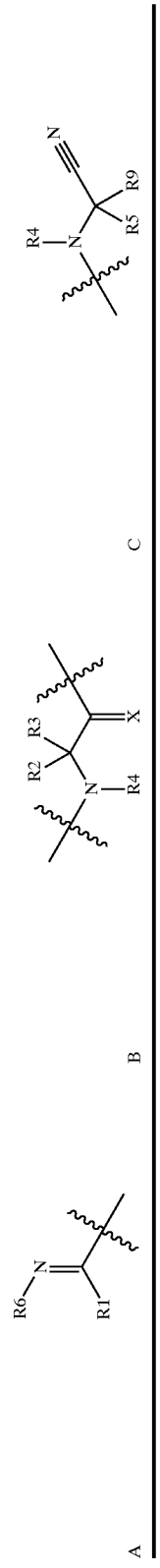

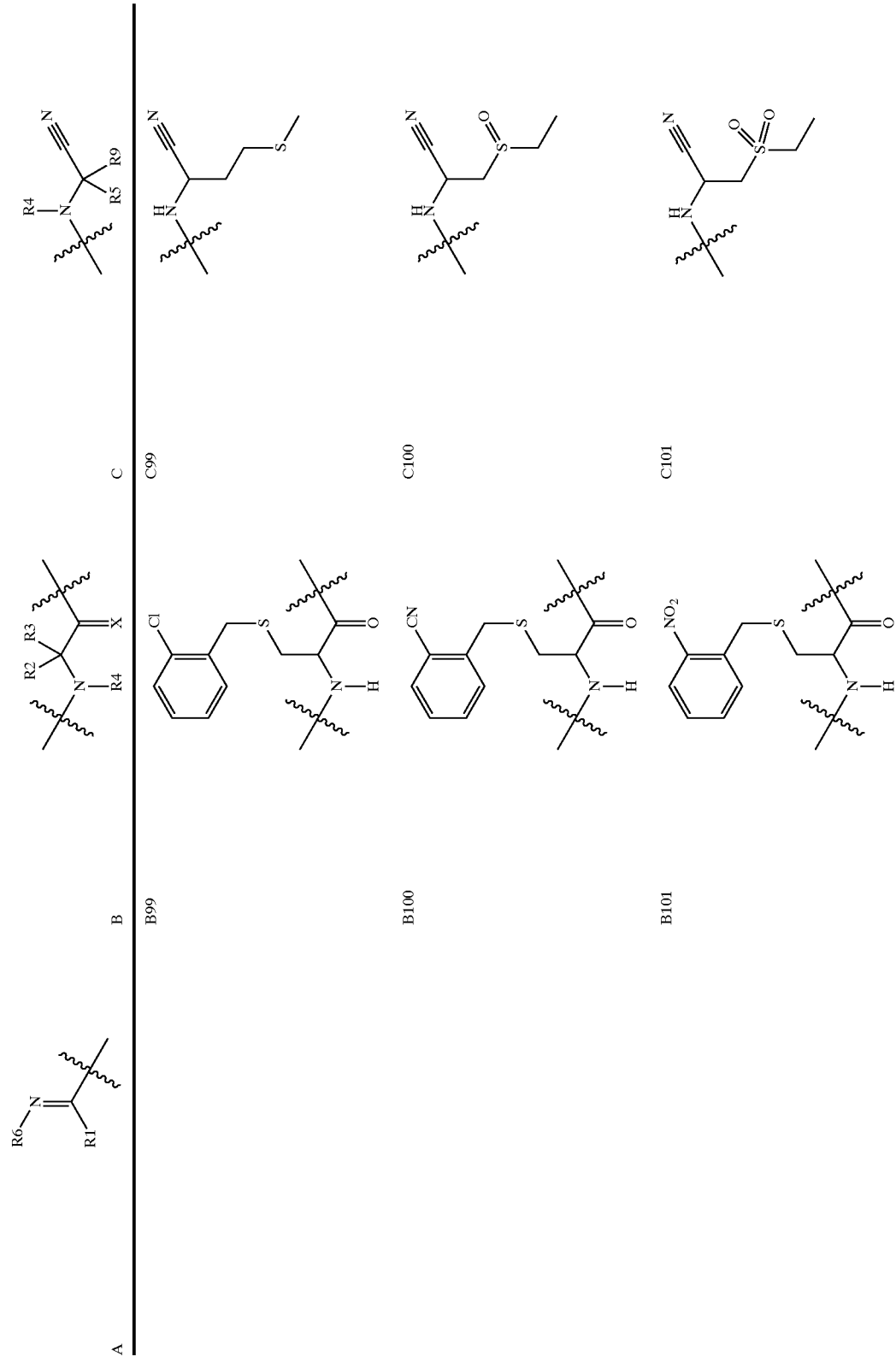

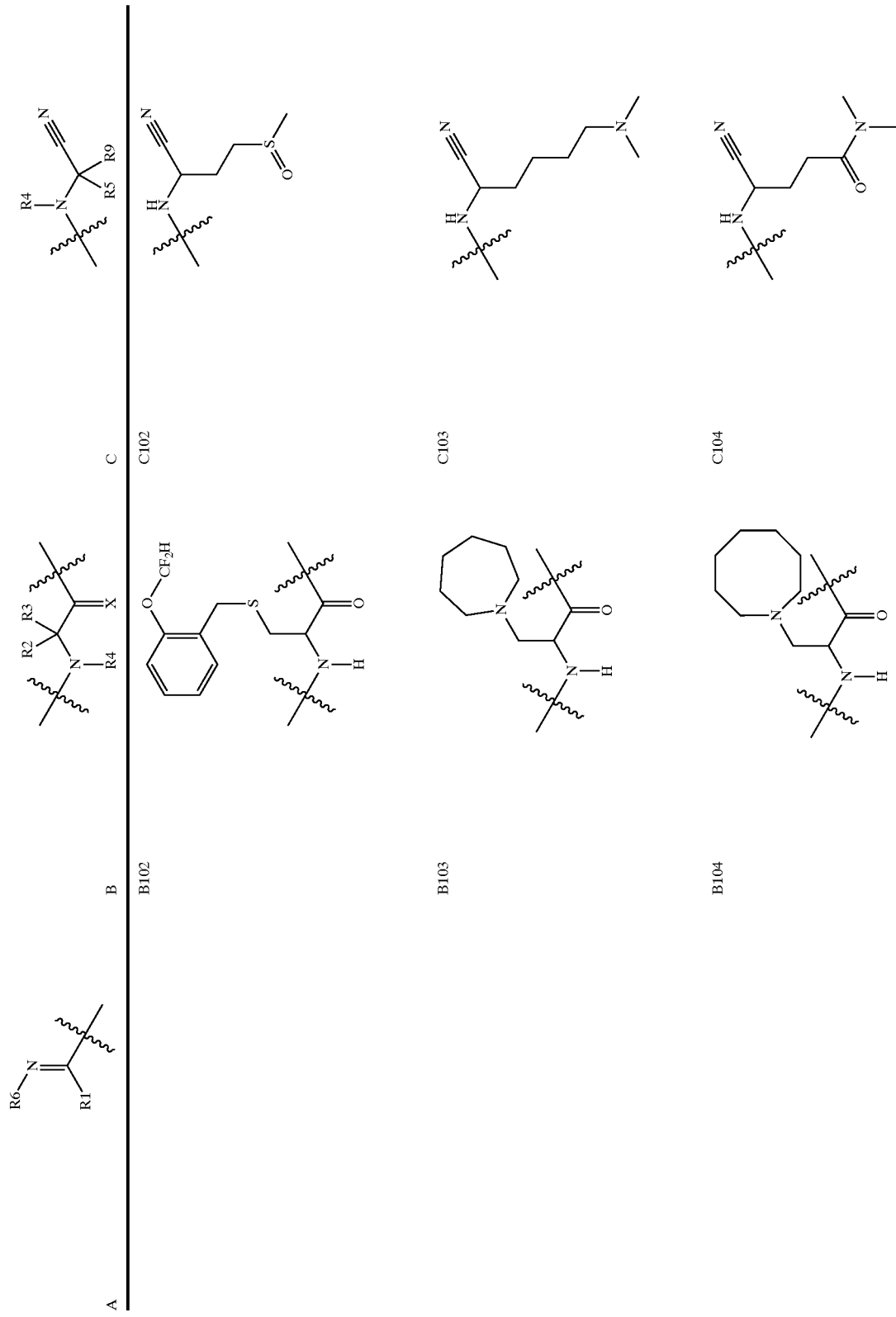

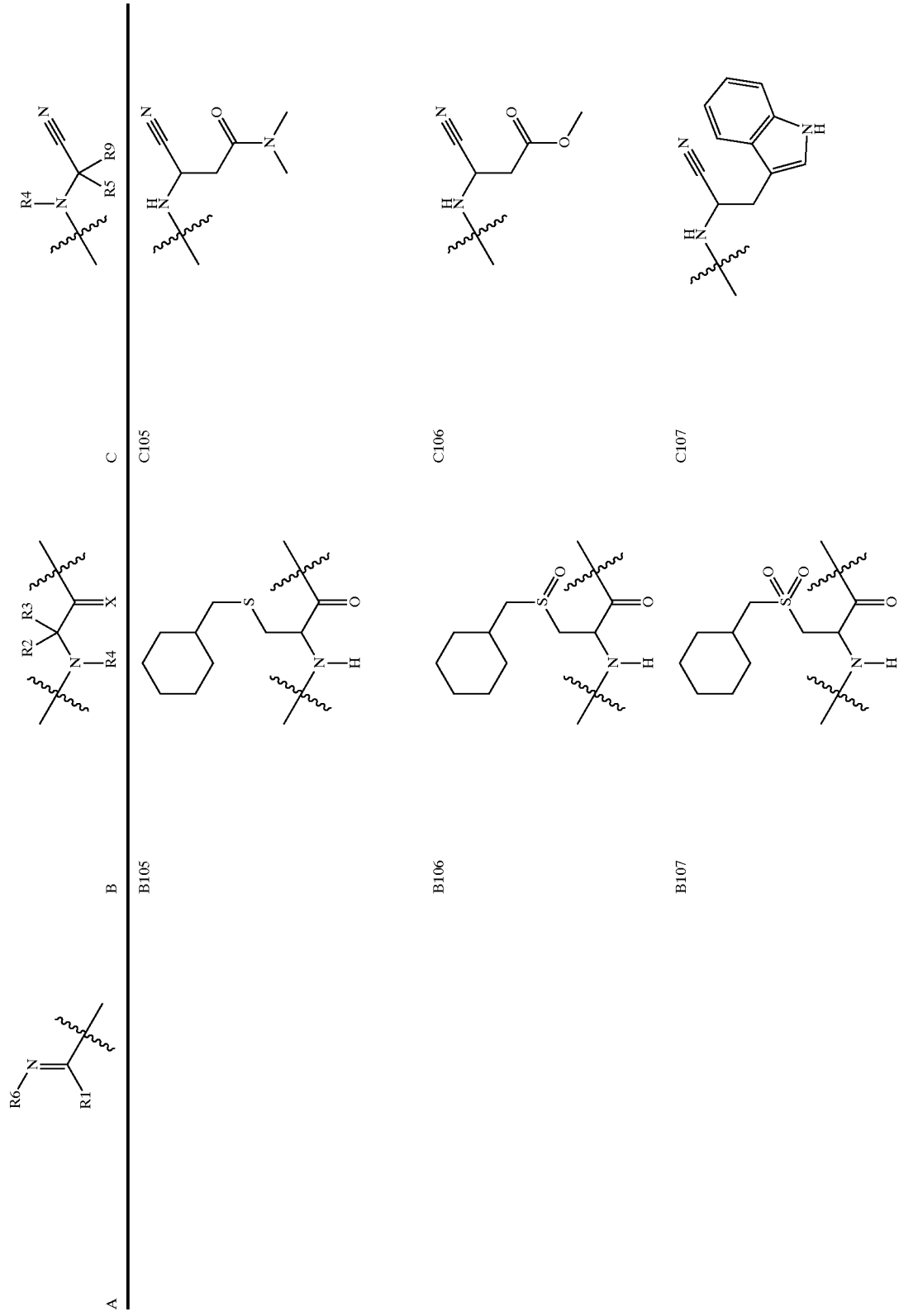

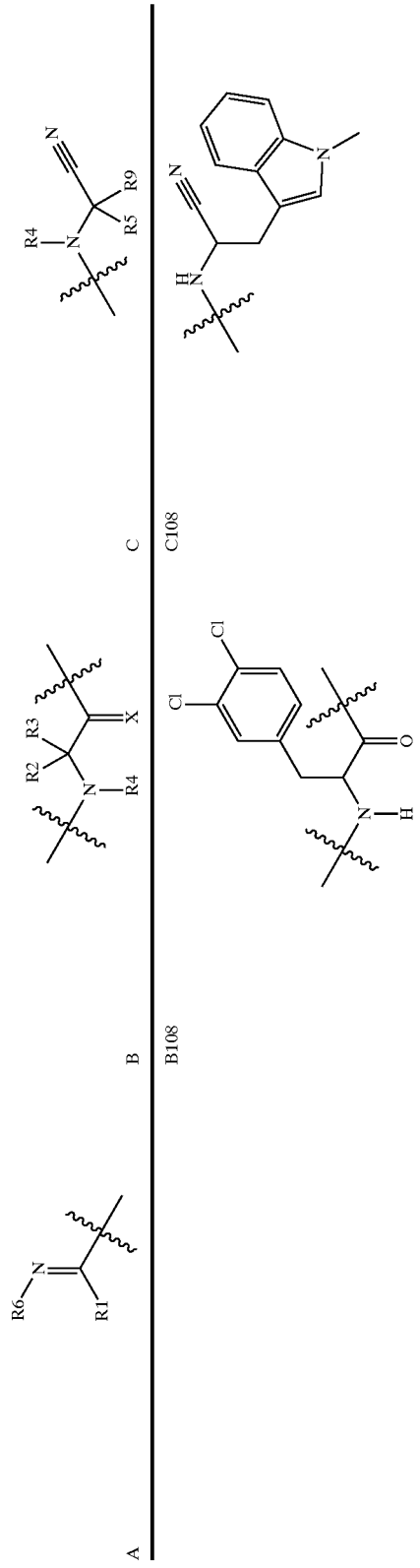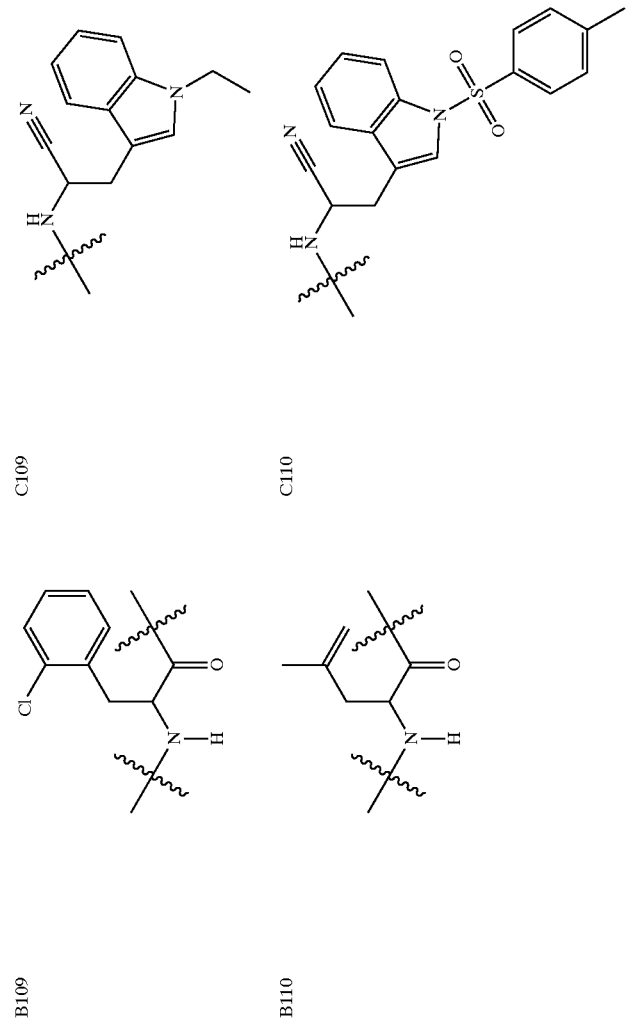

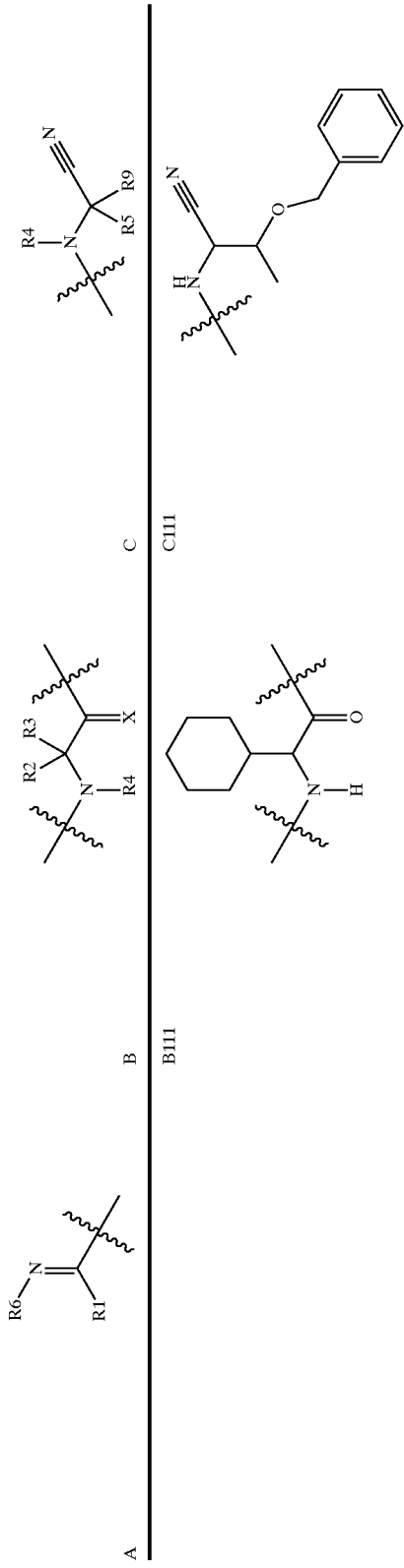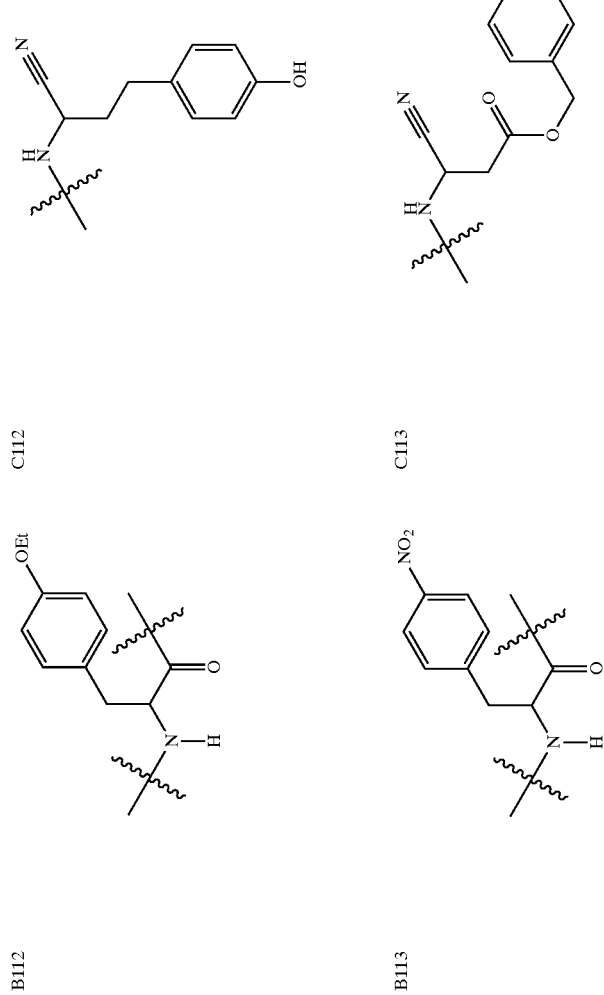

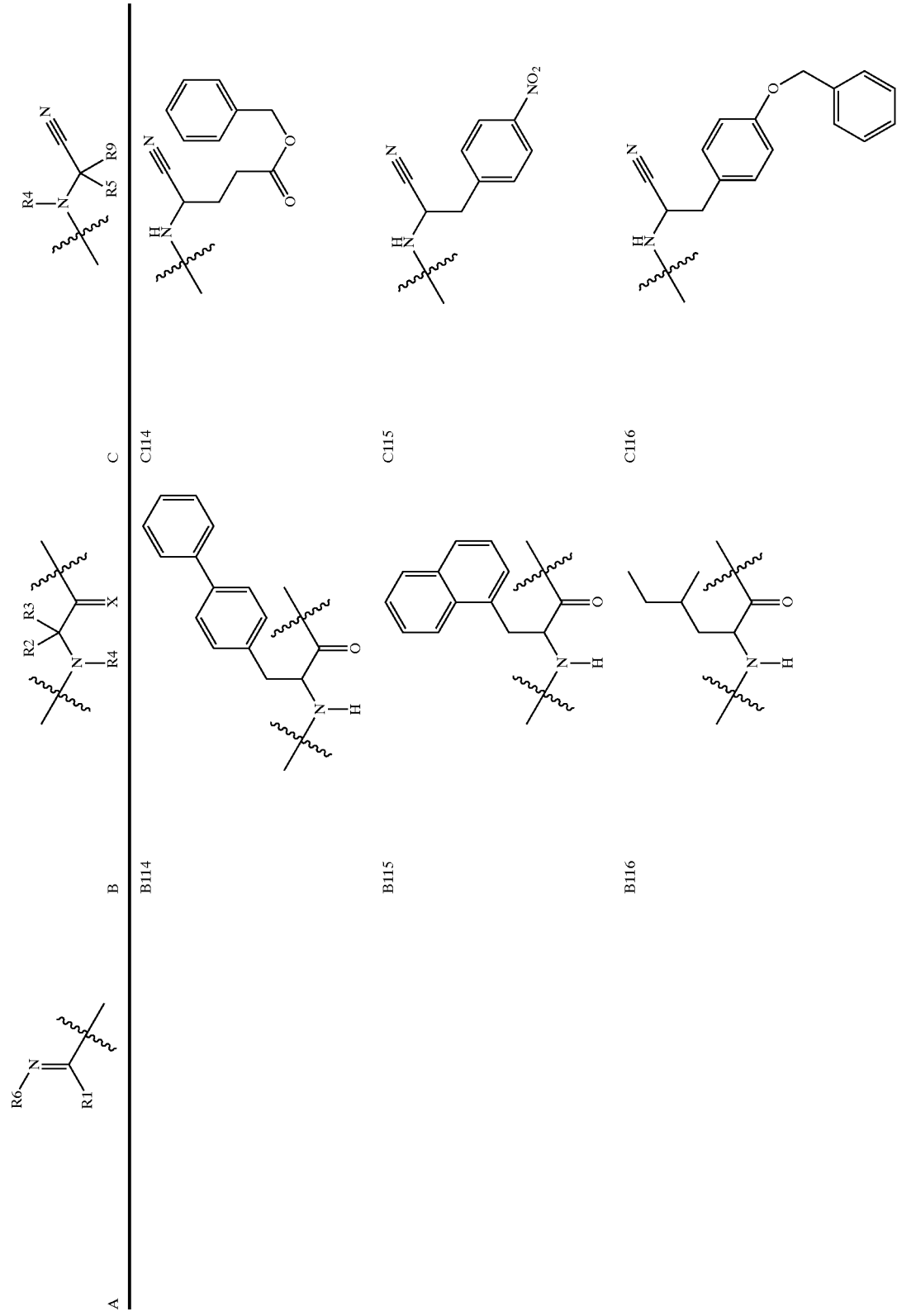

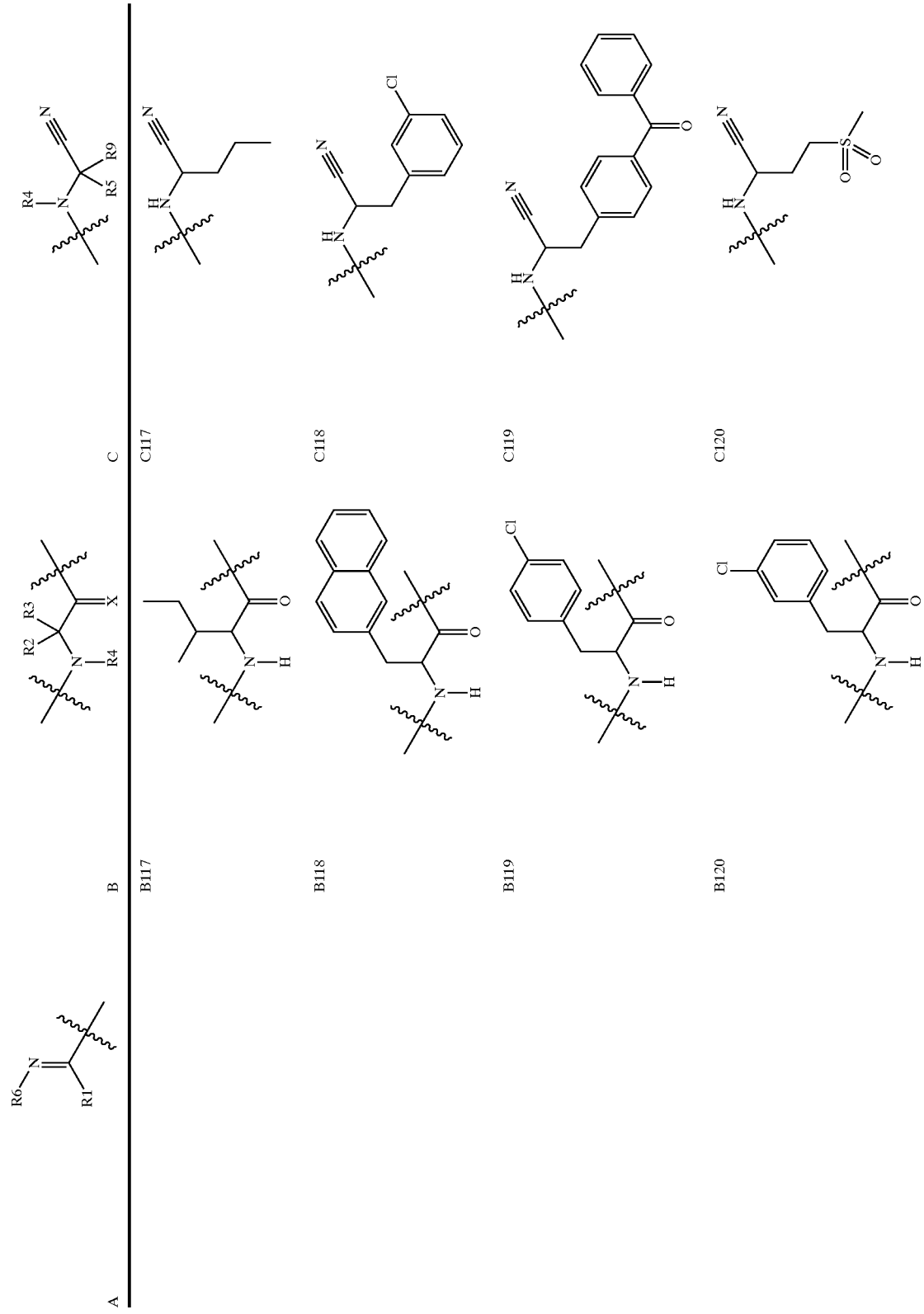

| A | B | C |
|---|---|---|
| 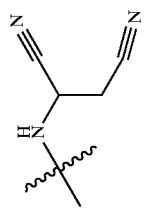 | B121 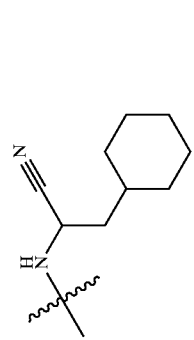 | C121 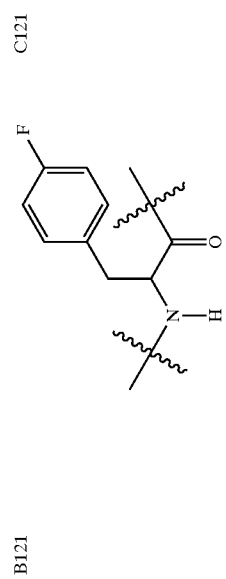 |
| | B122 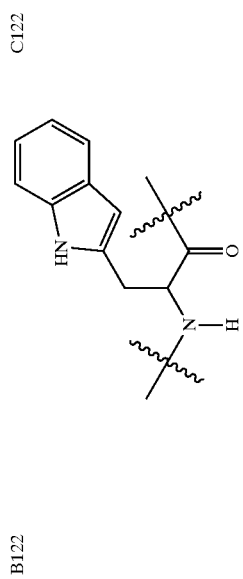 | C122 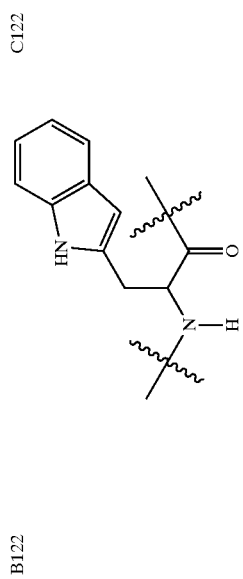 |
| | B123 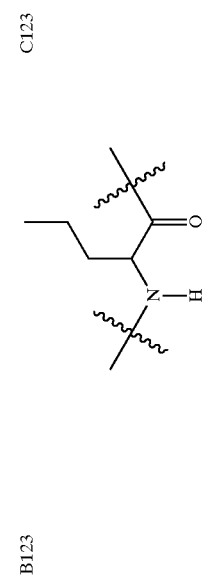 | C123 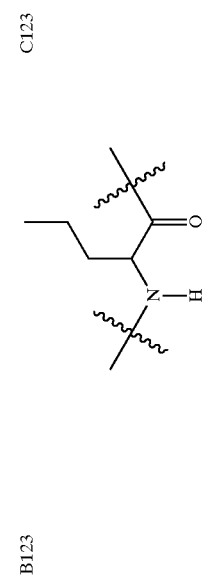 |

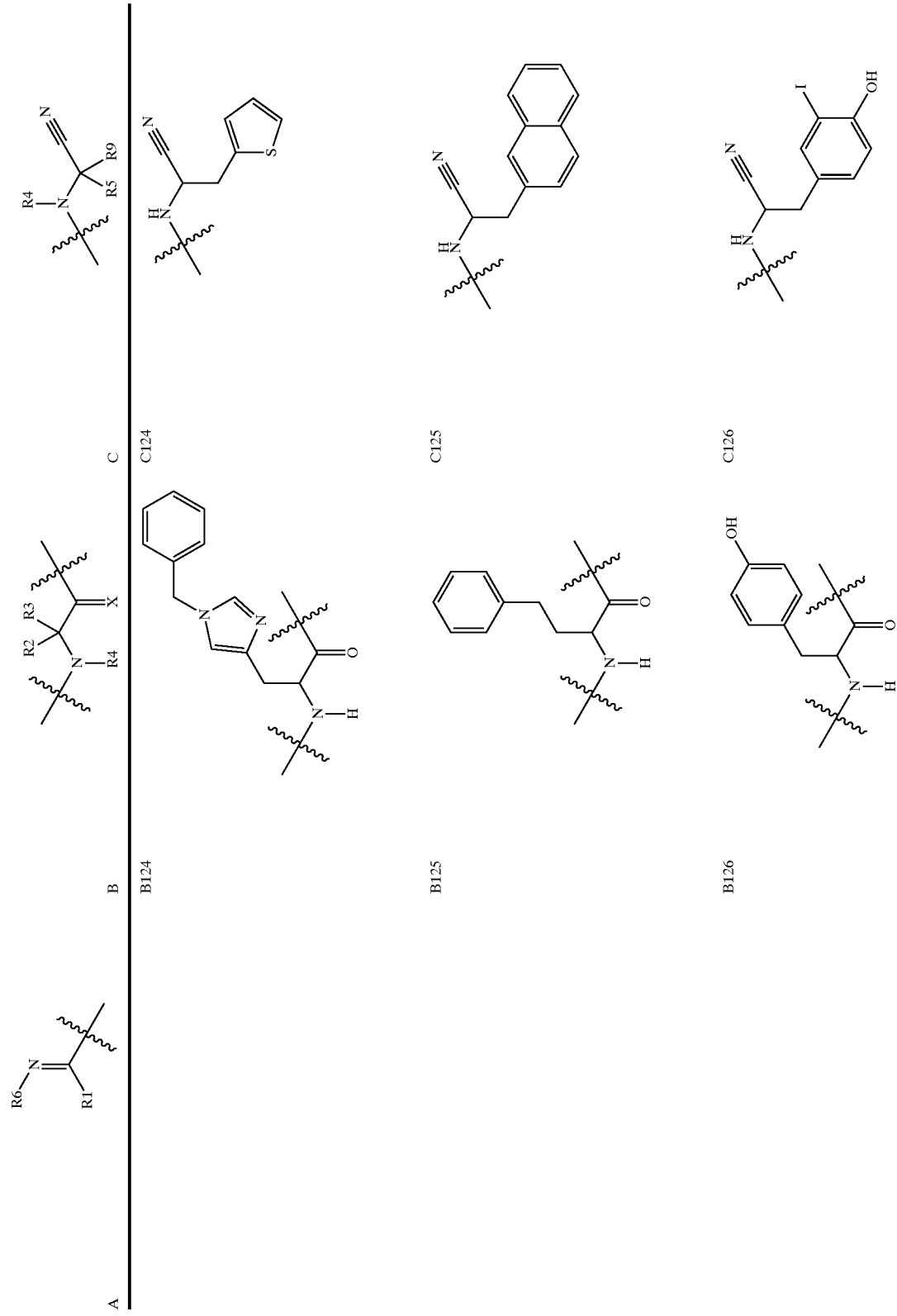

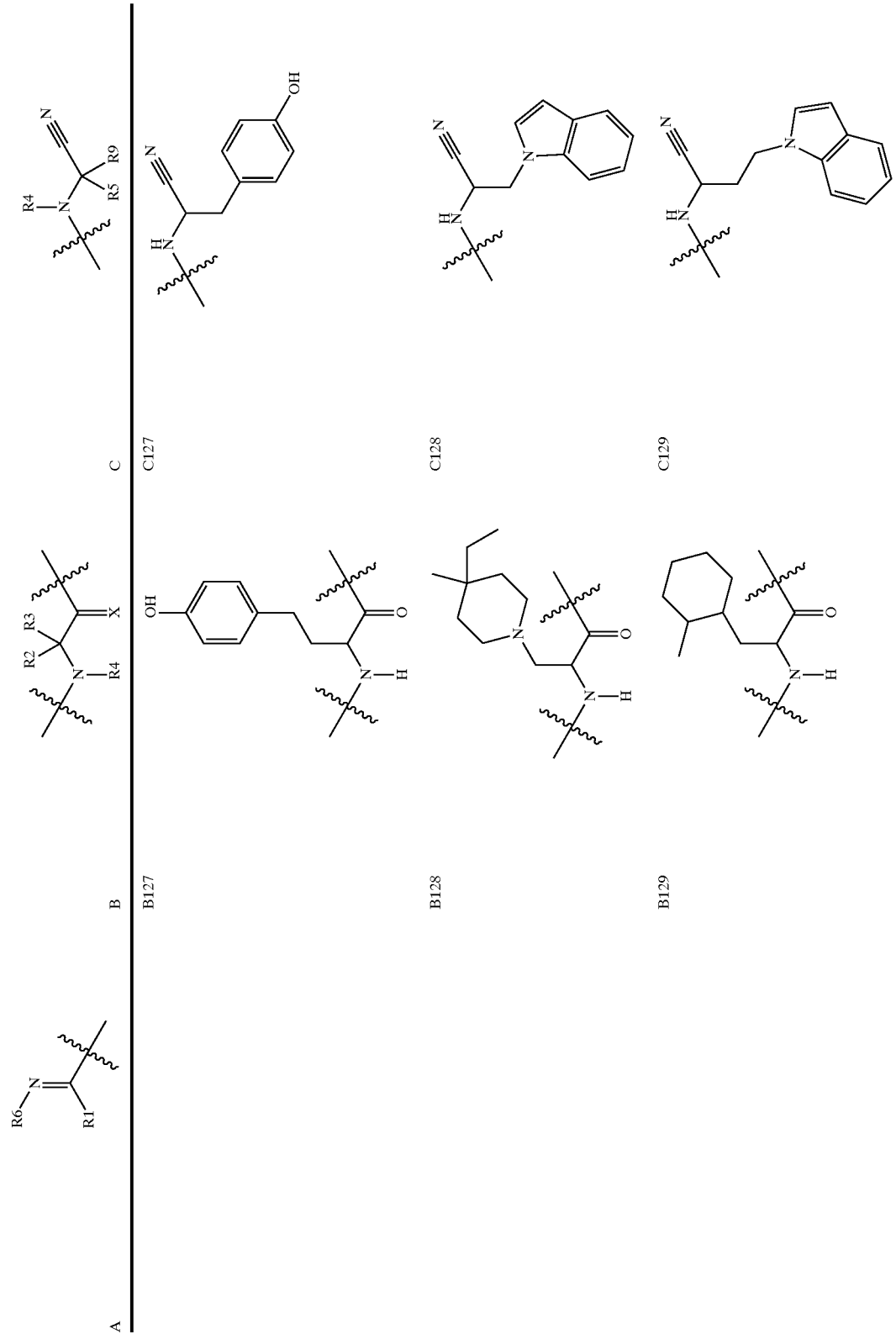

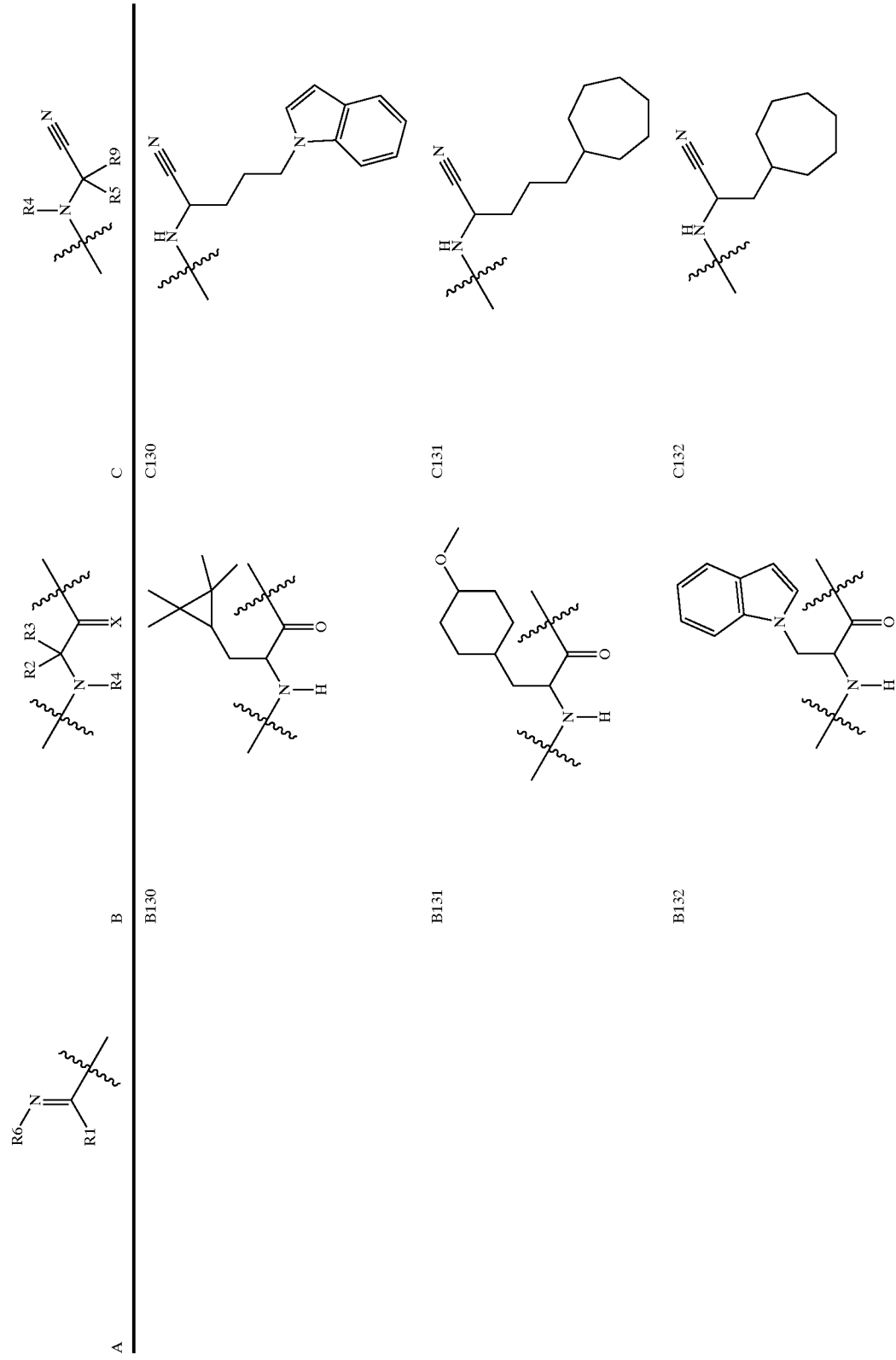

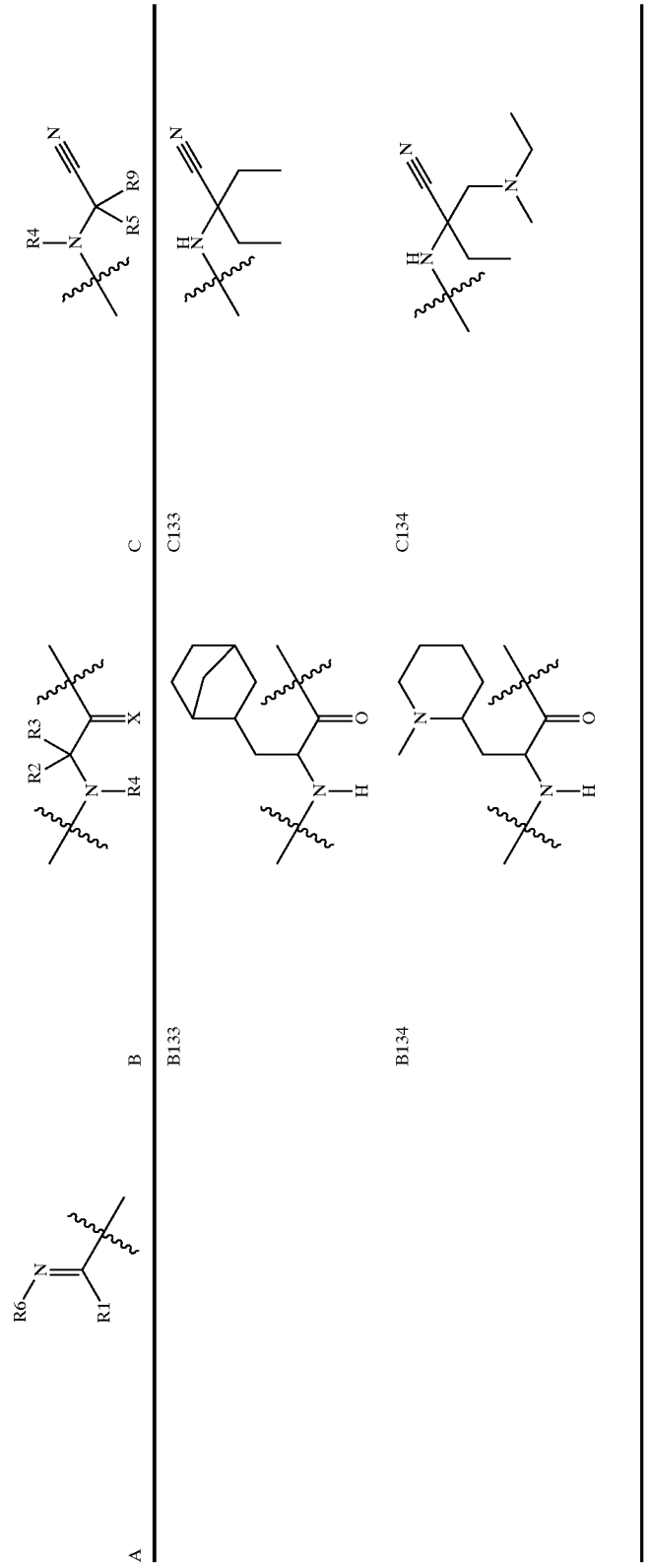

or the pharmaceutically acceptable salts, esters and tautomers thereof.
8. The compound of the formula (Ia) according to claim 7 and wherein:
for the formula (Ia), the components
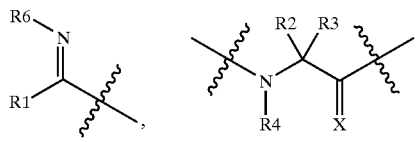 ,  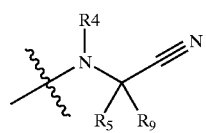 and
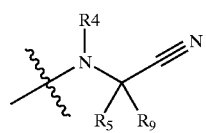
are chosen from any combination of A, B and C as follows:

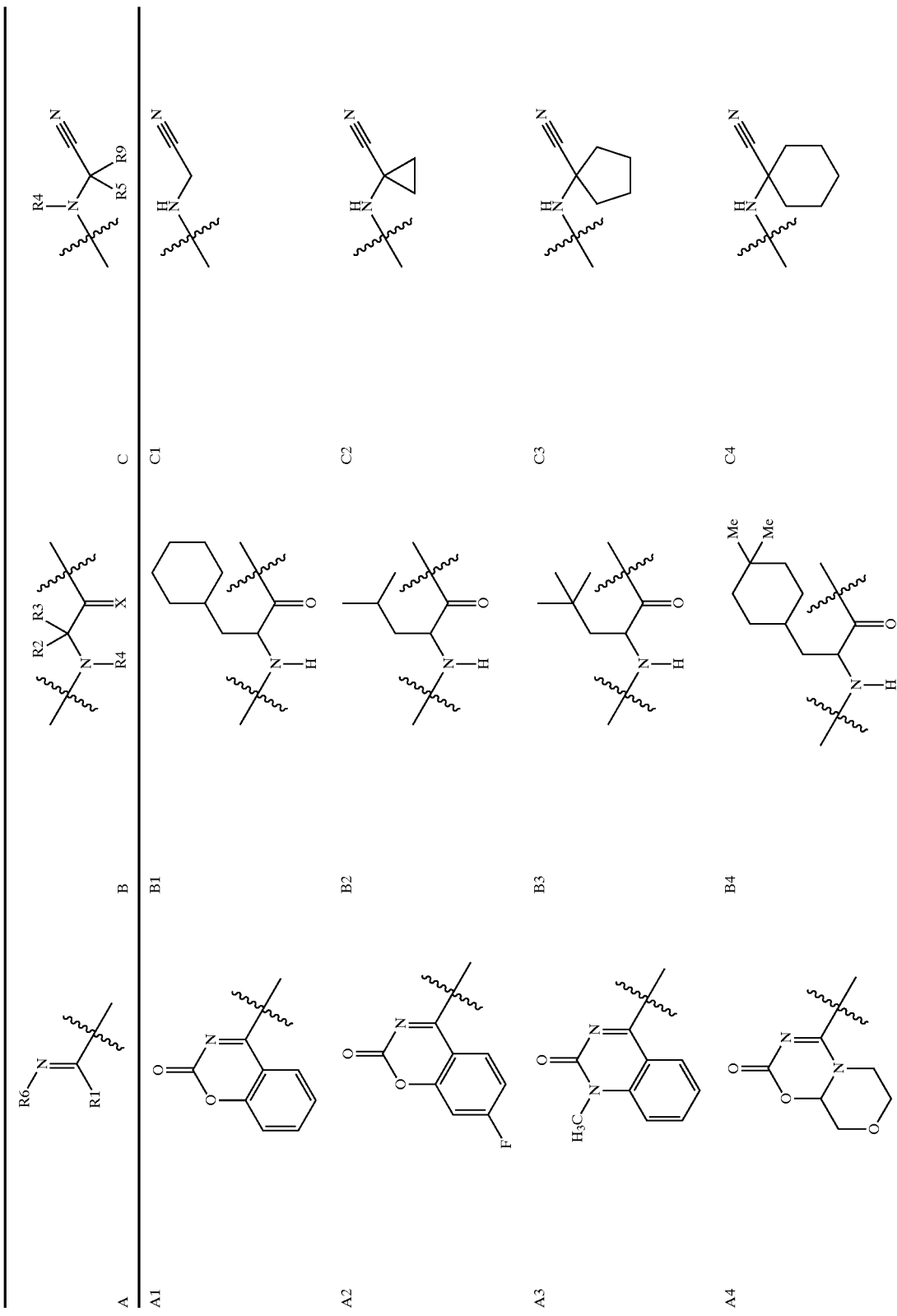

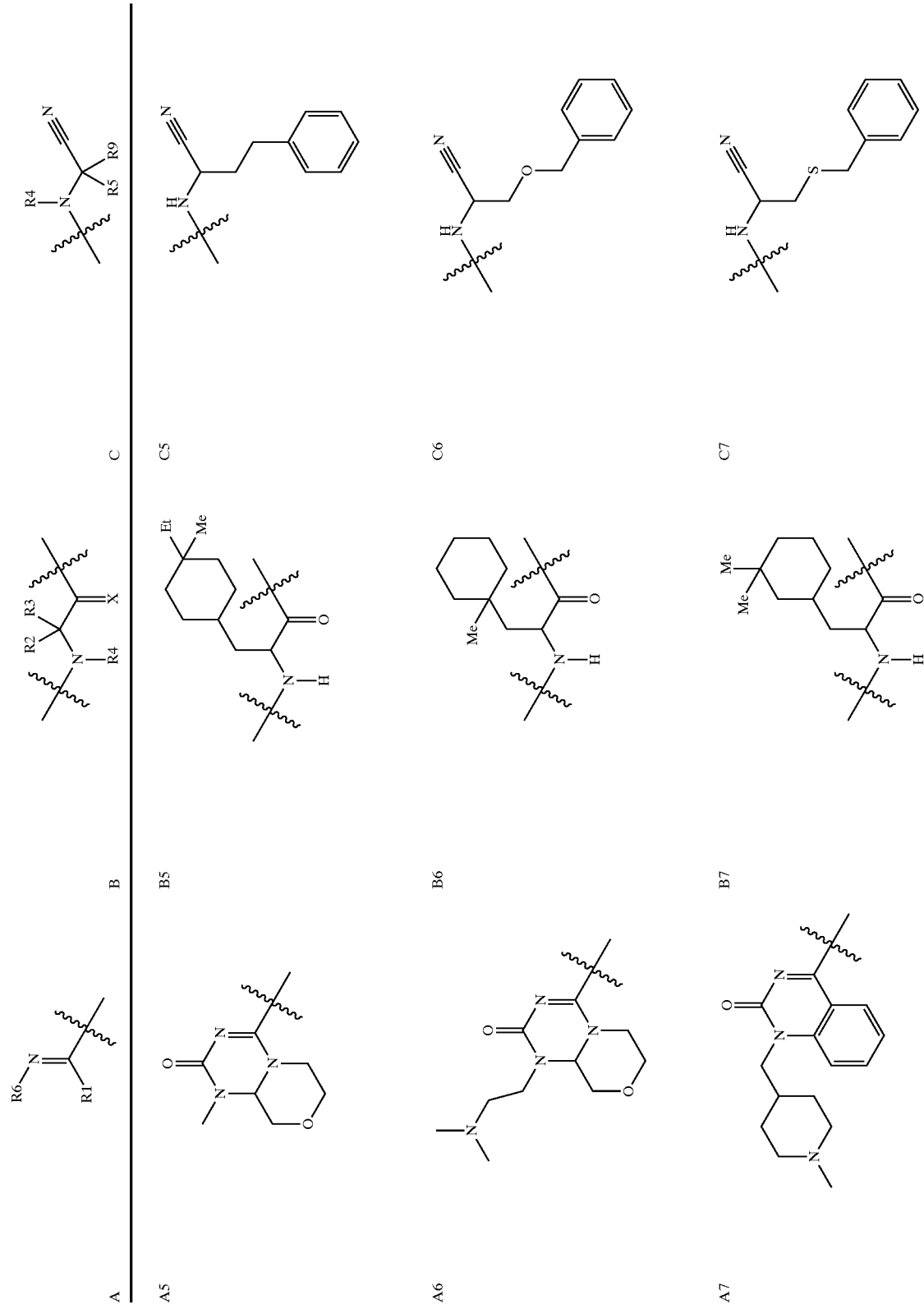

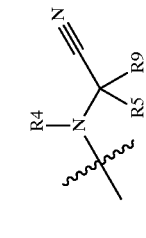 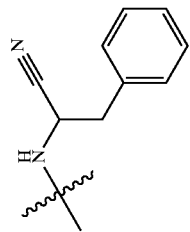 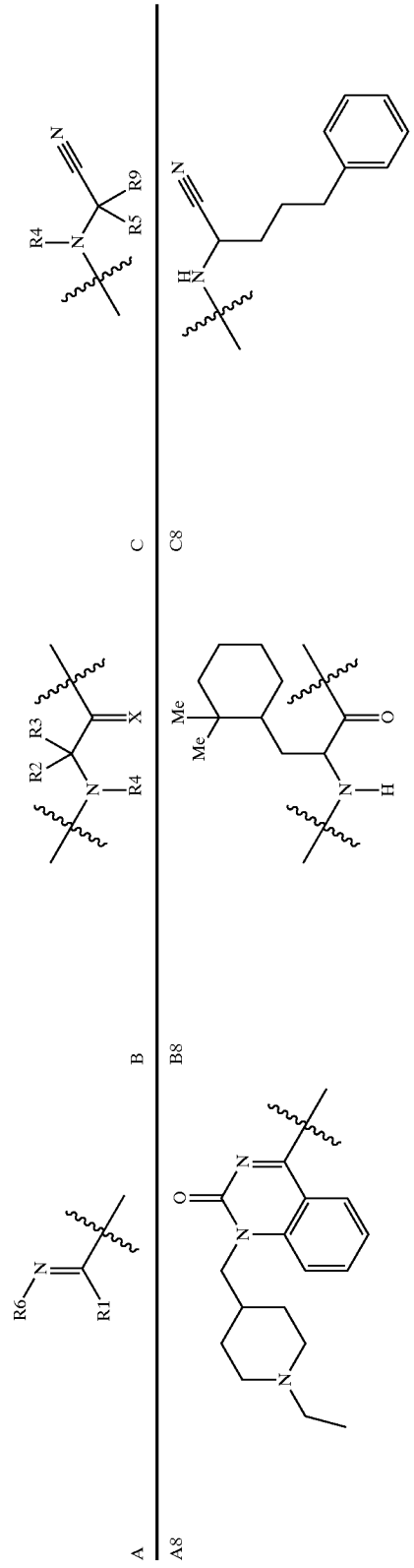 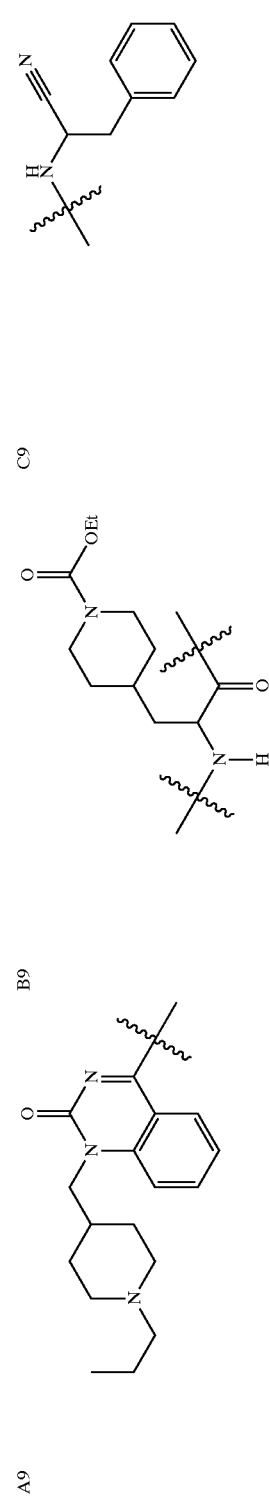 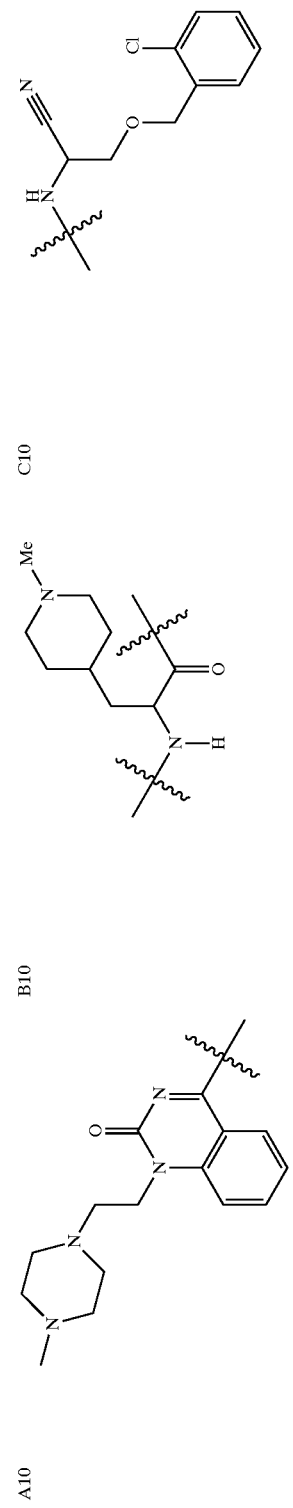

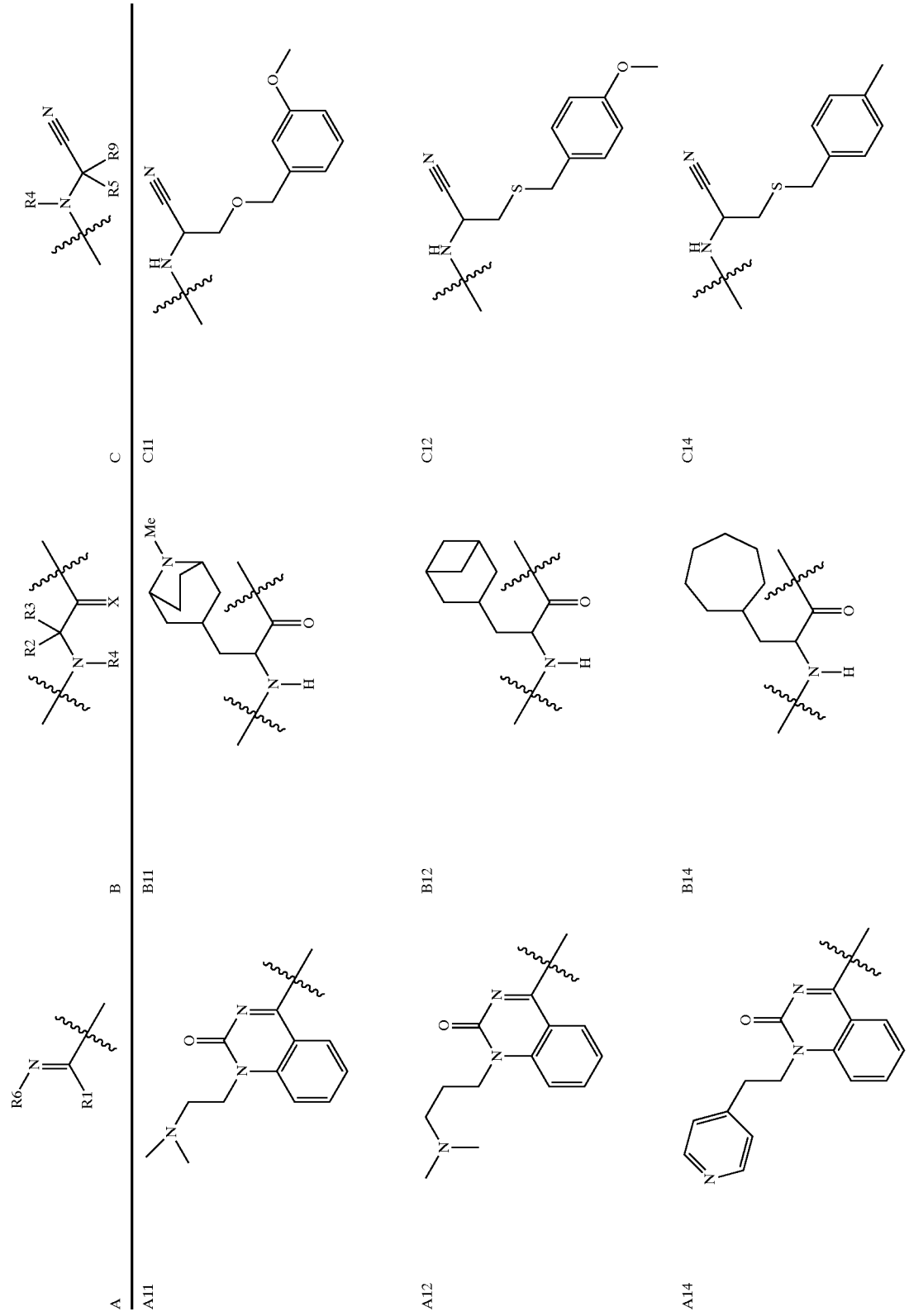

-continued
| A | B | C |
|---|---|---|
| 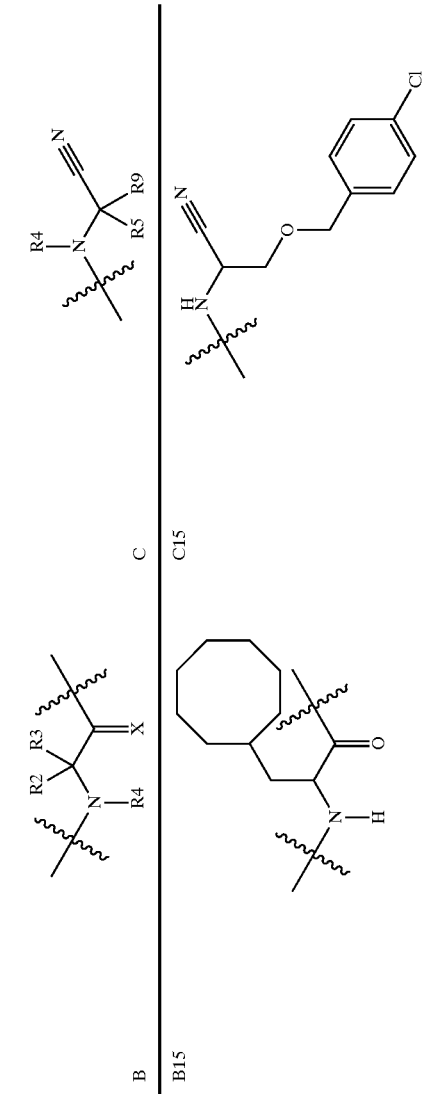 | | 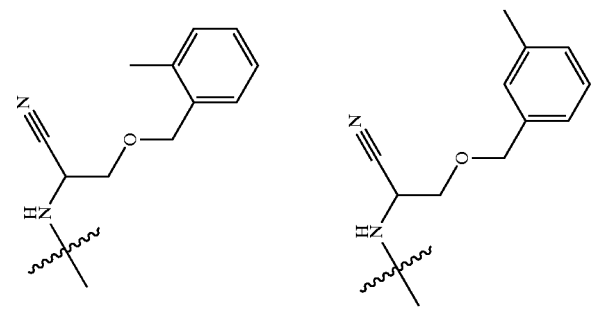 |
| A15 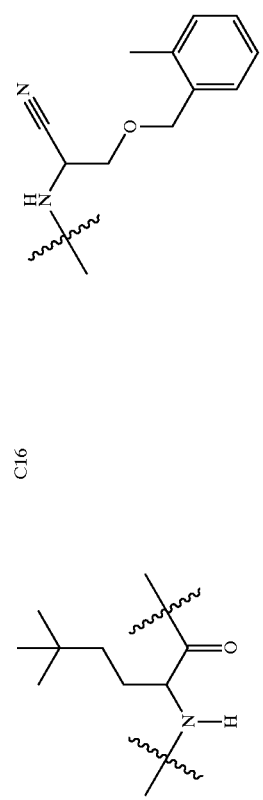 | B15 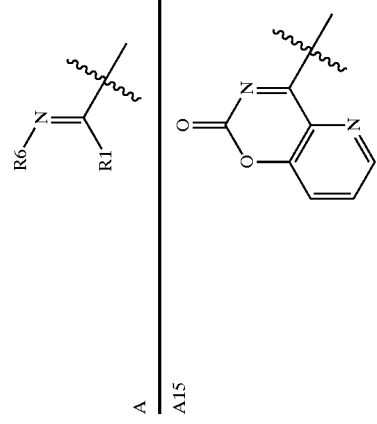 | C15 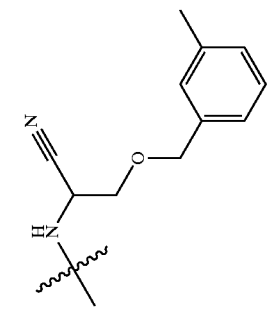 |
| A16 | B16 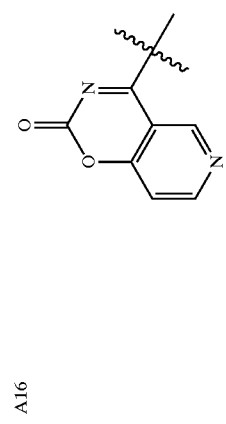 | C16 |
| A17 | B17 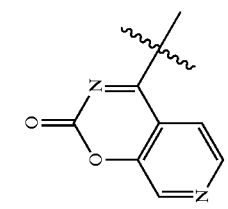 | C17 |

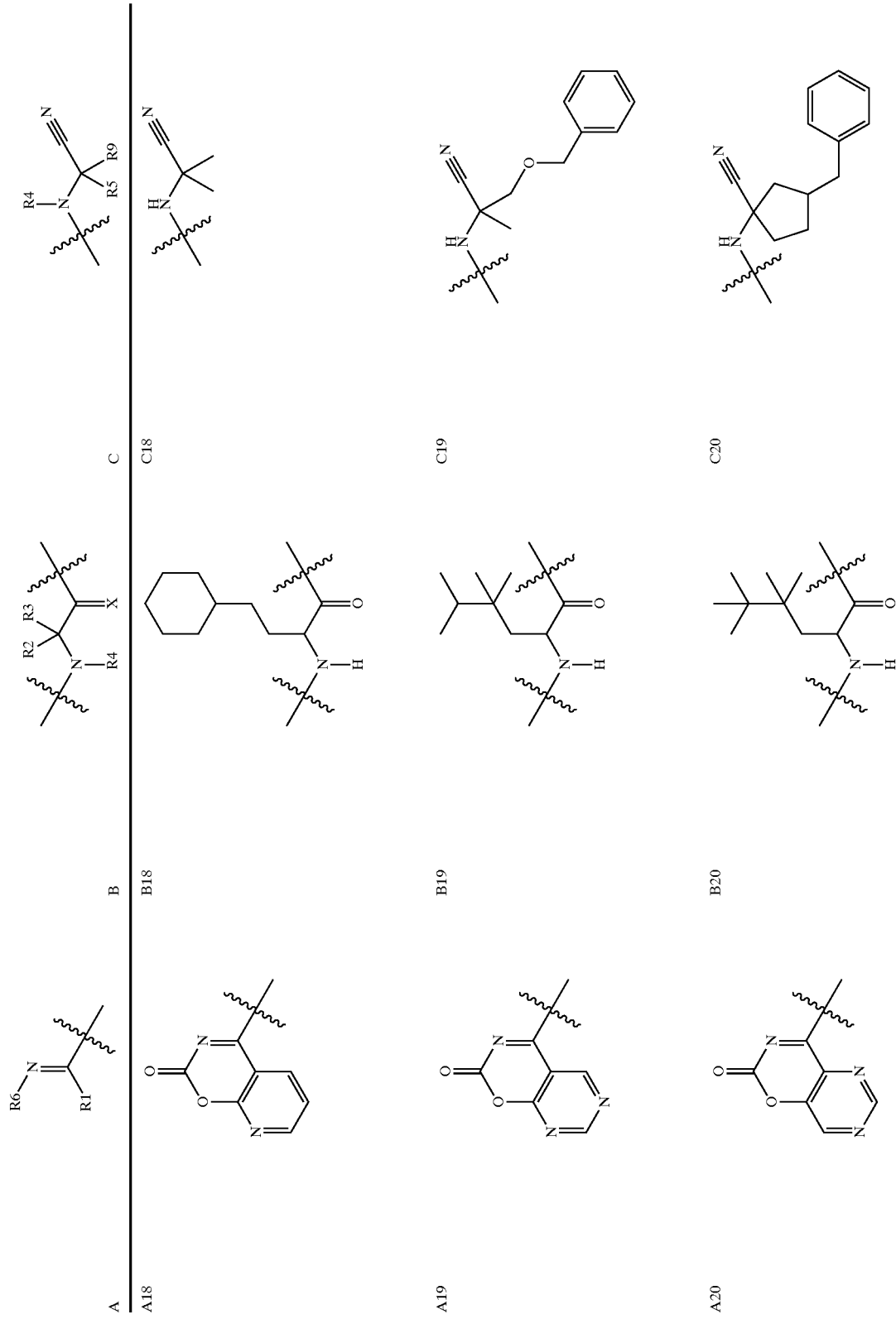

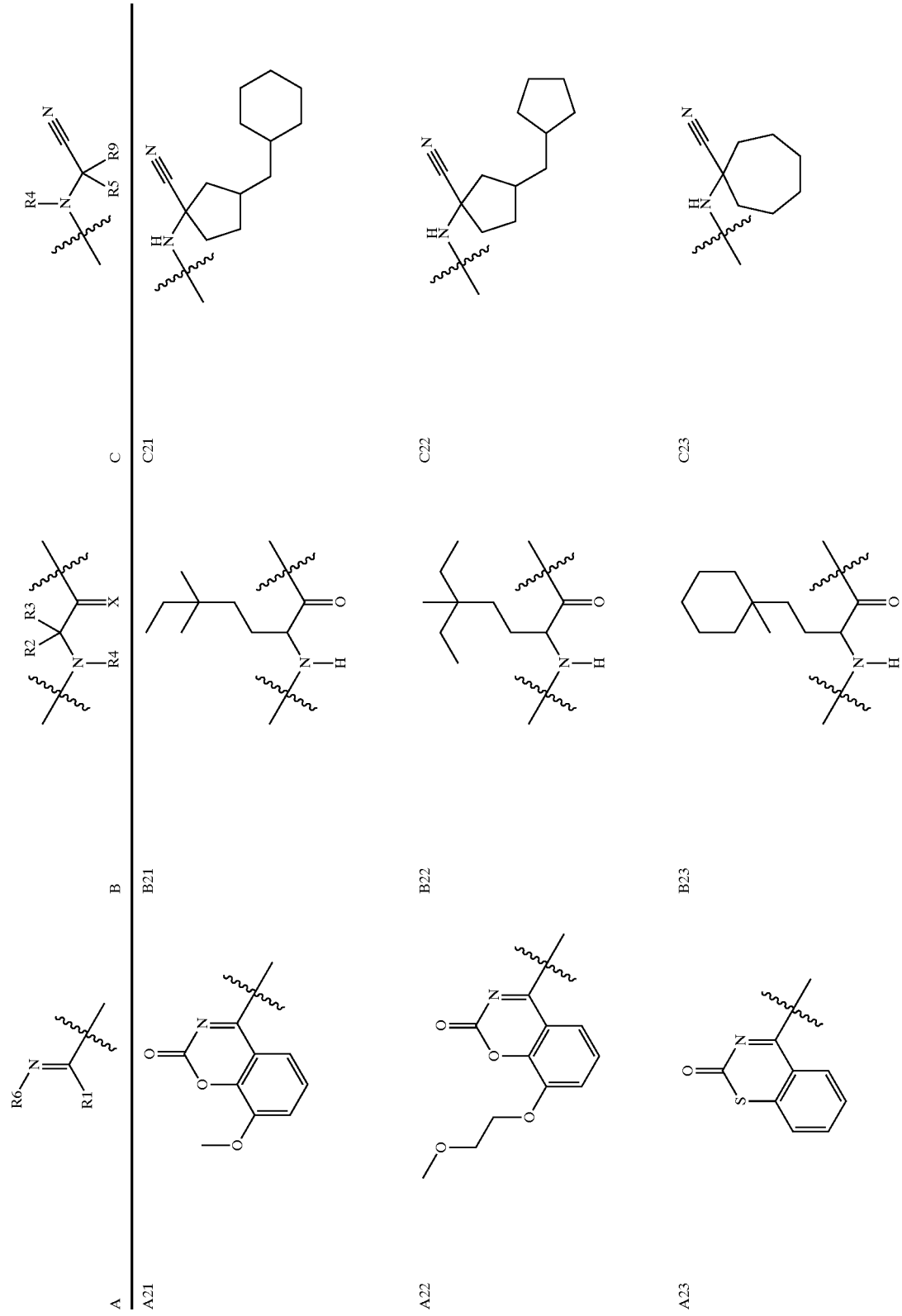

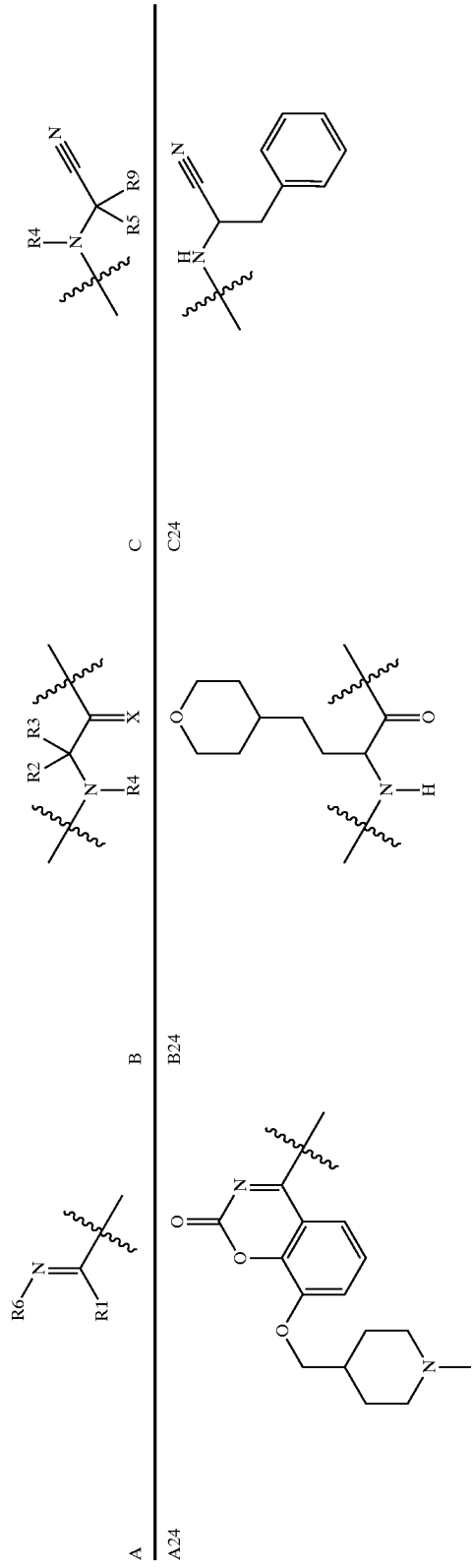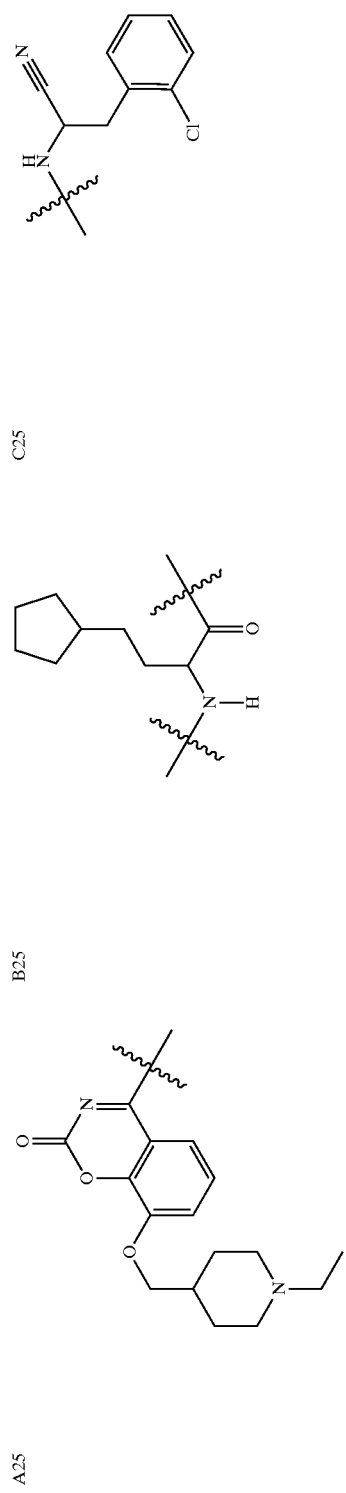

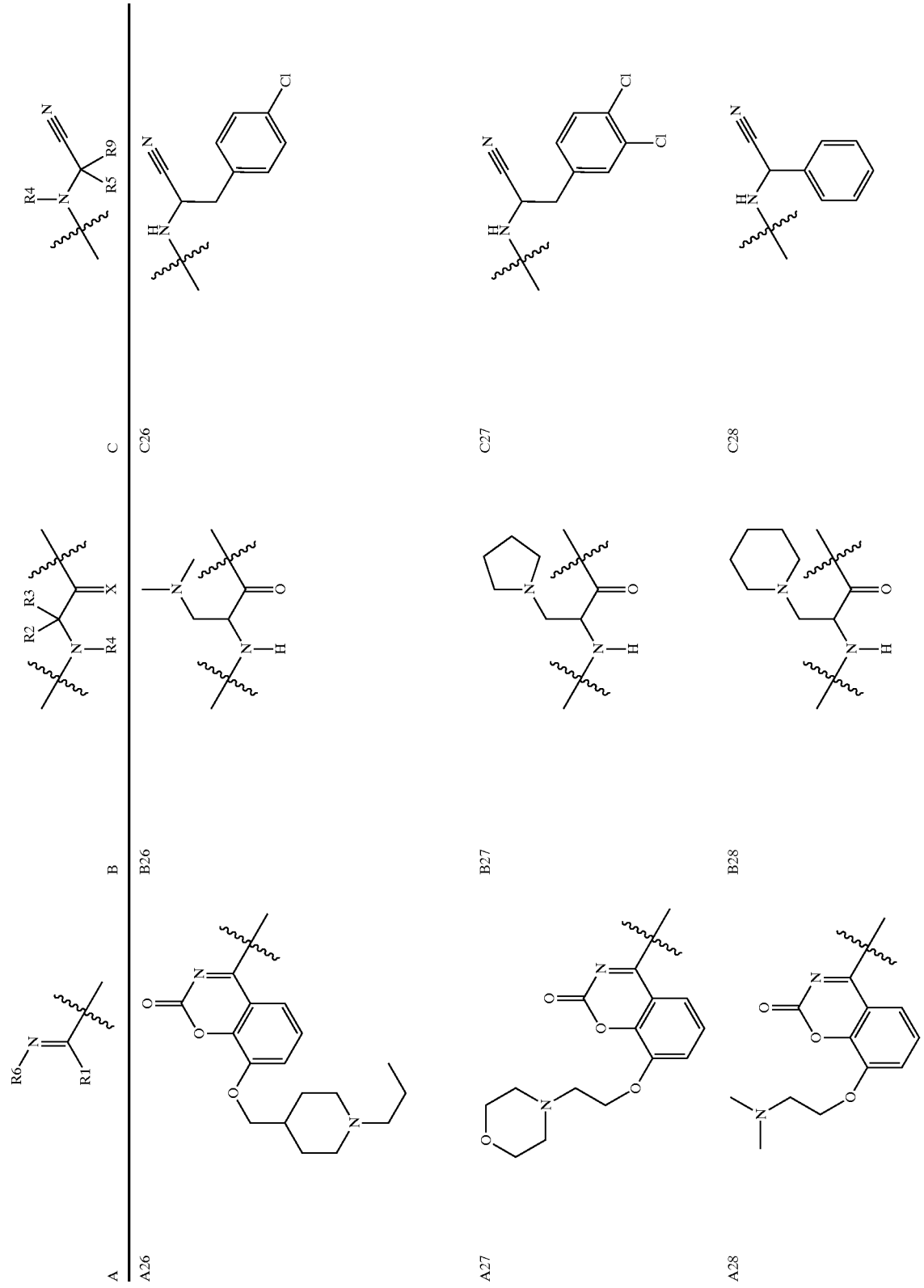

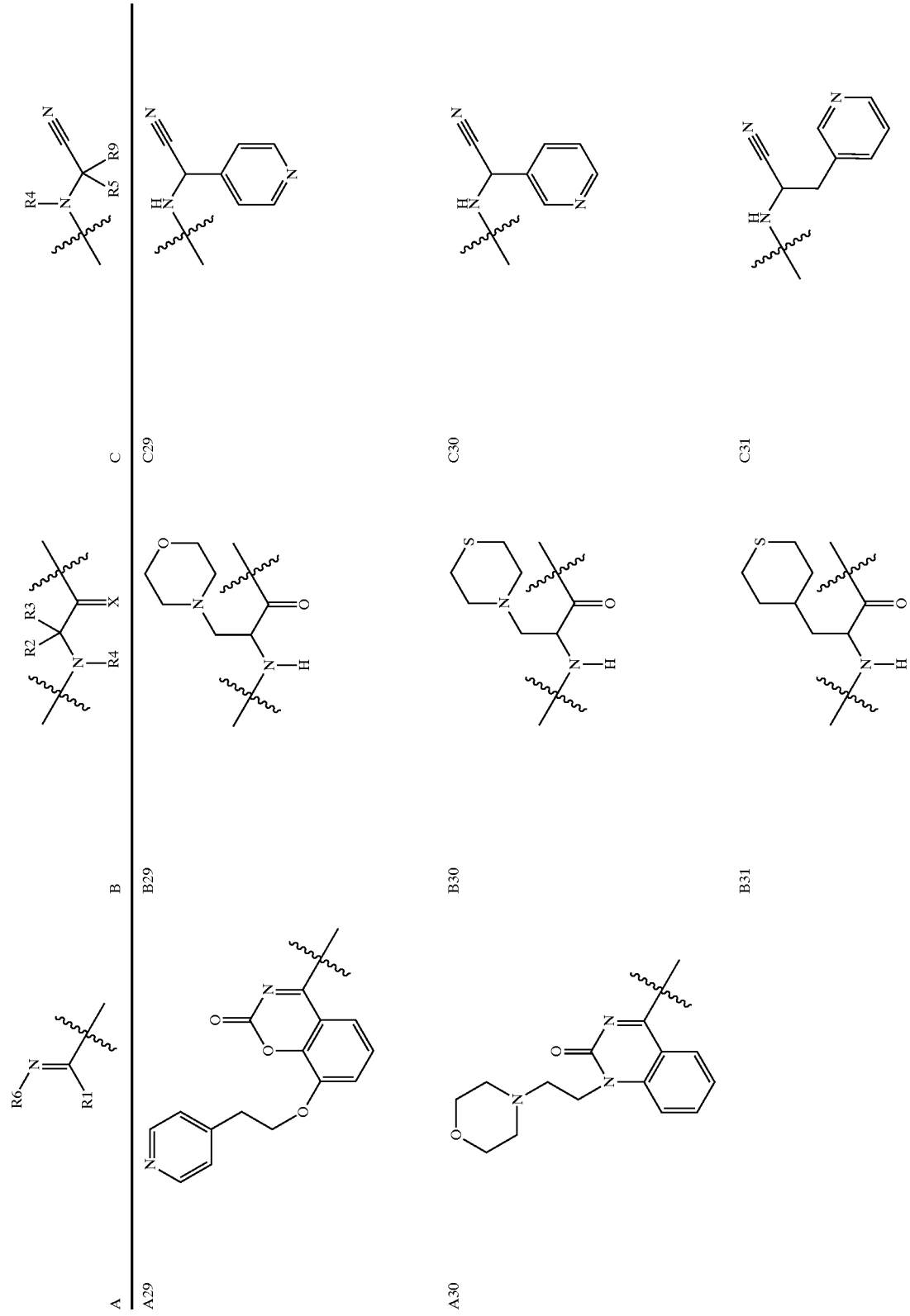

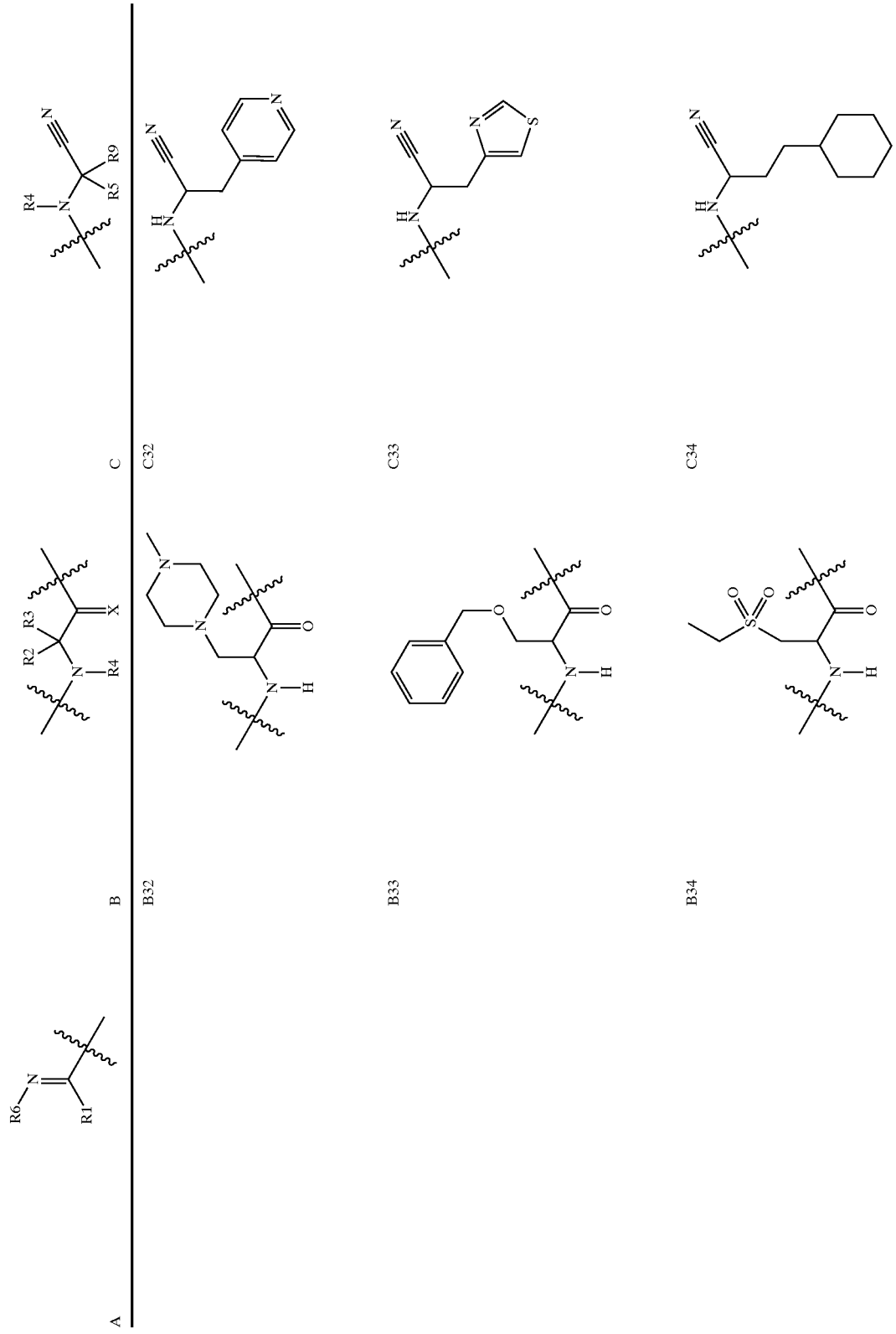

-continued
| A | B | C |
|---|---|---|
|  | | |
| | B35 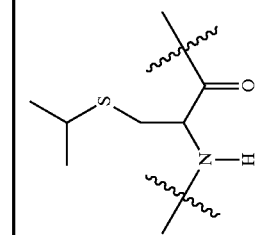 | C35 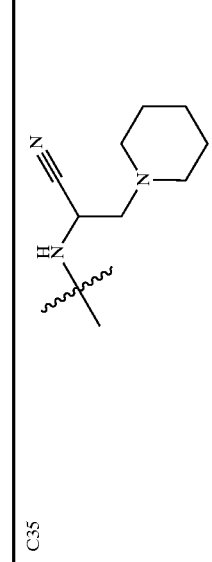 |
| | B36 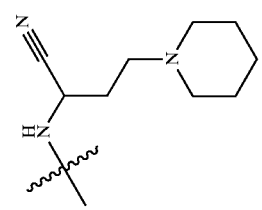 | C36 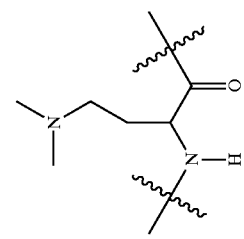 |
| | B37 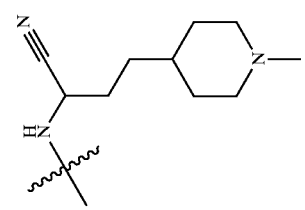 | C37 |

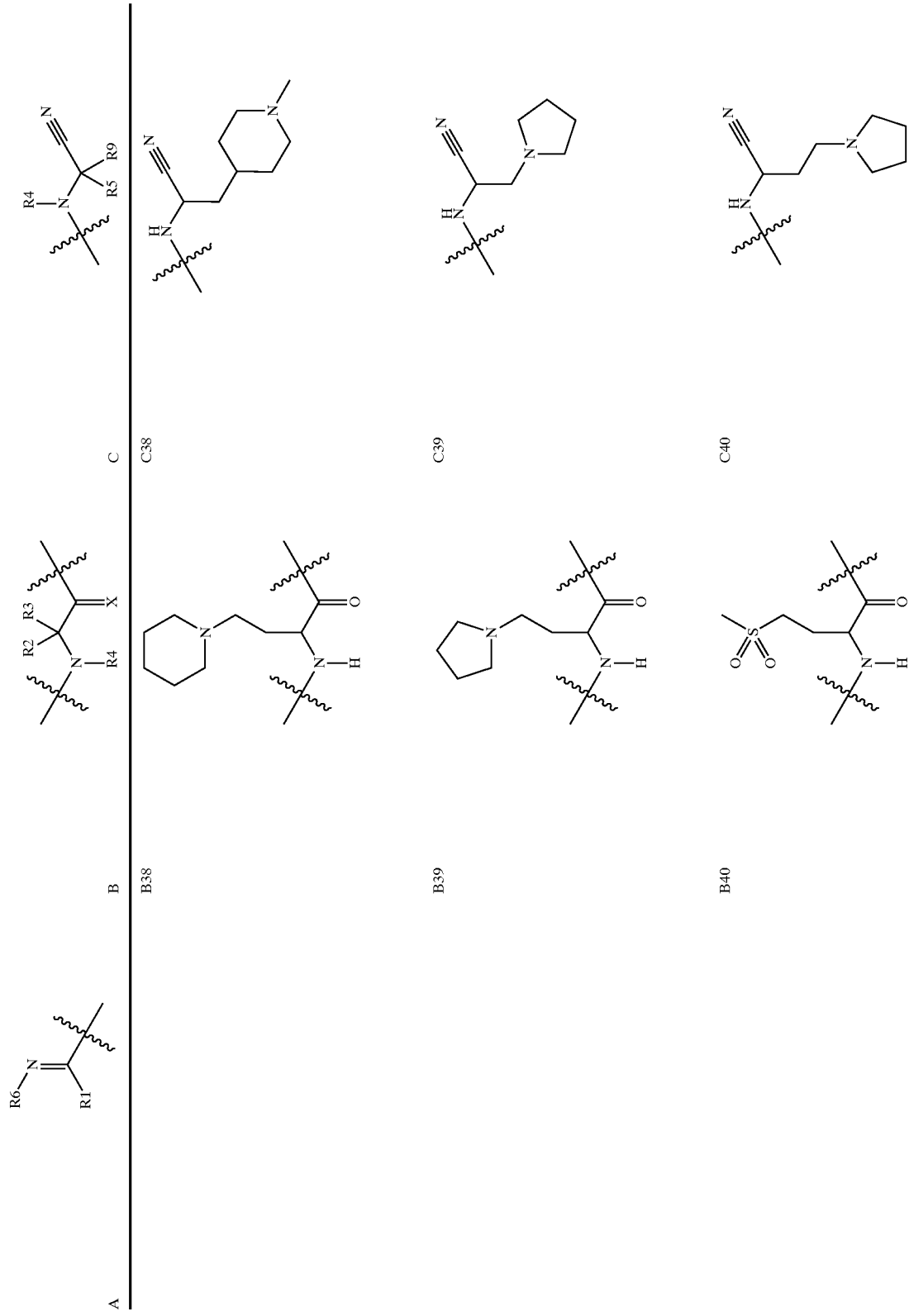

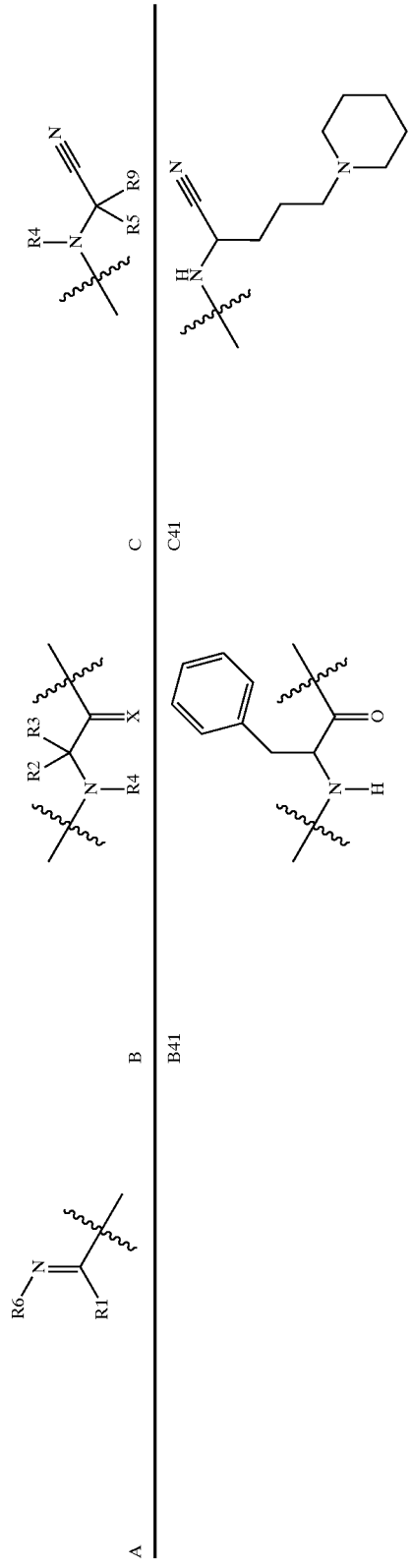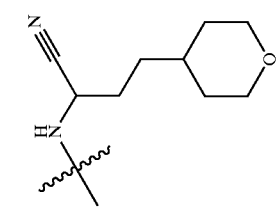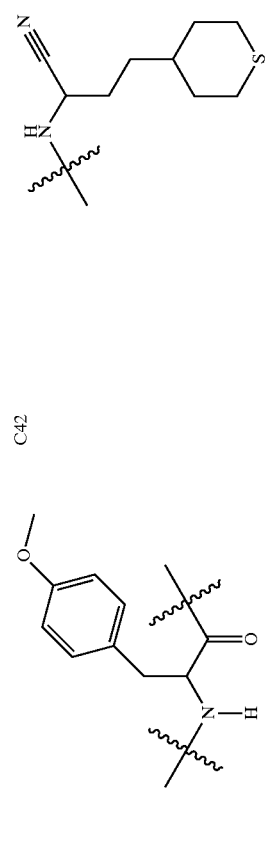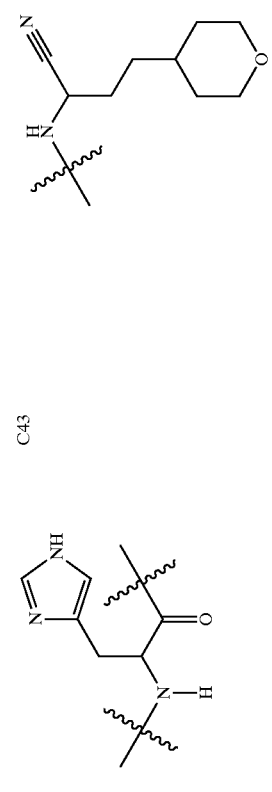

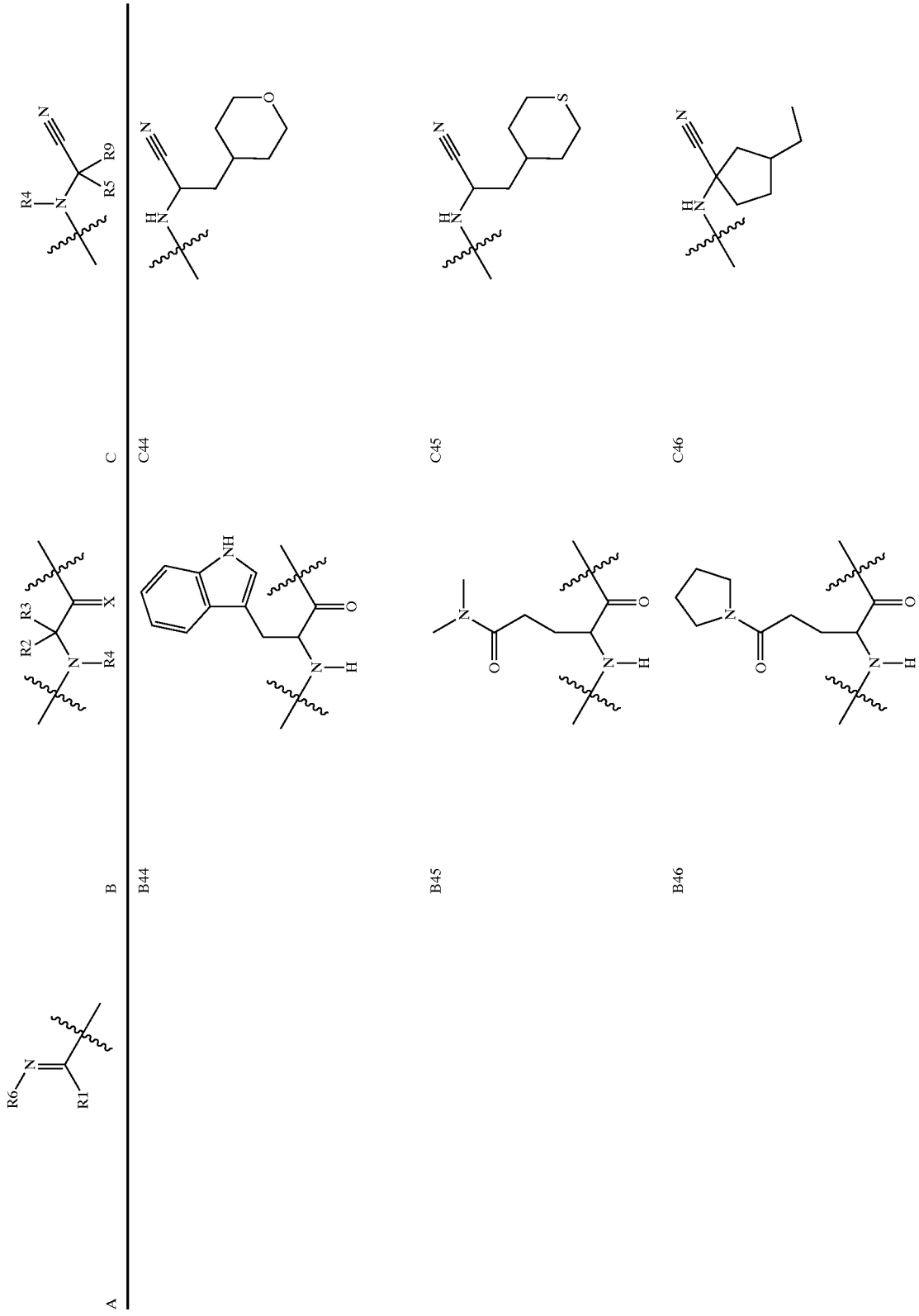

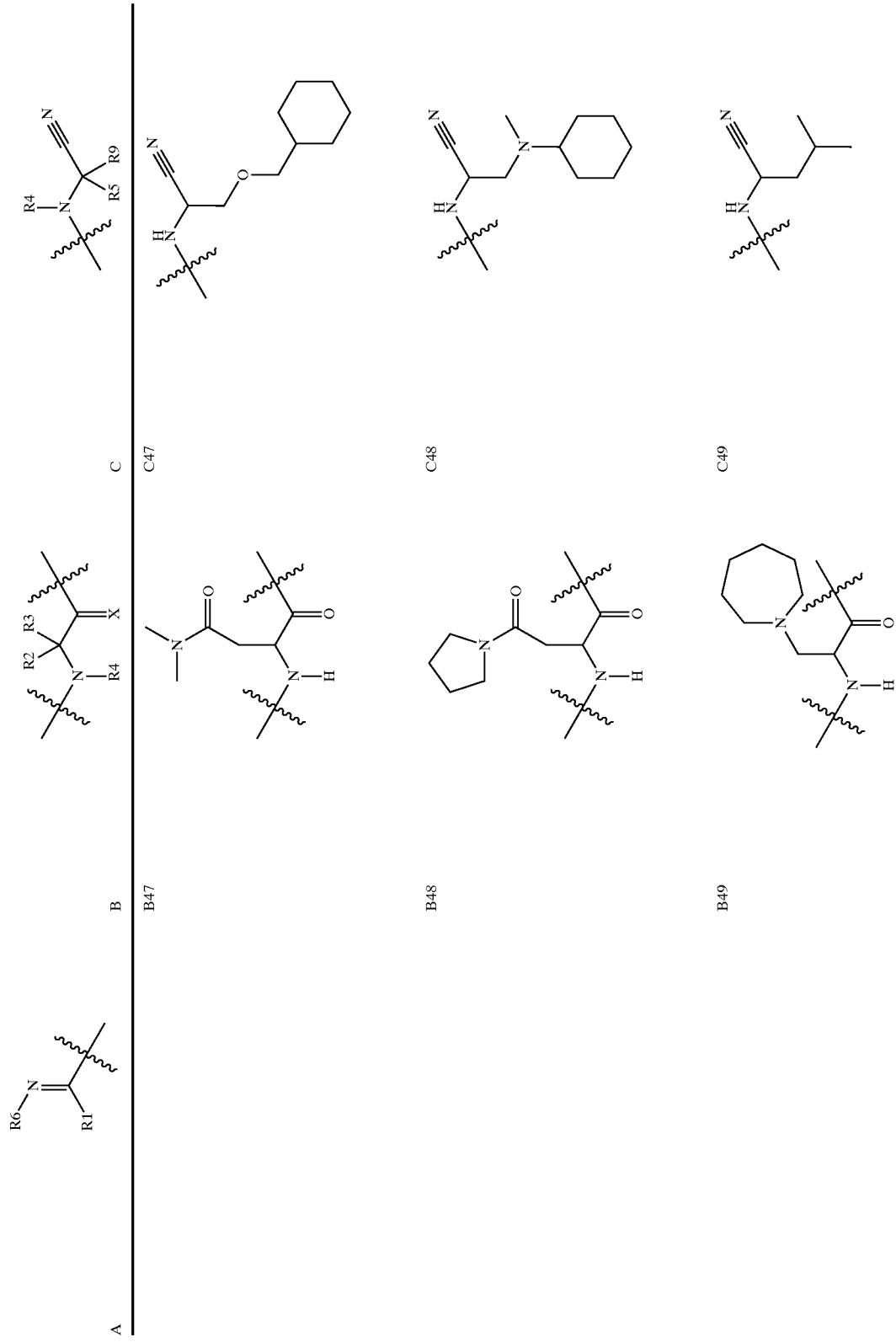

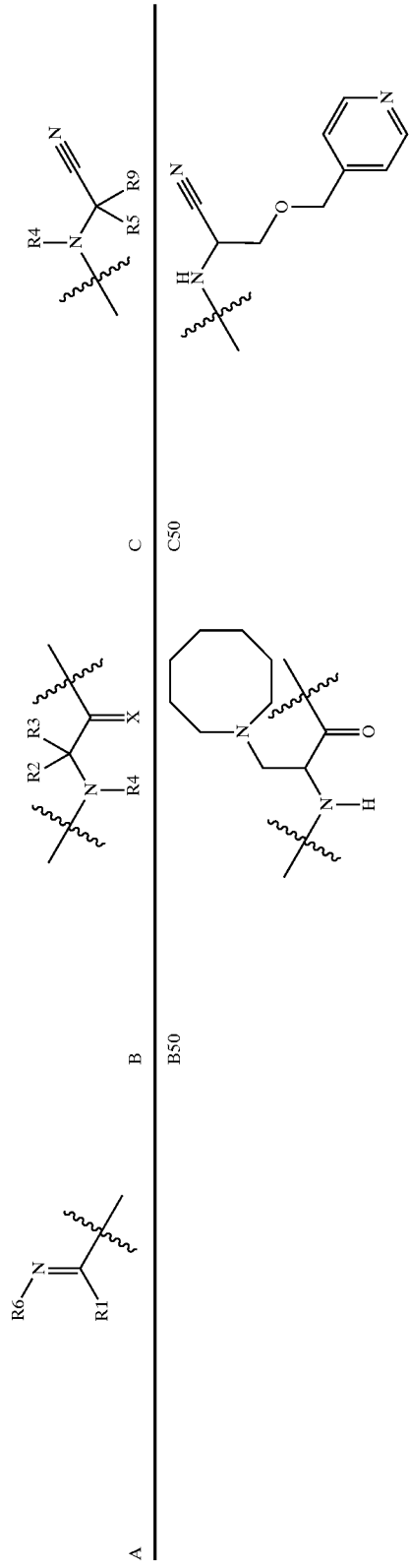
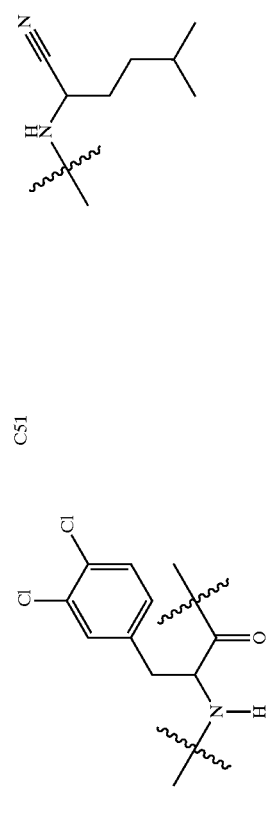
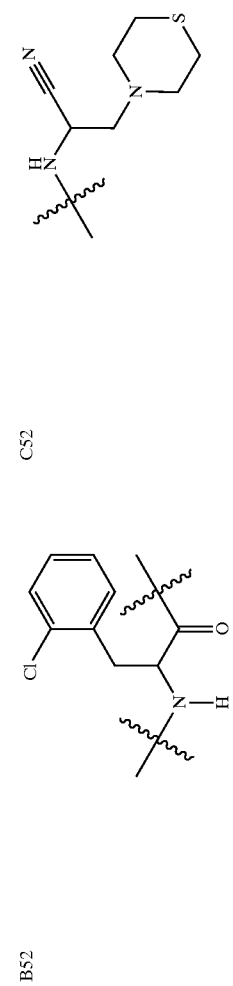

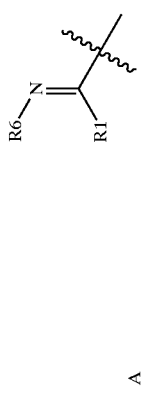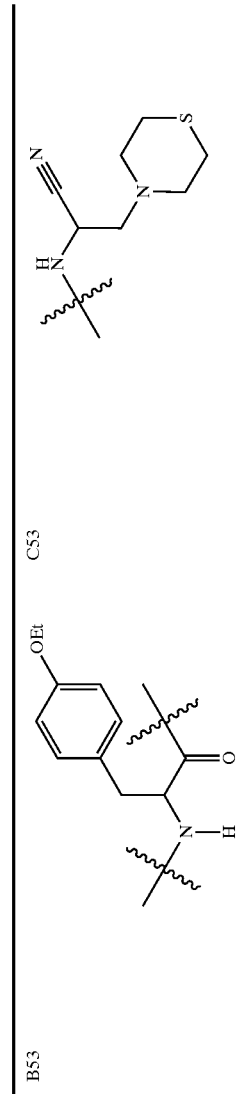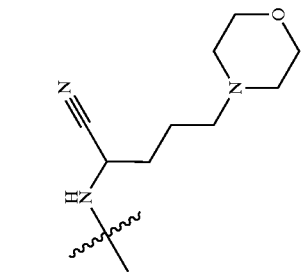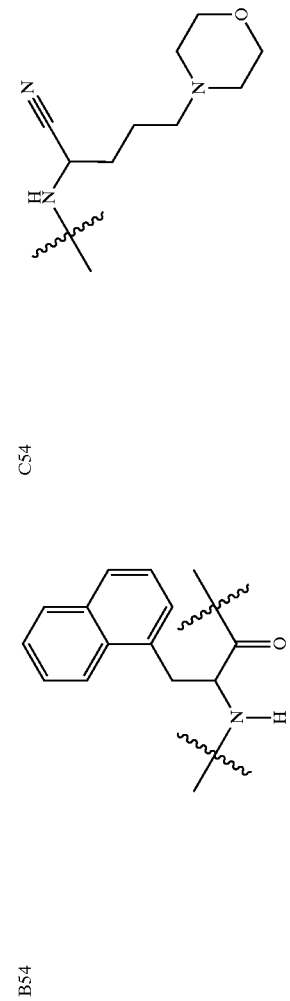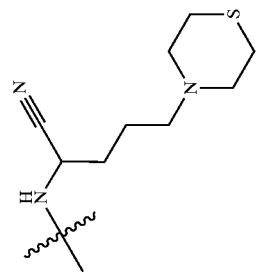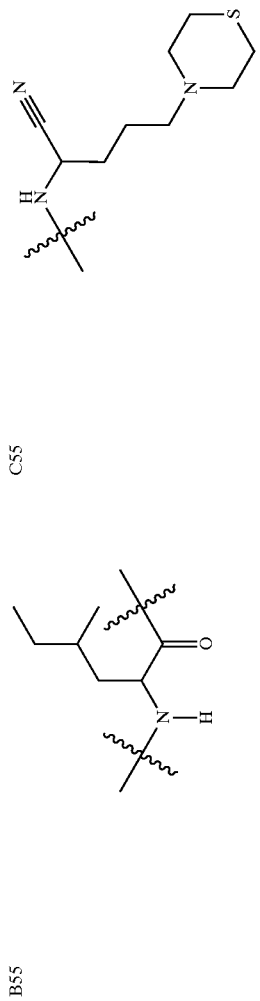

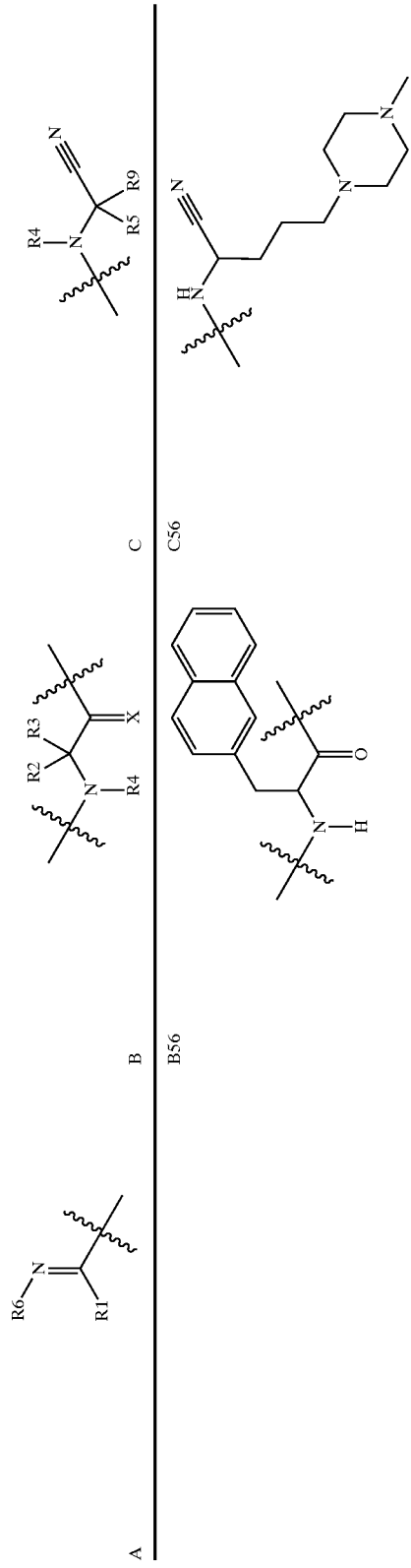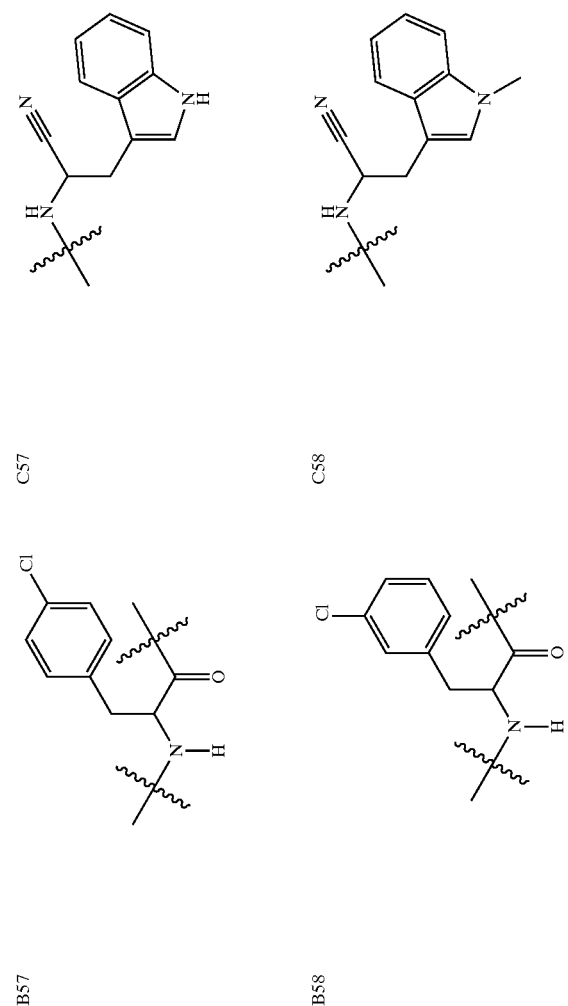

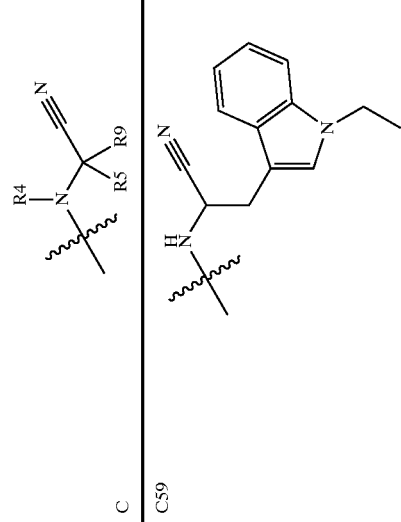
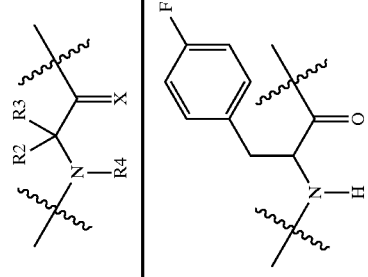
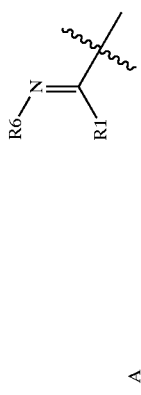
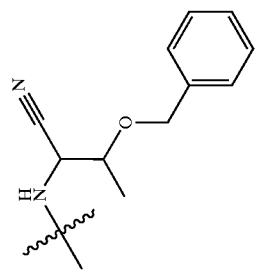
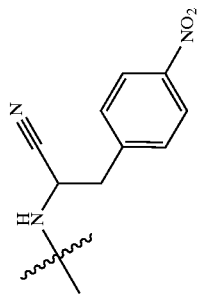
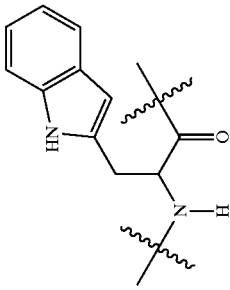
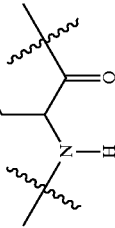

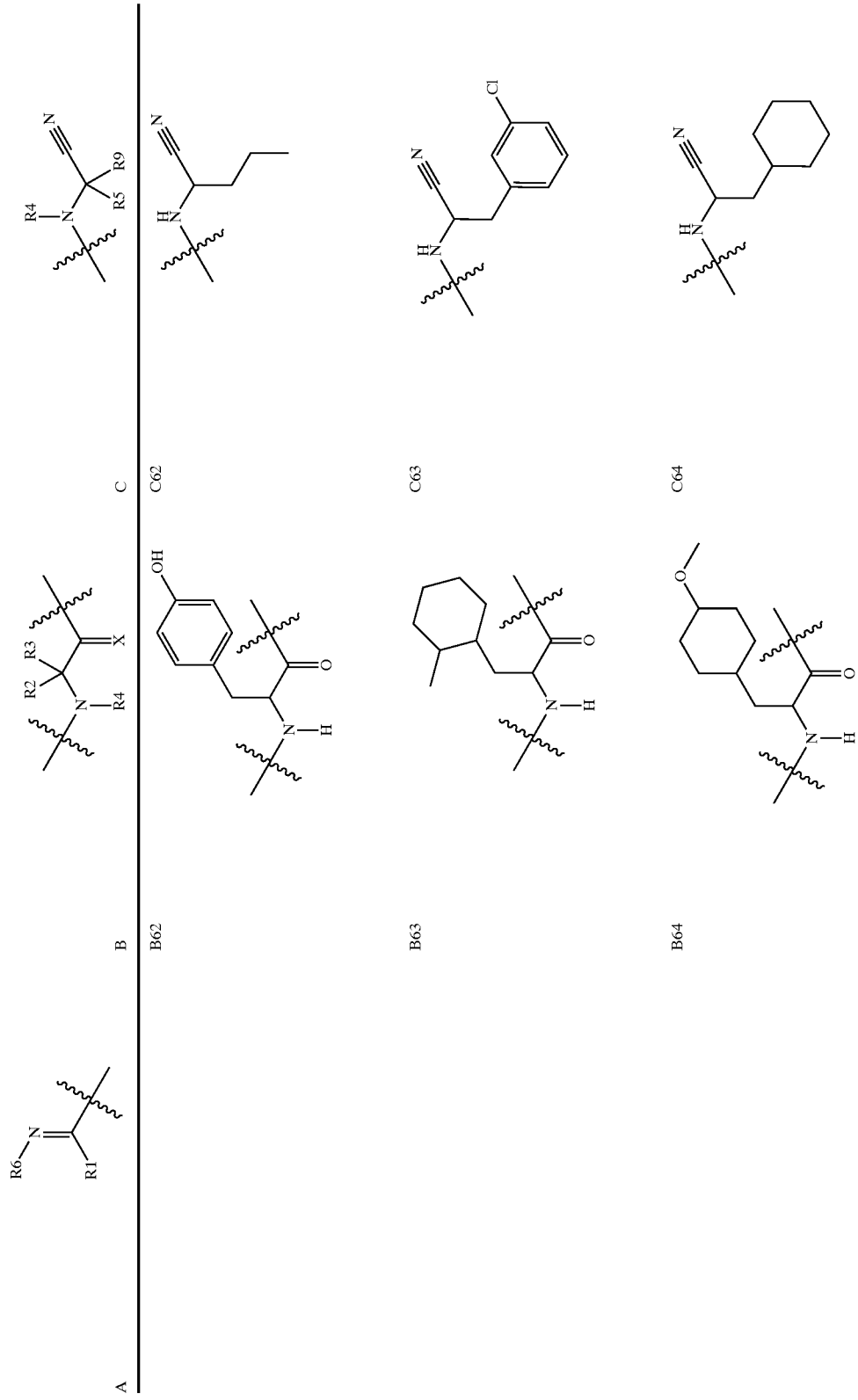

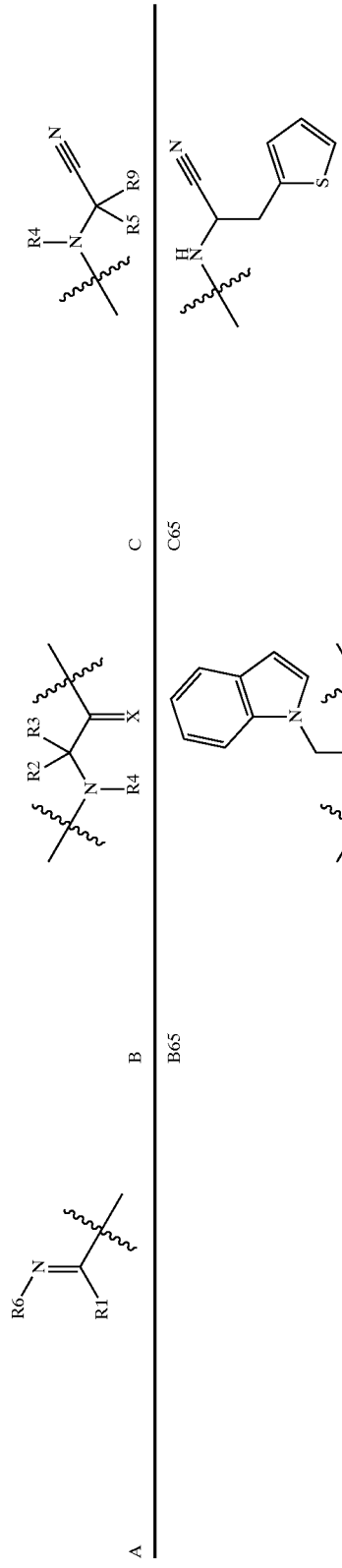
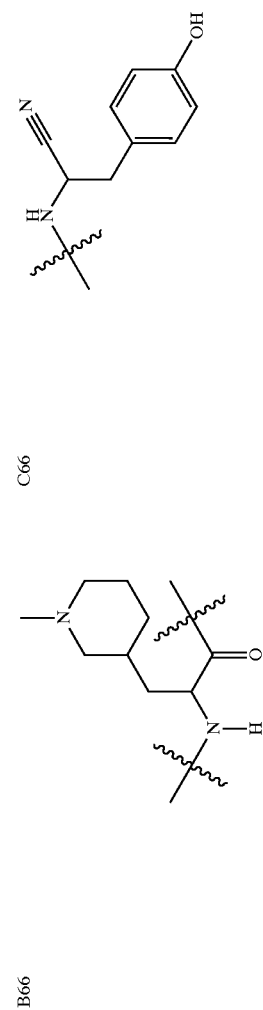

| A | B | C |
|---|---|---|
|  | | |
| | B67 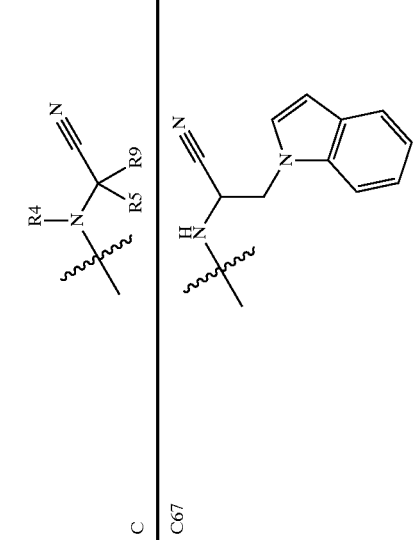 | C67 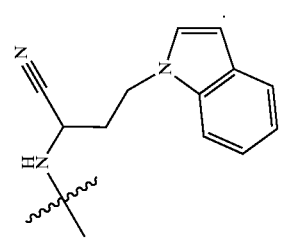 |
| | B68 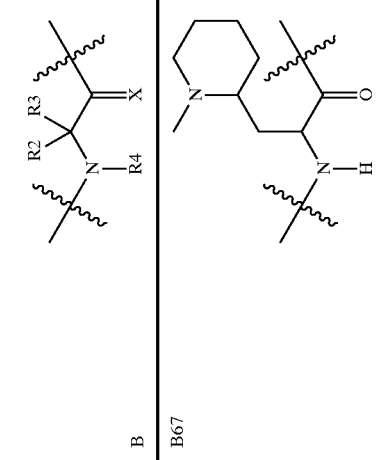 | C68 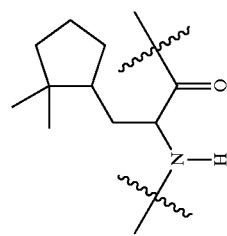 |

9. A compound of the formula (Ia)
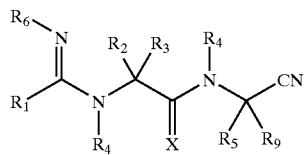
(Ia)
wherein for the formula (Ia), the components
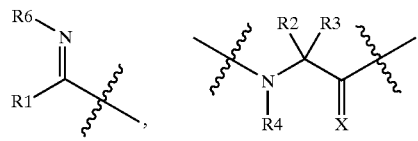
and
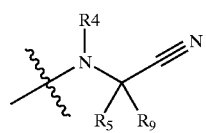
are chosen from any combination of A, B and C as follows:

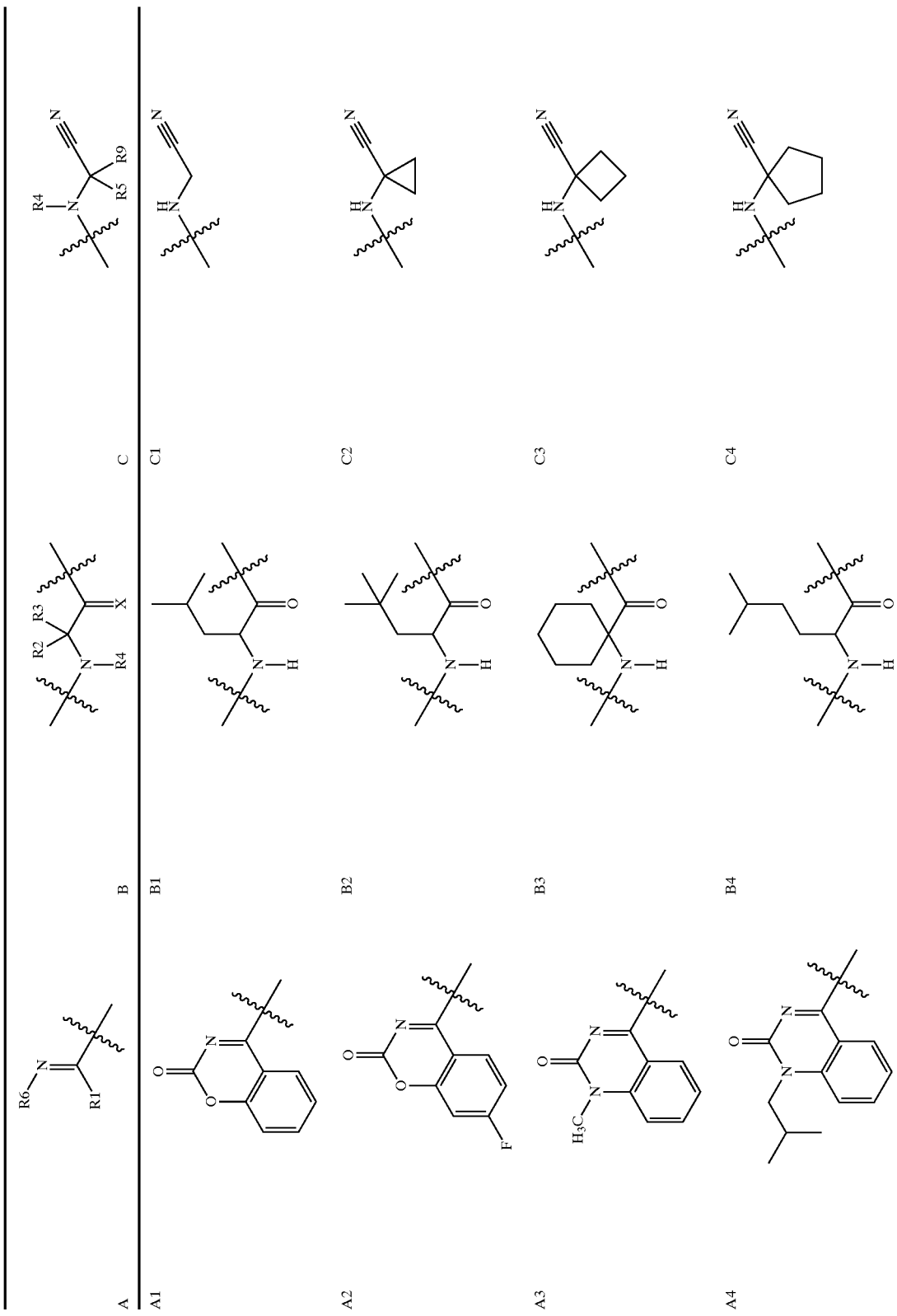

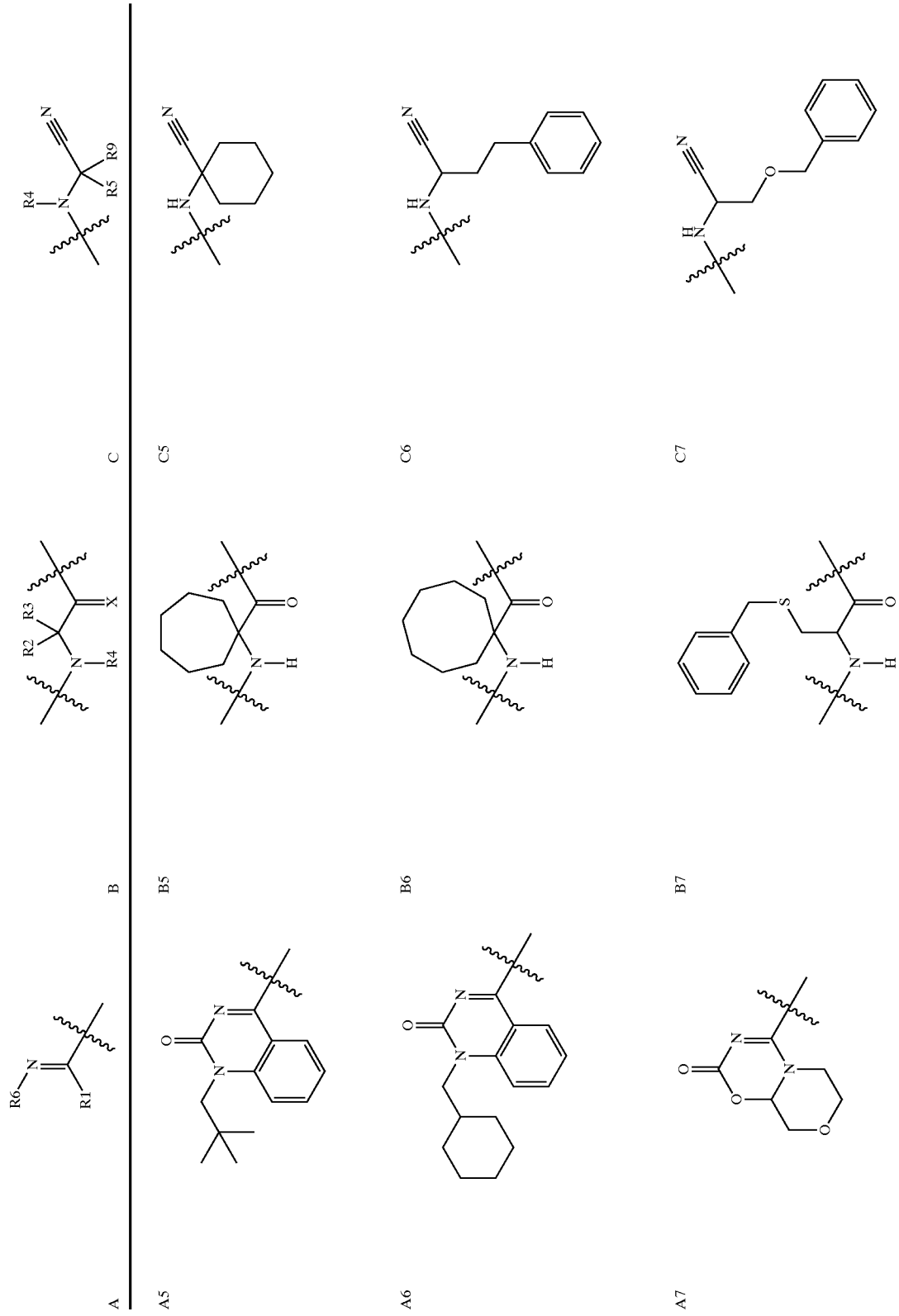

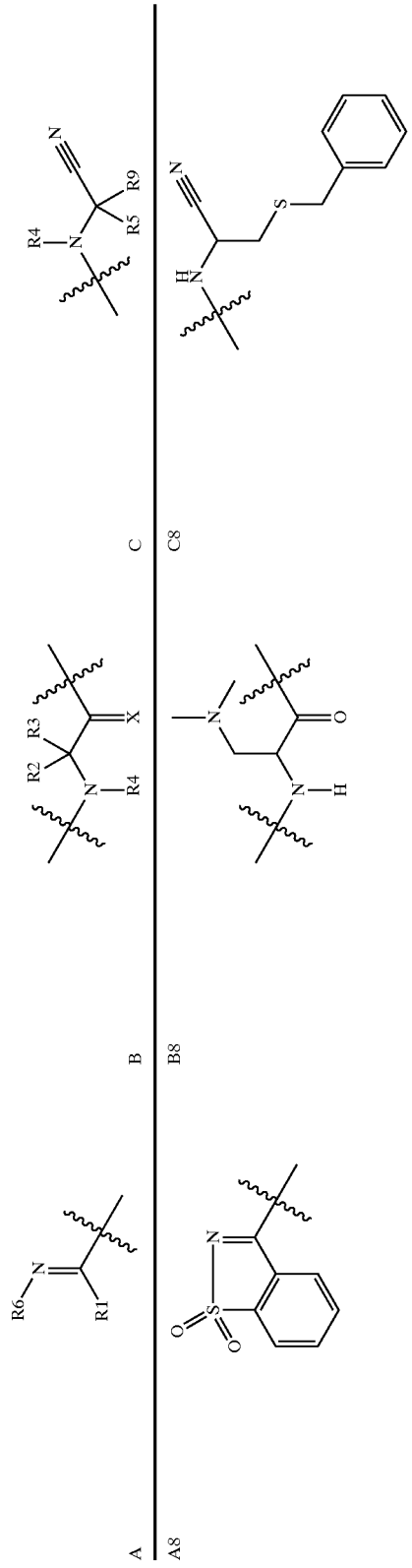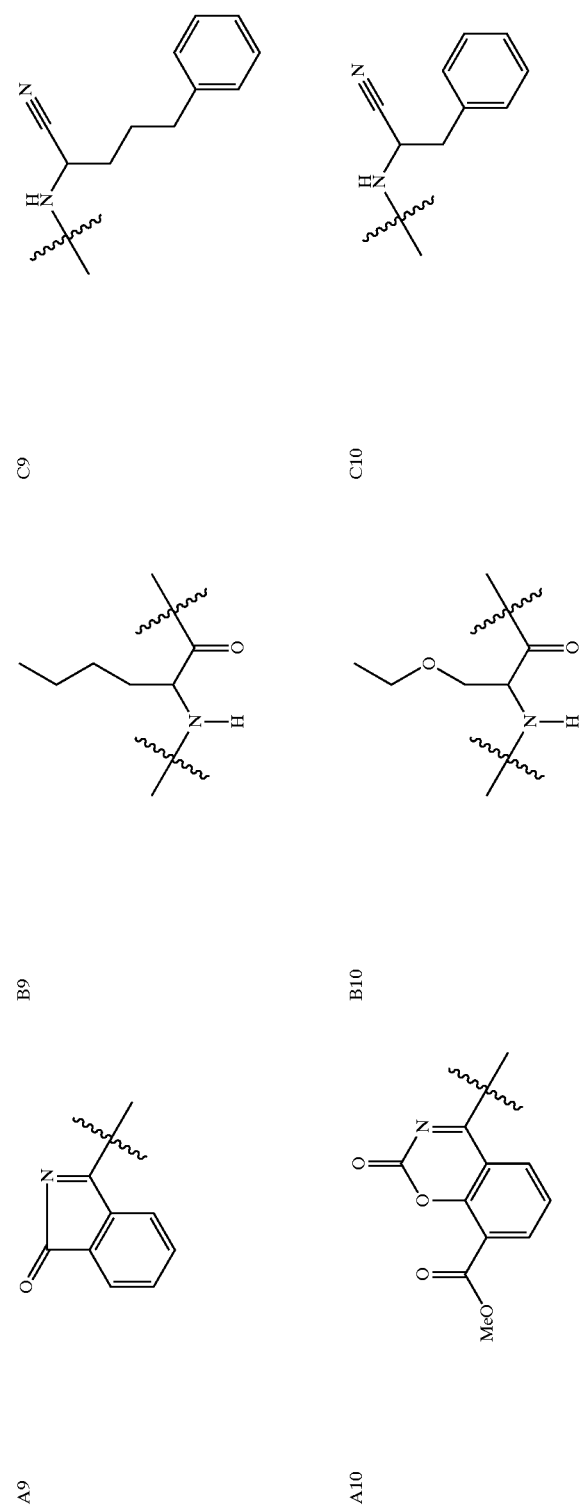

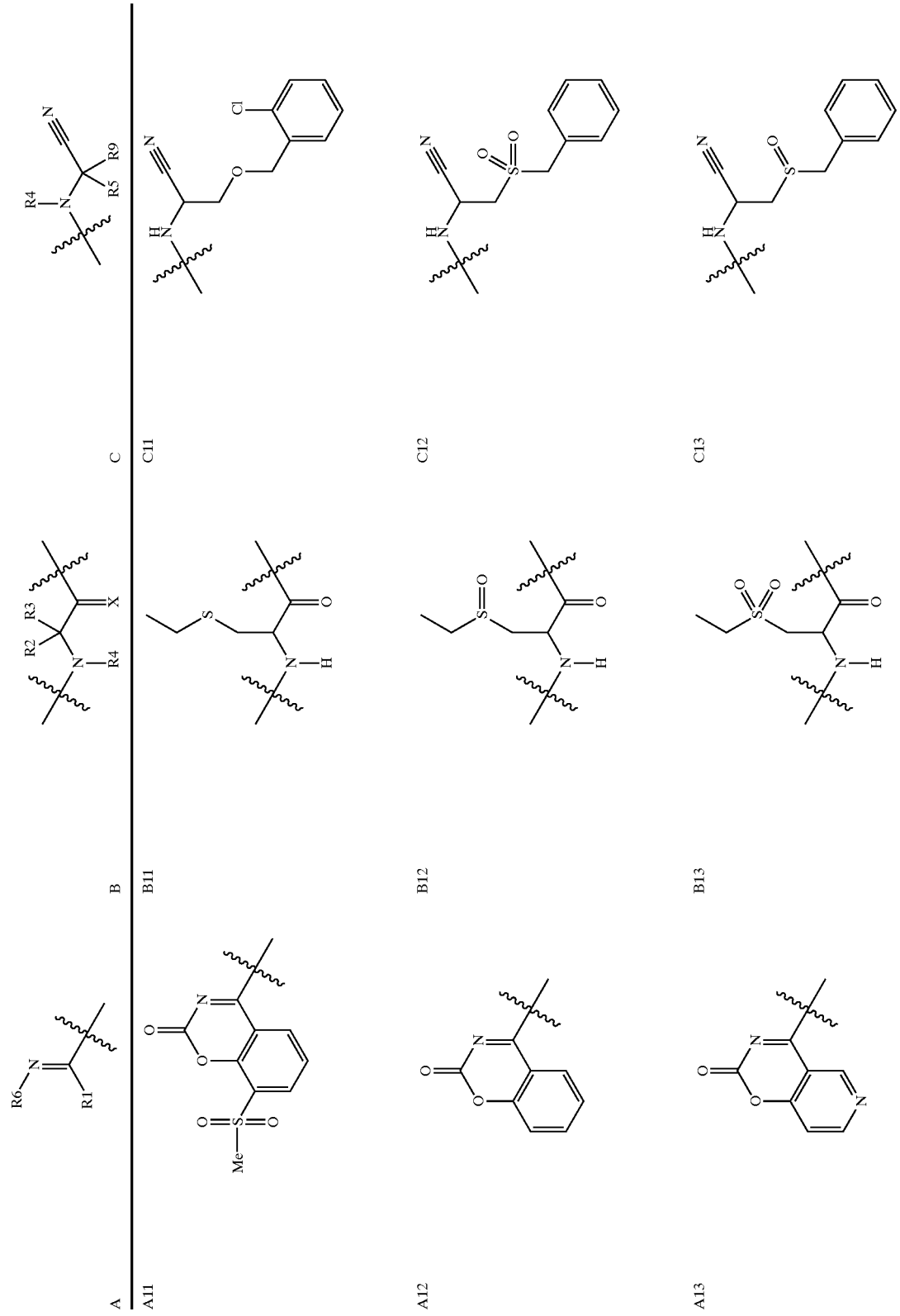

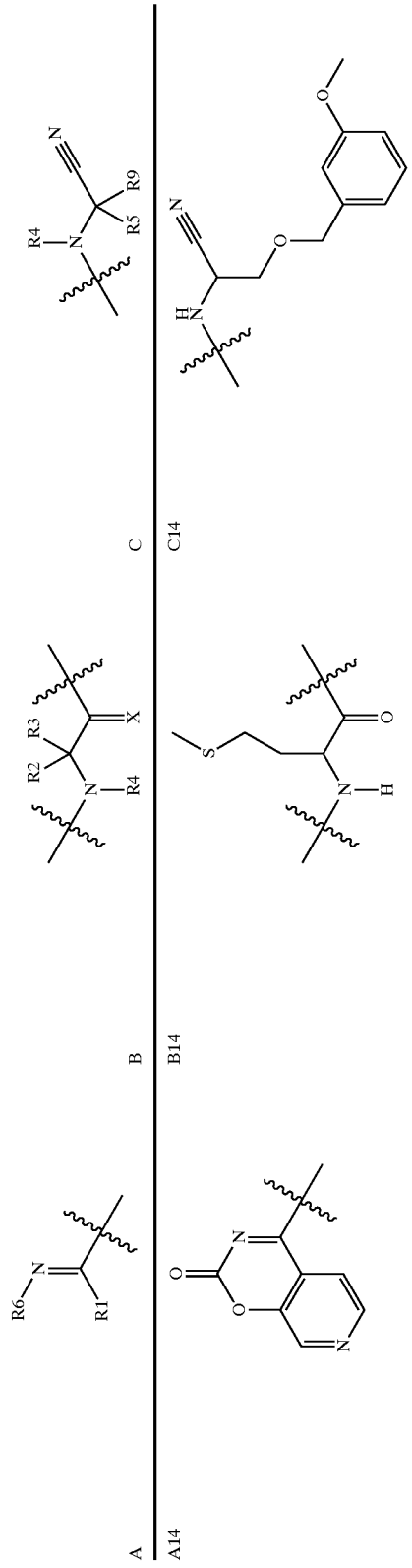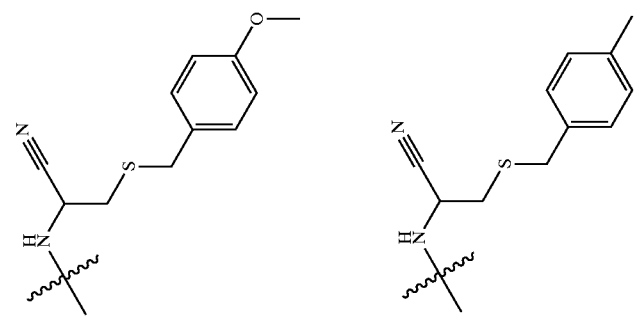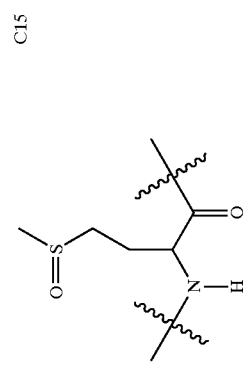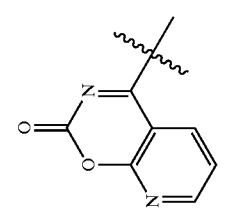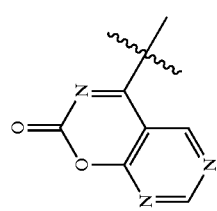

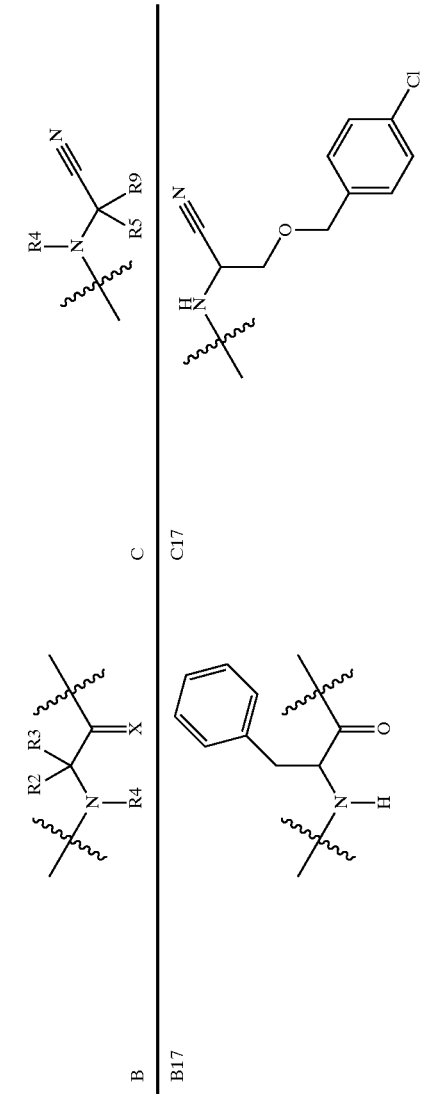
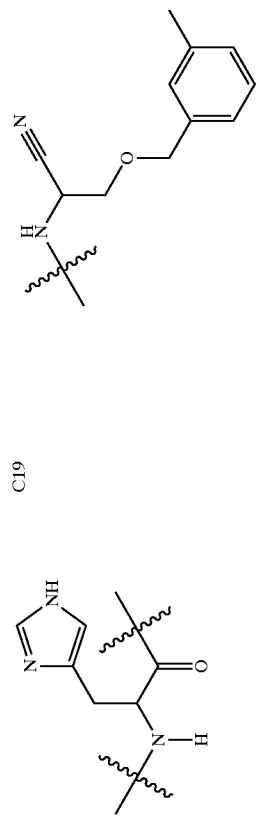
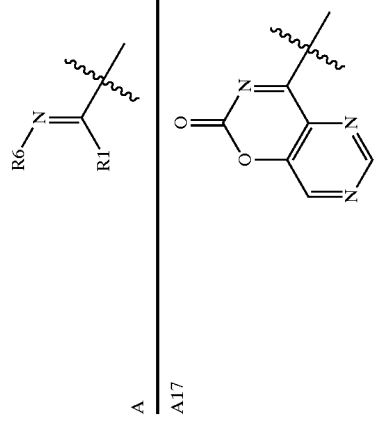
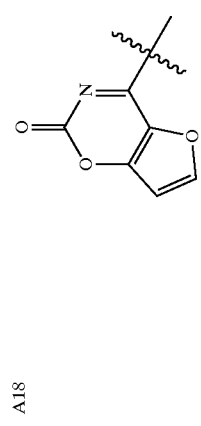
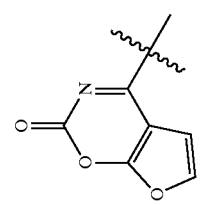

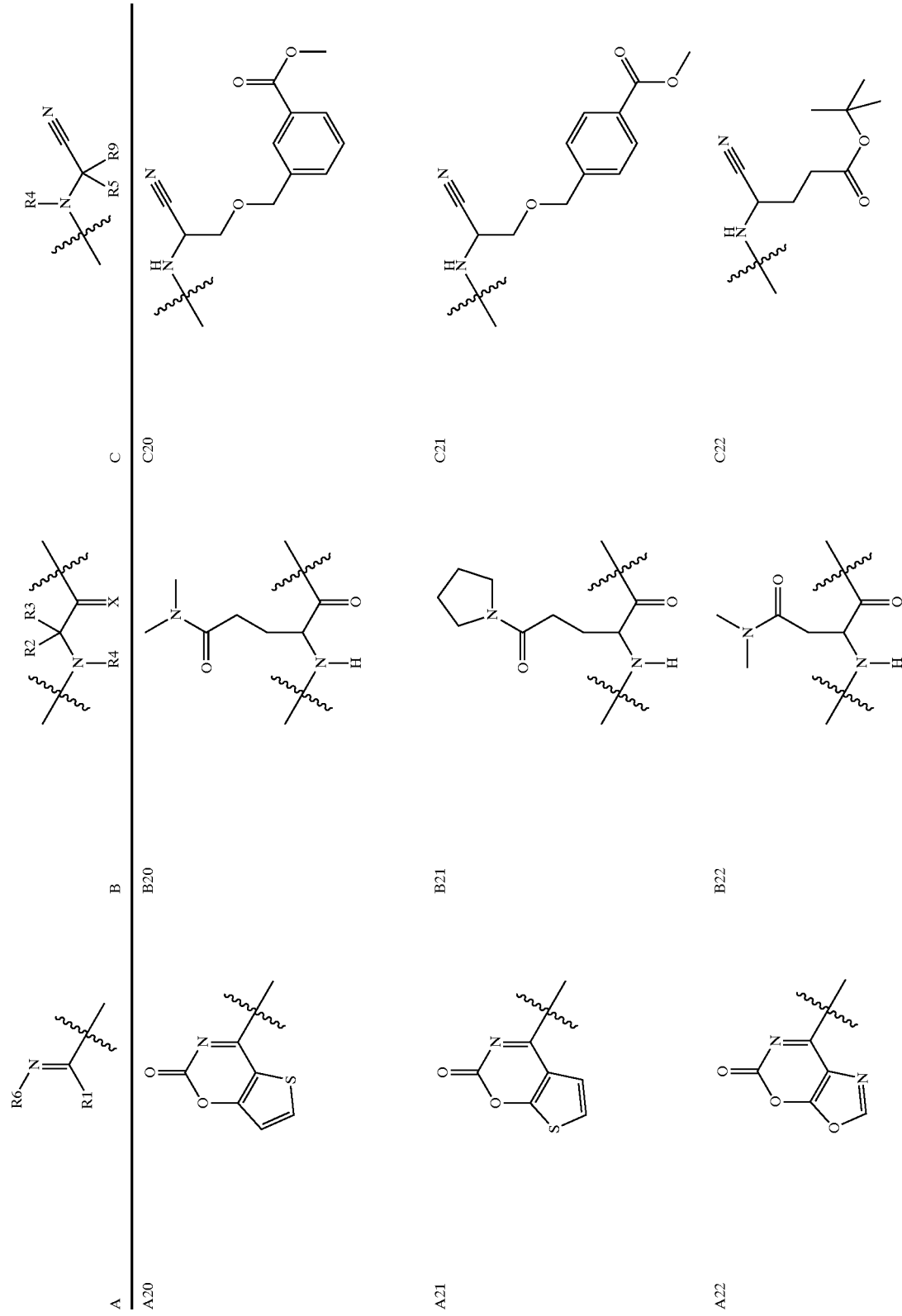

-continued
| A | B | C |
|---|---|---|
| 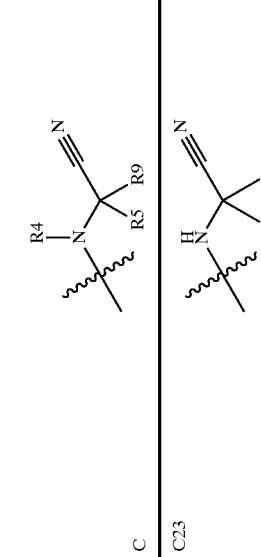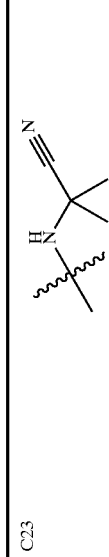 | 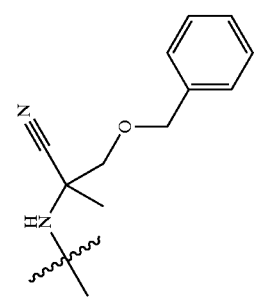 | 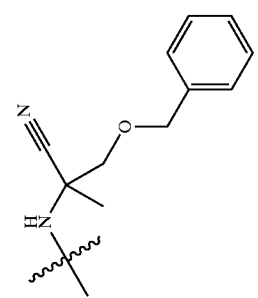 |
| A23 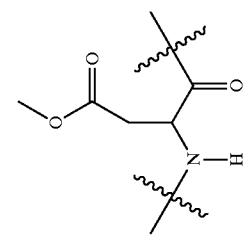 | B23 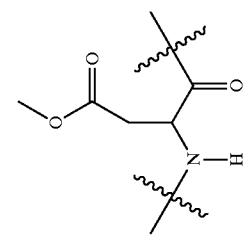 | C23 |
| A24 | B24 | C24 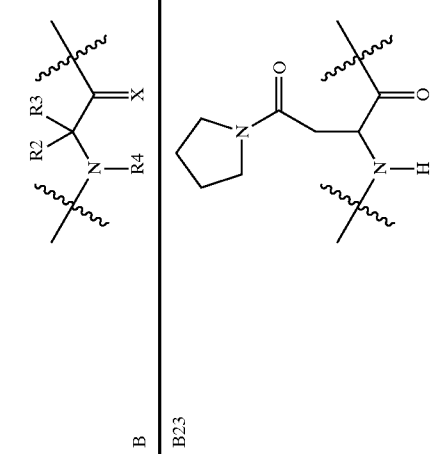 |
| A25 | B25 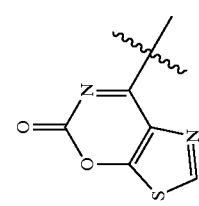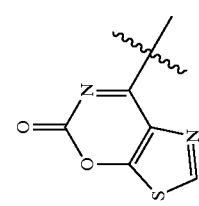 | C25 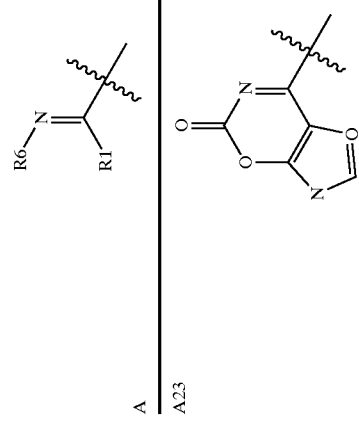 |

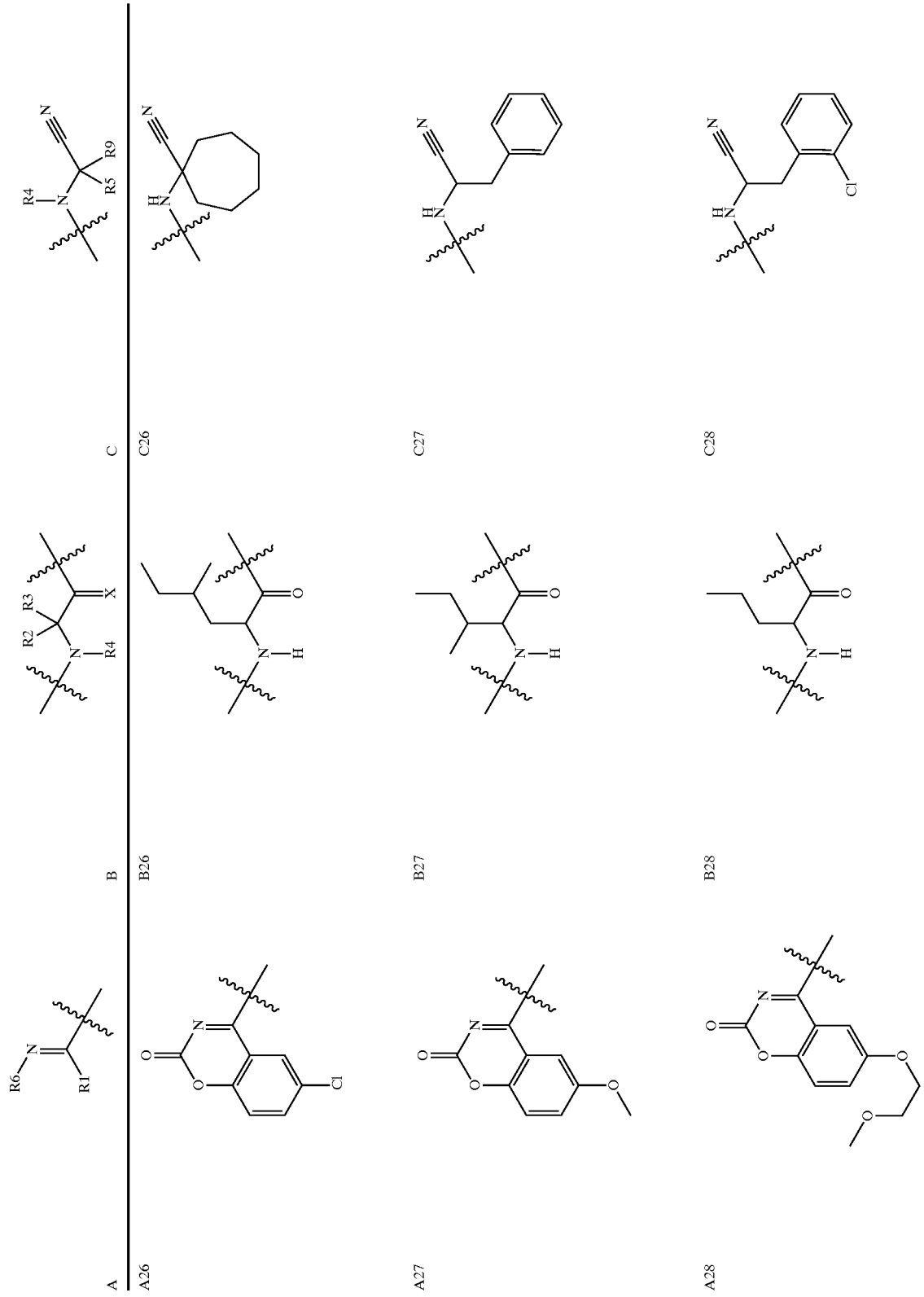

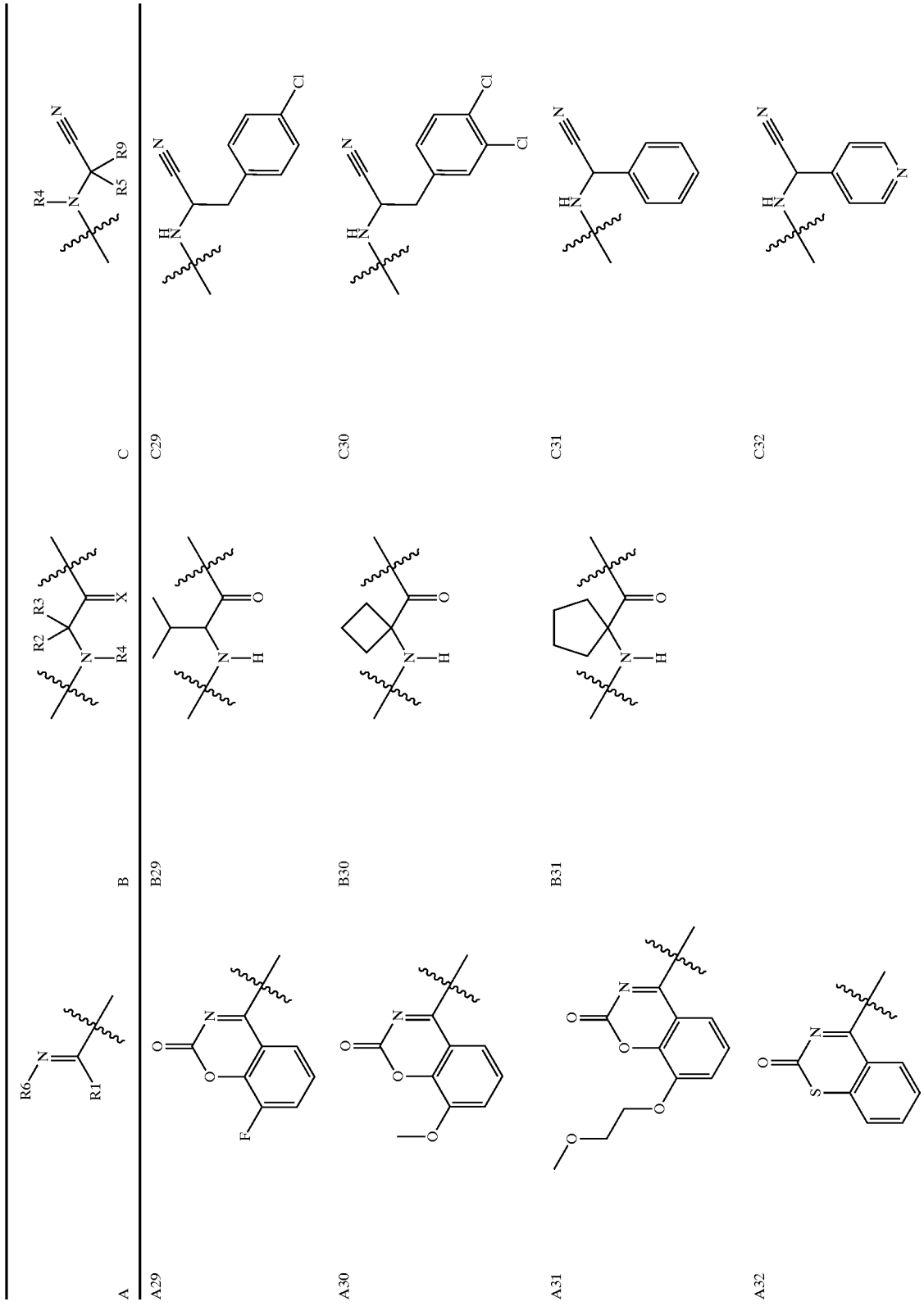

-continued
| A | B | C |
|---|---|---|
| 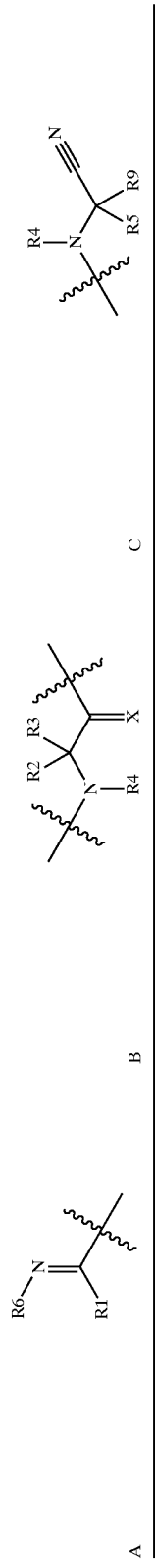 | | |
| A34 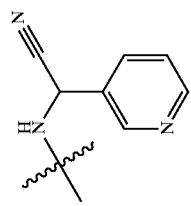 | | C33 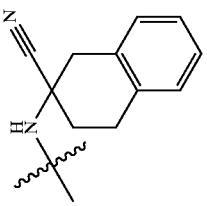 |
| A35 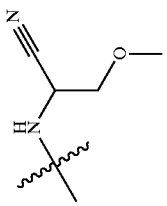 | | C34 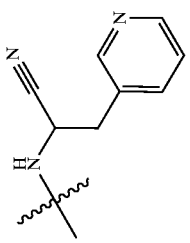 |
| A36 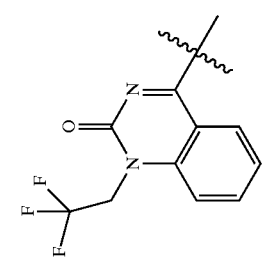 | | C35 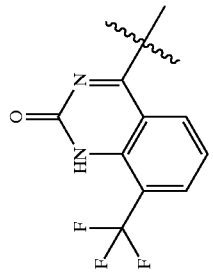 |
| | | C36 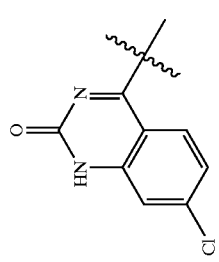 |

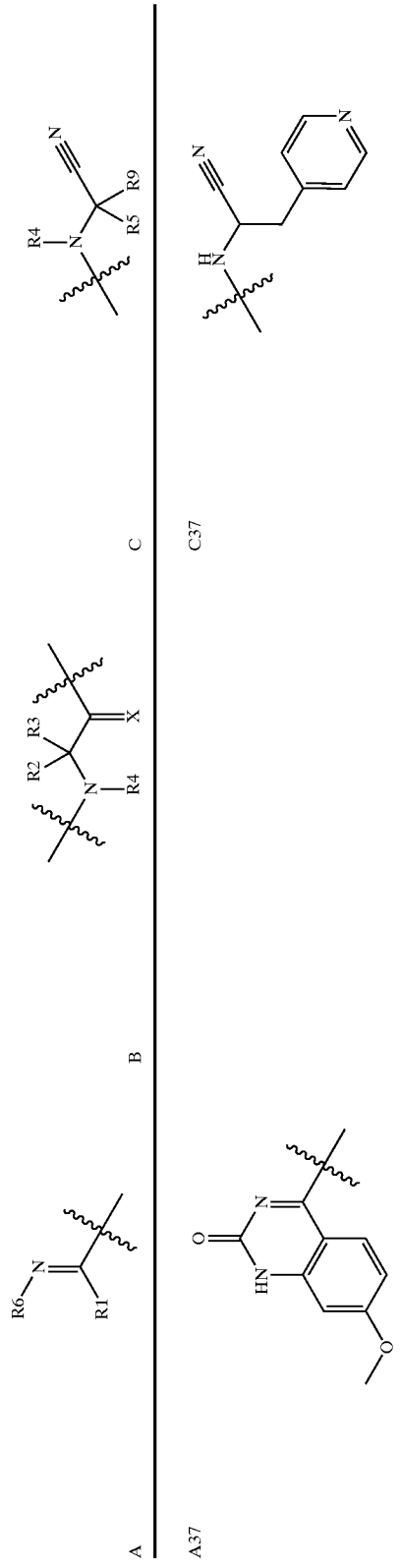

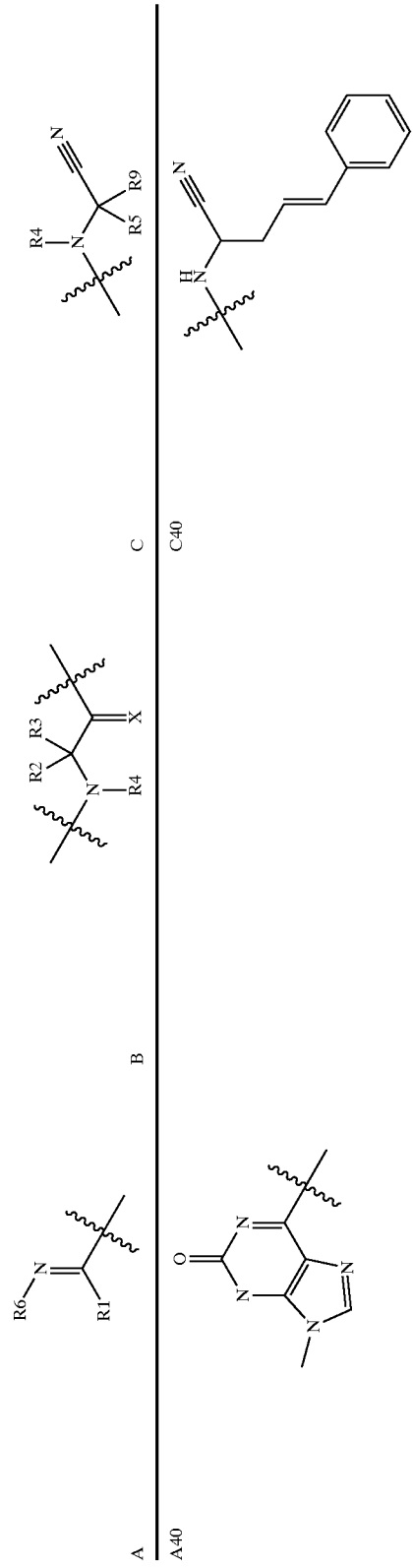

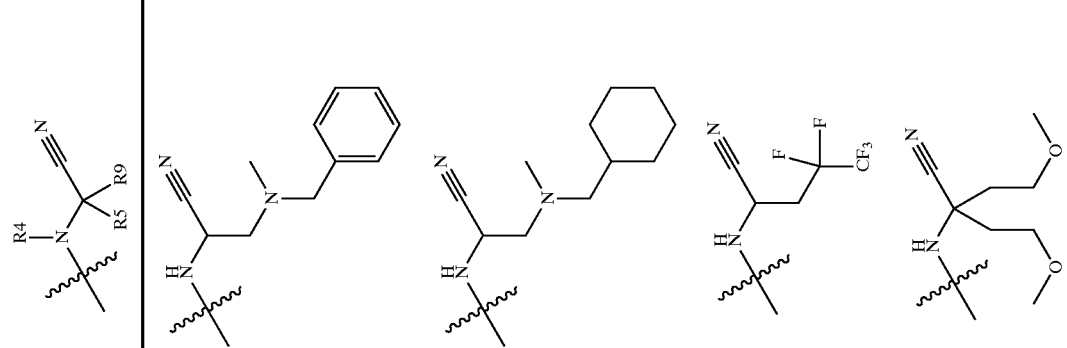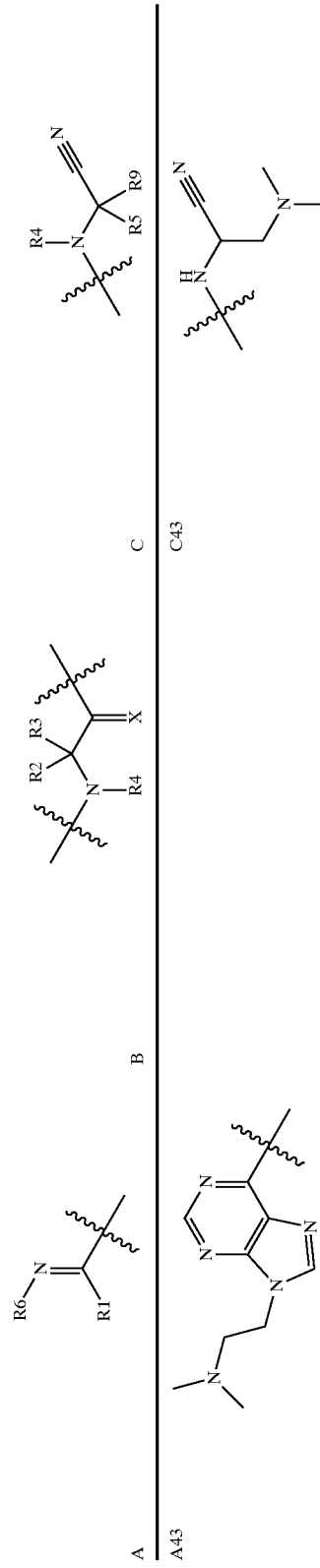

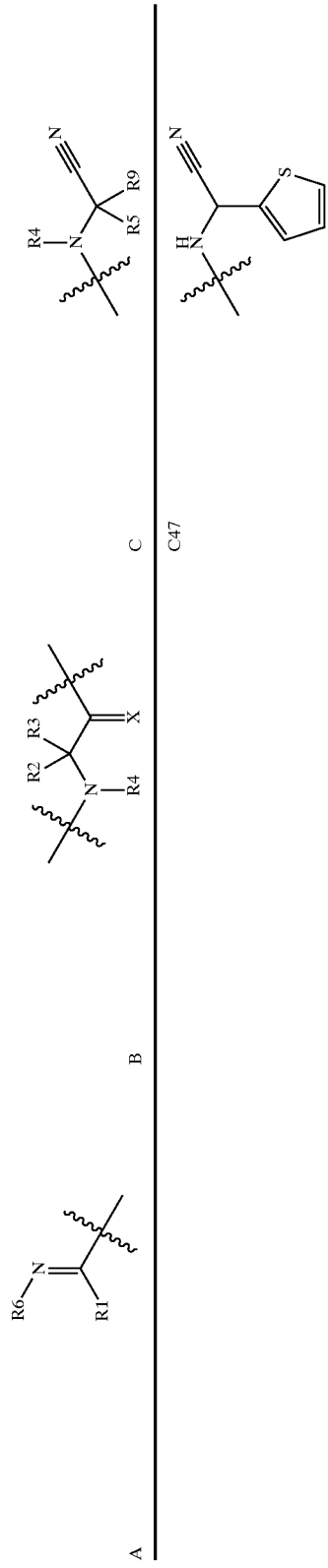

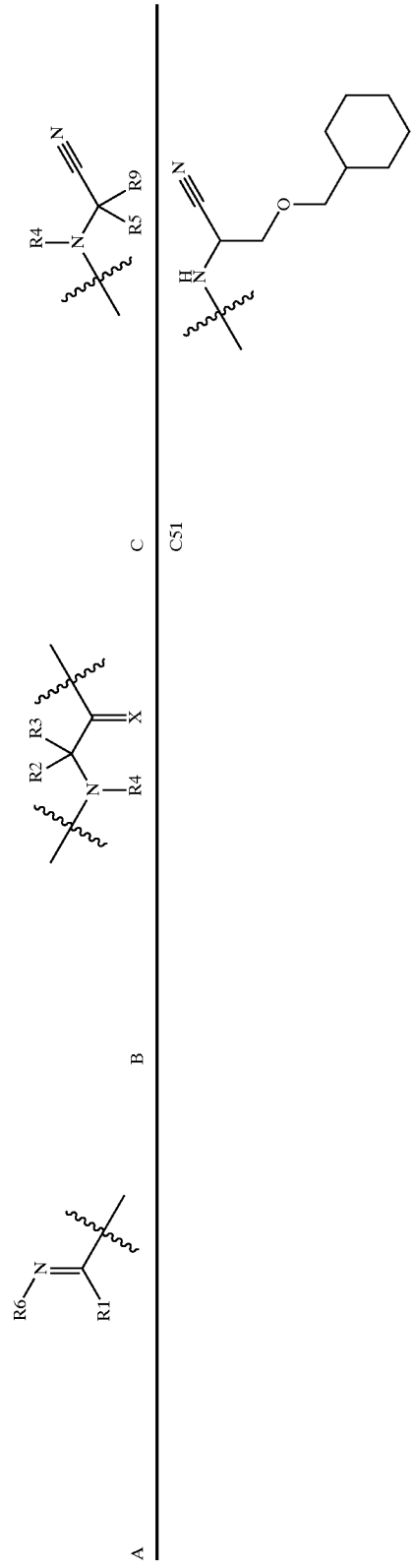

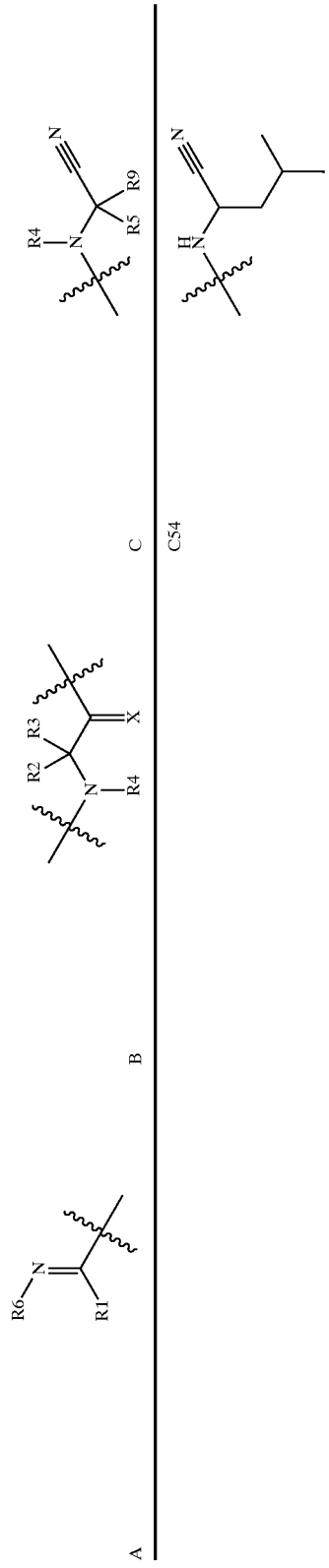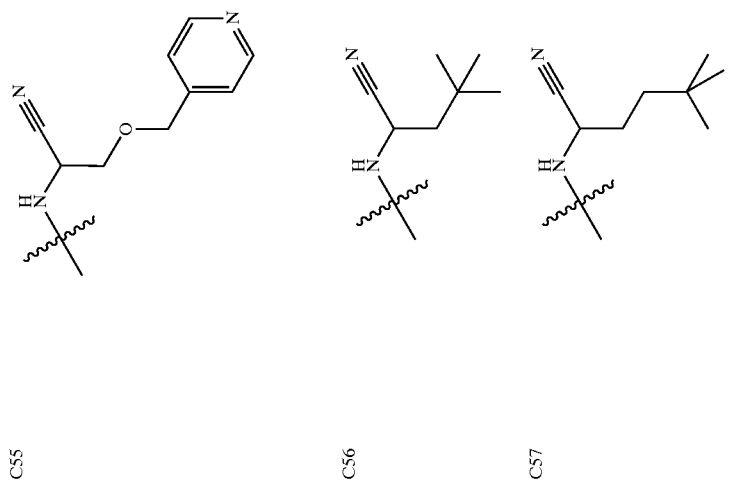

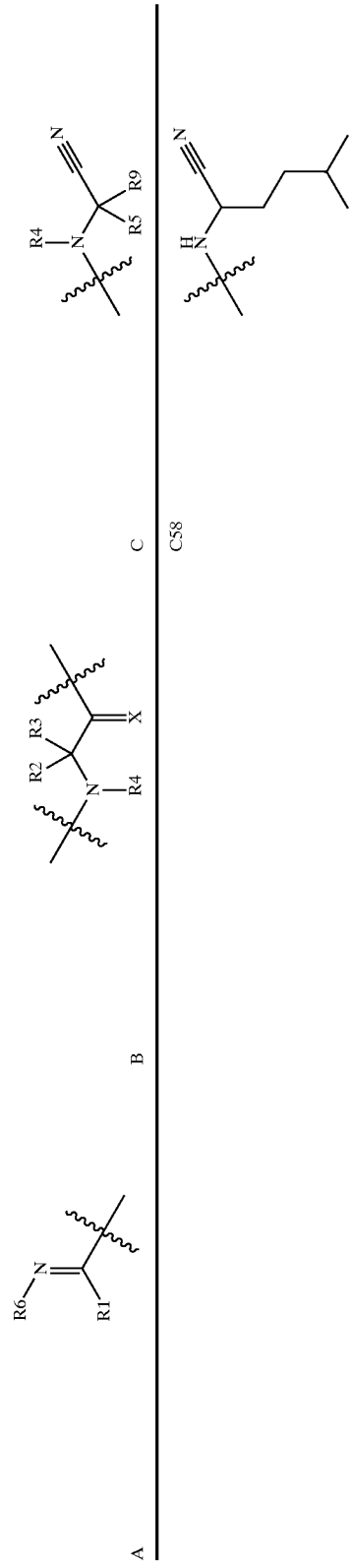

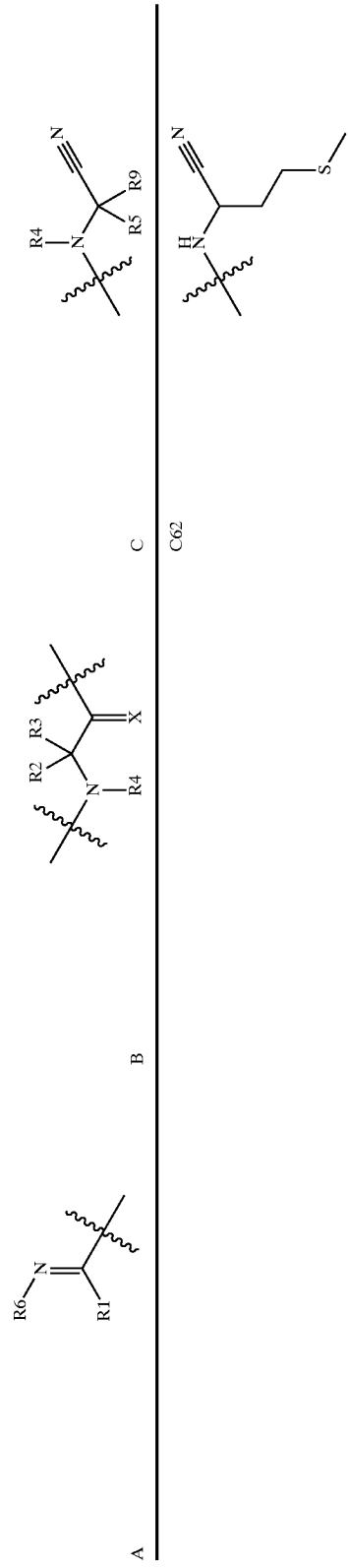

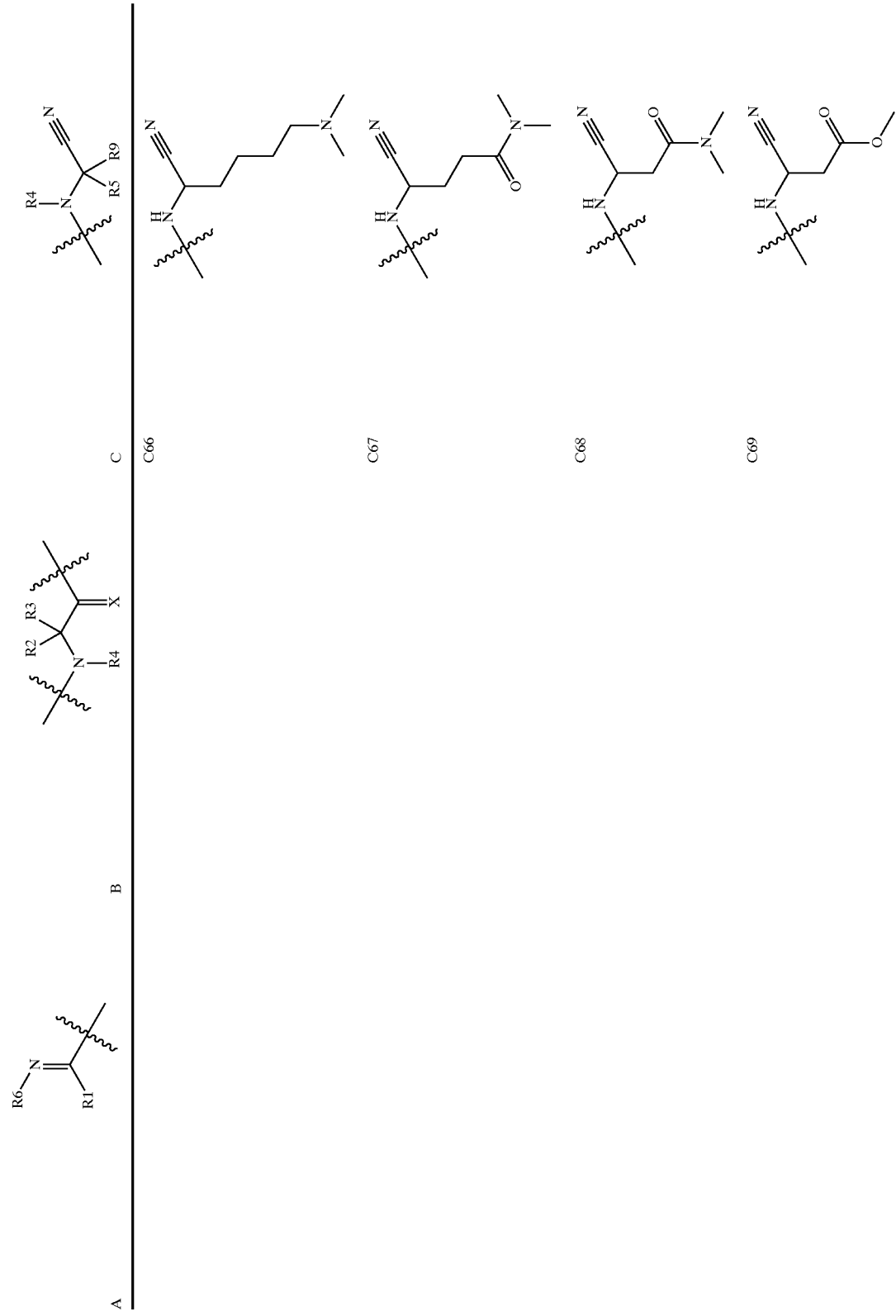

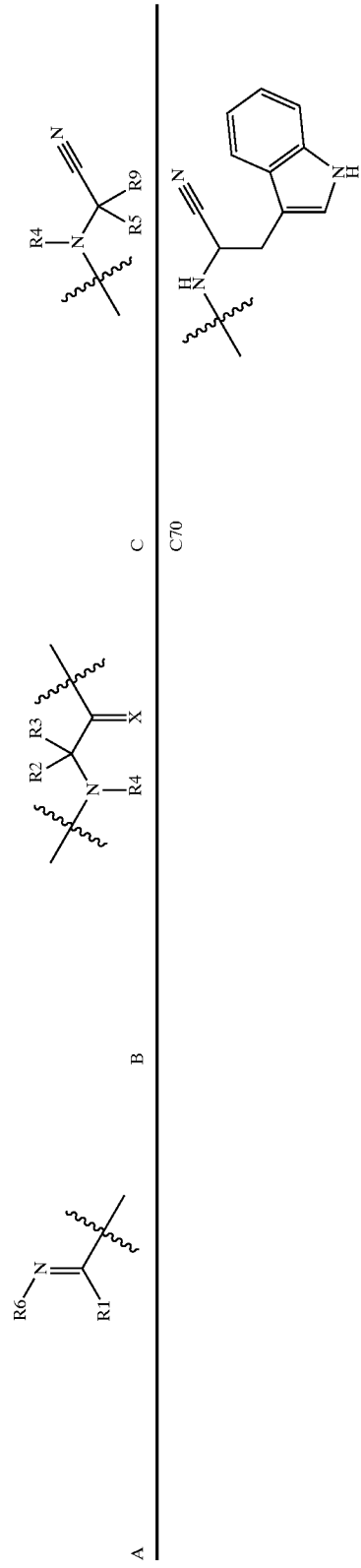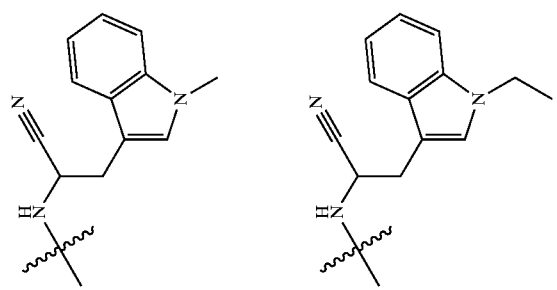

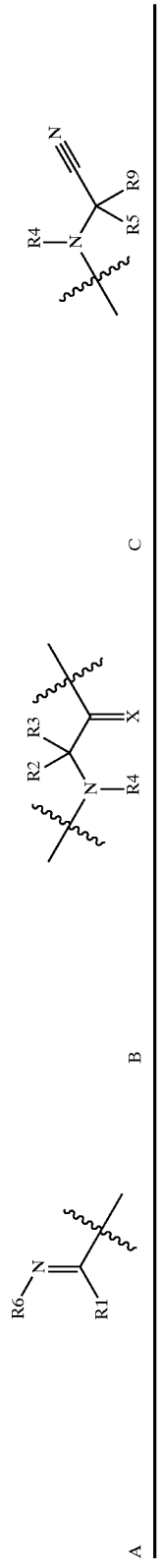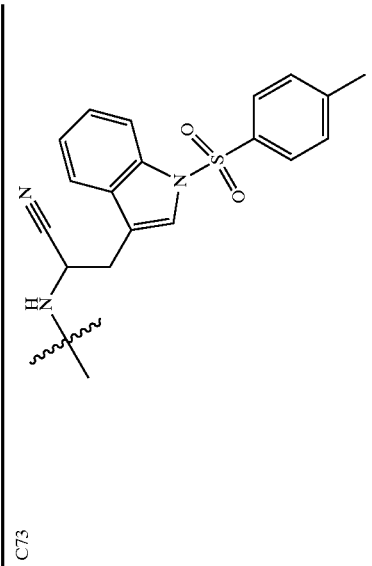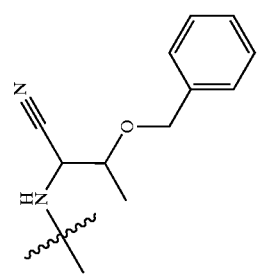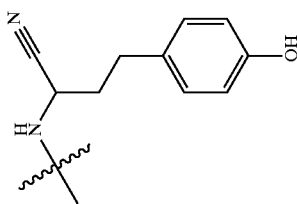

| A | B | C |
|---|---|---|
| 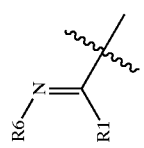 | 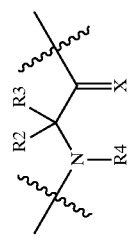 | 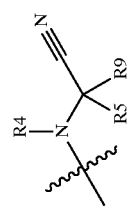 C76 |
| | | 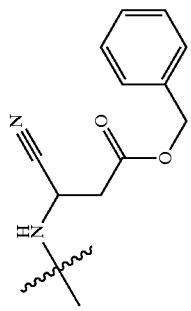 C77 |
| | | 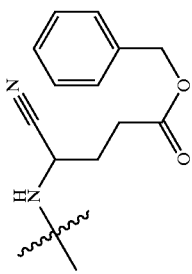 C78 |
| | | 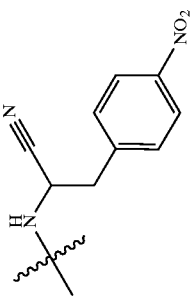 |

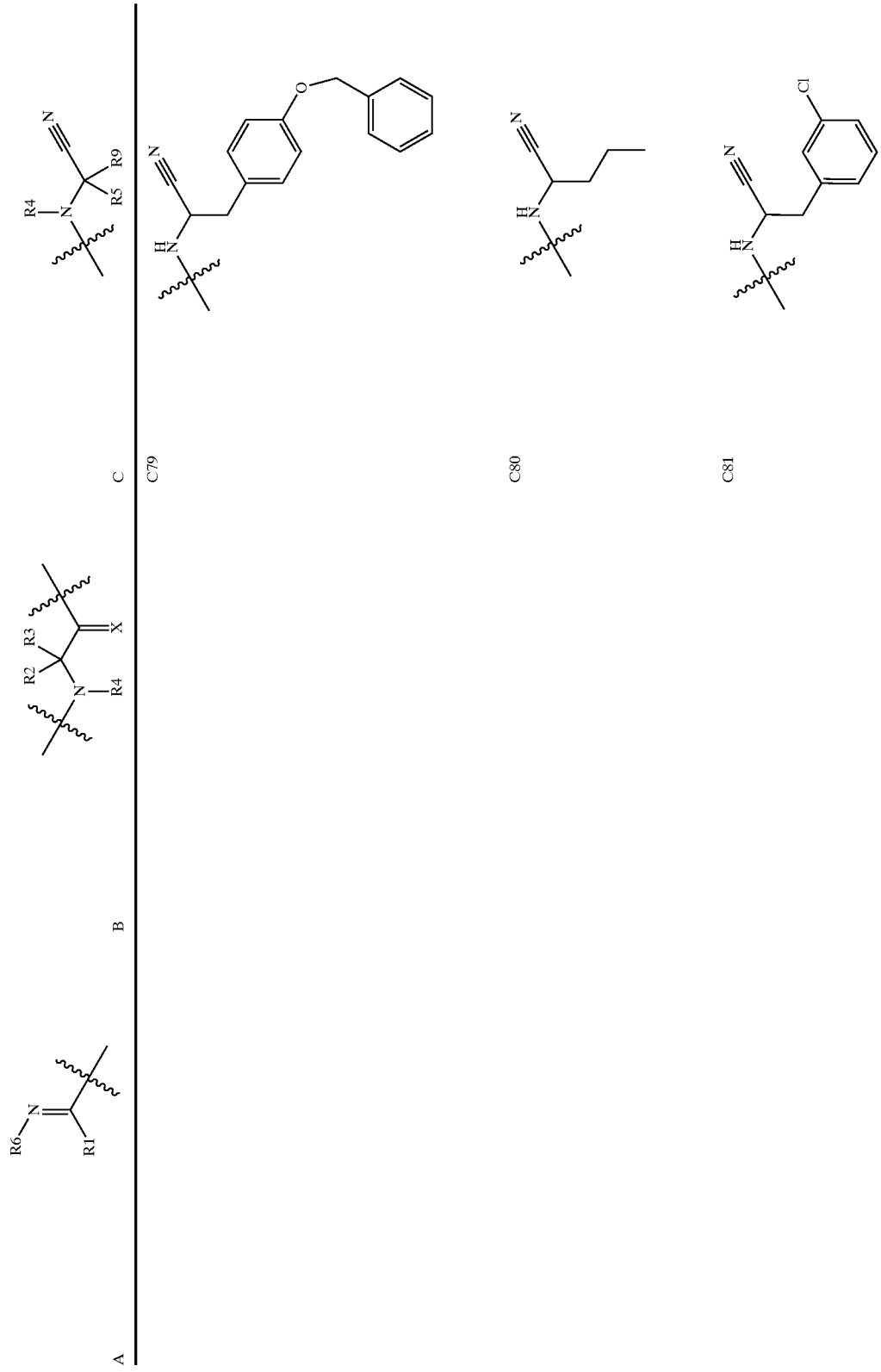

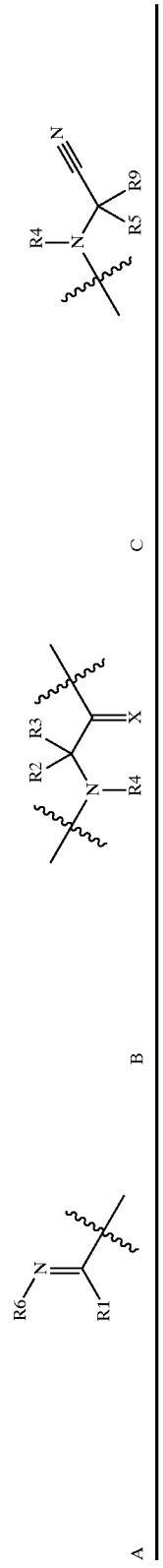
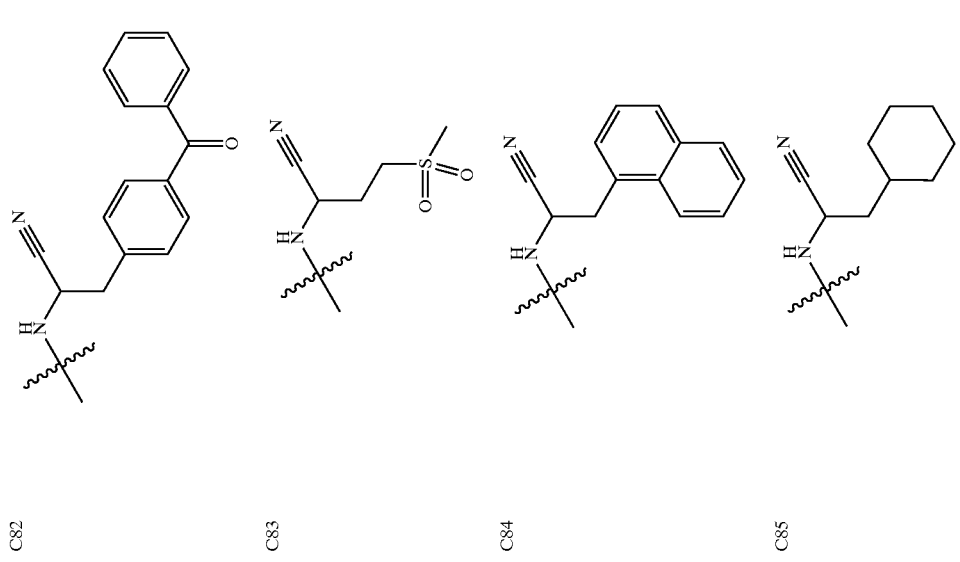

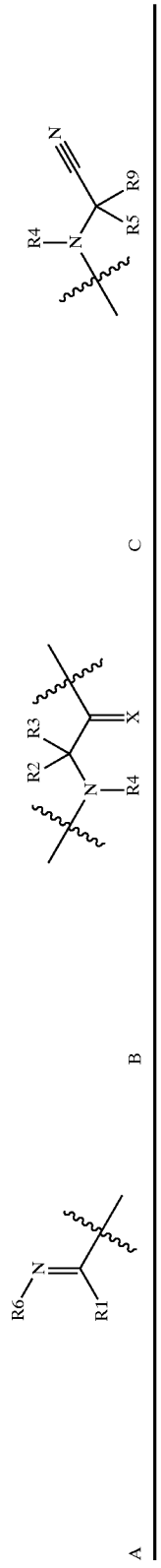
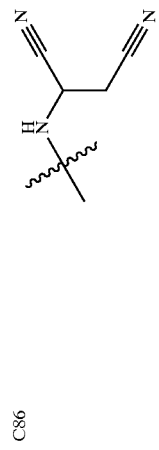
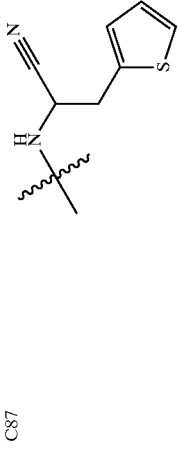
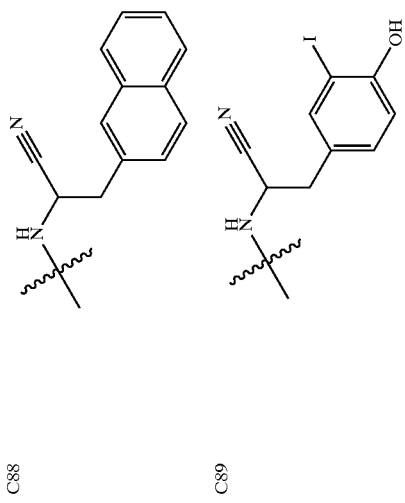

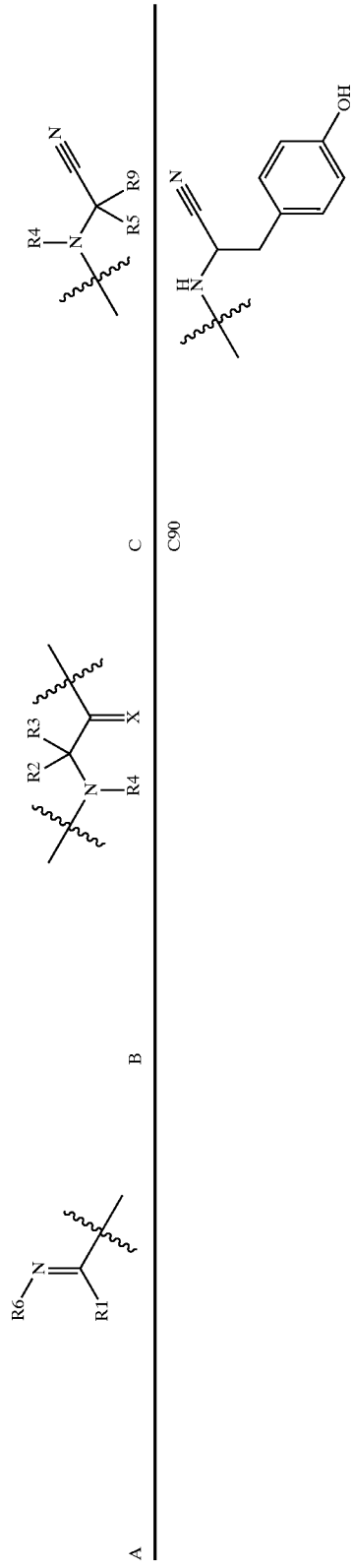
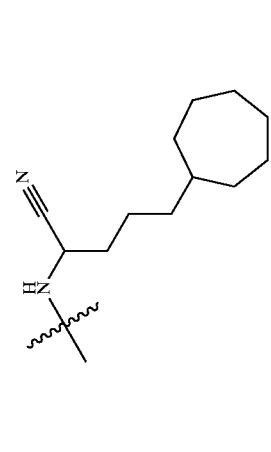
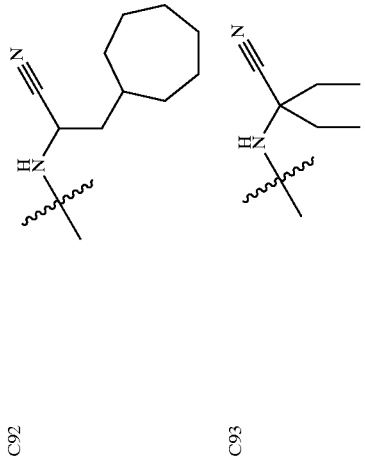

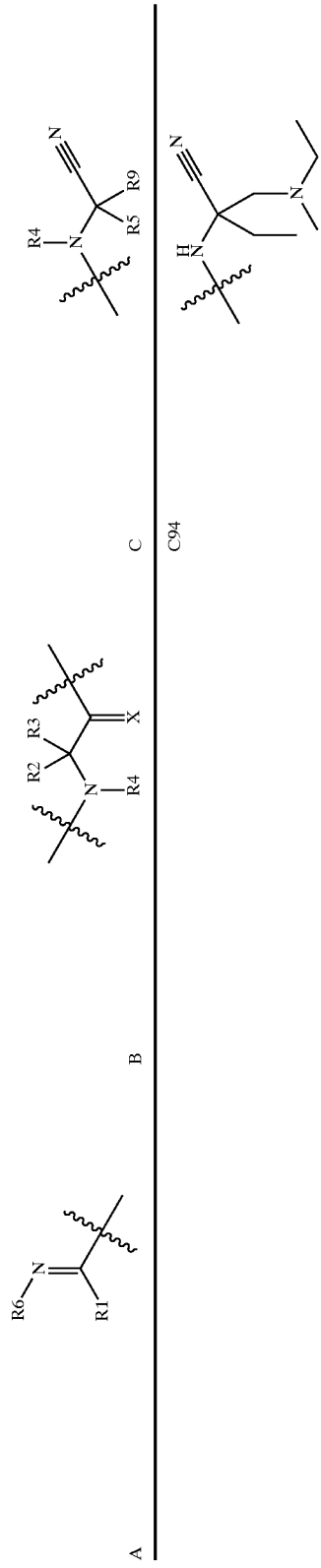

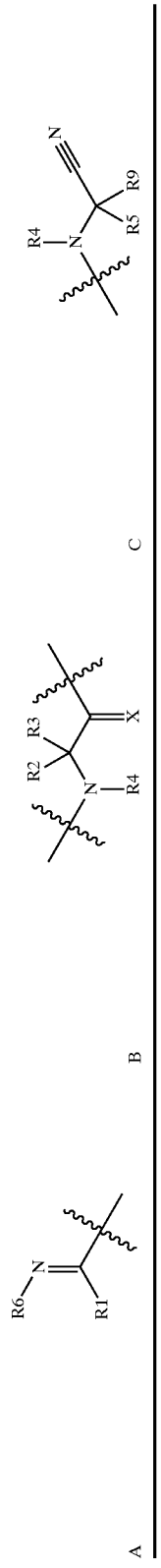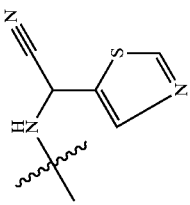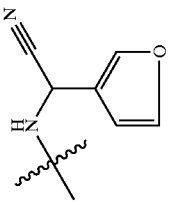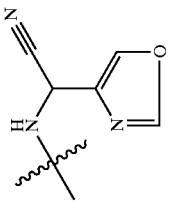

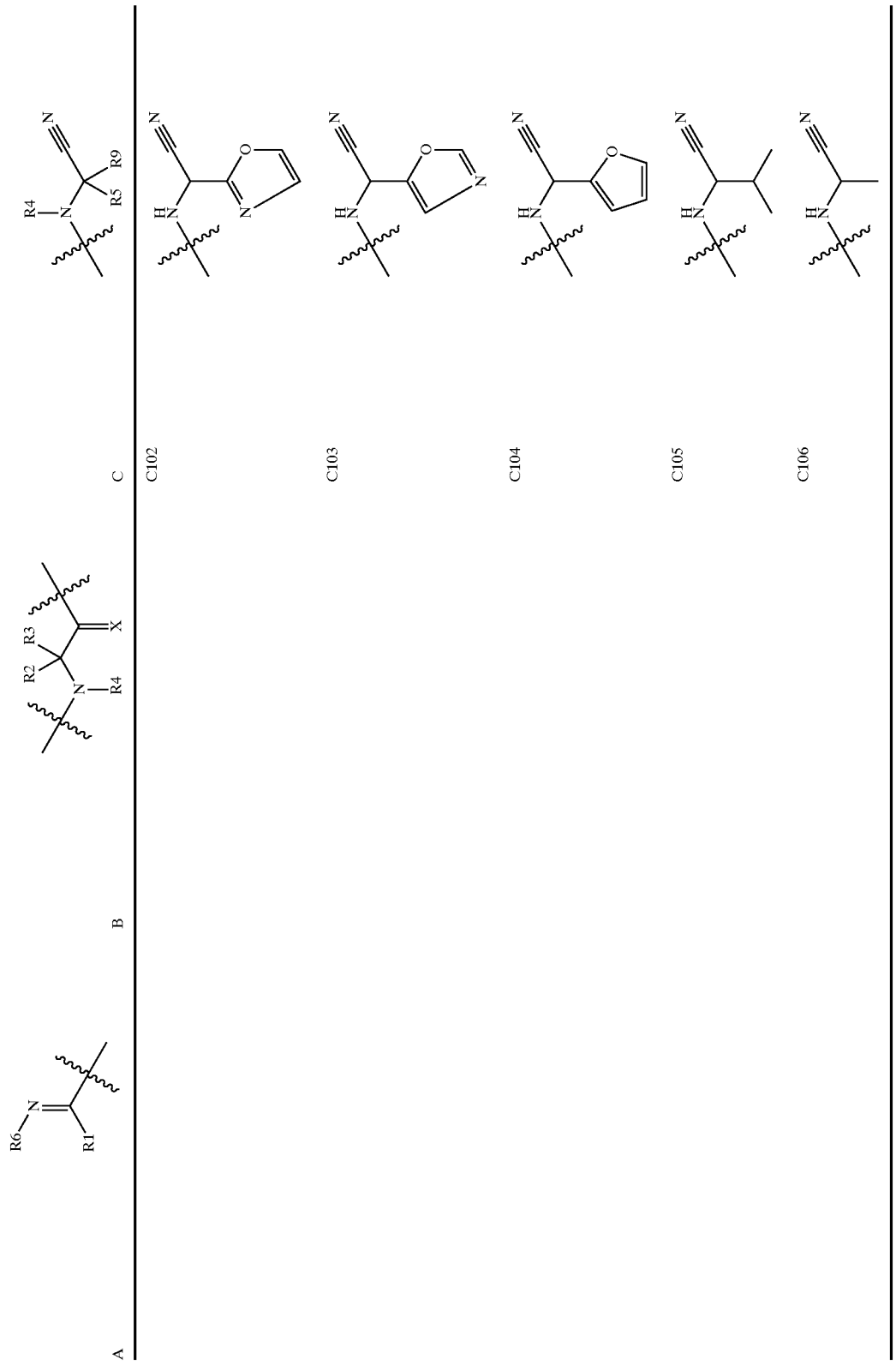

or the pharmaceutically acceptable salts, esters and tautomers thereof.

10. A compound chosen from:
4,4-Dimethyl-2-[1-(1-methyl-piperidin-4-yl)-2-oxo-2,3-dihydro-1H-quinazolin-4-ylideneamino]-pentanoic acid (1-cyano-cyclohexyl)-amide;
N-(1-Cyano-cyclohexyl)-3-cycloheptyl-2-[1-(1-methyl-piperidin-4-yl)-2-oxo-2,3-dihydro-1H-quinazolin-4-ylideneamino]-propionamide;
N-(1-Cyano-cyclohexyl)-3-cyclooctyl-2-{1-[2-(4-methyl-piperazin-1-yl)-ethyl]-2-oxo-2,3-dihydro-1H-quinazolin-4-ylideneamino}-propionamide;
2-[1-(2-Dimethylamino-ethyl)-2-oxo-2,3-dihydro-1H-quinazolin-4-ylideneamino]-4,4-dimethyl-pentanoic acid (1-cyano-cyclopentyl)-amide;
N-(1-Cyano-cyclopentyl)-2-[1-(3-dimethylamino-propyl)-2-oxo-2,3-dihydro-1H-quinazolin-4-ylideneamino]-3-(1,4,4-trimethyl-cyclohexyl)-propionamide;
N-Cyanomethyl-2-(4,4-dimethyl-cyclohexyl)-2-[2-oxo-1-(2-pyridin-4-yl-ethyl)-2,3-dihydro-1H-quinazolin-4-ylideneamino]-acetamide;
4-Methyl-4-(1-methyl-cyclopropyl)-2-[2-oxo-1-(3-pyrrolidin-1-yl-propyl)-2,3-dihydro-1H-quinazolin-4-ylideneamino]-pentanoic acid (1-cyano-cyclopentyl)-amide;
N-(1-Cyano-cyclopentyl)-4-(1-methyl-cyclopropyl)-2-[2-oxo-1-(3-piperidin-1-yl-propyl)-2,3-dihydro-1H-quinazolin-4-ylideneamino]-butyramide;
5,5-Dimethyl-2-[1-(1-methyl-piperidin-4-ylmethyl)-2-oxo-2,3-dihydro-1H-quinazolin-4-ylideneamino]-hexanoic acid cyanomethyl-amide;
4,4-Dimethyl-2-[1-(1-methyl-piperidin-4-ylmethyl)-2-oxo-2,3-dihydro-1H-quinazolin-4-ylideneamino]-pentanoic acid (1-cyano-cyclopropyl)-amide;
N-(1-Cyano-cyclopentyl)-3-cyclohexyl-2-[1-(1-methyl-piperidin-4-ylmethyl)-2-oxo-2,3-dihydro-1H-quinazolin-4-ylideneamino]-propionamide;
N-(Benzylsulfanylmethyl-cyano-methyl)-3-(4,4-diethyl-cyclohexyl)-2-{1-[2-(1-methyl-piperidin-4-yl)-ethyl]-2-oxo-2,3-dihydro-1H-quinazolin-4-ylideneamino}-propionamide;
4-Bicyclo[2.2.1]hept-1-yl-N-(1-cyano-3-phenyl-propyl)-2-{1-[2-(1-methyl-piperidin-4-yl)-ethyl]-2-oxo-2,3-dihydro-1H-quinazolin-4-ylideneamino}-butyramide;
4,4-Dimethyl-2-{1-[2-(1-methyl-piperidin-4-yl)-ethyl]-2-oxo-2,3-dihydro-1H-quinazolin-4-ylideneamino}-pentanoic acid (1-cyano-cyclopentyl)-amide;
N-(Benzyloxymethyl-cyano-methyl)-3-cyclohexyl-2-{1-[2-(4-methyl-piperazin-1-yl)-ethyl]-2-oxo-2,3-dihydro-1H-quinazolin-4-ylideneamino}-propionamide;
N-(1-Cyano-cyclopropyl)-3-cyclohexyl-2-{1-[2-(4-methyl-piperazin-1-yl)-ethyl]-2-oxo-2,3-dihydro-1H-quinazolin-4-ylideneamino}-propionamide;
4,4-Dimethyl-2-{1-[2-(4-methyl-piperazin-1-yl)-ethyl]-2-oxo-2,3-dihydro-1H-quinazolin-4-ylideneamino}-pentanoic acid (1-cyano-cyclopentyl)-amide;
(S)-5,5-Dimethyl-2-(2-oxo-2H-benzo[e][1,3]oxazin-4-ylamino)-heptanoic acid (1-cyano-cyclopropyl)-amide;
(S)-4,4-Dimethyl-2-(2-oxo-2H-benzo[e][1,3]oxazin-4-ylamino)-pentanoic acid (1-cyano-cyclopropyl)-amide;
(S)-4-methyl-2-(2-oxo-2H-benzo[e][1,3]oxazin-4-ylamino)-pentanoic acid (1-cyano-cyclopropyl)-amide;
(S)-2-(7-Fluoro-2-oxo-2H-benzo[e][1,3]oxazin-4-ylamino)-4,4-dimethyl-pentanoic acid (1-cyano-cyclopropyl)-amide;
(S)-5,5-Dimethyl-2-(1-methyl-2-oxo-1,2-dihydro-quinazolin-4-ylamino)-heptanoic acid (1-cyano-cyclopropyl)-amide;
(S)-4,4-Dimethyl-2-(1-methyl-2-oxo-1,2-dihydro-quinazolin-4-ylamino)-pentanoic acid (1-cyano-cyclopropyl)-amide;
(S)-4,4,5,5-Tetramethyl-2-(1-methyl-2-oxo-1,2-dihydro-quinazolin-4-ylamino)-hexanoic acid (1-cyano-cyclopropyl)-amide;
(S)-4,4,5,5-Tetramethyl-2-(2-oxo-2H-benzo[e][1,3]oxazin-4-ylamino)-hexanoic acid (1-cyano-cyclopropyl)-amide;
2-(7-Fluoro-2-oxo-2H-benxo[e][1,3]oxazin-4-ylamino)-5,5-dimethyl-heptanoic acid (1-cyano-cyclopropyl)-amide;
4-Methyl-2-(2-oxo-2H-benzo[e][1,3]oxazin-4-ylamino)-pentanoic acid (1-cyano-cyclopropyl)-amide;
2-(7-Fluoro-2-oxo-2H-benzo[e][1,3]oxazin-4-ylamino)-4-methyl-pentanoic acid (1-cyano-cyclopropyl)-amide;
N-Cyano-dimethyl-methyl)-3-cyclohexyl-2-(2-oxo-2H-benzo[e][1,3]oxazin-4-ylamino)-propionamide;
N-(1-Cyano-cyclopropyl)-3-cyclohexyl-2-(2-oxo-2H-benzo[e][1,3]oxazin-4-ylamino)-propionamide;
N-(1-Cyano-cyclopropyl)-3-cyclohexyl-2-(7-fluoro-2-oxo-2H-benzo[e][1,3]oxazin-4-ylamino)-propionamide;
N-(Cyano-benzyloxymethyl-methyl)-3-cyclohexyl-2-(2-oxo-2H-benzo[e][1,3]oxazin-4-ylamino)-propionamide;
4,4-Dimethyl-2-(2-oxo-2H-benxo[e][1,3]oxazin-4-ylamino)-pentanoic acid (cyano-benzyloxymethyl-methyl)-amide;
2-(1,1-Dioxo-1H-1λ⁶-benzo[d]isothiazol-3-ylamino)-4,4-dimethyl-pentanoic acid (cyano-benzyloxymethyl-methyl)-amide;
N-(Cyano-benzyloxymethyl-methyl)-3-cyclohexyl-2-(1,1-dioxo-1H-1-λ⁶-benzo[d]isothiazol-3-ylamino)-propionamide;
N-(1-Cyano-cylopropyl)-3-cyclohexyl-2-(1,1-dioxo-1H-1λ-⁶-benzo[d]isothiazol-3-ylamino)-propionamide;
N-(Cyano-dimethyl-methyl)-3-cyclohexyl-2-(1,1-dioxo-1H-1λ⁶-benzo[d]isothiazol-3-ylamino)-propionamide;
2-(1,1-Dioxo-1H-1λ⁶-benzo[d]isothiazol-3-ylamino)-4,4-dimethyl-pentanoic acid cyanomethyl-amide;
2-(1,1-Dioxo-1H-1λ⁶-benzo[d]isothiazol-3-ylamino)-4,4-dimethyl-pentanoic acid (1-cyano-cyclopropyl)-amide;
2-(1,1-Dioxo-1H-1λ⁶-benzo[d]isothiazol-3-ylamino)-4-methyl-pentanoic acid (1-cyano-cyclopropyl)-amide and
2-(1,1-Dioxo-1H-1λ⁶-benzo[d]isothiazol-3-ylamino)-5,5-dimethyl-heptanoic acid (1-cyano-cyclopropyl)-amide or the pharmaceutically acceptable salts, esters and tautomers thereof.

11. A pharmaceutical composition comprising a pharmaceutically effective amount of a compound according to claim 1.

12. A process of making a compound of the formula (Ia) according to the equation:

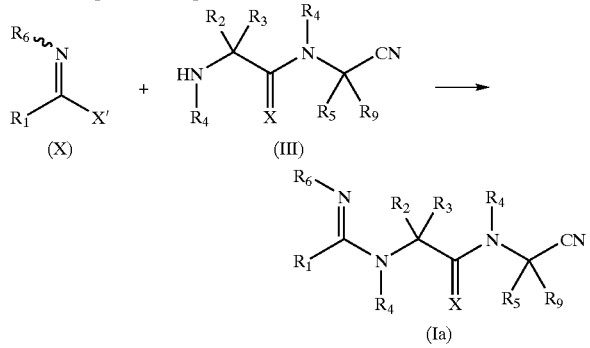

wherein for the formula (Ia), $R_1$, $R_2$, $R_3$, $R_4$, $R_5$, $R_6$, $R_9$ and X are as defined in claim 1, said process comprising:
reacting a dipeptide nitrile intermediate of the formula (III) shown above, or a basic salt thereof, with a compound intermediate of the formula X shown above, wherein X' is an appropriate leaving group, with or without an appropriate base to provide the product compound of the formula(Ia).

* * * * *